US010336774B2

(12) United States Patent
Chen et al.

(10) Patent No.: US 10,336,774 B2
(45) Date of Patent: Jul. 2, 2019

(54) N-AZASPIROCYCLOALKANE SUBSTITUTED N-HETEROARYL COMPOUNDS AND COMPOSITIONS FOR INHIBITING THE ACTIVITY OF SHP2

(71) Applicant: NOVARTIS AG, Basel (CH)

(72) Inventors: Christine Hiu-Tung Chen, Waltham, MA (US); Zhuoliang Chen, Belmont, MA (US); Michael Dore, Wilmington, MA (US); Jorge Garcia Fortanet, Wilmington, MA (US); John William Giraldes, Windsor Mill, MD (US); Rajesh Karki, Quincy, MA (US); Mitsunori Kato, Cambridge, MA (US); Matthew J. LaMarche, Reading, MA (US); Lawrence Blas Perez, Silver Spring, MD (US); Martin Sendzik, Belmont, MA (US); Troy Douglas Smith, Nashua, NH (US); Bakary-Barry Toure, Weston, MA (US); Sarah Williams, Emeryville, CA (US)

(73) Assignee: Novartis AG, Basel (CH)

(*) Notice: Subject to any disclaimer, the term of this patent is extended or adjusted under 35 U.S.C. 154(b) by 0 days.

(21) Appl. No.: 15/899,821

(22) Filed: Feb. 20, 2018

(65) Prior Publication Data
US 2018/0201623 A1 Jul. 19, 2018

Related U.S. Application Data

(62) Division of application No. 15/110,511, filed as application No. PCT/IB2015/050345 on Jan. 16, 2015, now Pat. No. 10,077,276.
(Continued)

(51) Int. Cl.
C07D 401/04 (2006.01)
C07D 401/14 (2006.01)
C07D 471/10 (2006.01)
C07D 498/10 (2006.01)
C07D 241/18 (2006.01)
C07D 241/20 (2006.01)
C07D 403/04 (2006.01)
(Continued)

(52) U.S. Cl.
CPC ......... C07D 498/10 (2013.01); C07D 241/18 (2013.01); C07D 241/20 (2013.01); C07D 401/04 (2013.01); C07D 401/14 (2013.01); C07D 403/04 (2013.01); C07D 471/10 (2013.01); C07D 491/107 (2013.01); C07D 495/10 (2013.01); C07B 2200/07 (2013.01)

(58) Field of Classification Search
CPC ... C07D 401/04; C07D 401/14; C07D 471/10
See application file for complete search history.

(56) References Cited

U.S. PATENT DOCUMENTS 4,613,603 A 9/1986 Biziere et al.
2003/0171359 A1 9/2003 Dahmann et al.
(Continued)

FOREIGN PATENT DOCUMENTS

CN 102753177 A 10/2012
EP 0 459 819 A2 4/1991
(Continued)

OTHER PUBLICATIONS

Whelligan, et al., "Aminopyrazine Inhibitors Binding to an Unusual Inactive Conformation of the Mitotic Kinase Nek2: SAR and Structural Characterization", Journal of Medicinal Chemistry, 2010, vol. 53, No. 21, pp. 7682-7698, American Chemical Society.
Ellingboe, et al., (Pyrimidinyloxy)acetic Acids and Pyrimidineacetic Acids as a Novel Class of Aldose Reductase Inhibitors, Journal of Medicinal Chemistry, 1990, vol. 33, pp. 2892-2899, American Chemical Society.
Aso, et al., "Discovery of pyrrolo[2,3-d]pyrimidin-4-ones as corticotropin-releasing factor 1 receptor agonists with a carbonyl-based hydrogen bonding acceptor", Bioorganic & Medicinal Chemistry Letters, 2011, pp. 2365-237, vol. 21, Elsevier Ltd.
Fortanet, et al., "Allosteric Inhibition of SHP2: Identification of a Potent, Selective, and Orally Efficacious Phosphatase Inhibitor", Journal of Medicinal Chemistry, Jun. 27, 2016, pp. 7773-7782, vol. 59, American Chemical Society.
(Continued)

Primary Examiner — Brian E McDowell
(74) Attorney, Agent, or Firm — Scott W. Reid

(57) ABSTRACT

The present invention relates to compounds of formula I:

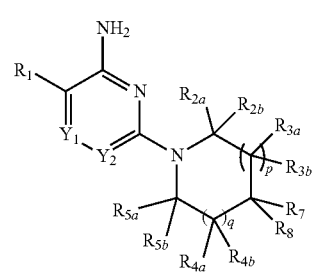

in which p, q, $Y_1$, $Y_2$, $R_1$, $R_{2a}$, $R_{2b}$, $R_{3a}$, $R_{3b}$, $R_{4a}$, $R_{4b}$, $R_{5a}$, $R_{5b}$, $R_7$ and $R_8$ are defined in the Summary of the Invention; capable of inhibiting the activity of SHP2. The invention further provides a process for the preparation of compounds of the invention, pharmaceutical preparations comprising such compounds and methods of using such compounds and compositions in the management of diseases or disorders associated with the aberrant activity of SHP2.

22 Claims, No Drawings
Specification includes a Sequence Listing.

Related U.S. Application Data

(60) Provisional application No. 61/928,754, filed on Jan. 17, 2014, provisional application No. 61/991,129, filed on May 9, 2014.

(51) Int. Cl.
*C07D 491/107* (2006.01)
*C07D 495/10* (2006.01)

(56) References Cited

U.S. PATENT DOCUMENTS

| | | |
|---|---|---|
| 2004/0229873 A1 | 11/2004 | Harbige et al. |
| 2005/0222159 A1 | 10/2005 | Tsutsumi et al. |
| 2008/0024964 A1 | 1/2008 | Lev et al. |
| 2011/0257184 A1 | 10/2011 | Qu et al. |
| 2011/0306606 A1 | 12/2011 | Ryu et al. |
| 2011/0319381 A1 | 12/2011 | Abouabdellah et al. |
| 2012/0252818 A1 | 10/2012 | Chiosis et al. |
| 2013/0116430 A1 | 5/2013 | Fujiwara et al. |
| 2015/0315207 A1 | 11/2015 | Morales et al. |

FOREIGN PATENT DOCUMENTS

| | | |
|---|---|---|
| EP | 799617 A2 | 10/1997 |
| JP | 6-340634 | 12/1994 |
| WO | 1991019305 A1 | 5/1991 |
| WO | 2000059893 A1 | 10/2000 |
| WO | 2002024679 A1 | 3/2002 |
| WO | 2005117909 A2 | 12/2005 |
| WO | 2007031529 A1 | 3/2007 |
| WO | 2008055959 A1 | 5/2008 |
| WO | 2008100412 A1 | 8/2008 |
| WO | 2008110611 A1 | 9/2008 |
| WO | 2009131687 A2 | 10/2009 |
| WO | 2009150230 A1 | 12/2009 |
| WO | 2009158571 A1 | 12/2009 |
| WO | 2010/011666 A2 | 1/2010 |
| WO | 2010008739 A1 | 1/2010 |
| WO | 2010048149 A2 | 4/2010 |
| WO | 2012121212 A2 | 10/2010 |
| WO | 2011078143 A1 | 6/2011 |
| WO | 11022440 A2 | 8/2011 |
| WO | 2012009217 A1 | 1/2012 |
| WO | 2012016217 A1 | 2/2012 |
| WO | 2012027495 A1 | 3/2012 |
| WO | 2012052948 A1 | 4/2012 |
| WO | 2013040044 A1 | 3/2013 |
| WO | 2013096093 A1 | 6/2013 |
| WO | 2013182546 A1 | 12/2013 |
| WO | 2014054053 A1 | 4/2014 |
| WO | 2014160521 A1 | 10/2014 |
| WO | 2015107493 A1 | 7/2015 |
| WO | 2015107494 A1 | 7/2015 |
| WO | 2015168466 A1 | 11/2015 |
| WO | 2016203404 A1 | 12/2016 |
| WO | 2016203405 A1 | 12/2016 |
| WO | 2016203406 A1 | 12/2016 |

OTHER PUBLICATIONS

RN 1326924-17-7, Database Registry [Online], Sep. 2, 2011, Retrieved from STN.

RN 1326900-40-6, Database Registry [Online], Sep. 2, 2011, Retrieved from STN.

RN 1326894-16-9, Database Registry [Online], Sep. 2, 2011, Retrieved from STN.

RN 1326879-96-2, Database Registry [Online], Sep. 2, 2011, Retrieved from STN.

RN 1115976-39-0, Database Registry [Online], Mar. 5, 2009, Retrieved from STN.

RN 1115976-35-6, Database Registry [Online], Mar. 5, 2009, Retrieved from STN.

RN 1115905-70-8, Database Registry [Online], Mar. 5, 2009, Retrieved from STN.

RN 1115905-69-5, Database Registry [Online], Mar. 5, 2009, Retrieved from STN.

RN 1115905-67-3, Database Registry [Online], Mar. 5, 2009, Retrieved from STN.

Large, Charles H., et al., "The relationship between sodium channel inhibition and anticonvulsant activity in a model of generalized seizure in the rat", Epilepsy Research, 85:96-106. 2009.

Hussein, Z. et al., "Pharmacokinetics of 619C89, a novel neuronal sodium channel inhibitor, in acute stroke patients after loading and discrete maintenance infusions", British Journal of Clinical Pharmacology, 41(6):505-511. 1996.

Palmer, Alan M., et al., "The role of sodium channels in disease", Drug News & Perspectives, 14(9):568-576. 2001.

N-AZASPIROCYCLOALKANE SUBSTITUTED N-HETEROARYL COMPOUNDS AND COMPOSITIONS FOR INHIBITING THE ACTIVITY OF SHP2

CROSS-REFERENCE TO RELATED APPLICATIONS

This application is a U.S. Divisional Patent Application of U.S. patent application Ser. No. 15/110,511, filed Jul. 8, 2016, which is a 371 U.S. national phase application of international application number PCT/IB2015/050345 filed 16 Jan. 2015, which application claims the benefit of priority under 35 U.S.C. § 119(e) to U.S. Provisional Patent Application No. 61/928,754, filed 17 Jan. 2014 and U.S. Provisional Patent Application No. 61/991,129, filed 9 May 2014. The disclosure of these applications are incorporated herein by reference in their entirety and for all purposes.

BACKGROUND

Field of the Invention

The present invention relates to compounds capable of inhibiting the activity of SHP2. The invention further provides a process for the preparation of compounds of the invention, pharmaceutical preparations comprising such compounds and methods of using such compounds and compositions in the management of diseases or disorders associated with the aberrant activity of SHP2.

Background of the Invention

The Src Homolgy-2 phosphatase (SHP2) is a non-receptor protein tyrosine phosphatase encoded by the PTPN11 gene that contributes to multiple cellular functions including proliferation, differentiation, cell cycle maintenance and migration. SHP2 is involved in signaling through the Ras-mitogen-activated protein kinase, the JAK-STAT or the phosphoinositol 3-kinase-AKT pathways.

SHP2 has two N-terminal Src homology 2 domains (N-SH2 and C-SH2), a catalytic domain (PTP), and a C-terminal tail. The two SH2 domains control the subcellular localization and functional regulation of SHP2. The molecule exists in an inactive, self-inhibited conformation stabilized by a binding network involving residues from both the N-SH2 and PTP domains. Stimulation by, for example, cytokines or growth factors leads to exposure of the catalytic site resulting in enzymatic activation of SHP2.

Mutations in the PTPN11 gene and subsequently in SHP2 have been identified in several human diseases, such as Noonan Syndrome, Leopard Syndrome, juvenile myelomonocytic leukemias, neuroblastoma, melanoma, acute myeloid leukemia and cancers of the breast, lung and colon. SHP2, therefore, represents a highly attractive target for the development of novel therapies for the treatment of various diseases. The compounds of the present invention fulfill the need of small molecules to that inhibit the activity of SHP2.

SUMMARY OF THE INVENTION

In one aspect, the present invention provides compounds of Formula I:

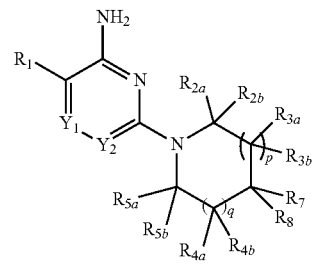

in which: p is selected from 0 and 1; q is selected from 0 and 1; $Y_1$ is selected from CH and N; $Y_2$ is selected from $CR_6$ and N; $R_1$ is $-XR_{1a}$; wherein $R_{1a}$ is selected from $C_{6-10}$aryl, $C_{3-8}$cycloalkyl, $C_{3-8}$cycloalkenyl and a 5-9 member heteroaryl group containing from 1 to 4 heteroatoms or groups independently selected from N, C(O), O and S; wherein said aryl or heteroaryl of $R_{1a}$ is substituted with 1 to 5 $R_9$ groups independently selected from halo, amino, hydroxy, $N_3$, $C_{1-4}$alkyl, dimethyl-amino, hydroxy-substituted-$C_{1-4}$alkyl, halo-substituted-$C_{1-4}$alkyl, amino-substituted-$C_{1-4}$alkyl, $-C(O)OR_{10}$ and $-NHC(O)R_{10}$; and X is selected from a bond, $S(O)_m$, O, C(O), $COR_{11}$, $CR_{10a}R_{10b}$, $NR_{11}$; wherein m is selected from 0, 1 and 2; each $R_{10a}$ and $R_{10b}$ is independently selected from halo and $C_{1-4}$alkyl; and $R_{11}$ is selected from hydrogen and $C_{1-4}$alkyl; $R_{2a}$ and $R_{2b}$ are independently selected from hydrogen, $C_{1-4}$alkyl, $C_{1-4}$alkoxy, amino, hydroxy, $C_{3-8}$cycloalkyl and $C_{1-4}$alkyl-amino; $R_{3a}$ and $R_{3b}$ are independently selected from halo, carbonyl, $C_{1-4}$alkyl, $C_{1-4}$alkoxy, amino, hydroxy, $C_{3-8}$cycloalkyl and $C_{1-4}$alkyl-amino; $R_{4a}$ and $R_{4b}$ are independently selected from hydrogen, halo, carbonyl, $C_{1-4}$alkyl, $C_{1-4}$alkoxy, amino, hydroxy, $C_{3-8}$cycloalkyl and $C_{1-4}$alkyl-amino; $R_{5a}$ and $R_{5b}$ are independently selected from hydrogen, carbonyl, $C_{1-4}$alkyl, $C_{1-4}$alkoxy, amino, hydroxy, $C_{3-8}$cycloalkyl and $C_{1-4}$alkyl-amino; wherein any two groups selected from $R_{2a}$, $R_{2b}$, $R_{3a}$, $R_{3b}$, $R_{4a}$, $R_{4b}$, $R_{5a}$, $R_{5b}$ and $R_7$ can form a 5 to 6 member unsaturated or partially saturated ring; $R_6$ is selected from hydrogen, halo, cyano, $C_{1-4}$alkyl, $C_{1-4}$alkoxy, amino-carbonyl, halo-substituted $C_{1-4}$alkyl, halo-substituted $C_{1-4}$alkoxy, hydroxy-substituted $C_{1-4}$alkyl, amino-substituted $C_{1-4}$alkyl, $-S(O)_{1-2}R_{6a}$, $-C(S)R_{6a}$, $-C(O)NR_{6a}R_{6b}$, $-C(NH)NR_{6a}R_{6b}$ and $-NR_{6a}C(O)R_{6b}$; wherein $R_{6a}$ and $R_{6b}$ are independently selected from hydrogen and $C_{1-4}$alkyl; $R_7$ and $R_8$ together with the carbon atom to which they are both attached form a 3 to 7 member saturated or partially unsaturated ring that can optionally contain 1 to 3 heteroatoms or groups independently selected from N, C(O), O and S(O)m; wherein m is selected from 0, 1 and 2; wherein said saturated ring formed by $R_7$ and $R_8$ can be unsubstituted or substituted with 1 to 3 groups independently selected from amino, hydroxy, methoxy, halo, methyl, methyl-amino and isobutyryloxy.

In a second aspect, the present invention provides a pharmaceutical composition which contains a compound of Formula I or a N-oxide derivative, tautomer, individual isomers and mixture of isomers thereof; or a pharmaceutically acceptable salt thereof, in admixture with one or more suitable excipients.

In a third aspect, the present invention provides a method of treating a disease in an animal in which modulation of SHP2 activity can prevent, inhibit or ameliorate the pathology and/or symptomology of the diseases, which method comprises administering to the animal a therapeutically effective amount of a compound of Formula I or a N-oxide derivative, individual isomers and mixture of isomers thereof, or a pharmaceutically acceptable salt thereof.

In a fourth aspect, the present invention provides a method of treating a disease in an animal in which modulation of SHP2 activity can prevent, inhibit or ameliorate the pathology and/or symptomology of the diseases, which method comprises administering to the animal a therapeutically effective amount of a compound of Formula I or a N-oxide derivative, individual isomers and mixture of isomers thereof, or a pharmaceutically acceptable salt thereof, in simultaneous or sequential combination with an anticancer therapeutic.

In a fifth aspect, the present invention provides the use of a compound of Formula I in the manufacture of a medicament for treating a disease in an animal in which SHP2 activity contributes to the pathology and/or symptomology of the disease.

In a sixth aspect, the present invention provides a process for preparing compounds of Formula I and the N-oxide derivatives, prodrug derivatives, protected derivatives, individual isomers and mixture of isomers thereof, and the pharmaceutically acceptable salts thereof.

Definitions

The general terms used hereinbefore and hereinafter preferably have within the context of this disclosure the following meanings, unless otherwise indicated, where more general terms wherever used may, independently of each other, be replaced by more specific definitions or remain, thus defining more detailed embodiments of the invention:

"Alkyl" refers to a fully saturated branched or unbranched hydrocarbon moiety having up to 20 carbon atoms. Unless otherwise provided, alkyl refers to hydrocarbon moieties having 1 to 7 carbon atoms ($C_{1-7}$alkyl), or 1 to 4 carbon atoms ($C_{1-4}$alkyl). Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. A substituted alkyl is an alkyl group containing one or more, such as one, two or three substituents selected from halogen, hydroxy or alkoxy groups. Halo-substituted-alkyl and halo-substituted-alkoxy, can be either straight-chained or branched and includes, methoxy, ethoxy, difluoromethyl, trifluoromethyl, pentafluoroethyl, difluoromethoxy, trifluoromethoxy, and the like.

"Aryl" means a monocyclic or fused bicyclic aromatic ring assembly containing six to ten ring carbon atoms. For example, aryl may be phenyl or naphthyl, preferably phenyl. "Arylene" means a divalent radical derived from an aryl group.

"Heteroaryl" is as defined for aryl above where one or more of the ring members is a heteroatom. For example $C_{5-10}$heteroaryl is a minimum of 5 members as indicated by the carbon atoms but that these carbon atoms can be replaced by a heteroatom. Consequently, $C_{5-10}$heteroaryl includes pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, etc.

"Cycloalkyl" means a saturated or partially unsaturated, monocyclic, fused bicyclic or bridged polycyclic ring assembly containing the number of ring atoms indicated. For example, $C_{3-10}$cycloalkyl includes cyclopropyl, cyclobutyl, cyclopentyl, cyclohexyl, cyclohexenyl, etc.

"Heterocycloalkyl" means cycloalkyl, as defined in this application, provided that one or more of the ring carbons indicated, are replaced by a moiety selected from —O—, —N═, —NR—, —C(O)—, —S—, —S(O)— or —S(O)$_2$—, wherein R is hydrogen, $C_{1-4}$alkyl or a nitrogen protecting group. For example, $C_{3-8}$heterocycloalkyl as used in this application to describe compounds of the invention includes morpholino, pyrrolidinyl, pyrrolidinyl-2-one, piperazinyl, piperidinyl, piperidinylone, 1,4-dioxa-8-aza-spiro[4.5]dec-8-yl, thiomorpholino, sulfanomorpholino, sulfonomorpholino, etc.

"Halogen" (or halo) preferably represents chloro or fluoro, but may also be bromo or iodo.

"SHP2" means "Src Homolgy-2 phosphatase" and is also known as SH-PTP2, SH-PTP3, Syp, PTP1D, PTP2C, SAP-2 or PTPN11.

Cancers harboring "PTPN11 mutations" include but are not limited to: N58Y; D61Y, V; E69K; A72V, T, D; E76G, Q, K (ALL); G60A; D61Y; E69V; F71K; A72V; T73I; E76G, K; R289G; G503V (AML); G60R, D61Y, V, N; Y62D; E69K; A72T, V; T73I; E76K, V, G, A, Q; E139D; G503A, R; Q506P (JMML); G60V; D61V; E69K; F71L; A72V; E76A (MDS); Y63C (CMML); Y62C; E69K; T507K (neuroblastoma); V46L; N58S; E76V (Lung cancer); R138Q (melanoma); E76G (colon cancer).

Compounds of formula I may have different isomeric forms. For example, any asymmetric carbon atom may be present in the (R)-, (S)- or (R,S)-configuration, preferably in the (R)- or (S)-configuration. Substituents at a double bond or especially a ring may be present in cis-(═Z-) or trans (═E-) form. The compounds may thus be present as mixtures of isomers or preferably as pure isomers, preferably as pure diastereomers or pure enantiomers.

Where the plural form (e.g. compounds, salts) is used, this includes the singular (e.g. a single compound, a single salt). "A compound" does not exclude that (e.g. in a pharmaceutical formulation) more than one compound of the formula I (or a salt thereof) is present, the "a" merely representing the indefinite article. "A" can thus preferably be read as "one or more", less preferably alternatively as "one".

Wherever a compound or compounds of the formula I are mentioned, this is further also intended to include N-oxides of such compounds and/or tautomers thereof.

The term "and/or an N-oxide thereof, a tautomer thereof and/or a (preferably pharmaceutically acceptable) salt thereof" especially means that a compound of the formula I may be present as such or in mixture with its N-oxide, as tautomer (e.g. due to keto-enol, lactam-lactim, amide-imidic acid or enamine-imine tautomerism) or in (e.g. equivalency reaction caused) mixture with its tautomer, or as a salt of the compound of the formula I and/or any of these forms or mixtures of two or more of such forms.

For the following compounds, the NH2 group attached to the pyrazine ring is critical for potency. Analysis of the crystallographic structure shows the NH2 group in an intramolecular interaction with the backbone carbonyl group of SHP2 residue E250:

| Compound | SHP2 IC50 |
|---|---|
| 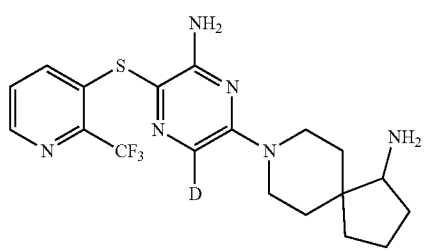 [SMILES: [2H]c1nc(Sc2cccnc2C(F)(F)F)c(N)nc1N1CCC2(CCCC2N)CC1] | 70 nM |
| | 5.7 μM |

The present invention also includes all suitable isotopic variations of the compounds of the invention, or pharmaceutically acceptable salts thereof. An isotopic variation of a compound of the invention or a pharmaceutically acceptable salt thereof is defined as one in which at least one atom is replaced by an atom having the same atomic number but an atomic mass different from the atomic mass usually found in nature. Examples of isotopes that may be incorporated into the compounds of the invention and pharmaceutically acceptable salts thereof include, but are not limited to, isotopes of hydrogen, carbon, nitrogen and oxygen such as as $^{2}H$, $^{3}H$, $^{11}C$, $^{13}C$, $^{14}C$, $^{15}N$, $^{17}O$, $^{18}O$, $^{35}S$, $^{18}F$, $^{36}Cl$ and $^{123}I$. Certain isotopic variations of the compounds of the invention and pharmaceutically acceptable salts thereof, for example, those in which a radioactive isotope such as $^{3}H$ or $^{14}C$ is incorporated, are useful in drug and/or substrate tissue distribution studies. In particular examples, $^{3}H$ and $^{14}C$ isotopes may be used for their ease of preparation and detectability. In other examples, substitution with isotopes such as $^{2}H$ may afford certain therapeutic advantages resulting from greater metabolic stability, such as increased in vivo half-life or reduced dosage requirements. Isotopic variations of the compounds of the invention or pharmaceutically acceptable salts thereof can generally be prepared by conventional procedures using appropriate isotopic variations of suitable reagents. For example, a compound of the invention can exist in a deutorated form as shown below:

DESCRIPTION OF PREFERRED EMBODIMENTS

The present invention relates to compounds capable of inhibiting the activity of SHP2. In one aspect of the invention, with respect to compounds of formula I, $—XR_{1a}$ is $—SR_{1a}$ and is selected from:

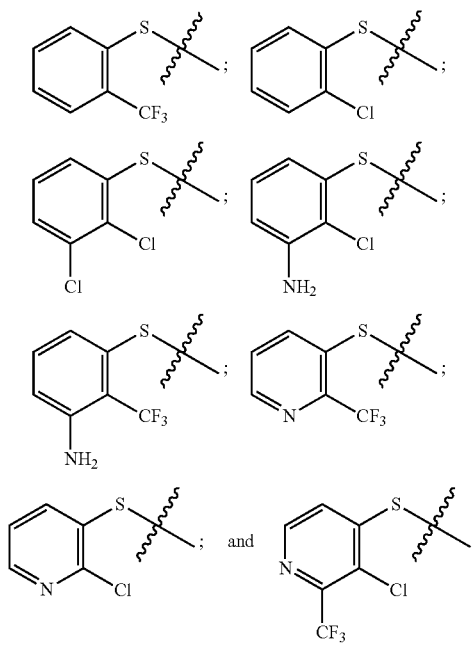

In another aspect of the invention, $—XR_{1a}$ is $—SR_{1a}$ and is selected from:

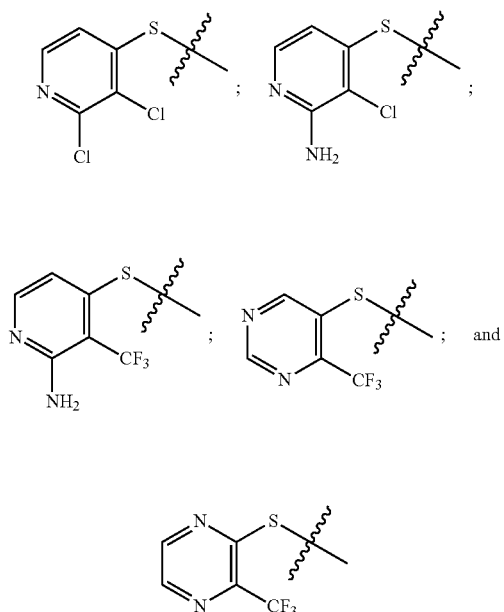

In another aspect of the invention, with respect to compounds of formula I:

is selected from:

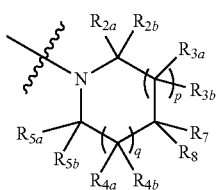

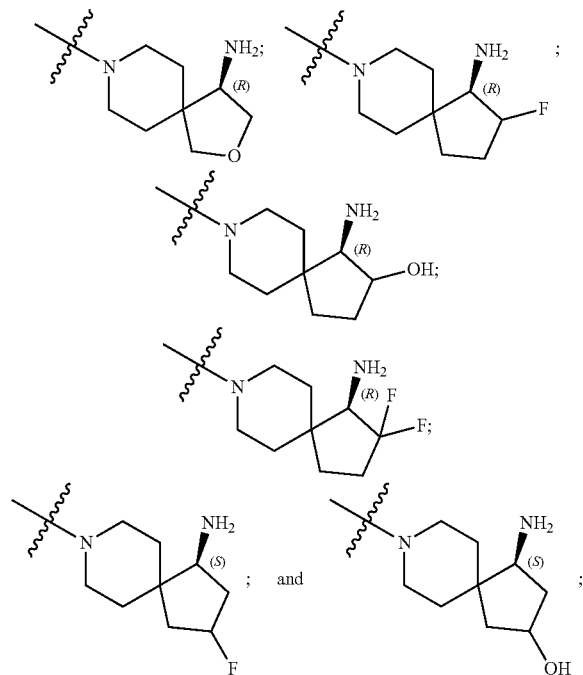

In another aspect, with respect to compounds of Formula I, are compounds of Formula Ia:

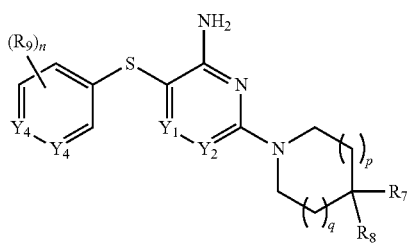

in which: n is selected from 1, 2, 3 and 4; p is selected from 0 and 1; q is selected from 0 and 1; $Y_1$ is selected from CH and N; $Y_2$ is selected from $CR_6$ and N; $Y_4$ is independently selected from N, C(O) and $CR_9$; wherein only one $Y_4$ is C(O); $R_6$ is selected from hydrogen, halo, methyl and amino-carbonyl; $R_7$ and $R_8$ together with the carbon atom to which they are both attached form a 3 to 7 member saturated or partially unsaturated ring that can optionally contain a heteroatom selected from N, O and S(O)m; wherein m is selected from 0, 1 and 2; wherein said saturated ring formed by $R_7$ and $R_8$ can be unsubstituted or substituted with a group selected from amino, amino-methyl and methyl-amino; $R_9$ is selected from halo, amino, dimethyl-amino, hydroxy, $N_3$, $C_{1-4}$alkyl, halo-substituted-$C_{1-4}$alkyl, $C_{1-4}$alkoxy, —C(O)O$R_{10}$ and —NHC(O)$R_{10}$; $R_{10}$ is selected from hydrogen, phenyl and naphthyl; wherein said phenyl of $R_{10}$ is unsubstituted or substituted with methoxy; or a pharmaceutically acceptable salt thereof.

In a further aspect of the invention, $R_7$ and $R_8$ together with the carbon atom to which they are both attached form a 5 member saturated or partially unsaturated ring that can optionally contain 1 to 2 heteroatoms or groups independently selected from N, O, C(O) and S(O)m; wherein m is selected from 0, 1 and 2; wherein said saturated ring formed by $R_7$ and $R_8$ is substituted with 1 to 3 groups independently selected from amino, hydroxy, methoxy, halo, methyl, methyl-amino and isobutyryloxy; or a pharmaceutically acceptable salt thereof.

In a further aspect of the invention are compounds, or the pharmaceutically acceptable salt thereof, selected from:

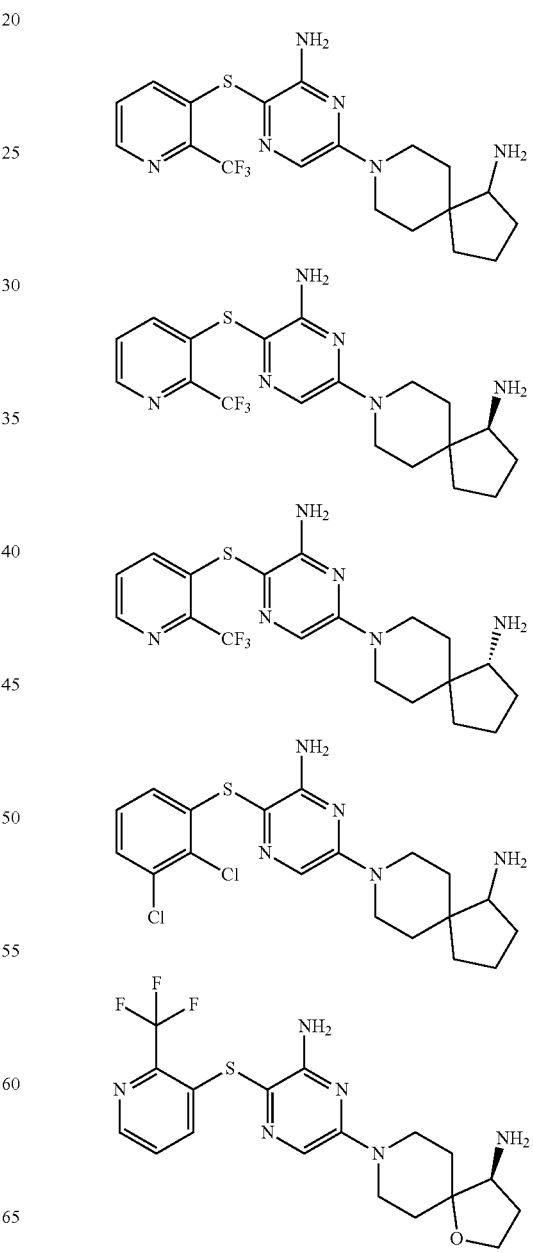

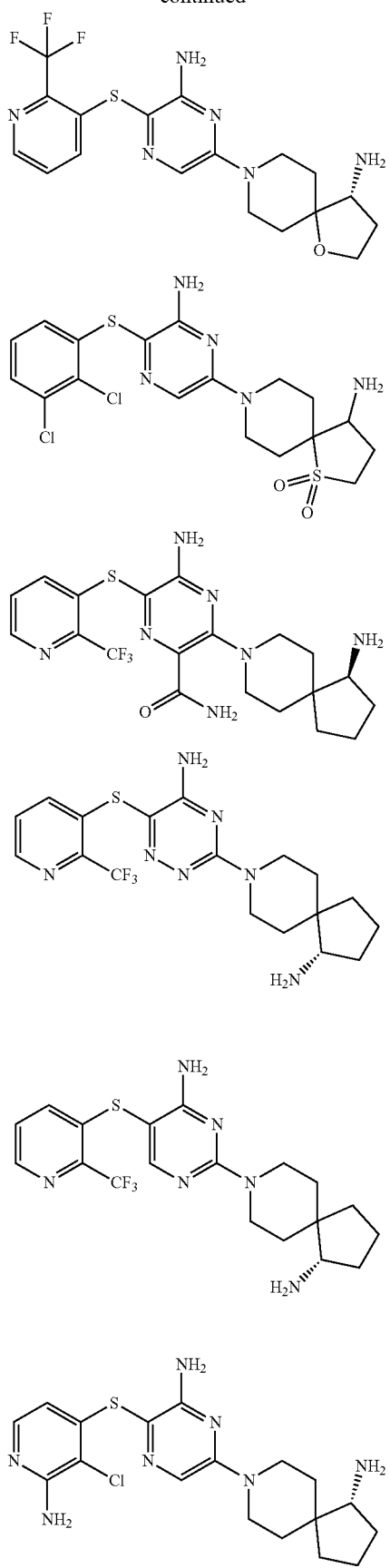
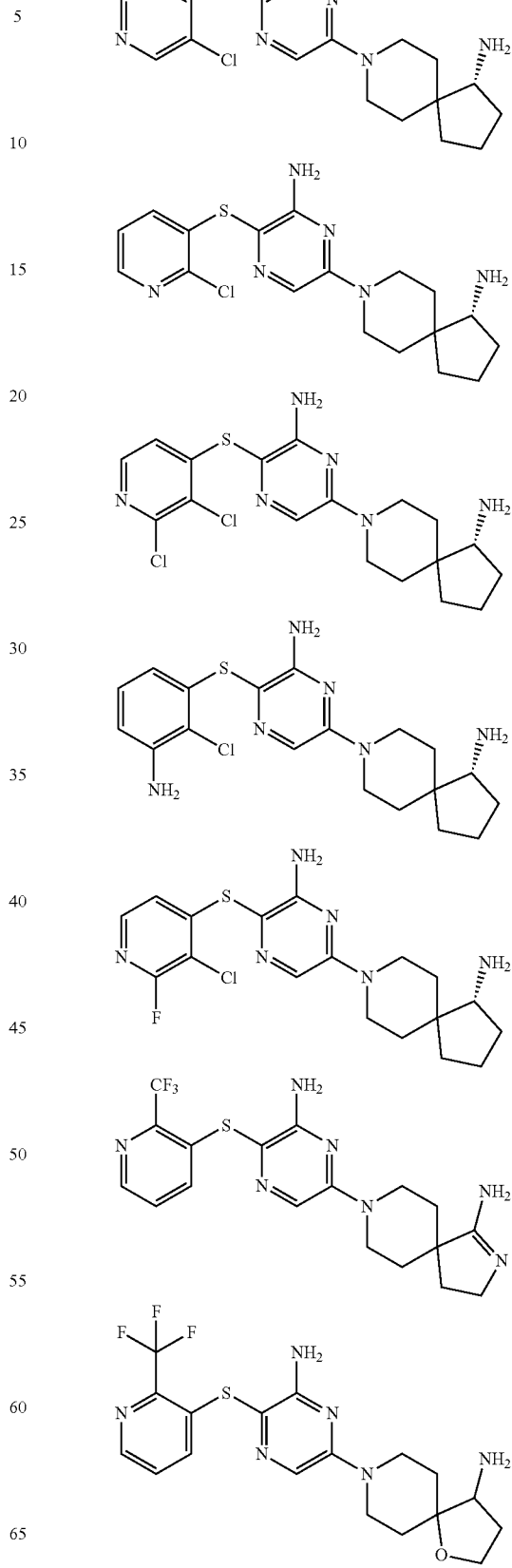

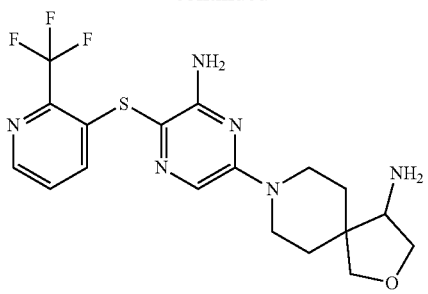
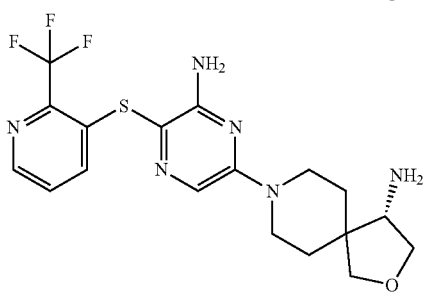
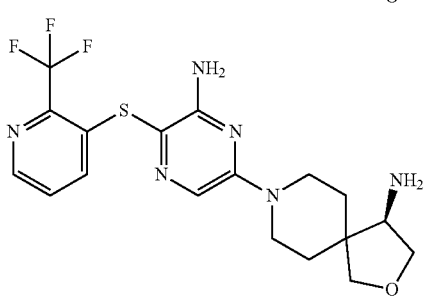
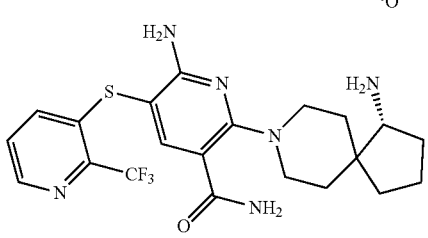
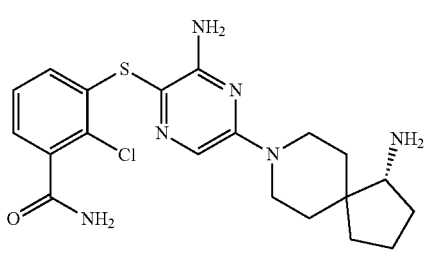
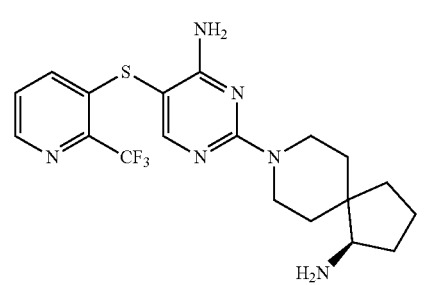
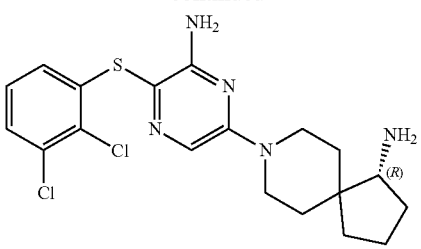
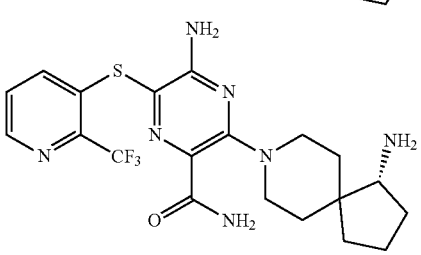
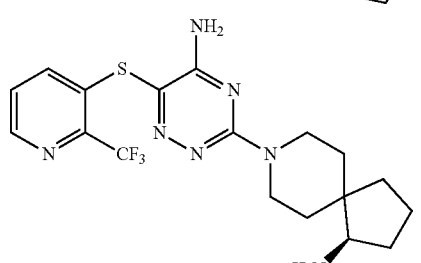
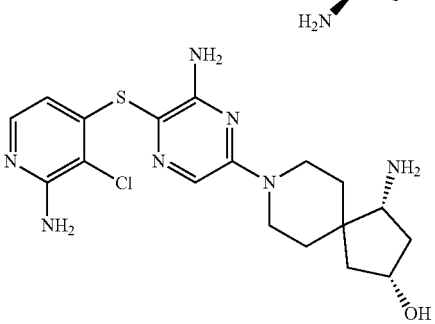
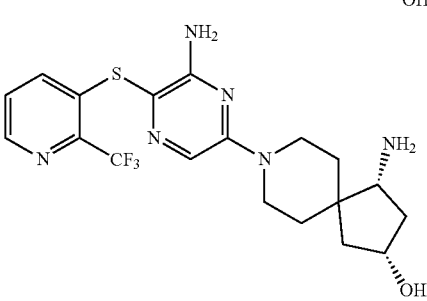
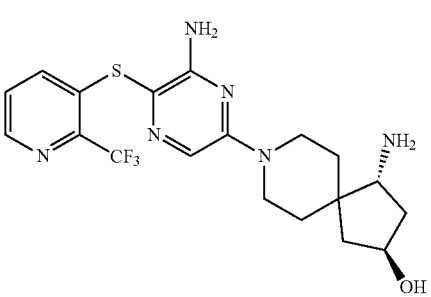

-continued
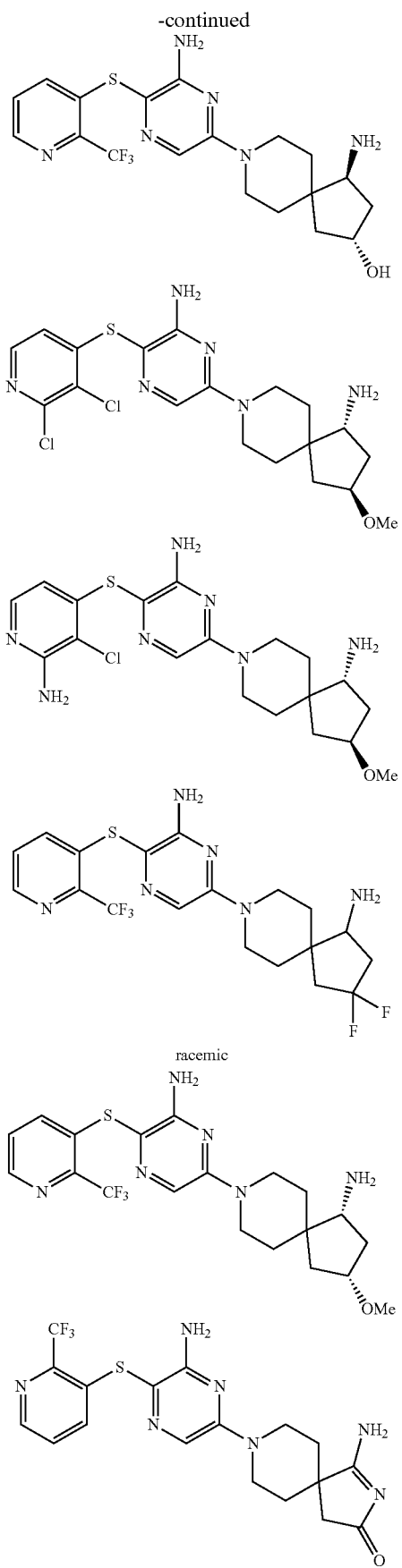
-continued
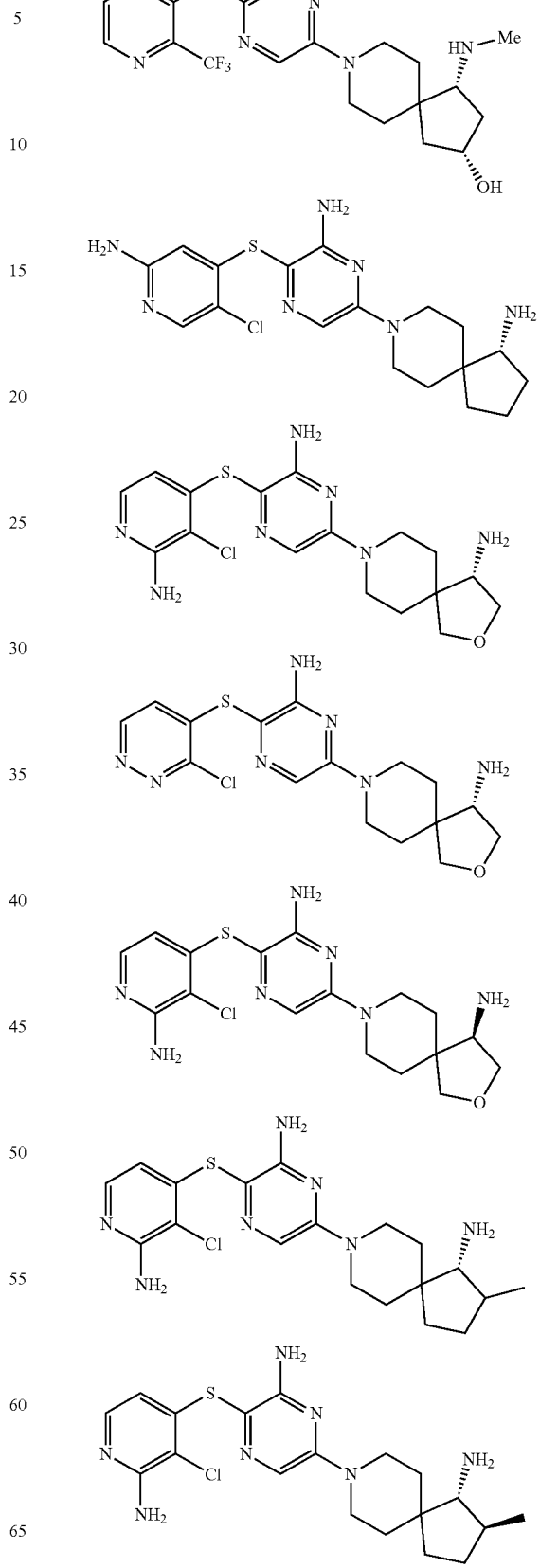

-continued
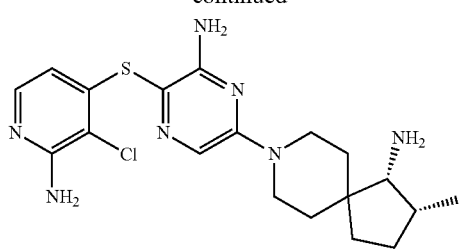
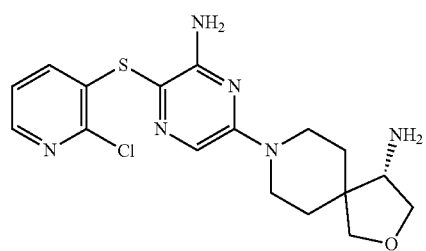
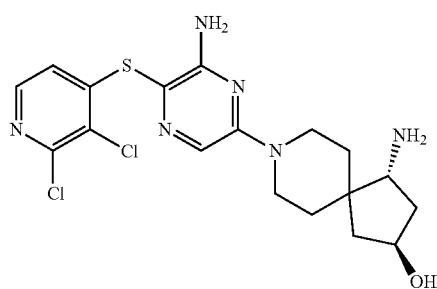
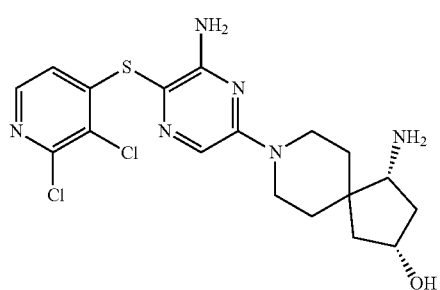
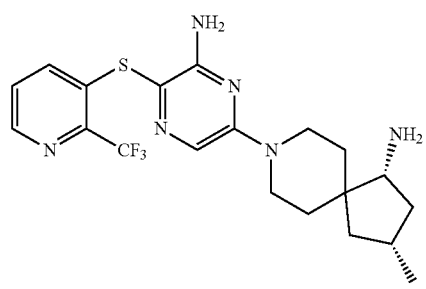
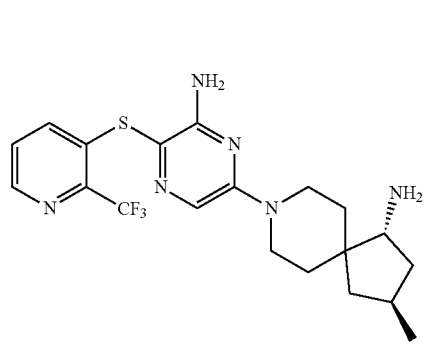
-continued
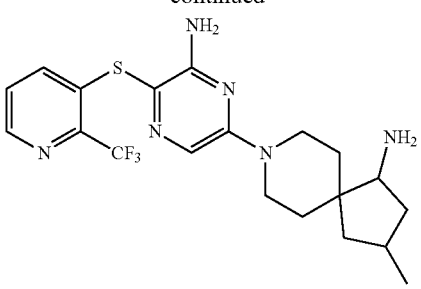
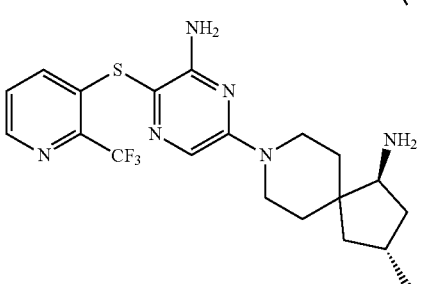
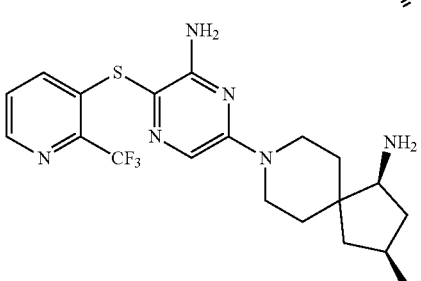
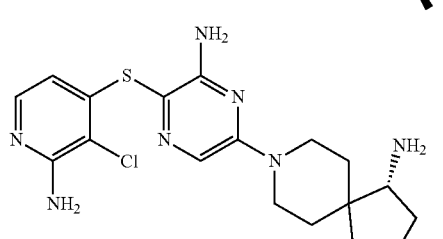
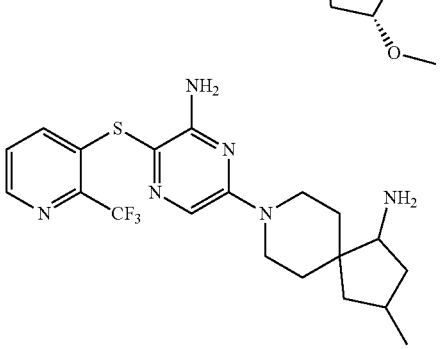
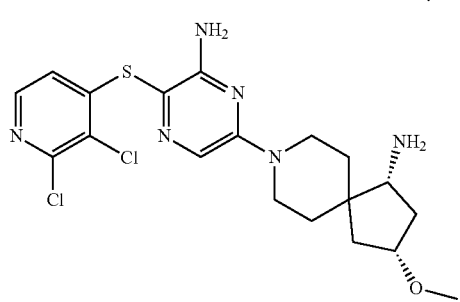

-continued
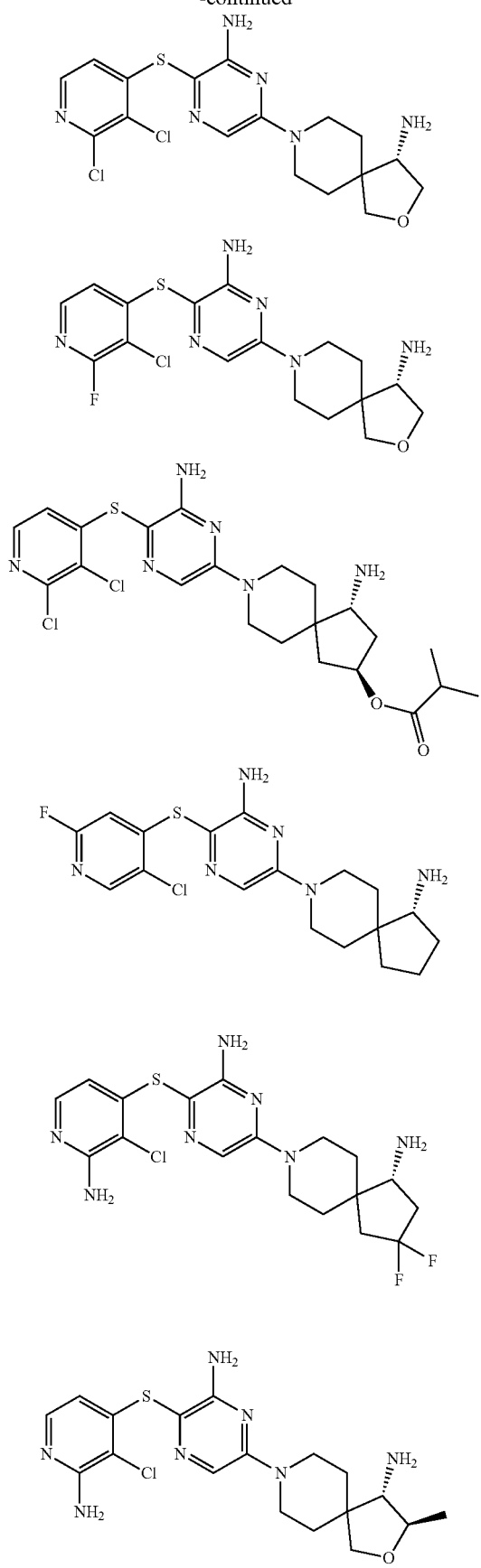
-continued
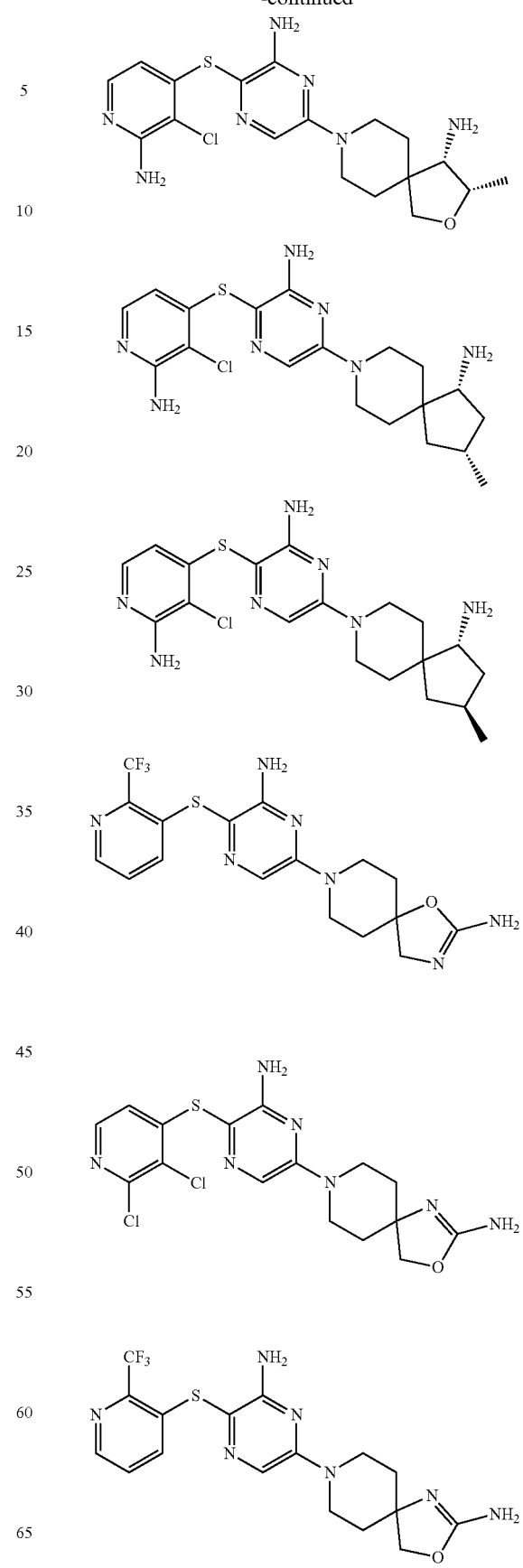

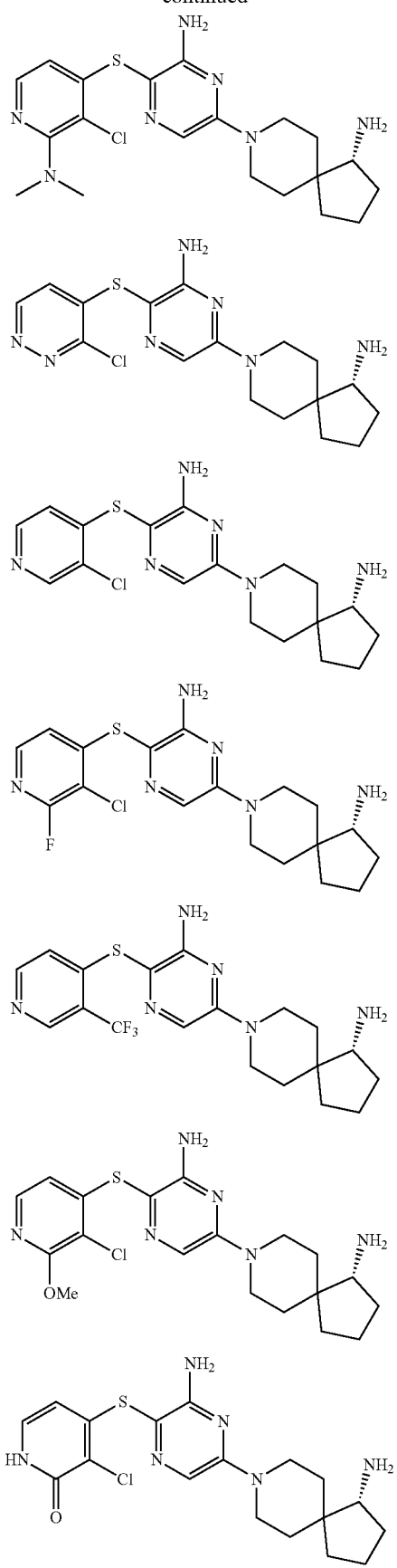
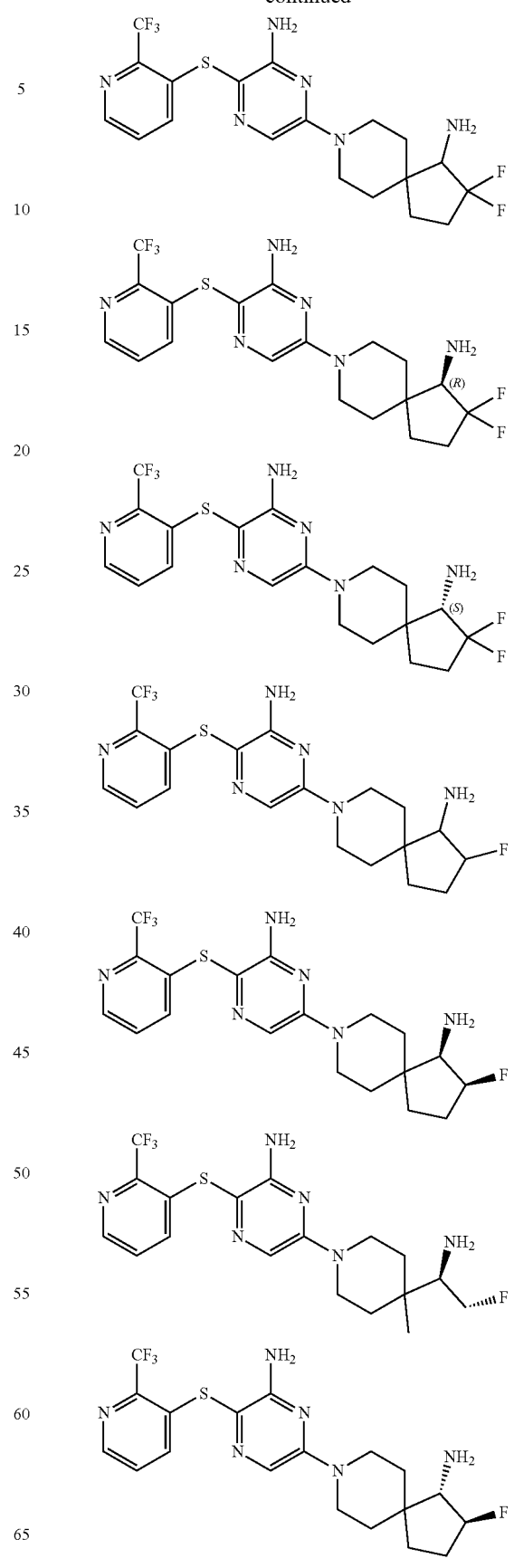

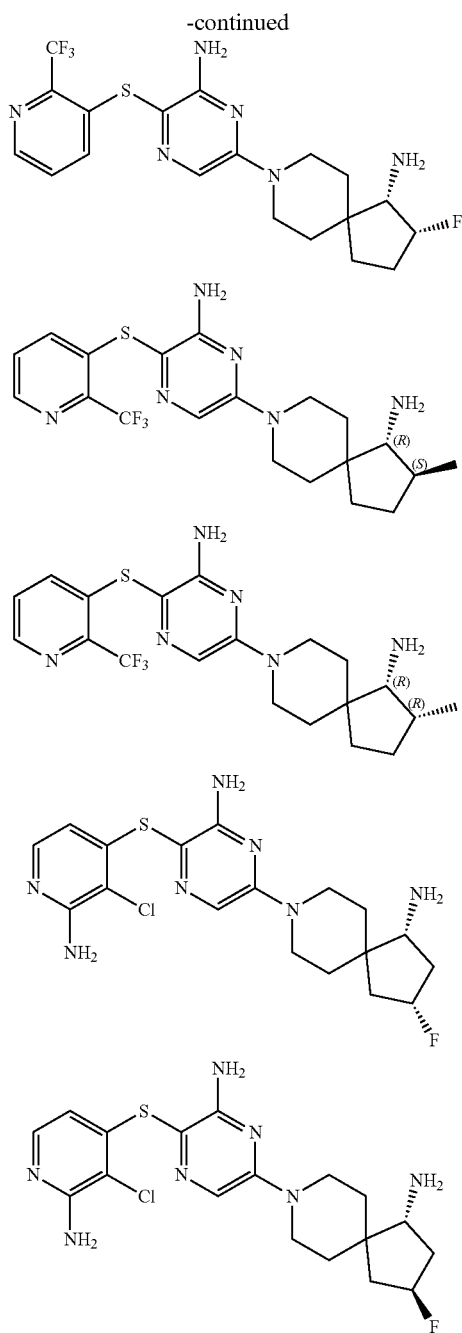

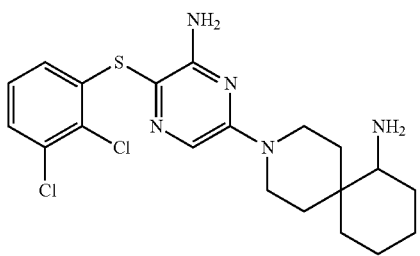 [SMILES: Nc1nc(N2CCC3(CCCCC3N)CC2)cnc1Sc1cccc(Cl)c1Cl]

In another aspect of the invention are compounds in which $R_7$ and $R_8$ together with the carbon atom to which they are both attached form a 4 member saturated or partially unsaturated ring that can optionally contain a heteroatom selected from N, O and S(O)m; wherein m is selected from 0, 1 and 2; wherein said saturated ring formed by $R_7$ and $R_8$ is substituted with a group selected from amino, aminomethyl and methyl-amino; or a pharmaceutically acceptable salt thereof.

In a further aspect of the invention are compounds, or the pharmaceutically acceptable salt thereof, selected from:

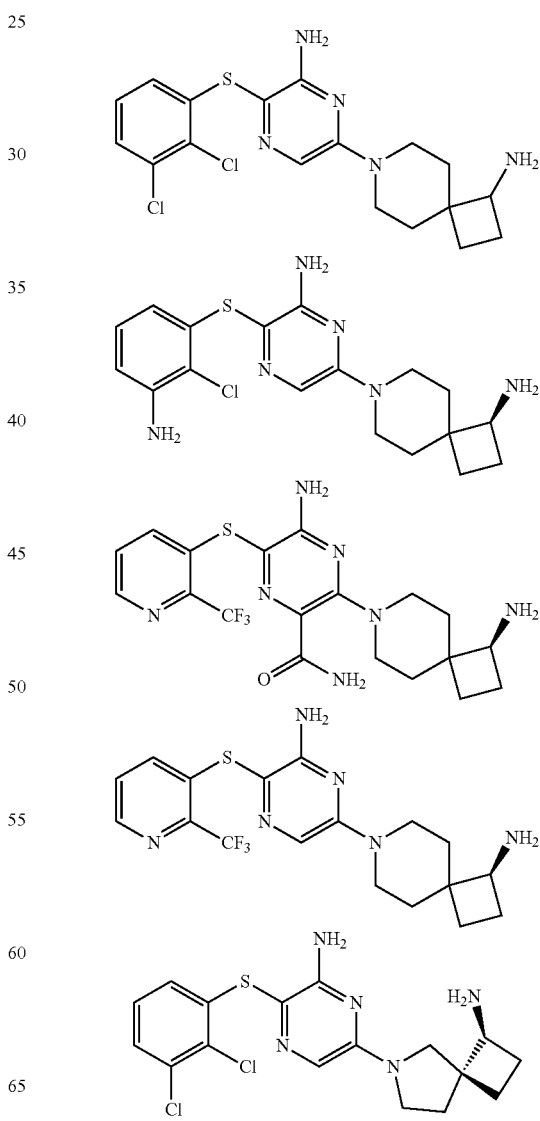

In another aspect of the invention are compounds in which $R_7$ and $R_8$ together with the carbon atom to which they are both attached form a 6 member saturated or partially unsaturated ring that can optionally contain a heteroatom selected from N, O and S(O)m; wherein m is selected from 0, 1 and 2; wherein said saturated ring formed by $R_7$ and $R_8$ is substituted with a group selected from amino, aminomethyl and methyl-amino; or a pharmaceutically acceptable salt thereof.

In a further aspect of the invention are compounds, or the pharmaceutically acceptable salt thereof, selected from:

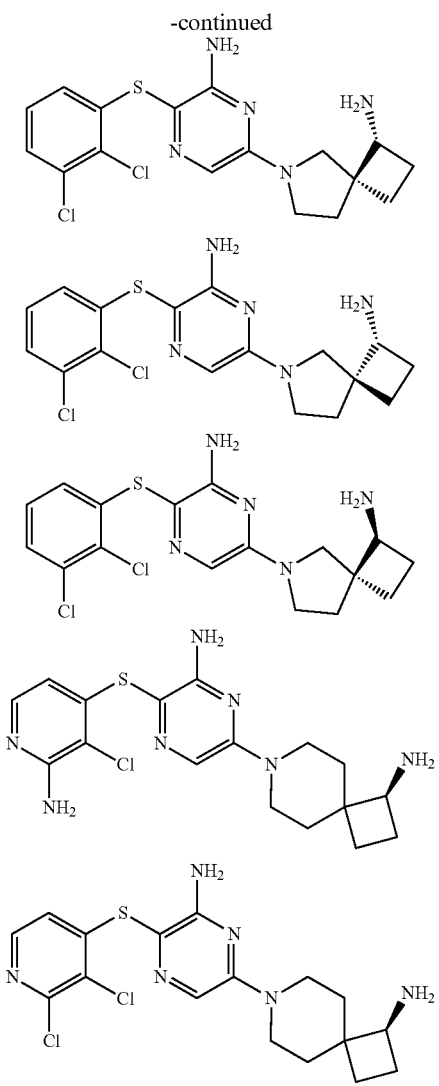

In another aspect of the invention are compounds in which p and q are both 0; or the pharmaceutically acceptable salt thereof.

In a further aspect of the invention are compounds, or the pharmaceutically acceptable salt thereof, selected from:

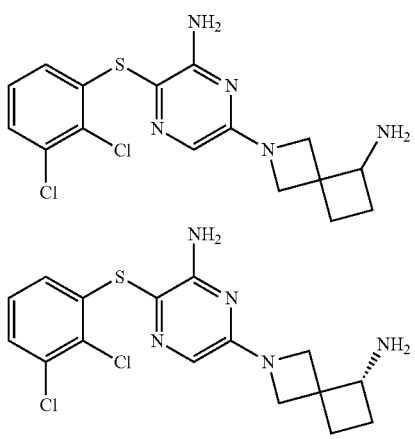

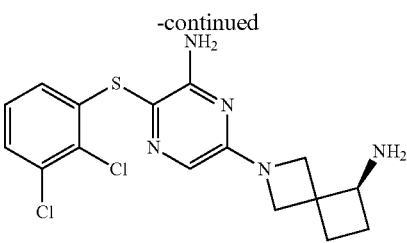

In another aspect of the invention are compounds of formula II:

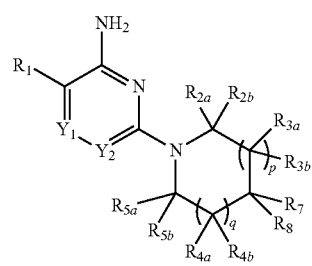

II in which: p is selected from 0 and 1; q is selected from 0 and 1; $Y_1$ is selected from CH and N; $Y_2$ is selected from $CR_6$ and N; $R_1$ is selected from $C_{6-10}$aryl, $C_{3-8}$cycloalkyl, $C_{3-8}$cycloalkenyl and a 5-9 member heteroaryl group containing from 1 to 4 heteroatoms selected from N, O and S; wherein said aryl or heteroaryl of $R_{1a}$ is substituted with 1 to 5 $R_9$ groups independently selected from halo, amino, hydroxy, $N_3$, $C_{1-4}$alkyl, hydroxy-substituted-$C_{1-4}$alkyl, halo-substituted-$C_{1-4}$alkyl, amino-substituted-$C_{1-4}$alkyl, —C(O)OR$_{10}$ and —NHC(O)R$_{10}$; wherein m is selected from 0, 1 and 2; each $R_{10a}$ and $R_{10b}$ is independently selected from halo and $C_{1-4}$alkyl; and $R_{11}$ is selected from hydrogen and $C_{1-4}$alkyl; $R_{2a}$ and $R_{2b}$ are independently selected from hydrogen, $C_{1-4}$alkyl, $C_{1-4}$alkoxy, amino, hydroxy, $C_{3-8}$cycloalkyl and $C_{1-4}$alkyl-amino; $R_{3a}$ and $R_{3b}$ are independently selected from halo, carbonyl, $C_{1-4}$alkyl, $C_{1-4}$alkoxy, amino, hydroxy, $C_{3-8}$cycloalkyl and $C_{1-4}$alkyl-amino; $R_{4a}$ and $R_{4b}$ are independently selected from hydrogen, halo, carbonyl, $C_{1-4}$alkyl, $C_{1-4}$alkoxy, amino, hydroxy, $C_{3-8}$cycloalkyl and $C_{1-4}$alkyl-amino; $R_{5a}$ and $R_{5b}$ are independently selected from hydrogen, carbonyl, $C_{1-4}$alkyl, $C_{1-4}$alkoxy, amino, hydroxy, $C_{3-8}$cycloalkyl and $C_{1-4}$alkyl-amino; wherein any two groups selected from $R_{2a}$, $R_{3a}$, $R_4$, $R_5$, $R_{6a}$ and $R_{7a}$ can form a 5 to 6 member unsaturated or partially unsaturated ring; $R_6$ is selected from hydrogen, halo, cyano, $C_{1-4}$alkyl, $C_{1-4}$alkoxy, amino-carbonyl, halo-substituted $C_{1-4}$alkyl, halo-substituted $C_{1-4}$alkoxy, hydroxy-substituted $C_{1-4}$alkyl and amino-substituted $C_{1-4}$alkyl; $R_7$ and $R_8$ together with the carbon atom to which they are both attached form a 3 to 7 member saturated or partially unsaturated ring that can optionally contain a heteroatom selected from N, O and S(O)m; wherein m is selected from 0, 1 and 2; wherein said saturated ring formed by $R_7$ and $R_8$ can be unsubstituted or substituted with a group selected from amino, amino-methyl and methyl-amino; or a pharmaceutically acceptable salt thereof.

In a further aspect of the invention are compounds of formula IIa:

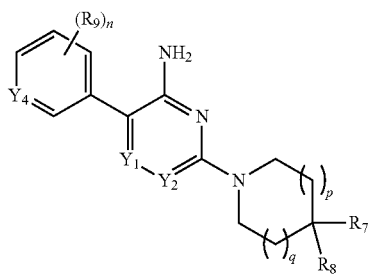

IIa in which: n is selected from 1, 2, 3 and 4; p is selected from 0 and 1; q is selected from 0 and 1; $Y_1$ is selected from CH and N; $Y_2$ is selected from $CR_6$ and N; $Y_4$ is selected from N and $CR_9$; $R_6$ is selected from hydrogen, halo, methyl and amino-carbonyl; $R_7$ and $R_8$ together with the carbon atom to which they are both attached form a 3 to 7 member saturated or partially unsaturated ring that can optionally contain a heteroatom selected from N, O and S(O)m; wherein m is selected from 0, 1 and 2; wherein said saturated ring formed by $R_7$ and $R_8$ can be unsubstituted or substituted with a group selected from amino, amino-methyl and methyl-amino; $R_9$ is selected from halo, amino, hydroxy, $N_3$, $C_{1-4}$alkyl, halo-substituted-$C_{1-4}$alkyl, $C_{1-4}$alkoxy, —C(O)OR$_{10}$ and —NHC(O)R$_{10}$; $R_{10}$ is selected from hydrogen, phenyl and naphthyl; wherein said phenyl of $R_{10}$ is unsubstituted or substituted with methoxy; or a pharmaceutically acceptable salt thereof.

In a further aspect of the invention are compounds in which $R_7$ and $R_8$ together with the carbon atom to which they are both attached form a 5 member saturated ring that can optionally contain a heteroatom selected from N, O and S(O)m; wherein m is selected from 0, 1 and 2; wherein said saturated ring formed by $R_7$ and $R_8$ is substituted with a group selected from amino, amino-methyl and methyl-amino; or a pharmaceutically acceptable salt thereof.

In a further aspect of the invention are compounds, or the pharmaceutically acceptable salt thereof, selected from:

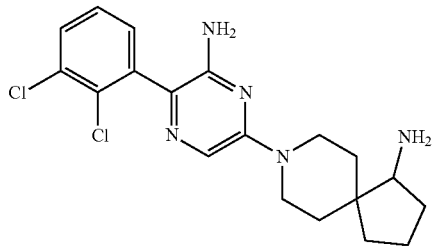

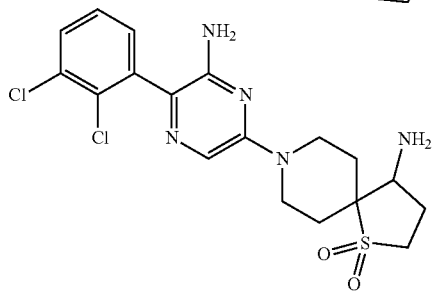

In another aspect of the invention are compounds in which $R_7$ and $R_8$ together with the carbon atom to which they are both attached form a 6 member saturated ring that can optionally contain a heteroatom selected from N, O and S(O)m; wherein m is selected from 0, 1 and 2; wherein said saturated ring formed by $R_7$ and $R_8$ is substituted with a group selected from amino, amino-methyl and methyl-amino; or a pharmaceutically acceptable salt thereof.

In a further aspect of the invention are compounds, or the pharmaceutically acceptable salt thereof, selected from:

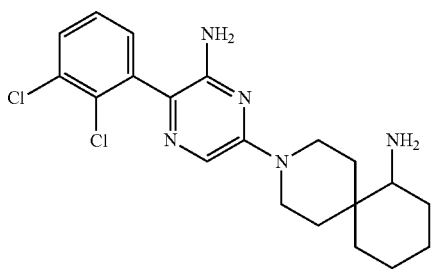 [SMILES: Nc1nc(N2CCC3(CCCCC3N)CC2)cnc1-c1cccc(Cl)c1Cl]

In another aspect of the invention are compounds in which $R_7$ and $R_8$ together with the carbon atom to which they are both attached form a 4 member saturated ring that can optionally contain a heteroatom selected from N, O and S(O)m; wherein m is selected from 0, 1 and 2; wherein said saturated ring formed by $R_7$ and $R_8$ is substituted with amino; or a pharmaceutically acceptable salt thereof.

In a further aspect of the invention are compounds, or the pharmaceutically acceptable salt thereof, selected from:

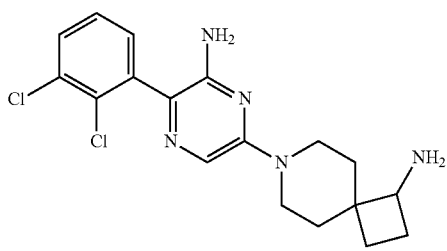

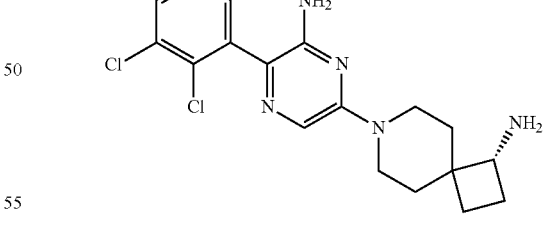

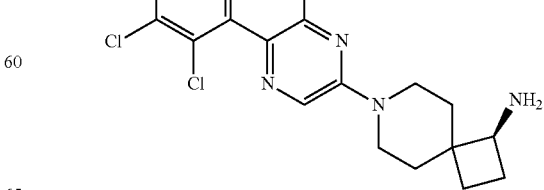

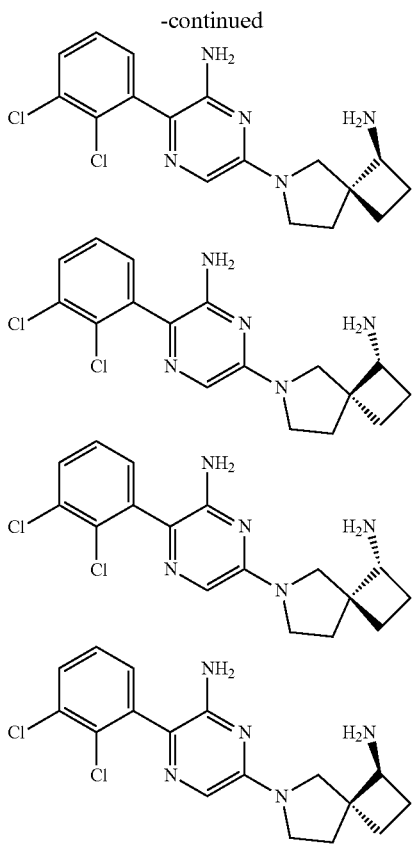

In another aspect of the invention are compounds in which p and q are both 0; or the pharmaceutically acceptable salt thereof.

In a further aspect of the invention are compounds, or the pharmaceutically acceptable salt thereof, selected from:

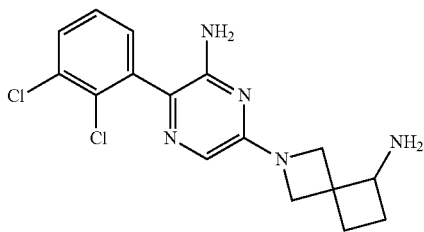 [SMILES: Nc1nc(N2CC3(CCC3N)C2)cnc1-c1cccc(Cl)c1Cl]

Pharmacology and Utility

The Src Homolgy-2 phosphatase (SHP2) is a protein tyrosine phosphatase encoded by the PTPN11 gene that contributes to multiple cellular functions including proliferation, differentiation, cell cycle maintenance and migration. SHP2 is involved in signaling through the Ras-mitogen-activated protein kinase, the JAK-STAT or the phosphoinositol 3-kinase-AKT pathways. SHP2 mediates activation of Erk1 and Erk2 (Erk1/2, Erk) MAP kinases by receptor tyrosine kinases such as ErbB1, ErbB2 and c-Met.

SHP2 has two N-terminal Src homology 2 domains (N-SH2 and C-SH2), a catalytic domain (PTP), and a C-terminal tail. The two SH2 domains control the subcellular localization and functional regulation of SHP2. The molecule exists in an inactive conformation, inhibiting its own activity via a binding network involving residues from both the N-SH2 and PTP domains. In response to growth factor stimulation, SHP2 binds to specific tyrosine-phosphorylated sites on docking proteins such as Gab1 and Gab2 via its SH2 domains. This induces a conformational change that results in SHP2 activation.

Mutations in PTPN11 have been identified in several human diseases, such as Noonan Syndrome, Leopard Syndrome, juvenile myelomonocytic leukemias, neuroblastoma, melanoma, acute myeloid leukemia and cancers of the breast, lung and colon. SHP2 is an important downstream signaling molecule for a variety of receptor tyrosine kinases, including the receptors of platelet-derived growth factor (PDGF-R), fibroblast growth factor (FGF-R) and epidermal growth factor (EGF-R). SHP2 is also an important downstream signaling molecule for the activation of the mitogen activated protein (MAP) kinase pathway which can lead to cell transformation, a prerequisite for the development of cancer. Knock-down of SHP2 significantly inhibited cell growth of lung cancer cell lines with SHP2 mutation or EML4/ALK translocations as well as EGFR amplified breast cancers and esophageal cancers. SHP2 is also activated downstream of oncogenes in gastric carcinoma, anaplastic large-cell lymphoma and glioblastoma.

Noonan Syndrome (NS) and Leopard Syndrome (LS)—PTPN11 mutations cause LS (multiple lentigenes, electrocardiographic conduction abnormalities, ocular hypertelorism, pulmonic stenosis, abnormal genitalia, retardation of growth, sensorineural deafness) and NS (congenital anomalies including cardiac defects, craniofacial abnormalities and short stature). Both disorders are part of a family of autosomal dominant syndromes caused by germline mutations in components of the RAS/RAF/MEK/ERK mitogen activating protein kinase pathway, required for normal cell growth and differentiation. Aberrant regulation of this pathway has profound effects, particularly on cardiac development, resulting in various abnormalities, including valvuloseptal defects and/or hypertrophic cardiomyopathy (HCM). Perturbations of the MAPK signaling pathway have been established as central to these disorders and several candidate genes along this pathway have been identified in humans, including mutations in KRAS, NRAS, SOS1, RAF1, BRAF, MEK1, MEK2, SHOC2, and CBL. The gene most commonly mutated in NS and LS is PTPN11. Germline mutations in PTPN11 (SHP2) are found in ~50% of the cases with NS and nearly all patients with LS that shares certain features with NS. For NS, Y62D and Y63C substitutions in the protein are largely invariant and are among the most common mutations. Both these mutations affect the catalytically inactive conformation of SHP2 without perturbing the binding of the phosphatase to its phosphorylated signaling partners.

Juvenile Myelomonocytic Leukemias (JMML)—Somatic mutations in PTPN11 (SHP2) occur in about 35% of the patients with JMML, a childhood myeloproliferative disorder (MPD). These gain-of-function mutations are typically point mutations in the N-SH2 domain or in the phosphatase domain, which prevent self-inhibition between the catalytic domain and the N-SH2 domain, resulting in SHP2 activity.

Acute Myeloid Leukemia—PTPN11 mutations have been identified in: ~10% of pediatric acute leukemias, such as myelodysplastic syndrome (MDS); ~7% of B cell acute lymphoblastic leukemia (B-ALL); and ~4% of acute myeloid leukemia (AML).

NS and leukemia mutations cause changes in amino acids located at the interface formed by the N-SH2 and PTP domains in the self-inhibited SHP2 conformation, disrupting the inhibitory intramolecular interaction, leading to hyperactivity of the catalytic domain.

SHP2 acts as a positive regulator in receptor tyrosine kinase (RTK) signaling. Cancers containing RTK alterations (EGFR$^{amp}$, Her2$^{amp}$, FGFR$^{amp}$, Met$^{amp}$, translocated/activated RTK, i.e. ALK, BCR/ABL) include Esophageal, Breast, Lung, Colon, Gastric, Glioma, Head and Neck cancers.

Esophageal cancer (or oesophageal cancer) is a malignancy of the esophagus. There are various subtypes, primarily squamous cell cancer (<50%) and adenocarcinoma. There is a high rate of RTK expression in esophageal adenocarcinoma and squamous cell cancer. A SHP2 inhibitor of the invention can, therefore, be employed for innovative treatment strategies.

Breast cancer is a major type of cancer and a leading cause of death in women, where patients develop resistance to current drugs. There are four major subtypes of breast cancers including luminal A, luminal B, Her2 like, and triple negative/Basal-like. Triple negative breast cancer (TNBC) is an aggressive breast cancer lacking specific targeted therapy. Epidermal growth factor receptor I (EGFR) has emerged as a promising target in TNBC. Inhibition of Her2 as well as EGFR via SHP2 may be a promising therapy in breast cancer.

Lung Cancer—NSCLC is currently a major cause of cancer-related mortality. accounting for about 85% of lung cancers (predominantly adenocarcinomas and squamous cell carcinomas). Although cytotoxic chemotherapy remains an important part of treatment, targeted therapies based on genetic alterations such as EGFR and ALK in the tumor are more likely to benefit from a targeted therapy.

Colon Cancer—Approximately 30% to 50% of colorectal tumors are known to have a mutated (abnormal) KRAS, and BRAF mutations occur in 10 to 15% of colorectal cancers. For a subset of patients whose colorectal tumors have been demonstrated to over express EGFR, these patients exhibit a favorable clinical response to anti-EGFR therapy.

Gastic Cancer is one of the most prevalent cancer types. Aberrant expression of tyrosine kinases, as reflected by the aberrant tyrosine phosphorylation in gastric cancer cells, is known in the art. Three receptor-tyrosine kinases, c-met (HGF receptor), FGF receptor 2, and erbB2/neu are frequently amplified in gastric carcinomas. Thus, subversion of different signal pathways may contribute to the progression of different types of gastric cancers.

Neuroblastoma is a pediatric tumor of the developing sympathetic nervous system, accounting for about 8% of childhood cancers. Genomic alterations of the anaplastic lymphoma kinase (ALK) gene have been postulated to contribute to neuroblastoma pathogenesis.

Squamous-cell carcinoma of the head and neck (SCCHN). High levels of EGFR expression are correlated with poor prognosis and resistance to radiation therapy in a variety of cancers, mostly in squamous-cell carcinoma of the head and neck (SCCHN). Blocking of the EGFR signaling results in inhibition of the stimulation of the receptor, cell proliferation, and reduced invasiveness and metastases. The EGFR is, therefore, a prime target for new anticancer therapy in SCCHN.

The present invention relates to compounds capable of inhibiting the activity of SHP2. The invention further provides a process for the preparation of compounds of the invention and pharmaceutical preparations comprising such compounds. Another aspect of the present invention relates to a method of treating SHP2-mediated disorders comprising the step of administering to a patient in need thereof a therapeutically effective amount of a compound of formula I as defined in the Summary of the Invention.

In certain embodiments, the present invention relates to the aforementioned method, wherein said SHP2-mediated disorders are cancers selected from, but not limited to: JMML; AML; MDS; B-ALL; neuroblastoma; esophageal; breast cancer; lung cancer; colon cancer; Gastric cancer, Head and Neck cancer.

The compounds of the present invention may also be useful in the treatment of other diseases or conditions related to the aberrant activity of SHP2. Thus, as a further aspect, the invention relates to a method of treatment of a disorder selected from: NS; LS; JMML; AML; MDS; B-ALL; neuroblastoma; esophageal; breast cancer; lung cancer; colon cancer; gastric cancer; head and neck cancer.

A SHP2 inhibitor of the present invention may be usefully combined with another pharmacologically active compound, or with two or more other pharmacologically active compounds, particularly in the treatment of cancer. For example, a compound of the formula (I), or a pharmaceutically acceptable salt thereof, as defined above, may be administered simultaneously, sequentially or separately in combination with one or more agents selected from chemotherapy agents, for example, mitotic inhibitors such as a taxane, a vinca alkaloid, paclitaxel, docetaxel, vincristine, vinblastine, vinorelbine or vinflunine, and other anticancer agents, e.g. cisplatin, 5-fluorouracil or 5-fluoro-2-4(1H,3H)-pyrimidinedione (5FU), flutamide or gemcitabine.

Such combinations may offer significant advantages, including synergistic activity, in therapy.

In certain embodiments, the present invention relates to the aforementioned method, wherein said compound is administered parenterally.

In certain embodiments, the present invention relates to the aforementioned method, wherein said compound is administered intramuscularly, intravenously, subcutaneously, orally, pulmonary, intrathecally, topically or intranasally.

In certain embodiments, the present invention relates to the aforementioned method, wherein said compound is administered systemically.

In certain embodiments, the present invention relates to the aforementioned method, wherein said patient is a mammal.

In certain embodiments, the present invention relates to the aforementioned method, wherein said patient is a primate.

In certain embodiments, the present invention relates to the aforementioned method, wherein said patient is a human.

In another aspect, the present invention relates to a method of treating an SHP2-mediated disorder, comprising the step of: administering to a patient in need thereof a therapeutically effective amount of a chemothereutic agent in combination with a therapeutically effective amount of a compound of formula I as defined in the Summary of the Invention.

Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) nasally; (9) pulmonary; or (10) intrathecally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. Preferred dosing is one administration per day.

While it is possible for a compound of the present invention to be administered alone, it is preferable to administer the compound as a pharmaceutical formulation (composition).

The compounds according to the invention may be formulated for administration in any convenient way for use in human or veterinary medicine, by analogy with other pharmaceuticals.

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

Microemulsification technology can improve bioavailability of some lipophilic (water insoluble) pharmaceutical agents. Examples include Trimetrine (Dordunoo, S. K., et al., Drug Development and Industrial Pharmacy, 17(12), 1685-1713, 1991 and REV 5901 (Sheen, P. C., et al., J Pharm Sci 80(7), 712-714, 1991). Among other things, microemulsification provides enhanced bioavailability by preferentially directing absorption to the lymphatic system instead of the circulatory system, which thereby bypasses the liver, and prevents destruction of the compounds in the hepatobiliary circulation.

While all suitable amphiphilic carriers are contemplated, the presently preferred carriers are generally those that have Generally-Recognized-as-Safe (GRAS) status, and that can both solubilize the compound of the present invention and microemulsify it at a later stage when the solution comes into a contact with a complex water phase (such as one found in human gastrointestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Commercially available amphiphilic carriers are particularly contemplated, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc (produced and distributed by a number of companies in USA and worldwide).

Hydrophilic polymers suitable for use in the present invention are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. Preferred polymers are those having a molecular weight of from about 100 or 120 daltons up to about 5,000 or 10,000 daltons, and more preferably from about 300 daltons to about 5,000 daltons. In a particularly preferred embodiment, the polymer is polyethyleneglycol having a molecular weight of from about 100 to about 5,000 daltons, and more preferably having a molecular weight of from about 300 to about 5,000 daltons. In a particularly preferred embodiment, the polymer is polyethyleneglycol of 750 daltons (PEG(750)). Polymers may also be defined by the number of monomers therein; a preferred embodiment of the present invention utilizes polymers of at least about three monomers, such PEG polymers consisting of three monomers (approximately 150 daltons).

Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, a formulation of the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

Cyclodextrins are cyclic oligosaccharides, consisting of 6, 7 or 8 glucose units, designated by the Greek letter alpha, beta or gamma, respectively. Cyclodextrins with fewer than six glucose units are not known to exist. The glucose units are linked by alpha-1,4-glucosidic bonds. As a consequence of the chair conformation of the sugar units, all secondary hydroxyl groups (at C-2, C-3) are located on one side of the ring, while all the primary hydroxyl groups at C-6 are situated on the other side. As a result, the external faces are hydrophilic, making the cyclodextrins water-soluble. In contrast, the cavities of the cyclodextrins are hydrophobic, since they are lined by the hydrogen of atoms C-3 and C-5, and by ether-like oxygens. These matrices allow complexation with a variety of relatively hydrophobic compounds, including, for instance, steroid compounds such as 17.beta.-estradiol (see, e.g., van Uden et al. Plant Cell Tiss. Org. Cult. 38:1-3-113 (1994)). The complexation takes place by Van der Waals interactions and by hydrogen bond formation. For a general review of the chemistry of cyclodextrins, see, Wenz, Agnew. Chem. Int. Ed. Engl., 33:803-822 (1994).

The physico-chemical properties of the cyclodextrin derivatives depend strongly on the kind and the degree of substitution. For example, their solubility in water ranges from insoluble (e.g., triacetyl-beta-cyclodextrin) to 147% soluble (w/v) (G-2-beta-cyclodextrin). In addition, they are soluble in many organic solvents. The properties of the cyclodextrins enable the control over solubility of various formulation components by increasing or decreasing their solubility.

Numerous cyclodextrins and methods for their preparation have been described. For example, Parmeter (I), et al. (U.S. Pat. No. 3,453,259) and Gramera, et al. (U.S. Pat. No. 3,459,731) described electroneutral cyclodextrins. Other derivatives include cyclodextrins with cationic properties [Parmeter (II), U.S. Pat. No. 3,453,257], insoluble crosslinked cyclodextrins (Solms, U.S. Pat. No. 3,420,788), and cyclodextrins with anionic properties [Parmeter (III), U.S. Pat. No. 3,426,011]. Among the cyclodextrin derivatives with anionic properties, carboxylic acids, phosphorous acids, phosphinous acids, phosphonic acids, phosphoric acids, thiophosphonic acids, thiosulphinic acids, and sulfonic acids have been appended to the parent cyclodextrin [see, Parmeter (III), supra]. Furthermore, sulfoalkyl ether cyclodextrin derivatives have been described by Stella, et al. (U.S. Pat. No. 5,134,127).

Liposomes consist of at least one lipid bilayer membrane enclosing an aqueous internal compartment. Liposomes may be characterized by membrane type and by size. Small unilamellar vesicles (SUVs) have a single membrane and typically range between 0.02 and 0.05 µm in diameter; large unilamellar vesicles (LUVS) are typically larger than 0.05 µm Oligolamellar large vesicles and multilamellar vesicles have multiple, usually concentric, membrane layers and are typically larger than 0.1 µm. Liposomes with several non-concentric membranes, i.e., several smaller vesicles contained within a larger vesicle, are termed multivesicular vesicles.

One aspect of the present invention relates to formulations comprising liposomes containing a compound of the present invention, where the liposome membrane is formulated to provide a liposome with increased carrying capacity. Alternatively or in addition, the compound of the present invention may be contained within, or adsorbed onto, the liposome bilayer of the liposome. The compound of the present invention may be aggregated with a lipid surfactant and carried within the liposome's internal space; in these cases, the liposome membrane is formulated to resist the disruptive effects of the active agent-surfactant aggregate.

According to one embodiment of the present invention, the lipid bilayer of a liposome contains lipids derivatized with polyethylene glycol (PEG), such that the PEG chains extend from the inner surface of the lipid bilayer into the interior space encapsulated by the liposome, and extend from the exterior of the lipid bilayer into the surrounding environment.

Active agents contained within liposomes of the present invention are in solubilized form. Aggregates of surfactant and active agent (such as emulsions or micelles containing the active agent of interest) may be entrapped within the interior space of liposomes according to the present invention. A surfactant acts to disperse and solubilize the active agent, and may be selected from any suitable aliphatic, cycloaliphatic or aromatic surfactant, including but not limited to biocompatible lysophosphatidylcholines (LPCs) of varying chain lengths (for example, from about $C_{14}$ to about $C_{20}$). Polymer-derivatized lipids such as PEG-lipids may also be utilized for micelle formation as they will act to inhibit micelle/membrane fusion, and as the addition of a polymer to surfactant molecules decreases the CMC of the surfactant and aids in micelle formation. Preferred are surfactants with CMCs in the micromolar range; higher CMC surfactants may be utilized to prepare micelles entrapped within liposomes of the present invention, however, micelle surfactant monomers could affect liposome bilayer stability and would be a factor in designing a liposome of a desired stability.

Liposomes according to the present invention may be prepared by any of a variety of techniques that are known in the art. See, e.g., U.S. Pat. No. 4,235,871; Published PCT applications WO 96/14057; New RRC, Liposomes: A practical approach, IRL Press, Oxford (1990), pages 33-104; Lasic D D, Liposomes from physics to applications, Elsevier Science Publishers BV, Amsterdam, 1993.

For example, liposomes of the present invention may be prepared by diffusing a lipid derivatized with a hydrophilic polymer into preformed liposomes, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art.

In one aspect of the present invention, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323 (Apr. 12, 1988).

The release characteristics of a formulation of the present invention depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In all cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween® and Pluronic®. Pore forming agents which add microstructure to the matrices (i.e., water soluble compounds such as inorganic salts and sugars) are added as particulates. The range should be between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

Pharmaceutical Combinations

The invention especially relates to the use of a compound of the formula I (or a pharmaceutical composition comprising a compound of the formula I) in the treatment of one or more of the diseases mentioned herein; wherein the response to treatment is beneficial as demonstrated, for example, by the partial or complete removal of one or more of the symptoms of the disease up to complete cure or remission.

A compound of formula (I) can also be used in combination with the following compounds and antibody-drug conjugates:

BCR-ABL inhibitors: Imatinib (Gleevec®); Inilotinib hydrochloride; Nilotinib (Tasigna®); Dasatinib (BMS-345825); Bosutinib (SKI-606); Ponatinib (AP24534); Bafetinib (INNO406); Danusertib (PHA-739358), AT9283 (CAS 1133385-83-7); Saracatinib (AZD0530); and N-[2-[(1S,4R)-6-[[4-(Cyclobutylamino)-5-(trifluoromethyl)-2-pyrimidinyl]amino]-1,2,3,4-tetrahydronaphthalen-1,4-imin-9-yl]-2-oxoethyl]-acetamide (PF-03814735, CAS 942487-16-3); and LGX818.

ALK inhibitors: PF-2341066 (XALKORI®; crizotinib); 5-chloro-N4-(2-(isopropylsulfonyl)phenyl)-N2-(2-methoxy-4-(4-(4-methylpiperazin-1-yl)piperidin-1-yl)phenyl)pyrimidine-2,4-diamine; GSK1838705A; and CH5424802.

BRAF inhibitors: Vemurafanib (PLX4032); and Dabrafenib.

FLT3 inhibitors—sunitinib malate (sold under the tradename Sutent® by Pfizer); PKC412 (midostaurin); tanutinib, sorafenib, sunitinib, midostaurin, lestaurtinib, KW-2449, quizartinib (AC220) and crenolanib.

MEK Inhibitors—trametinib.

Vascular Endothelial Growth Factor (VEGF) receptor inhibitors: Bevacizumab (sold under the trademark Avastin® by Genentech/Roche), axitinib, (N-methyl-2-[[3-[(E)-2-pyridin-2-ylethenyl]-1H-indazol-6-yl]sulfanyl]benzamide, also known as AG013736, and described in PCT Publication No. WO 01/002369), Brivanib Alaninate ((S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate, also known as BMS-582664), motesanib (N-(2,3-dihydro-3,3-dimethyl-1H-indol-6-yl)-2-[(4-pyridinylmethyl)amino]-3-pyridinecarboxamide, and described in PCT Publication No. WO 02/066470), pasireotide (also known as SOM230, and described in PCT Publication No. WO 02/010192), sorafenib (sold under the tradename Nexavar®);

HER2 receptor inhibitors: Trastuzumab (sold under the trademark Herceptin® by Genentech/Roche), neratinib (also known as HKI-272, (2E)-N-[4-[[3-chloro-4-[(pyridin-2-yl)methoxy]phenyl]amino]-3-cyano-7-ethoxyquinolin-6-yl]-4-(dimethylamino)but-2-enamide, and described PCT Publication No. WO 05/028443), lapatinib or lapatinib ditosylate (sold under the trademark Tykerb® by GlaxoSmithKline); Trastuzumab emtansine (in the United States, ado-trastuzumab emtansine, trade name Kadcyla)—an antibody-drug conjugate consisting of the monoclonal antibody trastuzumab (Herceptin) linked to the cytotoxic agent mertansine (DM1);

CD20 antibodies: Rituximab (sold under the trademarks Riuxan® and MabThera® by Genentech/Roche), tositumomab (sold under the trademarks Bexxar® by GlaxoSmithKline), ofatumumab (sold under the trademark Arzerra® by GlaxoSmithKline);

Tyrosine kinase inhibitors: Erlotinib hydrochloride (sold under the trademark Tarceva® by Genentech/Roche), Linifanib (N-[4-(3-amino-1H-indazol-4-yl)phenyl]-N'-(2-fluoro-5-methylphenyl)urea, also known as ABT 869, available from Genentech), sunitinib malate (sold under the tradename Sutent® by Pfizer), bosutinib (4-[(2,4-dichloro-5-methoxyphenyl)amino]-6-methoxy-7-[3-(4-methylpiperazin-1-yl)propoxy]quinoline-3-carbonitrile, also known as SKI-606, and described in U.S. Pat. No. 6,780,996), dasatinib (sold under the tradename Sprycel® by Bristol-Myers Squibb), armala (also known as pazopanib, sold under the tradename Votrient® by GlaxoSmithKline), imatinib and imatinib mesylate (sold under the tradenames Gilvec® and Gleevec® by Novartis);

DNA Synthesis inhibitors: Capecitabine (sold under the trademark Xeloda® by Roche), gemcitabine hydrochloride (sold under the trademark Gemzar® by Eli Lilly and Company), nelarabine ((2R,3S,4R,5R)-2-(2-amino-6-methoxypurin-9-yl)-5-(hydroxymethyl)oxolane-3,4-diol, sold under the tradenames Arranon® and Atriance® by GlaxoSmithKline);

Antineoplastic agents: oxaliplatin (sold under the tradename Eloxatin® ay Sanofi-Aventis and described in U.S. Pat. No. 4,169,846);

Epidermal growth factor receptor (EGFR) inhibitors: Gefitnib (sold under the tradename Iressa®), N-[4-[(3-Chloro-4-fluorophenyl)amino]-7-[[(3"S")-tetrahydro-3-furanyl]oxy]-6-quinazolinyl]-4(dimethylamino)-2-butenamide, sold under the tradename Tovok® by Boehringer Ingelheim), cetuximab (sold under the tradename Erbitux® by Bristol-Myers Squibb), panitumumab (sold under the tradename Vectibix® by Amgen);

HER dimerization inhibitors: Pertuzumab (sold under the trademark Omnitarg®, by Genentech);

Human Granulocyte colony-stimulating factor (G-CSF) modulators: Filgrastim (sold under the tradename Neupogen® by Amgen);

Immunomodulators: Afutuzumab (available from Roche®), pegfilgrastim (sold under the tradename Neulasta® by Amgen), lenalidomide (also known as CC-5013, sold under the tradename Revlimid®), thalidomide (sold under the tradename Thalomid®);

CD40 inhibitors: Dacetuzumab (also known as SGN-40 or huS2C6, available from Seattle Genetics, Inc);

Pro-apoptotic receptor agonists (PARAs): Dulanermin (also known as AMG-951, available from Amgen/Genentech);

Hedgehog antagonists: 2-chloro-N-[4-chloro-3-(2-pyridinyl)phenyl]-4-(methylsulfonyl)-benzamide (also known as GDC-0449, and described in PCT Publication No. WO 06/028958);

PI3K inhibitors: 4-[2-(1H-Indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036082 and WO 09/055730), 2-Methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806);

Phospholipase A2 inhibitors: Anagrelide (sold under the tradename Agrylin®);

BCL-2 inhibitors: 4-[4-[[2-(4-chlorophenyl)-5,5-dimethyl-1-cyclohexen-1-yl]methyl]-1-piperazinyl]-N-[[4-[[(1R)-3-(4-morpholinyl)-1-[(phenylthio)methyl]propyl]amino]-3-[(trifluoromethyl)sulfonyl]phenyl]sulfonyl]benzamide (also known as ABT-263 and described in PCT Publication No. WO 09/155386);

Mitogen-activated protein kinase kinase (MEK) inhibitors: XL-518 (Cas No. 1029872-29-4, available from ACC Corp.);

Aromatase inhibitors: Exemestane (sold under the trademark Aromasin® by Pfizer), letrozole (sold under the tradename Femara® by Novartis), anastrozole (sold under the tradename Arimidex®);

Topoisomerase I inhibitors: Irinotecan (sold under the trademark Camptosar® by Pfizer), topotecan hydrochloride (sold under the tradename Hycamtin® by GlaxoSmithKline);

Topoisomerase II inhibitors: etoposide (also known as VP-16 and Etoposide phosphate, sold under the tradenames Toposar®, VePesid® and Etopophos®), teniposide (also known as VM-26, sold under the tradename Vumon®);

mTOR inhibitors: Temsirolimus (sold under the tradename Torisel® by Pfizer), ridaforolimus (formally known as deferolimus, (1R,2R,4S)-4-[(2R)-2 [(1R,9S,12S,15R,16E,18R,19R,21R, 23S,24E,26E,28Z,30S,32S,35R)-1,18-dihydroxy-19,30-dimethoxy-15,17,21,23, 29,35-hexamethyl-2,3,10,14,20-pentaoxo-11,36-dioxa-4-azatricyclo[30.3.1.0$^{4,9}$] hexatriaconta-16,24,26,28-tetraen-12-yl]propyl]-2-methoxycyclohexyl dimethylphosphinate, also known as AP23573 and MK8669, and described in PCT Publication No. WO 03/064383), everolimus (sold under the tradename Afinitor® by Novartis);

Osteoclastic bone resorption inhibitors: 1-Hydroxy-2-imidazol-1-yl-phosphonoethyl) phosphonic acid monohydrate (sold under the tradename Zometa® by Novartis);

CD33 Antibody Drug Conjugates: Gemtuzumab ozogamicin (sold under the tradename Mylotarg® by Pfizer/Wyeth);

CD22 Antibody Drug Conjugates: Inotuzumab ozogamicin (also referred to as CMC-544 and WAY-207294, available from Hangzhou Sage Chemical Co., Ltd.);

CD20 Antibody Drug Conjugates: Ibritumomab tiuxetan (sold under the tradename Zevalin®);

Somatostain analogs: octreotide (also known as octreotide acetate, sold under the tradenames Sandostatin® and Sandostatin LAR®);

Synthetic Interleukin-11 (IL-11): oprelvekin (sold under the tradename Neumega® by Pfizer/Wyeth);

Synthetic erythropoietin: Darbepoetin alfa (sold under the tradename Aranesp® by Amgen);

Receptor Activator for Nuclear Factor κ B (RANK) inhibitors: Denosumab (sold under the tradename Prolia® by Amgen);

Thrombopoietin mimetic peptibodies: Romiplostim (sold under the tradename Nplate® by Amgen;

Cell growth stimulators: Palifermin (sold under the tradename Kepivance® by Amgen);

Anti-Insulin-like Growth Factor-1 receptor (IGF-1R) antibodies: Figitumumab (also known as CP-751,871, available from ACC Corp), robatumumab (CAS No. 934235-44-6);

Anti-CS1 antibodies: Elotuzumab (HuLuc63, CAS No. 915296-00-3);

CD52 antibodies: Alemtuzumab (sold under the tradename Campath®);

CTLA-4 inhibitors: Tremelimumab (IgG2 monoclonal antibody available from Pfizer, formerly known as ticilimumab, CP-675,206), ipilimumab (CTLA-4 antibody, also known as MDX-010, CAS No. 477202-00-9);

PD1 inhibitors: Nivolumab (also referred to herein as MDX-1106, MDX-1106-04, ONO-4538, BMS0936558, CAS Registry No: 946414-94-4) disclosed in, for example, U.S. Pat. No. 8,008,449, and having a sequence disclosed therein (or a sequence substantially identical or similar thereto, for example, a sequence having at least 85%, 90%, 95% identity or greater to the sequence specified in U.S. Pat. No. 8,008,449); Pembrolizumab (also referred to herein as Lambrolizumab, MK-3475, MK03475, SCH-900475 or KEYTRUDA), disclosed in, for example, U.S. Pat. No. 8,354,509 and WO 2009/114335, and having a sequence disclosed therein (or a sequence substantially identical or similar thereto, for example, a sequence having at least 85%, 90%, 95% identity or greater to the sequence specified in U.S. Pat. No. 8,354,509 and WO2009/114335); an immunoadhesin (for example, an immunoadhesin comprising an extracellular or PD-1 binding portion of PD-L1 or PD-L2 fused to a constant region (e.g., an Fc region of an immunoglobulin sequence); Pidilizumab (CT-011; Cure Tech) is a humanized IgG1k monoclonal antibody that binds to PD1 (Pidilizumab and other humanized anti-PD-1 monoclonal antibodies are disclosed in WO2009/101611); and AMP-224 (B7-DCIg; Amplimmune), disclosed in WO2010/027827 and WO2011/066342), is a PD-L2 Fc fusion soluble receptor that blocks the interaction between PD1 and B7-H1; other PD-1 inhibitors, for example, anti-PD1 antibodies disclosed in U.S. Pat. No. 8,609,089, US 2010028330, and/or US 20120114649.

PDL1 inhibitors: MSB0010718C (also referred to as A09-246-2; Merck Serono) is a monoclonal antibody that binds to PD-L1 and is disclosed in, for example, WO 2013/0179174, (and having a sequence substantially identical or similar thereto, for example, a sequence having at least 85%, 90%, 95% identity or higher to the sequence specified in WO 2013/0179174); and anti-PD-L1 binding antagonist selected from YW243.55.570, MPDL3280A (Genetech/Roche) is a human Fc optimized IgG1 monoclonal antibody that binds to PD-L1 (MDPL3280A and other human monoclonal antibodies to PD-L1 are disclosed in U.S. Pat. No. 7,943,743 and U.S Publication No.: 20120039906); MEDI-4736, MSB-0010718C, or MDX-1105 (MDX-1105, also known as BMS-936559, is an anti-PD-L1 antibody described in WO2007/005874; antibody YW243.55.570 is an anti-PD-L1 described in WO 2010/077634).

LAG-3 inhibitors: BMS-986016 (also referred to as BMS986016; Bristol-Myers Squibb) is a monoclonal antibody that binds to LAG-3. BMS-986016 and other humanized anti-LAG-3 antibodies are disclosed in US 2011/0150892, WO2010/019570, and WO2014/008218.

GITR agonists: exemplary GITR agonists include, for example, GITR fusion proteins and anti-GITR antibodies (for example, bivalent anti-GITR antibodies), such as, a GITR fusion protein described in U.S. Pat. No. 6,111,090, European Patent No.: 090505B1, U.S. Pat. No. 8,586,023, PCT Publication Nos.: WO 2010/003118 and 2011/090754, or an anti-GITR antibody described, for example, in U.S. Pat. No. 7,025,962, European Patent No.: 1947183B1, U.S. Pat. Nos. 7,812,135, 8,388,967, 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

Histone deacetylase inhibitors (HDI): Voninostat (sold under the tradename Zolinza® by Merck).

anti-CTLA4 antibodies include Tremelimumab (IgG2 monoclonal antibody available from Pfizer, formerly known as ticilimumab, CP-675,206); and Ipilimumab (CTLA-4 antibody, also known as MDX-010, CAS No. 477202-00-9).

anti-TIM-3 antibody or antigen-binding fragment thereof.

Alkylating agents: Temozolomide (sold under the tradenames Temodar® and Temodal® by Schering-Plough/Merck), dactinomycin (also known as actinomycin-D and sold under the tradename Cosmegen®), melphalan (also known as L-PAM, L-sarcolysin, and phenylalanine mustard, sold under the tradename Alkeran®), altretamine (also known as hexamethylmelamine (HMM), sold under the tradename Hexalen®), carmustine (sold under the tradename BiCNU®), bendamustine (sold under the tradename Treanda®), busulfan (sold under the tradenames Busulfex® and Myleran®), carboplatin (sold under the tradename Paraplatin®), lomustine (also known as CCNU, sold under the tradename CeeNU®), cisplatin (also known as CDDP, sold under the tradenames Platinol® and Platinol®-AQ), chlorambucil (sold under the tradename Leukeran®), cyclophosphamide (sold under the tradenames Cytoxan® and Neosar®), dacarbazine (also known as DTIC, DIC and imidazole carboxamide, sold under the tradename DTIC-Dome®), altretamine (also known as hexamethylmelamine (HMM) sold under the tradename Hexalen®), ifosfamide (sold under the tradename Ifex®), procarbazine (sold under the tradename Matulane®), mechlorethamine (also known as nitrogen mustard, mustine and mechloroethamine hydrochloride, sold under the tradename Mustargen®), streptozocin (sold under the tradename Zanosar®), thiotepa (also known as thiophosphoamide, TESPA and TSPA, sold under the tradename Thioplex®;

Biologic response modifiers: bacillus calmette-guerin (sold under the tradenames theraCys® and TICE® BCG), denileukin diftitox (sold under the tradename Ontak®);

Anti-tumor antibiotics: doxorubicin (sold under the tradenames Adriamycin® and Rubex®), bleomycin (sold under the tradename Lenoxane®), daunorubicin (also known as dauorubicin hydrochloride, daunomycin, and rubidomycin hydrochloride, sold under the tradename Cerubidine®), daunorubicin liposomal (daunorubicin citrate liposome, sold under the tradename DaunoXome®), mitoxantrone (also known as DHAD, sold under the tradename Novantrone®), epirubicin (sold under the tradename Ellence™), idarubicin (sold under the tradenames Idamycin®, Idamycin PFS®), mitomycin C (sold under the tradename Mutamycin®);

Anti-microtubule agents: Estramustine (sold under the tradename Emcyl®);

Cathepsin K inhibitors: Odanacatib (also know as MK-0822, N-(1-cyanocyclopropyl)-4-fluoro-$N^2$-{(1S)-2,2, 2-trifluoro-1-[4'-(methylsulfonyl)biphenyl-4-yl]ethyl}-L-leucinamide, available from Lanzhou Chon Chemicals, ACC Corp., and ChemieTek, and described in PCT Publication no. WO 03/075836);

Epothilone B analogs: Ixabepilone (sold under the tradename Lxempra® by Bristol-Myers Squibb);

Heat Shock Protein (HSP) inhibitors: Tanespimycin (17-allylamino-17-demethoxygeldanamycin, also known as KOS-953 and 17-AAG, available from SIGMA, and described in U.S. Pat. No. 4,261,989);

TpoR agonists: Eltrombopag (sold under the tradenames Promacta® and Revolade® by GlaxoSmithKline);

Anti-mitotic agents: Docetaxel (sold under the tradename Taxotere® by Sanofi-Aventis);

Adrenal steroid inhibitors: aminoglutethimide (sold under the tradename Cytadren®);

Anti-androgens: Nilutamide (sold under the tradenames Nilandron® and Anandron®), bicalutamide (sold under tradename Casodex®), flutamide (sold under the tradename Fulexin™);

Androgens: Fluoxymesterone (sold under the tradename Halotestin®);

Proteasome inhibitors: Bortezomib (sold under the tradename Velcade®);

CDK1 inhibitors: Alvocidib (also known as flovopirdol or HMR-1275, 2-(2-chlorophenyl)-5,7-dihydroxy-8-[(3S,4R)-3-hydroxy-1-methyl-4-piperidinyl]-4-chromenone, and described in U.S. Pat. No. 5,621,002);

Gonadotropin-releasing hormone (GnRH) receptor agonists: Leuprolide or leuprolide acetate (sold under the tradenames Viadure® by Bayer AG, Eligard® by Sanofi-Aventis and Lupron® by Abbott Lab);

Taxane anti-neoplastic agents: Cabazitaxel (1-hydroxy-7β,10β-dimethoxy-9-oxo-5β,20-epoxytax-11-ene-2α,4, 13α-triyl-4-acetate-2-benzoate-13-[(2R,3S)-3-{[(tert-butoxy)carbonyl]amino}-2-hydroxy-3-phenylpropanoate), larotaxel ((2α,3λ,4α,5β,7α,10β,13α)-4,10-bis(acetyloxy)-13-({(2R,3S)-3-[(tert-butoxycarbonyl) amino]-2-hydroxy-3-phenylpropanoyl}oxy)-1-hydroxy-9-oxo-5,20-epoxy-7, 19-cyclotax-11-en-2-yl benzoate);

5HT1a receptor agonists: Xaliproden (also known as SR57746, 1-[2-(2-naphthyl)ethyl]-4-[3-(trifluoromethyl) phenyl]-1,2,3,6-tetrahydropyridine, and described in U.S. Pat. No. 5,266,573);

HPC vaccines: Cervarix® sold by GlaxoSmithKline, Gardasil® sold by Merck;

Iron Chelating agents: Deferasinox (sold under the tradename Exjade® by Novartis);

Anti-metabolites: Claribine (2-chlorodeoxyadenosine, sold under the tradename Leustatin®), 5-fluorouracil (sold under the tradename Adrucil®), 6-thioguanine (sold under the tradename Purinethol®), pemetrexed (sold under the tradename Alimta®), cytarabine (also known as arabinosylcytosine (Ara-C), sold under the tradename Cytosar-U®), cytarabine liposomal (also known as Liposomal Ara-C, sold under the tradename DepoCyt™), decitabine (sold under the tradename Dacogen®), hydroxyurea (sold under the tradenames Hydrea®, Droxia™ and Mylocel™), fludarabine (sold under the tradename Fludara®), floxuridine (sold under the tradename FUDR®), cladribine (also known as 2-chlorodeoxyadenosine (2-CdA) sold under the tradename Leustatin™), methotrexate (also known as amethopterin, methotrexate sodim (MTX), sold under the tradenames Rheumatrex® and Trexall™), pentostatin (sold under the tradename Nipent®);

Bisphosphonates: Pamidronate (sold under the tradename Aredia®), zoledronic acid (sold under the tradename Zometa®);

Demethylating agents: 5-azacitidine (sold under the tradename Vidaza®), decitabine (sold under the tradename Dacogen®);

Plant Alkaloids: Paclitaxel protein-bound (sold under the tradename Abraxane®), vinblastine (also known as vinblastine sulfate, vincaleukoblastine and VLB, sold under the tradenames Alkaban-AQ® and Velban®), vincristine (also known as vincristine sulfate, LCR, and VCR, sold under the tradenames Oncovin® and Vincasar Pfs®), vinorelbine (sold under the tradename Navelbine®), paclitaxel (sold under the tradenames Taxol and Onxal™);

Retinoids: Alitretinoin (sold under the tradename Panretin®), tretinoin (all-trans retinoic acid, also known as ATRA, sold under the tradename Vesanoid®), Isotretinoin (13-cis-retinoic acid, sold under the tradenames Accutane®, Amnesteem®, Claravis®, Clarus®, Decutan®, Isotane®, Izotech®, Oratane®, Isotret®, and Sotret®), bexarotene (sold under the tradename Targretin®);

Glucocorticosteroids: Hydrocortisone (also known as cortisone, hydrocortisone sodium succinate, hydrocortisone sodium phosphate, and sold under the tradenames AlaCort®, Hydrocortisone Phosphate, Solu-Cortef®, Hydrocort Acetate® and Lanacort®), dexamethazone ((8S,9R,10S,11S,13S,14S,16R,17R)-9-fluoro-11,17-dihydroxy-17-(2-hydroxyacetyl)-10,13,16-trimethyl-6,7,8,9,10,11,12,13,14,15,16,17-dodecahydro-3H-cyclopenta[a]phenanthren-3-one), prednisolone (sold under the tradenames Delta-Cortel®, Orapred®, Pediapred® and Prelone®), prednisone (sold under the tradenames Deltasone®, Liquid Red®, Meticorten® and Orasone®), methylprednisolone (also known as 6-Methylprednisolone, Methylprednisolone Acetate, Methylprednisolone Sodium Succinate, sold under the tradenames Duralone®, Medralone®, Medrol®, M-Prednisol® and Solu-Medrol®);

Cytokines: interleukin-2 (also known as aldesleukin and IL-2, sold under the tradename Proleukin®), interleukin-11 (also known as oprevelkin, sold under the tradename Neumega®), alpha interferon alfa (also known as IFN-alpha, sold under the tradenames Intron® A, and Roferon-A®);

Estrogen receptor downregulators: Fulvestrant (sold under the tradename Faslodex®);

Anti-estrogens: tamoxifen (sold under the tradename Novaldex®);

Toremifene (sold under the tradename Fareston®);

Selective estrogen receptor modulators (SERMs): Raloxifene (sold under the tradename Evista®);

Leutinizing hormone releasing hormone (LHRH) agonists: Goserelin (sold under the tradename Zoladex®);

Progesterones: megestrol (also known as megestrol acetate, sold under the tradename Megace®);

Miscellaneous cytotoxic agents: Arsenic trioxide (sold under the tradename Trisenox®), asparaginase (also known as L-asparaginase, Erwinia L-asparaginase, sold under the tradenames Elspar® and Kidrolase®);

A compound of formula (I) can also be used in combination with the following adjunct therapies:

Anti-nausea drugs: NK-1 receptor antagonists: Casopitant (sold under the tradenames Rezonic® and Zunrisa® by GlaxoSmithKline); and Cytoprotective agents: Amifostine (sold under the tradename Ethyol®), leucovorin (also known as calcium leucovorin, citrovorum factor and folinic acid).

Immune checkpoint inhibitors: In one embodiment, the combination therapies disclosed herein include an inhibitor of an inhibitory molecule of an immune checkpoint molecule. The term "immune checkpoints" refers to a group of molecules on the cell surface of CD4 and CD8 T cells. These molecules can effectively serve as "brakes" to down-modulate or inhibit an anti-tumor immune response. Immune checkpoint molecules include, but are not limited to, Programmed Death 1 (PD-1), Cytotoxic T-Lymphocyte Antigen 4 (CTLA-4), B7H1, B7H4, OX-40, CD137, CD40, and LAG3, which directly inhibit immune cells, immunotherapeutic agents which can act as immune checkpoint inhibitors useful in the methods of the present invention, include, but are not limited to, inhibitors of PD-L1, PD-L2, CTLA4, TIM3, LAG3, VISTA, BTLA, TIGIT, LAIR1, CD160, 2B4 and/or TGFR beta. Inhibition of an inhibitory molecule can be performed by inhibition at the DNA, RNA or protein level. In embodiments, an inhibitory nucleic acid (e.g., a dsRNA, siRNA or shRNA), can be used to inhibit expression of an inhibitory molecule. In other embodiments, the inhibitor of an inhibitory signal is, a polypeptide e.g., a soluble ligand, or an antibody or antigen-binding fragment thereof, that binds to the inhibitory molecule.

In certain embodiments, the anti-PD-1 molecules described herein are administered in combination with one or more other inhibitors of PD-1, PD-L1 and/or PD-L2 known in the art. The antagonist may be an antibody, an antigen binding fragment thereof, an immunoadhesin, a fusion protein, or oligopeptide.

In certain embodiments, the combination therapies disclosed herein include a modulator of a costimulatory molecule or an inhibitory molecule, e.g., a co-inhibitory ligand or receptor.

In one embodiment, the costimulatory modulator, e.g., agonist, of a costimulatory molecule is chosen from an agonist (e.g., an agonistic antibody or antigen-binding fragment thereof, or soluble fusion) of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand.

In another embodiment, the combination therapies disclosed herein include a costimulatory molecule, e.g., an agonist associated with a positive signal that includes a costimulatory domain of CD28, CD27, ICOS and GITR.

In one embodiment, the anti-PD-1 antibody molecule is administered after treatment, e.g., after treatment of a melanoma, with an anti-CTLA4 antibody (e.g., ipilimumab) with or without a BRAF inhibitor (e.g., vemurafenib or dabrafenib). Exemplary doses that can be use include a dose of anti-PD-1 antibody molecule of about 1 to 10 mg/kg, e.g., 3 mg/kg, and a dose of an anti-CTLA-4 antibody, e.g., ipilimumab, of about 3 mg/kg.

In another embodiment, the anti-PD-1 or PD-L1 antibody molecule is administered in combination with an anti-LAG-3 antibody or an antigen-binding fragment thereof. In another embodiment, the anti-PD-1 or PD-L1 antibody molecule is administered in combination with an anti-TIM-3 antibody or antigen-binding fragment thereof. In yet other embodiments, the anti-PD-1 or PD-L1 antibody molecule is administered in combination with an anti-LAG-3 antibody and an anti-TIM-3 antibody, or antigen-binding fragments thereof. The combination of antibodies recited herein can be administered separately, e.g., as separate antibodies, or linked, e.g., as a bispecific or trispecific antibody molecule. In one embodiment, a bispecific antibody that includes an anti-PD-1 or PD-L1 antibody molecule and an anti-TIM-3 or anti-LAG-3 antibody, or antigen-binding fragment thereof, is administered. In certain embodiments, the combination of antibodies recited herein is used to treat a cancer, e.g., a cancer as described herein (e.g., a solid tumor). The efficacy of the aforesaid combinations can be tested in animal models known in the art. For example, the animal models to test the synergistic effect of anti-PD-1 and anti-LAG-3 are described, e.g., in Woo et al. (2012) *Cancer Res.* 72(4):917-27).

In some embodiments, the combination therapy disclosed herein (e.g., an anti-PD-1 or PD-L1 antibody molecule, alone or in combination with another immunomodulator (e.g., an anti-LAG-3, or anti-TIM-3 antibody molecule). In one embodiment, the anti-PD-1 or PD-L1 antibody molecule is administered in combination with an anti-LAG-3 antibody or an antigen-binding fragment thereof. In another embodiment, the anti-PD-1 or PD-L1 antibody molecule is administered in combination with an anti-TIM-3 antibody or antigen-binding fragment thereof. In yet other embodiments, the anti-PD-1 or PD-L1 antibody molecule is administered in combination with an anti-LAG-3 antibody and an anti-TIM-3 antibody, or antigen-binding fragments thereof. The combination of antibodies recited herein can be administered separately, e.g., as separate antibodies, or linked, e.g., as a bispecific or trispecific antibody molecule. In one embodiment, a bispecific antibody that includes an anti-PD-1 or PD-L1 antibody molecule and an anti-TIM-3 or anti-LAG-3 antibody, or antigen-binding fragment thereof, is administered. In certain embodiments, the combination of antibodies recited herein is used to treat a cancer, e.g., a cancer as described herein (e.g., a solid tumor). The efficacy of the aforesaid combinations can be tested in animal models known in the art. For example, the animal models to test the synergistic effect of anti-PD-1 and anti-LAG-3 are described, e.g., in Woo et al. (2012) *Cancer Res.* 72(4):917-27).24

In certain embodiments, the antibody molecule is in the form of a bispecific or multispecific antibody molecule. In one embodiment, the bispecific antibody molecule has a first binding specificity to PD-1 or PD-L1 and a second binding specifity, e.g., a second binding specificity to TIM-3, LAG-3, or PD-L2. In one embodiment, the bispecific antibody molecule binds to PD-1 or PD-L1 and TIM-3. In another embodiment, the bispecific antibody molecule binds to PD-1 or PD-L1 and LAG-3. In another embodiment, the bispecific antibody molecule binds to PD-1 or PD-L1. In yet another embodiment, the bispecific antibody molecule binds to PD-1 and PD-L2. In another embodiment, the bispecific antibody molecule binds to TIM-3 and LAG-3. Any combination of the aforesaid molecules can be made in a multispecific antibody molecule, e.g., a trispecific antibody that includes a first binding specificity to PD-1 or PD-1, and a second and third binding specifities to two or more of: TIM-3, LAG-3, or PD-L2.

None of the quotations of references made within the present disclosure is to be understood as an admission that the references cited are prior art that would negatively affect the patentability of the present invention.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Compounds of Formula I can be prepared by proceeding as in the following

Reaction Scheme I:

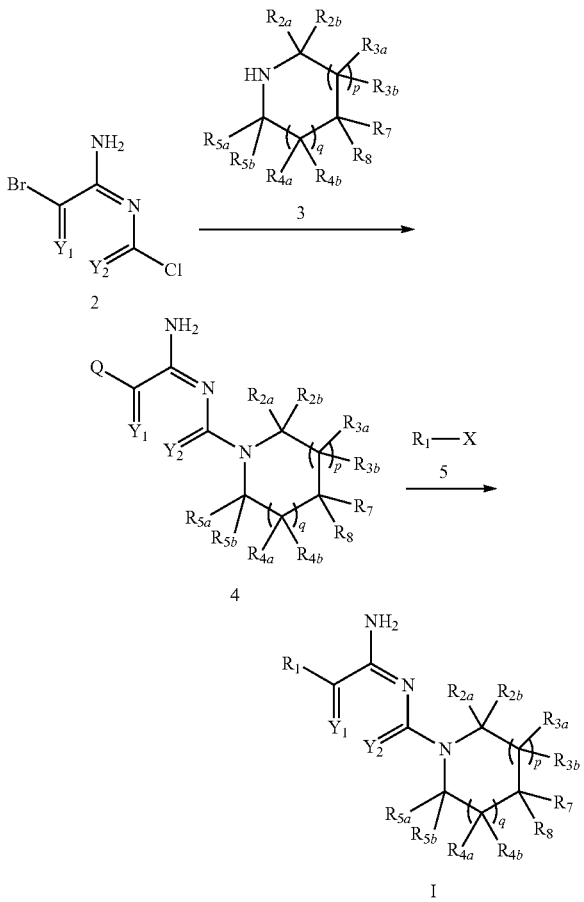

in which p, q, $Y_1$, $Y_2$, $R_{2a}$, $R_{2b}$, $R_{3a}$, $R_{3b}$, $R_{4a}$, $R_{4b}$, $R_{5a}$, $R_{5b}$, $R_7$ and $R_8$ are as defined for Formula I in the Summary of the Invention, Q is a halogen (like bromine) or a thiol, boronate or stannate which reacts with a halogen on compound 5, and X is a reactive group which reacts with Q (such as a boronate, stannane, alcohol, thiol, halogen, and the like). Compound 4 may be prepared by reacting compound 2 with compound 3 through a reaction under suitable acid or base conditions in the presence or absence of a transition metal under ambient temperature, or under thermal or microwave conditions. Alternatively, the halogen of compound 2 may be replaced by other halogens or suitable activating groups such as triflates, mesylates, tosylates, nonaflates, boronates, organostannanes, organosilyls, organozincs, lithium, magnesium, and the like.

A compound of formula I can be prepared by reacting compound 4 with a suitable coupling partner (e.g. compound 5) depending on X. For example, compound 5 is shown in reaction scheme I as a substituted phenyl group linked via X. Alternatively, compound 5 could be aryl-alcohol, aryl-thio, aryl-boronate, aryl-stannate, heteroaryl-alcohol, aryl-thiol, heteroaryl-thiol, aryl-boronate, aryl-stannane, olefin, or other aryl-metals or heteroaryl-metals, and the like. The coupling partners may also be substituted. This reaction may be conducted under suitable acid or base conditions, in the presence or absence of a transition metal such as palladium, under ambient temperature, or under thermal or microwave conditions. Other halogens or suitable activating groups (e.g., triflates, mesylates, tosylates, and nonaflates) may be used in place of Br for these transformations.

Alternatively, the coupling partners could be reversed and compound 2 may be derivatized to a stannane, boronate, organo-zinc, organo-lithium, organo-magnesium, organo-silicon, organo-cuprate and coupled with a suitable aryl-halide, heteroaryl-halide, olefin or suitable reactive functional group (e.g., triflates, mesylates, tosylates and nonaflates), and the like.

These reactions may be conducted in the order described or in reverse order, under a variety of solvents, temperatures, pressures, and under suitable atmospheres. The reactions may be conducted under acid, base, and or transition metal conditions.

Detailed examples of the synthesis of compounds of Formula I can be found in the Examples, infra.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base.

Compounds of the formula I can also be modified by appending appropriate functionalities to enhance selective biological properties. Modifications of this kind are known in the art and include those that increase penetration into a given biological system (e.g. blood, lymphatic system, central nervous system, testis), increase bioavailability, increase solubility to allow parenteral administration (e.g. injection, infusion), alter metabolism and/or alter the rate of secretion. Examples of this type of modifications include but are not limited to esterification, e.g. with polyethylene glycols, derivatisation with pivaloyloxy or fatty acid substituents, conversion to carbamates, hydroxylation of aromatic rings and heteroatom substitution in aromatic rings. Whereever compounds of the formula I, and/or N-oxides, tautomers and/or (preferably pharmaceutically acceptable) salts thereof are mentioned, this comprises such modified formulae, while preferably the molecules of the formula I, their N-oxides, their tautomers and/or their salts are meant.

Alternatively, the salt forms of the compounds of the invention can be prepared using salts of the starting materials or intermediates. In view of the close relationship between the novel compounds of the formula I in free form and those in the form of their salts, including those salts that can be used as intermediates, for example in the purification or identification of the novel compounds, any reference to the compounds or a compound of the formula I hereinbefore and hereinafter is to be understood as referring to the compound in free form and/or also to one or more salts thereof, as appropriate and expedient, as well as to one or more solvates, e.g. hydrates.

Salts are formed, for example, as acid addition salts, preferably with organic or inorganic acids, from compounds of formula I with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, malonic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 4-toluenesulfonic acid, 2-naphthalenesulfonic acid, 1,5-naphthalene-disulfonic acid, 2- or 3-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3rd edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:
(a) that of reaction scheme I; and
(b) optionally converting a compound of the invention into a pharmaceutically acceptable salt;
(c) optionally converting a salt form of a compound of the invention to a non-salt form;
(d) optionally converting an unoxidized form of a compound of the invention into a pharmaceutically acceptable N-oxide;
(e) optionally converting an N-oxide form of a compound of the invention to its unoxidized form;
(f) optionally resolving an individual isomer of a compound of the invention from a mixture of isomers;
(g) optionally converting a non-derivatized compound of the invention into a pharmaceutically acceptable prodrug derivative; and
(h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The following examples and intermediates serve to illustrate the invention without limiting the scope thereof. Some abbreviations used in the examples are as follows: acetic acid (AcOH); triethylamine (TEA); tetrahydrofuran (THF); aqueous (aq.); atmosphere (atm.); 2,2'-bis-diphenylphosphanyl-[1,1']binaphthalenyl (BINAP); 4-dimethylaminopyridine (DMAP); tert-butoxycarbonyl (Boc); 1,1-carbonyldiimidazole (CDI); di-tert-butyl dicarbonate (BOC$_2$O); benzotriazole-1-yl-oxy-tris-(dimethylamino)-phosphonium hexafluorophosphate (BOP); dichloromethane (DCM); diethyl ether (Et$_2$O); p-toluene sulfonic acid (PTSA); ethyl acetate (EtOAc); ethanol (EtOH); lithium bis(trimethylsilyl)amide (LHMDS); diisopropyl azodicarboxylate (DIAD); N,N-diisopropyl-ethylamine (DIEA or DIPEA); N,N-dimethylformamide (DMF); dimethyl sulfoxide (DMSO); diphenylphosphoryl azide (DPPA); hour(s) (h); 2-(1H-7-azabenzotriazol-1-yl)-1,1,3,3-tetramethyluronium hexafluorophosphate (HATU); High Performance Liquid Chromatography (HPLC); lithium aluminium hydride (LAH); liquid chromatography coupled with mass spectrometry (LCMS); lithium diisopropylamide (LDA); methanol (MeOH); milliliter(s) (mL); minute(s) (min); microwave (MW); n-butyl-lithium (n-BuLi); 1,1-bis(diphenylphosphino)-ferrocenedichloropalladium (II) (PdCl$_2$(dppf)); tris(dibenzylideneacetone)dipalladium (0) (Pd$_2$(dba)$_3$); dichlorobis(triphenylphosphine)palladium (II) (PdCl$_2$(PPh$_3$)$_2$); room temperature (RT); trifluoroacetic acid (TFA); tetrahydrofuran (THF); thin layer chromatography (TLC); retention time (t$_R$); & 4,5-bis(diphenylphosphino)-9,9-dimethylxanthene (Xantphos).

Intermediate 1

6-chloro-3-((2-(trifluoromethyl)pyridin-3-yl)thio)pyrazin-2-amine

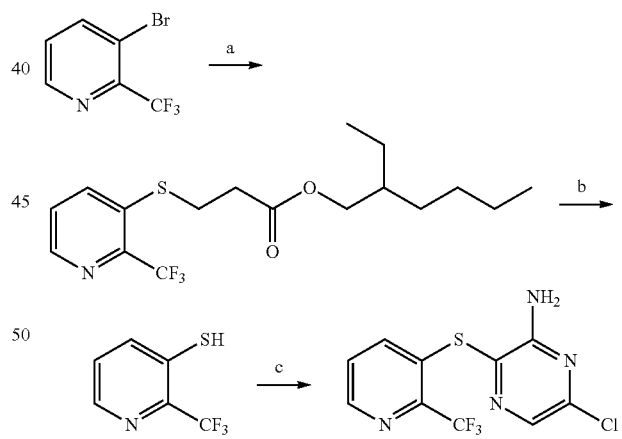

Step a:
To a solution of 3-bromo-2-(trifluoromethyl)pyridine (1.0 g, 4.42 mmol), XantPhos (256 mg, 0.442 mmol), Pd$_2$(dba)$_3$ (203 mg, 0.221 mmol) in dioxane (12 mL) was added (at RT and under N$_2$) 2-ethylhexyl-3-mercaptopropanoate (1.1 mL, 4.87 mmol) followed by addition of DIPEA (1.55 mL, 8.85 mmol). The resulting solution was stirred in a microwave reactor for 1 h at 110° C. After cooling to RT, the reaction was filtered through a pad of Celite followed by EtOAc (25 mL) wash. The combined filtrates were concentrated and the resulting residue was purified by silica chromatography (0 to 30% gradient of EtOAc/heptane) to give 2-ethylhexyl 3-((2-

(trifluoromethyl)pyridin-3-yl)thio)propanoate (1.41 g, 3.88 mmol). MS m/z 364.0 (M+H)+.

Step b:

To a solution of 2-ethylhexyl 3-((2-(trifluoromethyl)pyridin-3-yl)thio)propanoate (1.0 g, 2.75 mmol) in THF (8 mL) was added at −78° C. and under $N_2$ potassium tert-butoxide (1 M in THF, 8.25 mL, 8.25 mmol). After stirring vigorously at −78° C. for 20 min, the reaction was quenched with $K_2CO_3$ aq (2 M, 500 µL) and the volatiles were removed under reduced pressure. The resulting residue was poured into a separation funnel containing $K_2CO_3$ aq (2 M, 30 mL) and it was extracted with $Et_2O$ (2×20 mL). The aqueous phase was acidified with 6 M HCl until pH 4 and the resulting cloudy suspension was extracted with $CHCl_3$:IPA (9:1; 3×20 mL) to give 2-(trifluoromethyl)pyridine-3-thiol (380 mg, 2.12 mmol). MS m/z 180.0 (M+H)+.

Step c:

To a solution of 2-(trifluoromethyl)pyridine-3-thiol (285 mg, 1.591 mmol), 3-bromo-6-chloropyrazin-2-amine (414 mg, 1.988 mmol), XantPhos (101 mg, 0.175 mmol), and $Pd_2(dba)_3$ (72.8 mg, 0.08 mmol) in dioxane (2 mL) was added (at RT and under $N_2$) DIPEA (556 µL, 3.18 mmol). The resulting solution was stirred in a microwave reactor for 1.5 h at 130° C. After cooling to RT, the reaction was diluted with EtOAc and it was filtered through a pad of Celite followed by EtOAc (25 mL) wash. The combined filtrates were concentrated and the resulting residue was purified by silica chromatography (0 to 30% gradient of EtOAc/heptane) to give 6-chloro-3-((2-(trifluoromethyl)pyridin-3-yl)thio)pyrazin-2-amine (1.41 g, 3.88 mmol). $^1$H NMR (400 MHz, CHLOROFORM-d) δ ppm 8.64 (dd, J=4.55, 1.26 Hz, 1H), 7.90 (s, 1H), 7.82 (dd, J=8.08, 0.76 Hz, 1H), 7.46 (dd, J=8.08, 4.80 Hz, 1H); $^{19}$F NMR (376 MHz, CHLOROFORM-d) δ ppm −64.34 (s, 1F). MS m/z 307.1 (M+H)+.

Intermediate 2

6-(4-amino-4-methylpiperidin-1-yl)-3-(2,3-dichlorophenyl)pyrazin-2-amine

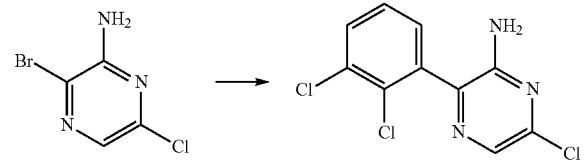 [SMILES: Nc1nc(Cl)cnc1Br ; Nc1nc(Cl)cnc1-c1cccc(Cl)c1Cl]

A suspension of 3-bromo-6-chloropyrazin-2-amine (1.2 g, 5.76 mmol), (2,3-dichlophenyl)boronic acid (1.1 g, 5.76 mmol), potassium phosphate (3.67 g, 17.27 mmol), and $PdCl_2(dppf)$.DCM adduct (235 mg, 0.288 mmol) in MeCN:$H_2O$ (9:1, 15 mL, degassed) was stirred in a microwave reactor for 4 h at 120° C. After cooling to RT, the reaction was filtered through a pad of Celite followed by EtOAc (25 mL) wash. The combined filtrates were concentrated and the resulting residue was purified by silica chromatography (0 to 30% gradient of EtOAc/heptane) to give 6-(4-amino-4-methylpiperidin-1-yl)-3-(2,3-dichlorophenyl)pyrazin-2-amine (633 mg, 2.306 mmol). MS m/z 276.4 (M+H)+.

Intermediate 3

6-chloro-3-((2,3-dichlorophenyl)thio)pyrazin-2-amine

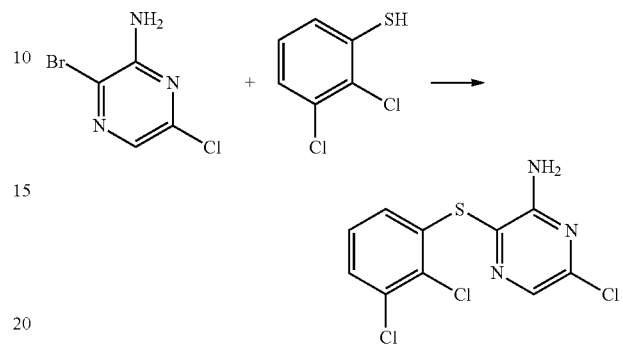

A mixture of 3-bromo-6-chloropyrazin-2-amine (5.0 g, 23.99 mmol), 2,3-dichlorobenzenethiol (6.44 g, 36.0 mmol), copper(I)iodide (914 mg, 4.80 mmol), potassium phosphate (10.18 g, 48.0 mmol), and 1,10-phenanthroline (1.73 mg, 9.59 mmol) in dioxane (50 mL, degassed) was stirred for 16 h at 85° C. After cooling to RT, the reaction was diluted with EtOAc, and it was filtered through a pad of Celite followed by EtOAc (50 mL) wash. The volatiles were removed under reduced pressure and the resulting residue was purified by silica chromatography (0 to 25% gradient of DCM/toluene) to give 6-chloro-3-((2,3-dichlorophenyl)thio)pyrazin-2-amine (3.7 g, 12.07 mmol). MS m/z 306.0 (M+H)+.

Intermediate 4

(R) and (S)-2-(7-azaspiro[3.5]nonan-1-yl)isoindoline-1,3-dione

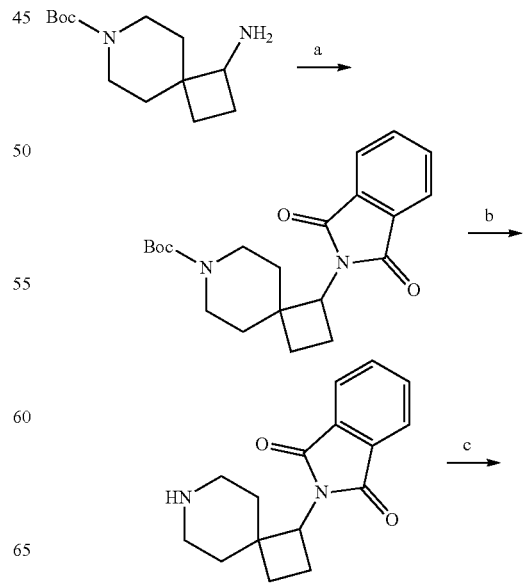

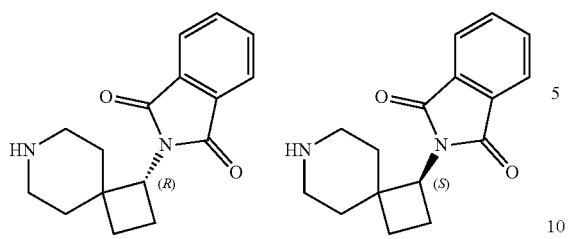

Step a:

A suspension of tert-butyl 1-amino-7-azaspiro[3.5]nonane-7-carboxylate (250 mg, 1.04 mmol), phthalic anhydride (193 mg, 1.3 mmol), activated molecular sieves (3 angstroms, 250 mg), and DIPEA (545 μL, 3.12 mmol) in toluene (4 mL) was stirred for 16 h at 105° C. After cooling to RT, the mixture was filtered through a pad of Celite followed by EtOAc (10 mL) wash. The volatiles were removed under reduced pressure and the resulting residue was purified by silica chromatography (5 to 40% gradient of EtOAc/heptane) to give tert-butyl 1-(1,3-dioxoisoindolin-2-yl)-7-azaspiro[3.5]nonane-7-carboxylate (233 mg, 0.629 mmol). MS m/z 370.4 (M+H)+.

Step b:

A solution of tert-butyl 1-(1,3-dioxoisoindolin-2-yl)-7-azaspiro[3.5]nonane-7-carboxylate (233 mg, 0.629 mmol) and HCl (4 M in dioxane, 800 μL, 3.21 mmol) in dioxane (5 mL) was stirred for 16 h at RT. The volatiles were removed on the rotavap to give the HCl salt of the title compound (195 mg, 0.636 mmol). MS m/z 270.3 (M+H)+.

Step c:

Chiral SFC purification was performed under the following conditions; column: Cellulose LUX-2 21×250 mm, flow rate: 75 g per minute, mobile phase: 50% MeOH and 10 mM NH$_4$OH in CO$_2$, detection: 220 nm UV to obtain two peaks R$_t$ (P1)=3.6 min (enantiomer R); R$_t$ (P2)=7.4 min (enantiomer S).

Intermediate 5

2-(1,1-dioxido-1-thia-8-azaspiro[4.5]decan-4-yl)isoindoline-1,3-dione

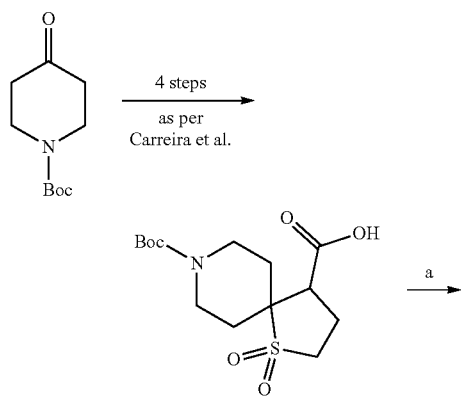

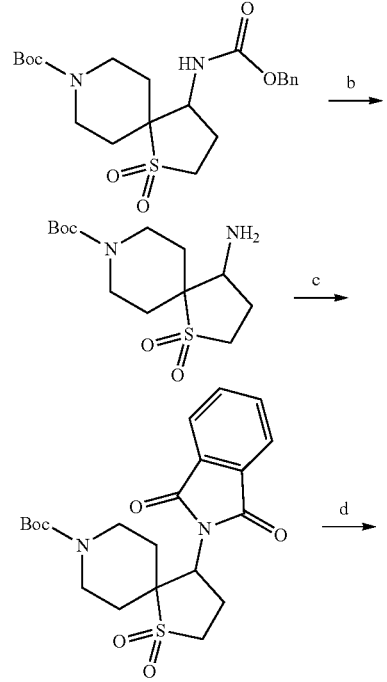

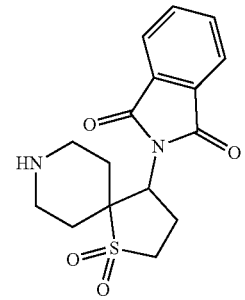

Step a:

A solution of 8-(tert-butoxycarbonyl)-1-thia-8-azaspiro[4.5]decane-4-carboxylic acid 1,1-dioxide (prepared from tert-butyl 4-oxopiperidine-1-carboxylate in 4 steps as described in Carreira et al., *Org Lett.*, 2011, 13, 6134-6136; 2.00 g, 6.00 mmol), diphenyl phosphorazidate (2.0 g, 7.26 mmol), and Et$_3$N (1.0 mL, 7.26 mmol) in toluene (37 mL) was stirred for 1.5 h at 115° C. Benzyl alcohol (1.50 mL, 14.52 mmol) was added and the resulting mixture was stirred for 16 h at 100° C. After cooling to RT, the reaction mixture was poured into a separation funnel containing NaHCO$_3$ sat. aq. (30 mL) and it was extracted with EtOAc (3×20 mL). The combined organic phases were dried over MgSO$_4$, filtered and the volatiles were removed under reduced pressure. The resulting residue was purified by silica chromatography (10 to 90% gradient of EtOAc/heptane) to give tert-butyl 4-(((benzyloxy)carbonyl)amino)-1-thia-8-azaspiro[4.5]decane-8-carboxylate 1,1-dioxide (1.57 g. 3.58 mmol) as a white solid. MS m/z 339.4 (M+H)+.

Step b:

A suspension of tert-butyl 4-(((benzyloxy)carbonyl)amino)-1-thia-8-azaspiro[4.5]decane-8-carboxylate 1,1-dioxide (570 mg. 1.30 mmol) and Pd/C (10% on charcoal, 138 mg) in THF (8 mL) was vigorously stirred under H$_2$ atmosphere for 16 h. The reaction was filtered through a plug of Celite followed by EtOAc (20 mL) wash. The volatiles were removed under reduced pressure to give tert-butyl 4-amino- 1-thia-8-azaspiro[4.5]decane-8-carboxylate 1,1-dioxide which was used in next step without further purification.

Step c:

A suspension of tert-butyl 4-amino-1-thia-8-azaspiro[4.5]decane-8-carboxylate 1,1-dioxide (415 mg, 1.363 mmol), phthalic anhydride (252 mg, 1.704 mmol), and activated molecular sieves (3 angstroms, 500 mg) in toluene (7 mL) was vigorously stirred for 16 h at 115° C. After cooling to RT, the mixture was filtered through a pad of Celite followed by EtOAc (10 mL) wash, and the volatiles were removed under reduced pressure. The resulting residue was purified by silica chromatography (0 to 10% gradient of MeOH/DCM) to give tert-butyl 4-(1,3-dioxoisoindolin-2-yl)-1-thia-8-azaspiro[4.5]decane-8-carboxylate 1,1-dioxide (385 mg, 0.886 mmol) as a white foam. MS m/z 433.1 (M−H)⁻.

Step d:

A solution of tert-butyl 4-(1,3-dioxoisoindolin-2-yl)-1-thia-8-azaspiro[4.5]decane-8-carboxylate 1,1-dioxide (385 mg, 0.886 mmol) and HCl (4 M in dioxane, 2.22 mL, 8.86 mmol) in dioxane (4 mL) was stirred for 16 h at RT. The mixture was diluted with dioxane (20 mL) and filtered to give 2-(1,1-dioxido-1-thia-8-azaspiro[4.5]decan-4-yl)isoindoline-1,3-dione (HCl salt, 328 mg, 0.884 mmol) as a white solid. MS m/z 335.4 (M+H)⁺.

Intermediate 6

(R)-2-methyl-N—((S)-7-azaspiro[3.5]nonan-1-yl)propane-2-sulfinamide

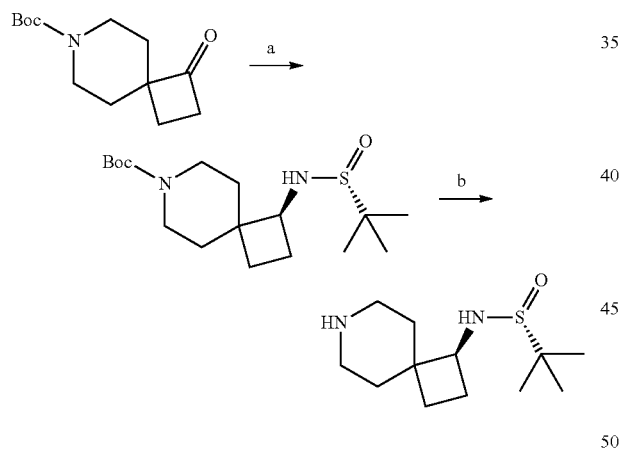

Step a:

A solution of tert-butyl 1-oxo-7-azaspiro[3.5]nonane-7-carboxylate (5.24 g, 21.9 mmol), titanium(IV) isopropoxide (16.2 mL, 54.7 mmol), and (R)-2-methylpropane-2-sulfinamide (3.45 g, 28.5 mmol) in THF (99 mL) was stirred for 12 h at 65° C. After cooling to −78° C., MeOH (9.9 mL) was added followed by lithium borohydride (1.43 g, 65.7 mmol). The resulting mixture was stirred at −78° C. for 3 h and at RT for 1 h. MeOH was slowly added to quench the excess of borohydride followed by addition of brine. The resulting mixture was stirred for 15 min and then filtered through Celite. The aqueous mixture was extracted with EtOAc (3×20 mL). The organic phases were dried over MgSO₄, filtered, and the volatiles were removed under reduced pressure. The resulting residue was purified by silica chromatography (0 to 50% gradient of EtOAc/heptane to give (S)-tert-butyl 1-((R)-1,1-dimethylethylsulfinamido)-7-azaspiro[3.5]nonane-7-carboxylate (4.79 g. 13.90 mmol) as a white solid. MS m/z 345.3 (M+H)⁺.

Step b:

A solution of (S)-tert-butyl 1-((R)-1,1-dimethylethylsulfinamido)-7-azaspiro[3.5]nonane-7-carboxylate (0.4 g, 1.16 mmol) and TFA (450 µL, 5.81 mmol) in DCM (3.5 mL) was stirred for 30 min at 40° C. Na₂CO₃ sat. aq. was added until pH 11 and the aqueous mixture was extracted with DCM (3×15 mL). The combined organic phases were washed with brine, dried over Na₂SO₄, filtered, and the volatiles were removed under reduced pressure to give (R)-2-methyl-N—((S)-7-azaspiro[3.5]nonan-1-yl)propane-2-sulfinamide (237 mg, 0.97 mmol) as a white solid. MS m/z 245.5 (M+H)⁺.

Intermediate 7

N-(4-methoxybenzyl)-8-azaspiro[4.5]decan-1-amine

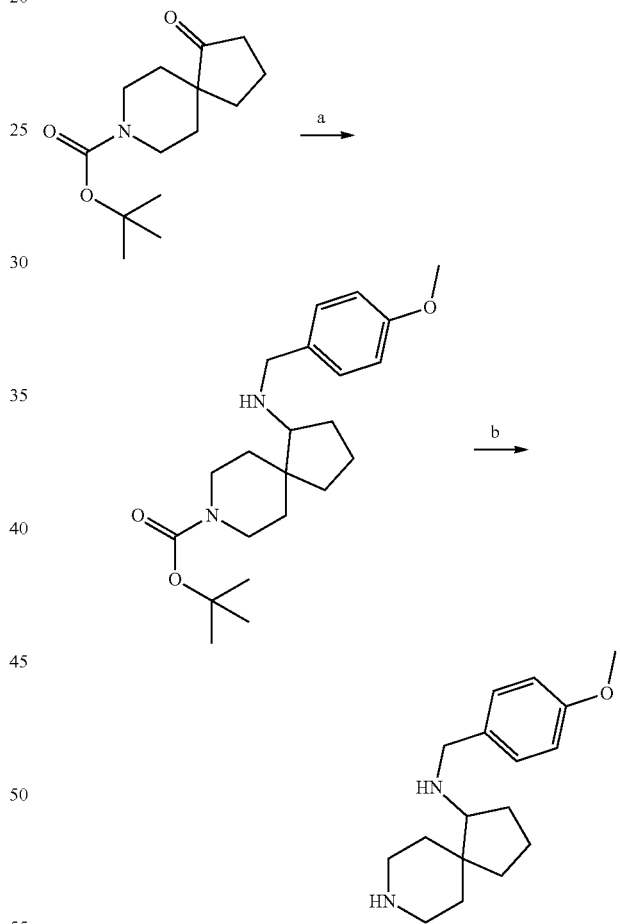

Step a:

To a solution of tert-butyl 1-oxo-8-azaspiro[4.5]decane-8-carboxylate (1.8 g, 7.11 mmol), and (4-methoxyphenyl)methanamine (1.07 g, 7.82 mmol) in DCE (7 mL) was added sodium cyanoborohydride (2.23 g, 35.5 mmol) in portions and stirred at RT for 65 h. The mixture was diluted with saturated aqueous sodium bicarbonate solution (10 mL) and extracted with EtOAc (3×20 mL). The combined organic phases were washed with brine and concentrated. The resulting residue was purified by silica chromatography (0 to 2% gradient of MeOH/DCM, 0.25% Et₃N modified, followed by 0 to 50% gradient of EtOAc/heptane) to give tert-butyl 1-((4-methoxybenzyl)amino)-8-azaspiro[4.5]decane-8-carboxylate (1.1 g, 2.94 mmol) as a colorless wax. MS m/z 375.3 (M+H)⁺.

Step b:

A solution of tert-butyl 1-((4-methoxybenzyl)amino)-8-azaspiro[4.5]decane-8-carboxylate (1.1 g, 2.94 mmol) and TFA (2 mL) in DCM (2 mL) was stirred for 15 min at 0° C. The volatiles were removed under reduced pressure. The resulting residue was diluted with aqueous NaHCO₃ (10 mL) and extracted with EtOAc (4×10 mL) to give N-(4-methoxybenzyl)-8-azaspiro[4.5]decan-1-amine (0.8 g, 2.92 mmol) as a colorless oil. MS m/z 275.2 (M+H)⁺.

N-(4-methoxybenzyl)-3-azaspiro[5.5]undecan-7-amine was obtained following the above procedure starting from tert-butyl 7-oxo-3-azaspiro[5.5]undecane-3-carboxylate.

Intermediate 8

N—((R)-1-(4-methoxyphenyl)ethyl)-8-azaspiro[4.5]decan-1-amine

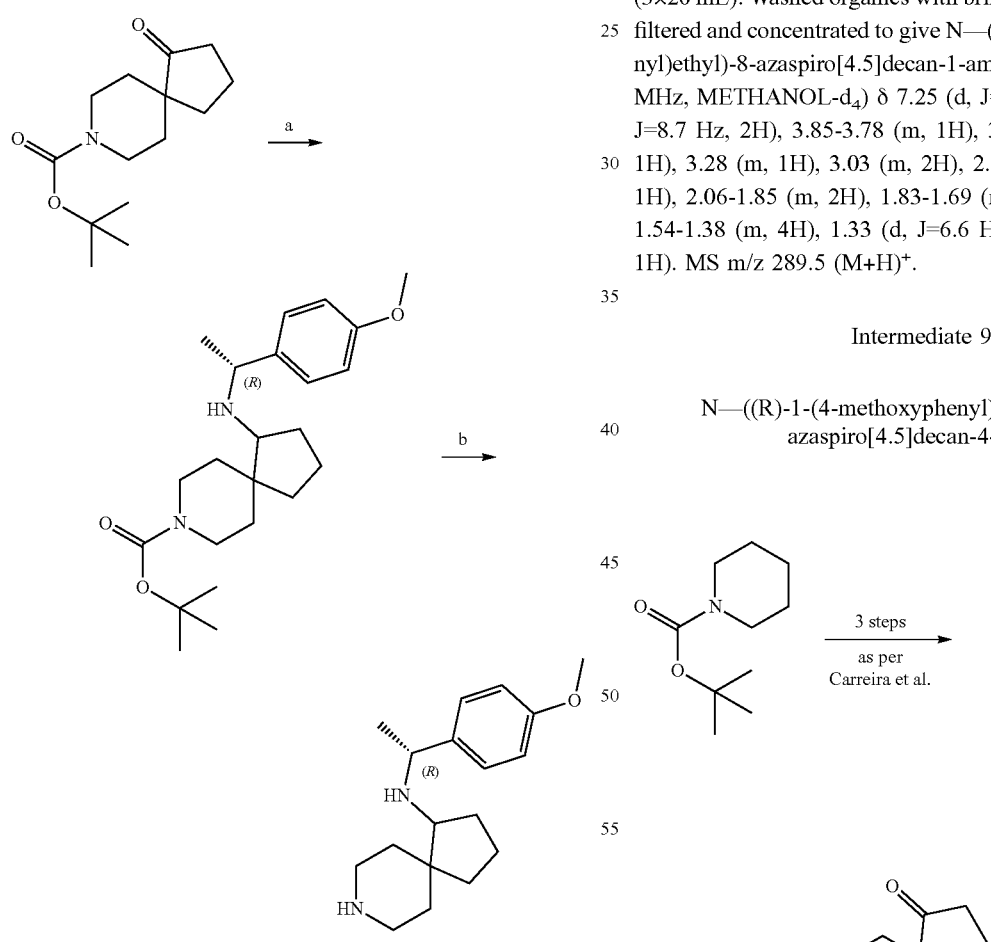

Step a:

To a solution of tert-butyl 1-oxo-8-azaspiro[4.5]decane-8-carboxylate (1.15 g, 4.54 mmol), and (R)-1-(4-methoxyphenyl)ethanamine (961 mg, 6.36 mmol) in DCE (3 mL) was added sodium cyanoborohydride in portions and stirred for 16 h at RT. The mixture was diluted with saturated aqueous sodium bicarbonate solution (5 mL) and extracted with EtOAc (3×10 mL). The combined organic phases were washed with brine and concentrated. The resulting residue containing a 9:1 mixture of diastereomers was purified by silica chromatography (0 to 20% gradient of EtOAc/heptane) to give tert-butyl 1-(((R)-1-(4-methoxyphenyl)ethyl)amino)-8-azaspiro[4.5]decane-8-carboxylate (major diastereomer; 431 mg, 1.11 mmol) pure. ¹H NMR (400 MHz, DMSO-d₆) δ ppm 7.18-7.24 (m, 2H), 6.81-6.86 (m, 2H), 3.76 (d, J=13.64 Hz, 1H), 3.72 (s, 3H), 3.64-3.70 (m, 2H), 2.65-2.92 (m, 2H), 2.05-2.14 (m, 1H), 1.80-1.91 (m, 1H), 1.65-1.75 (m, 1H), 1.42-1.60 (m, 4H), 1.40 (s, 9H), 1.28-1.35 (m, 1H), 1.20 (d, J=6.57 Hz, 3H), 1.09-1.17 (m, 2H), 0.80 (d, J=11.37 Hz, 1H). MS m/z 389.6 (M+H)⁺.

Step b:

To a solution of tert-butyl 1-(((R)-1-(4-methoxyphenyl)ethyl)amino)-8-azaspiro[4.5]decane-8-carboxylate (major diastereomer; 431 mg, 1.11 mmol) in DCM (2 mL) was added TFA (2 mL) and stirred for 10 min at RT. The reaction was concentrated with further addition of DCM, then diluted with saturated aqueous NaHCO₃ and extracted with DCM (3×20 mL). Washed organics with brine, dried over Na₂SO₄, filtered and concentrated to give N—((R)-1-(4-methoxyphenyl)ethyl)-8-azaspiro[4.5]decan-1-amine. ¹H NMR (400 MHz, METHANOL-d₄) δ 7.25 (d, J=8.6 Hz, 2H), 6.87 (d, J=8.7 Hz, 2H), 3.85-3.78 (m, 1H), 3.78 (s, 3H), 3.35 (m, 1H), 3.28 (m, 1H), 3.03 (m, 2H), 2.63 (dd, J=9.6, 7.3 Hz, 1H), 2.06-1.85 (m, 2H), 1.83-1.69 (m, 2H), 1.62 (m, 1H), 1.54-1.38 (m, 4H), 1.33 (d, J=6.6 Hz, 3H), 1.31-1.23 (m, 1H). MS m/z 289.5 (M+H)⁺.

Intermediate 9

N—((R)-1-(4-methoxyphenyl)ethyl)-1-oxa-8-azaspiro[4.5]decan-4-amine

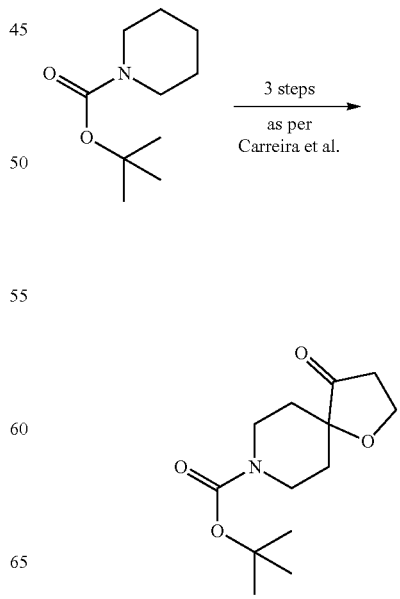

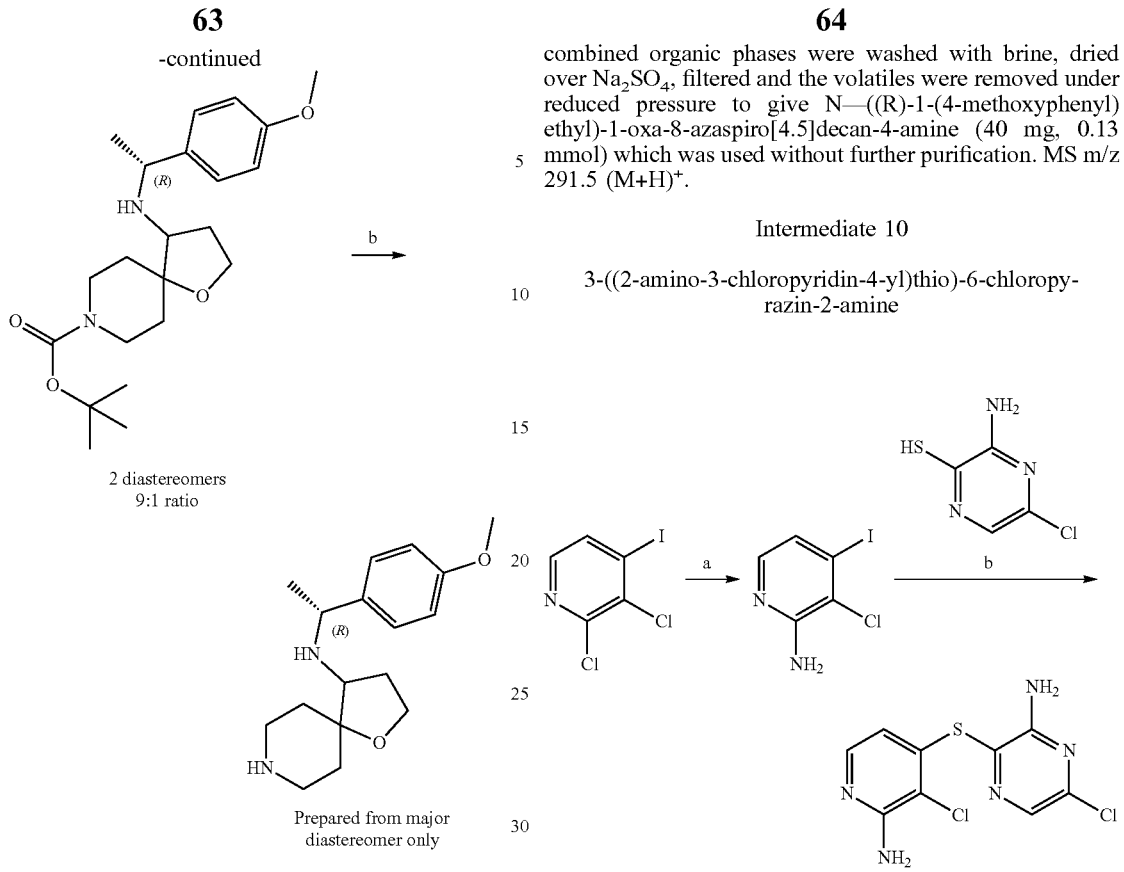

2 diastereomers
9:1 ratio

Prepared from major
diastereomer only

Step a:

To a solution of tert-butyl 4-oxo-1-oxa-8-azaspiro[4.5]decane-8-carboxylate (prepared from tert-butyl 4-oxopiperidine-1-carboxylate in 3 steps as described in Carreira et al., *Org Lett.*, 2013, 15, 4766-4769; 200 mg, 0.78 mmol), and (R)-1-(4-methoxyphenyl)ethanamine (474 mg, 3.13 mmol) in DCE (1 mL) was added sodium cyanoborohydride in portions (393 mg, 3.13 mmol). The resulting reaction was stirred for 16 h at RT. Lithium borohydride (34 mg, 1.6 mmol) was added and the mixture was stirred for 30 min at RT. The mixture was diluted with MeOH (2 mL) and the volatiles were removed under reduced pressure (two times). NaHCO$_3$ sat. aq. (5 mL) was added and the mixture was extracted with DCM (3×20 mL). The combined organic phases were dried over Na$_2$SO$_4$, filtered, and the volatiles were removed under reduced pressure. The resulting 9:1 mixture of diastereomers was purified by silica chromatography (0 to 40% gradient of EtOAc/heptane) to give tert-butyl 4-(((R)-1-(4-methoxyphenyl)ethyl)amino)-1-oxa-8-azaspiro[4.5]decane-8-carboxylate (65 mg, 0.17 mmol) diastereomerically pure. Major diastereomer: $^1$H NMR (400 MHz, CDCl$_3$) δ ppm 7.15 (d, J=8.6 Hz, 2H), 6.79 (d, J=8.6 Hz, 2H), 3.96-3.76 (m, 2H), 3.77-3.66 (m, 5H), 3.60 (t, J=8.1 Hz, 1H), 2.98 (m, 2H), 2.76 (t, J=7.8 Hz, 1H), 1.95 (m, 1H), 1.67-1.41 (m, 4H), 1.40 (s, 9H), 1.33 (d, J=3.1 Hz, 1H), 1.21 (d, J=6.5 Hz, 3H), 1.08-0.92 (m, 1H). MS m/z 391.6 (M+H)$^+$.

Step b:

A solution of tert-butyl 4-(((R)-1-(4-methoxyphenyl)ethyl)amino)-1-oxa-8-azaspiro[4.5]decane-8-carboxylate (major diastereomer, 65 mg, 0.17 mmol) and TFA (2 mL) in DCM (2 mL) stirred for 10 min at RT. The volatiles were removed under reduced pressure, diluted with NaHCO$_3$ sat. aq. (5 mL), and extracted with DCM (3×20 mL). The combined organic phases were washed with brine, dried over Na$_2$SO$_4$, filtered and the volatiles were removed under reduced pressure to give N—((R)-1-(4-methoxyphenyl)ethyl)-1-oxa-8-azaspiro[4.5]decan-4-amine (40 mg, 0.13 mmol) which was used without further purification. MS m/z 291.5 (M+H)$^+$.

Intermediate 10

3-((2-amino-3-chloropyridin-4-yl)thio)-6-chloropyrazin-2-amine

Step a:

Commercially available 2,3-dichloro-4-iodopyridine was converted to 3-chloro-4-iodopyridin-2-amine by procedure a, as described in Marie et al., *Molecules*, 2012, 17, 10683-10707.

Step b:

To a solution of 3-amino-5-chloropyrazine-2-thiol (100 mg, 0.619 mmol), 3-chloro-4-iodopyridin-2-amine (315 mg, 1.238 mmol), XantPhos (35.8 mg, 0.062 mmol), and Pd$_2$(dba)$_3$ (28.3 mg, 0.03 mmol) in dioxane (3 mL) was added (at RT and under N$_2$) DIPEA (324 μL, 1.856 mmol). The resulting solution was stirred in a microwave reactor for 2.5 h at 100° C. After cooling to RT, the reaction was diluted with EtOAc and it was filtered through a pad of Celite followed by EtOAc (10 mL) wash. The combined filtrates were concentrated and the resulting residue was purified by silica chromatography (0 to 5% gradient of MeOH/DCM) to give 3-((2-amino-3-chloropyridin-4-yl)thio)-6-chloropyrazin-2-amine (1.41 g, 3.88 mmol). $^1$H NMR (400 MHz, METHANOL-d$_4$) δ ppm 7.88 (s, 1H), 7.68 (d, J=5.56 Hz, 1H), 6.06 (d, J=5.56 Hz, 1H), 1.35-1.43 (m, 2H). MS m/z 288.2 (M+H)$^+$.

Intermediate 11

3-amino-5-chloropyrazine-2-thiol

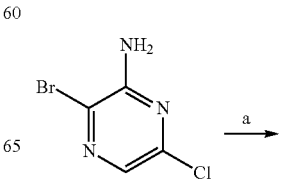

-continued

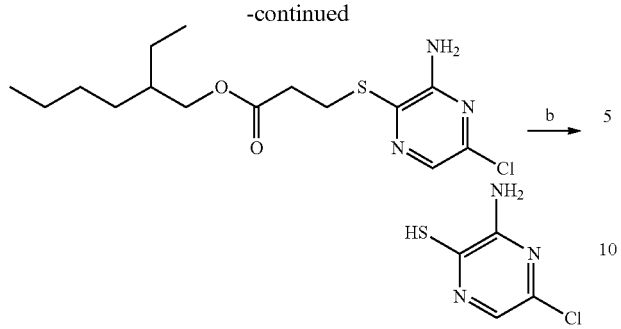

Step a:

A solution of 3-bromo-6-chloropyrazin-2-amine (4.95 g, 23.74 mmol) in dioxane (119 mL) was sparged with nitrogen for 10 min. Then, 2-ethylhexyl 3-mercaptopropanoate (3.79 mL, 24.92 mmol), Xantphos (1.37 g, 2.37 mmol), $Pd_2(dba)_3$ (1.08 g, 1.19 mmol), and DIPEA (8.29 mL, 47.5 mmol) were added. The resulting mixture was stirred at 105° C. for 24 h and the reaction mixture was filtered through Celite and concentrated. The crude was purified by silica chromatography (0-40% gradient of EtOAc/heptane) to afford 2-ethylhexyl 3-((3-amino-5-chloropyrazin-2-yl)thio)propanoate (6.24 g, 18.04 mmol) as a yellow oil. $^1$H NMR (400 MHz, CHLOROFORM-d) δ ppm 7.82 (s, 1H), 4.93 (br. s., 2H), 4.14-3.96 (m, 2H), 3.47 (t, J=6.9 Hz, 2H), 2.78 (t, J=6.9 Hz, 2H), 1.67-1.51 (m, 1H), 1.44-1.20 (m, 8H), 0.90 (t, J=7.4 Hz, 6H). MS m/z 346.0 (M+H)$^+$.

Step b:

To a solution of 2-ethylhexyl 3-((3-amino-5-chloropyrazin-2-yl)thio)propanoate (2.3 g, 6.65 mmol) in THF (33 mL) at −78° C., potassium tert-butoxide (1 M in THF, 19.95 mL, 19.95 mmol) was added and the resulting mixture was stirred at −78° C. for 1 h. MeOH (20 mL) was added and the resulting mixture was concentrated. The crude was dissolved in MeOH, filtered, and was purified by HPLC (gradient elution 5-20%, acetonitrile in water, 0.1% TFA modifier) to afford 3-amino-5-chloropyrazine-2-thiol (TFA salt: 1.3 g, 4.72 mmol) as a yellow solid. MS m/z 162.0 (M+H)$^+$.

Intermediate 12

6-chloro-3-((3-chloropyridin-4-yl)thio)pyrazin-2-amine

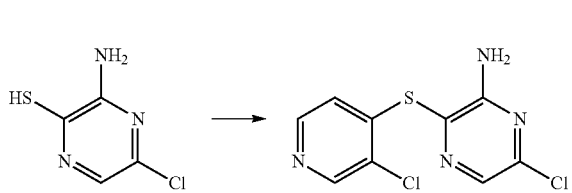 [SMILES: Nc1nc(Cl)cnc1S ; Nc1nc(Cl)cnc1Sc1ccncc1Cl]

A solution of 3-amino-5-chloropyrazine-2-thiol (TFA salt: 0.158 g, 0.978 mmol) in dioxane (4.9 mL) was sparged with nitrogen for 10 min. Then, 3-chloro-4-iodopyridine (0.468 g, 1.955 mmol), Xantphos (0.057 g, 0.098 mmol), $Pd_2(dba)_3$ (0.045 g, 0.049 mmol), and DIPEA (0.512 mL, 2.93 mmol) were added. The resulting mixture was stirred at 105° C. for 10 h, filtered through Celite and concentrated. The crude was purified by silica chromatography (0-40% gradient of EtOAc/heptane; heptane containing 2% of $Et_3N$) to afford 6-chloro-3-((3-chloropyridin-4-yl)thio)pyrazin-2-amine (75 mg, 0.274 mmol) as a white solid. $^1$H NMR (400 MHz, CHLOROFORM-d) δ ppm 8.46 (s, 1H), 8.22 (d, J=5.3 Hz, 1H), 7.96 (s, 1H), 6.68 (d, J=5.3 Hz, 1H), 5.17 (br. s., 2H). MS m/z 273.0 (M+H)$^+$.

Intermediate 13

6-chloro-3-((2-chloropyridin-3-yl)thio)pyrazin-2-amine

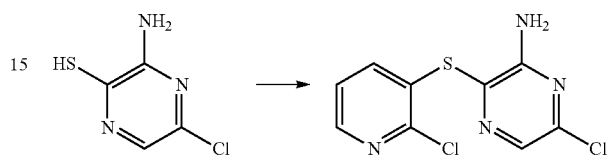

A solution of 3-amino-5-chloropyrazine-2-thiol (TFA salt: 0.2 g, 1.238 mmol) in dioxane (6.2 mL) was sparged with nitrogen for 10 min. Then, 2-chloro-3-iodopyridine (0.593 g, 2.475 mmol), Xantphos (0.072 g, 0.124 mmol), $Pd_2(dba)_3$ (0.057 g, 0.062 mmol), and DIPEA (0.65 mL, 3.71 mmol) were added. The resulting mixture was stirred at 105° C. for 10 h, filtered through Celite and concentrated. The crude was purified by silica chromtography (0-40% gradient of EtOAc/heptane, containing 2% of $Et_3N$) to afford 6-chloro-3-((2-chloropyridin-3-yl)thio)pyrazin-2-amine (95 mg, 0.348 mmol) as a white solid. $^1$H NMR (400 MHz, CHLOROFORM-d) δ ppm 8.28-8.38 (m, 1H), 7.91 (s, 1H), 7.51-7.59 (m, 1H), 7.22 (dd, J=7.9, 4.6 Hz, 1H), 5.25 (br. s., 2H). MS m/z 273.0 (M+H)$^+$.

Intermediate 14

6-chloro-3-((2,3-dichloropyridin-4-yl)thio)pyrazin-2-amine

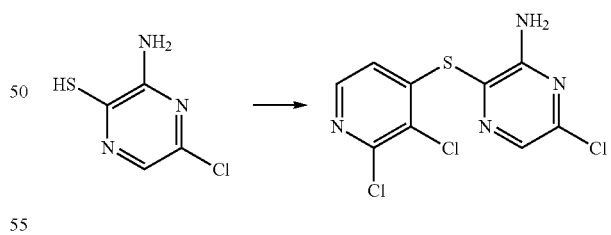

A solution of 3-amino-5-chloropyrazine-2-thiol (TFA salt: 0.50 g, 1.814 mmol) in dioxane (90 mL) was degassed with nitrogen for 10 min. Then, 2,3-dichloro-4-iodopyridine (0.0.99 g, 3.63 mmol), Xantphos (0.105 g, 0.181 mmol), $Pd_2(dba)_3$ (0.083 g, 0.091 mmol), and DIPEA (0.95 mL, 5.44 mmol) were added. The resulting mixture was stirred at 105° C. for 10 h, filtered through Celite and concentrated. The crude was purified by silica chromatography (0-10% gradient of EtOAc/DCM). $^1$H NMR (400 MHz, DMSO-$d_6$) δ ppm 8.13 (d, J=5.3 Hz, 1H), 7.95 (s, 1H), 7.30 (br. s, 2H), 6.83 (d, J=5.3 Hz, 1H). MS m/z 306.9 (M+H)$^+$.

Intermediate 15

6-chloro-3-((3-chloro-2-fluoropyridin-4-yl)thio)pyrazin-2-amine

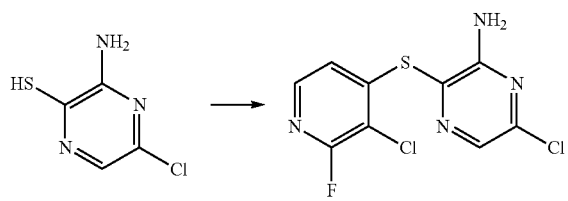 [SMILES: Nc1nc(Cl)cnc1S ; Nc1nc(Cl)cnc1Sc1ccnc(F)c1Cl]

A solution of 3-amino-5-chloropyrazine-2-thiol (TFA salt: 50 mg, 0.181 mmol) in dioxane (1.8 mL) was sparged with nitrogen for 10 min. Then, 3-chloro-2-fluoro-4-iodopyridine (0.140 g, 0.544 mmol), Xantphos (11 mg, 0.018 mmol), Pd$_2$(dba)$_3$ (8 mg, 0.009 mmol), and DIPEA (95 µL, 0.544 mmol) were added. The resulting mixture was stirred at 100° C. for 10 h, filtered through Celite, and concentrated. The crude was purified by silica chromatography (0 to 40% gradient of EtOAc/heptane; heptane containing 2% Et$_3$N) to afford 6-chloro-3-((3-chloro-2-fluoropyridin-4-yl)thio)pyrazin-2-amine (41 mg, 0.137 mmol) as a white solid. $^1$H NMR (400 MHz, CHLOROFORM-d) δ ppm 8.06 (s, 1H), 7.91 (d, J=5.3 Hz, 1H), 6.63 (d, J=5.3 Hz, 1H), 5.30 (br. s, 2H). MS m/z 291.0 (M+H)$^+$.

Intermediate 17

2-(2-oxa-8-azaspiro[4.5]decan-4-yl)isoindoline-1,3-dione

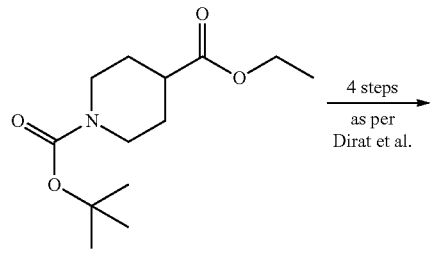

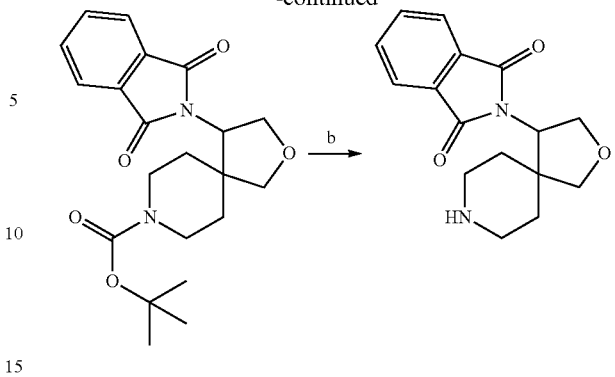

Following procedures of Dirat et al., PCT Int. Appl., 20044078750, 16 Sep. 2004, prepared tert-butyl 4-hydroxy-2-oxa-8-azaspiro[4.5]decane-8-carboxylate. $^1$H NMR (400 MHz, Chloroform-d) δ 4.13 (dd, J=10.1, 4.6 Hz, 1H), 4.03 (dd, J=4.6, 2.0 Hz, 1H), 3.78-3.71 (m, 2H), 3.69 (d, J=8.6 Hz, 1H), 3.67-3.58 (m, 2H), 3.29 (m, 1H), 3.16 (m, 1H), 1.78 (m, 2H), 1.58 (m, 1H), 1.50 (m, 2H), 1.47 (s, 9H). MS m/z 258.1 (M−H)$^+$ from 1-tert-butyl 4-ethyl piperidine-1,4-dicarboxylate in four steps, then converted to 2-(2-oxa-8-azaspiro[4.5]decan-4-yl)isoindoline-1,3-dione in two steps as follows.

Step a:

To a solution of tert-butyl 4-hydroxy-2-oxa-8-azaspiro[4.5]decane-8-carboxylate (306 mg, 1.19 mmol), phthalimide (262 mg, 1.78 mmol) and triphenylphosphine (468 mg, 1.78 mmol) in THF (10 mL) was added diisopropylazadicarboxylate (0.374 mL, 1.78 mmol) and stirred 16 h. Concentrated and purified by silica chromatography (0 to 50% gradient of ethyl acetate/heptane) to obtain racemic tert-butyl 4-(1,3-dioxoisoindolin-2-yl)-2-oxa-8-azaspiro[4.5]decane-8-carboxylate (190 mg, 0.49 mmol). $^1$H NMR (400 MHz, Chloroform-d) δ 7.88 (dd, J=5.4, 3.0 Hz, 2H), 7.77 (dd, J=5.5, 3.0 Hz, 2H), 4.65 (dd, J=8.7, 5.6 Hz, 1H), 4.40 (dd, J=9.5, 5.6 Hz, 1H), 4.26 (t, J=9.0 Hz, 1H), 4.08 (d, J=8.5 Hz, 1H), 3.98 (d, J=8.5 Hz, 1H), 3.84 (m, 1H), 3.58 (m, 1H), 3.20 (m, 1H), 2.94 (m, 1H), 1.73 (m, 2H), 1.56 (s, 9H), 1.42-1.36 (m, 2H).

Step b:

To a solution of racemic tert-butyl 4-(1,3-dioxoisoindolin-2-yl)-2-oxa-8-azaspiro[4.5]decane-8-carboxylate (190 mg, 0.49 mmol) in dichloromethane (3 mL) was added trifluoroacetic acid (1 mL). Concentrated with further addition of dichloromethane, then acetonitrile to obtain 2-(2-oxa-8-azaspiro[4.5]decan-4-yl)isoindoline-1,3-dione as a TFA salt (quantitative). MS m/z 287.0 (M+H)$^+$. Used without further characterization.

Intermediate 18

2-chloro-3-mercaptobenzamide

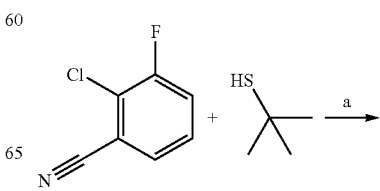

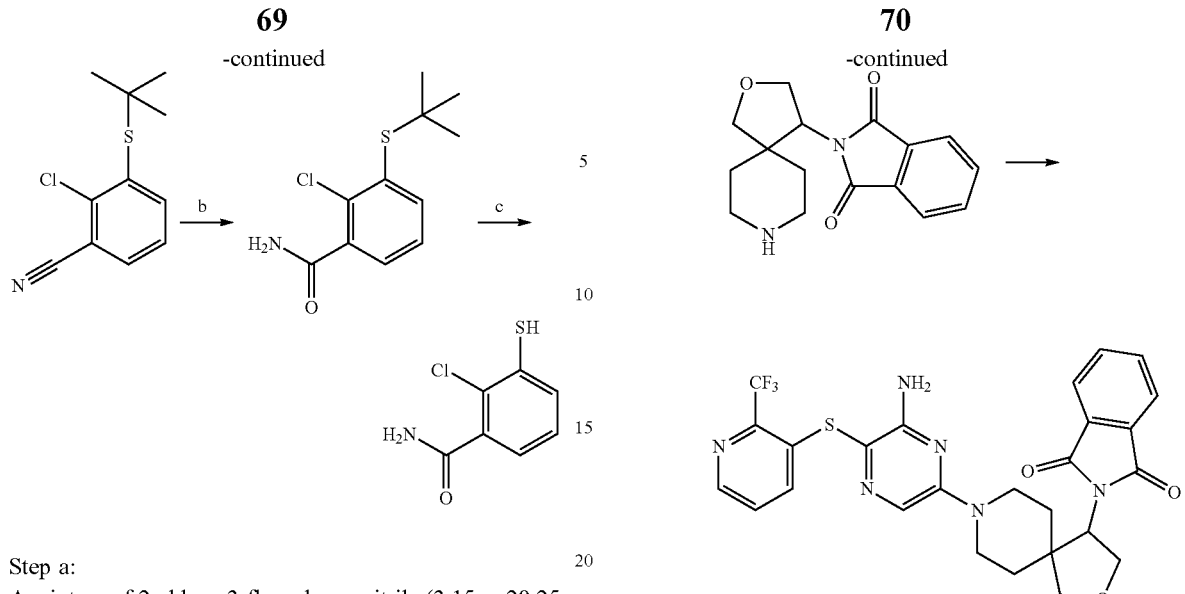

Step a:

A mixture of 2-chloro-3-fluorobenzonitrile (3.15 g, 20.25 mmol), 2-methylpropane-2-thiol (2.283 mL, 20.25 mmol) and Cs$_2$CO$_3$ (6.598 g, 20.25 mmol) in DMF (100 mL) was stirred for 48 h at 22° C. The reaction mixture was diluted with water (200 mL) and EtOAc (300 mL). EtOAc layer was washed with water (3×300 mL), brine (3×100 mL), dried over Na$_2$SO$_4$, filtered and concentrated. The resulting residue was purified by HPLC (gradient elution: 45 to 70% acetonitrile in water, 5 mM NH$_4$OH modifier), to give 3-(tert-butylthio)-2-chlorobenzonitrile (1.33 g, 5.89 mmol). MS m/z 226.1 (M+H)$^+$.

Step b:

A mixture of 3-(tert-butylthio)-2-chlorobenzonitrile (217 mg, 0.961 mmol) and NaOH (1 N, 2.88 mL, 2.88 mmol) in MeOH (11 mL) was irradiated in a microwave reactor for 35 min at 90° C. After cooling to RT, the reaction was concentrated and dissolved in MeOH. The solid was filtered off and the filtrate was concentrated to almost dryness and was purified by HPLC (gradient elution: 25 to 50% acetonitrile in water, 5 mM NH$_4$OH modifier), to give 3-(tert-butylthio)-2-chlorobenzamide (93.6 mg, 0.384 mmol). MS m/z 244 (M+H)$^+$.

Step c:

A mixture of 3-(tert-butylthio)-2-chlorobenzamide (190 mg, 0.779 mmol) and conc. HCl (2.36 mL, 78 mmol) was stirred for 45 min at 85° C. After cooling to RT, the reaction was concentrated to dryness to yield crude 2-chloro-3-mercaptobenzamide (HCl salt: 156 mg, 0.651 mmol). MS m/z 188 (M+H)$^+$.

Intermediate 19

2-(8-(6-amino-5-((2-(trifluoromethyl)pyridin-3-yl)thio)pyrazin-2-yl)-2-oxa-8-azaspiro[4.5]decan-4-yl)isoindoline-1,3-dione

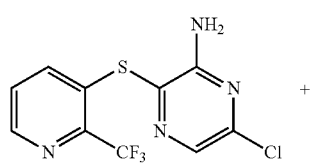

Coupled 2-(2-oxa-8-azaspiro[4.5]decan-4-yl)isoindoline-1,3-dione TFA salt with 6-chloro-3-((2-(trifluoromethyl)pyridin-3-yl)thio)pyrazin-2-amine (151 mg, 0.492 mmol) using the standard procedures described above. Diluted with DCM and purified by silica chromatography (0 to 60% gradient of ethyl acetate/heptane) to obtain 2-(8-(6-amino-5-((2-(trifluoromethyl)pyridin-3-yl)thio)pyrazin-2-yl)-2-oxa-8-azaspiro[4.5]decan-4-yl)isoindoline-1,3-dione (0.140 g, 0.178 mmol). MS m/z 557.1 (M+H)$^+$. Chiral SFC purification performed as follows; column: OJ-H 21×250 mm, flow rate: 80 g per minute, mobile phase: 45% MeOH and 5 mM NH$_4$OH in CO$_2$, detection: mass triggered to obtain single enantiomers peak 1 (P1), R$_t$: 2.77 min. MS m/z 557.1 (M+H)$^+$, and peak 2 (P2), R$_t$: 3.91 min. MS m/z 557.2 (M+H)$^+$. Phthalimide deprotection performed on each enantiomer separately without further characterization.

Intermediate 20

3-chloro-4-iodo-N,N-dimethylpyridin-2-amine

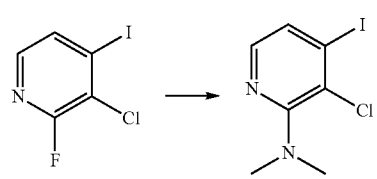

A solution of 3-chloro-2-fluoro-4-iodopyridine (0.26 g, 1.01 mmol) and dimethylamine (2 M in THF, 1.5 ml, 3.03 mmol) in DMSO (3.4 mL) was stirred at for 2 h at 70° C. After cooling to RT, water was added and the aqueous mixture was extracted with EtOAc. The combined organic phases were washed with water, brine, dried with Na$_2$SO$_4$, filtered and concentrated under reduced pressure to give 3-chloro-4-iodo-N,N-dimethylpyridin-2-amine (0.26 g, 0.922 mmol) as a colorless oil. $^1$H NMR (400 MHz, CHLOROFORM-d) δ ppm 7.75 (d, J=5.3 Hz, 1H), 7.33 (d, J=5.0 Hz, 1H), 3.00 (s, 6H). MS m/z 282.9 (M+H)$^+$.

Intermediate 21

3-chloro-4-iodo-2-methoxypyridine

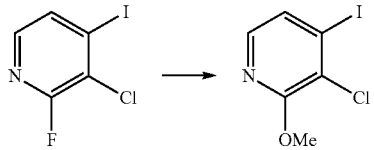 [SMILES: Fc1nccc(I)c1Cl ; COc1nccc(I)c1Cl]

A solution of 3-chloro-2-fluoro-4-iodopyridine (150 mg, 0.571 mmol) and NaOMe (0.5 M in MeOH, 3.4 ml, 1.71 mmol) in DMSO (1.9 mL) was stirred at for 1 h at 70° C. After cooling to RT, water was added and the aqueous mixture was extracted with EtOAc. The combined organic phases were washed with water, brine, dried over $Na_2SO_4$, filtered, and concentrated under reduced pressure to give 3-chloro-4-iodo-2-methoxypyridine (123 mg, 0.456 mmol) as a colorless oil. $^1$H NMR (400 MHz, DMSO-$d_6$) δ ppm 7.81 (d, J=5.3 Hz, 1H), 7.55 (d, J=5.3 Hz, 1H), 3.92 (s, 3H). MS m/z 269.9 (M+H)$^+$.

Intermediate 22

6-chloro-3-((3-(trifluoromethyl)pyridin-4-yl)thio)pyrazin-2-amine

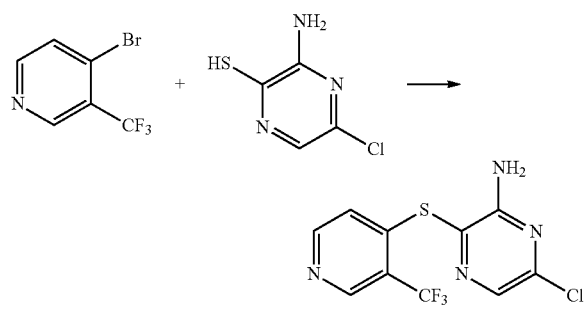

A mixture of 3-amino-5-chloropyrazine-2-thiol (750 mg, 4.09 mmol), 4-bromo-3-(trifluoromethyl)pyridine (1.63 g, 5.31 mmol), Xantphos (236 mg, 0.409 mmol), $Pd_2(dba)_3$ (187 mg, 0.204 mmol), and DIPEA (2.14 mL, 12.26 mmol) in dioxane (degassed, 50 mL) was stirred for 16 h at 100° C. After cooling to RT, the reaction was filtered through a pad of Celite followed by EtOAc (25 mL) wash. The combined filtrates were concentrated under reduced pressure and the resulting residue was purified by silica chromatography (0 to 40% gradient of EtOAc/DCM) to give 6-chloro-3-((3-(trifluoromethyl)pyridin-4-yl)thio)pyrazin-2-amine (722 mg, 2.35 mmol) as a light yellow solid. MS m/z 307.0 (M+H)$^+$.

The following compounds were synthesized using the above procedure or modifications to the above procedure using the corresponding iodo- or bromo-pyridyl and thiolate.

TABLE 1

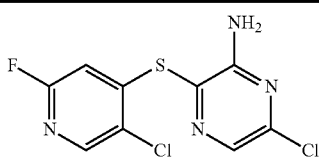

TABLE 1-continued

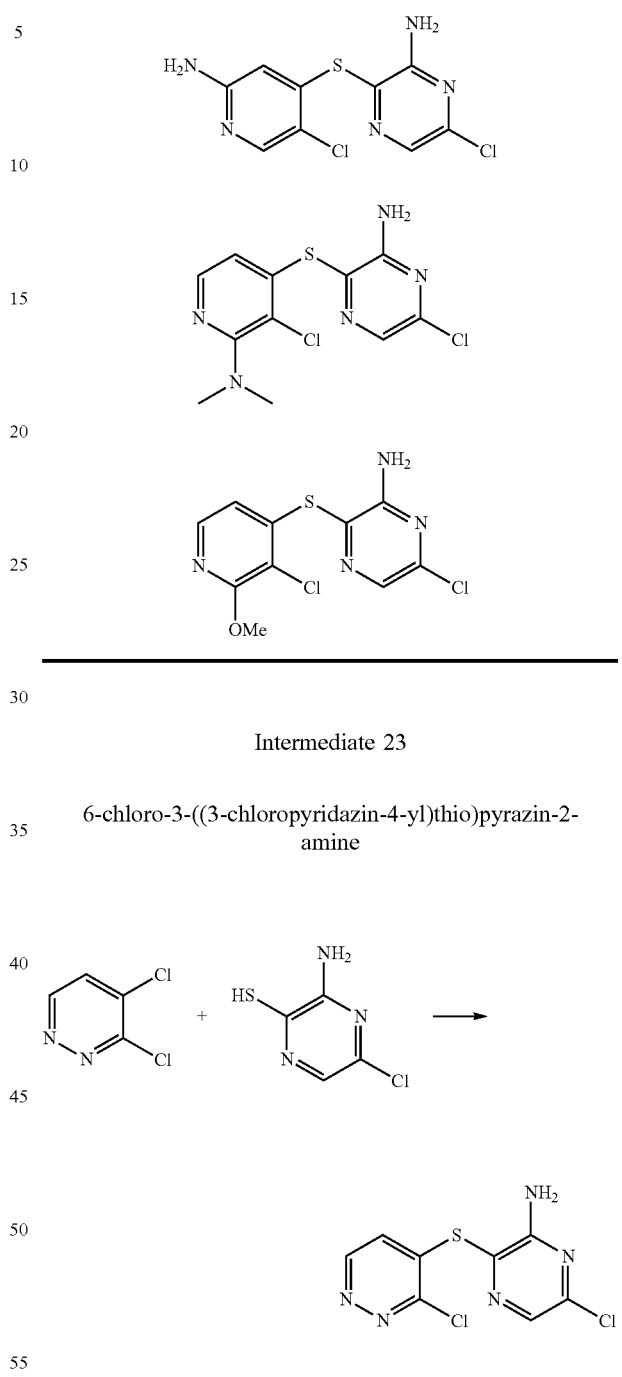

Intermediate 23

6-chloro-3-((3-chloropyridazin-4-yl)thio)pyrazin-2-amine

A mixture of 3-amino-5-chloropyrazine-2-thiol (100 mg, 0.545 mmol), 3,4-dicholoropyridazine (81 mg, 0.545 mmol), and DIPEA (0.142 mL, 0.817 mmol) in MeCN (5.5 mL) was stirred for 12 h at 50° C. After cooling to RT, the precipitate was collected by vacuum filtration to give 6-chloro-3-((3-chloropyridazin-4-yl)thio)pyrazin-2-amine (101 mg, 0.368 mmol) as a brown solid. $^1$H NMR (400 MHz, DMSO-$d_6$) δ ppm 8.90 (d, J=5.4 Hz, 1H), 7.95 (s, 1H), 7.31 (s, 2H), 7.15 (d, J=5.3 Hz, 1H). MS m/z 274.1 (M+H)$^+$.

Intermediate 24 tert-butyl 1-oxo-8-azaspiro[4.5]dec-2-ene-8-carboxylate

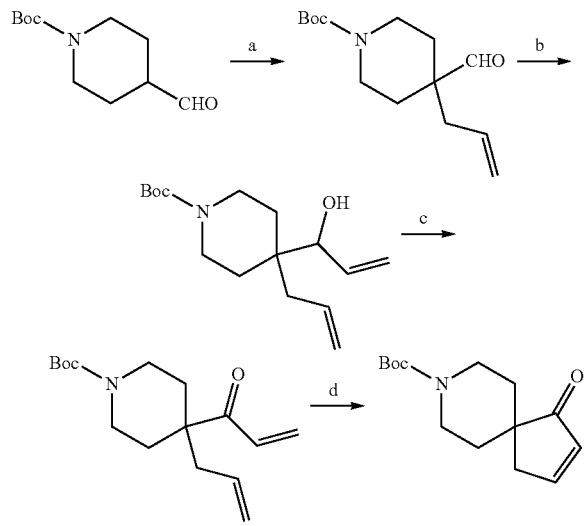

Step a:

A mixture of tert-butyl 4-formylpiperidine-1-carboxylate (35.0 g, 164 mmol), lithium tert-butoxyde (15.77 g, 197 mmol), and allylbromide (11.54 mL, 189 mmol) in DMF (328 mL) was stirred for 1 h at 0° C. The mixture was poured into a separation funnel containing sat. aq $NH_4Cl:H_2O$ (1:1, 500 mL) and it was extracted with $Et_2O$ (5×50 mL). The combined organic phases were dried over $MgSO_4$, filtered, and the volatiles were removed under reduced pressure. The resulting residue was purified by silica chromatography (0 to 25% gradient of EtOAc/heptane) to give tert-butyl 4-allyl-4-formylpiperidine-1-carboxylate (24 g, 95 mmol) as colorless oil. $^1$H NMR (400 MHz, CHLOROFORM-d) δ ppm 9.52 (s, 1H), 5.53-5.76 (m, 1H), 4.96-5.19 (m, 2H), 3.80 (br. s., 2H), 2.97 (t, J=11.49 Hz, 2H), 2.26 (d, J=7.33 Hz, 2H), 1.95 (dt, J=13.71, 3.13 Hz, 2H), 1.38-1.58 (m, 11H).

Step b:

To a solution of tert-butyl 4-allyl-4-formylpiperidine-1-carboxylate (24 g, 95 mmol) in THF (300 mL) was added (at −78° C. and under $N_2$) vinyl magnesium bromide (1 M in THF, 118 mL, 118 mmol). The resulting solution was slowly warmed up to RT within 1 h. The mixture was poured into a separation funnel containing sat. aq $NH_4Cl$ (250 mL) and it was extracted with EtOAc (4×50 mL). The combined organic phases were dried over $MgSO_4$, filtered and the volatiles were removed under reduced pressure to give tert-butyl 4-allyl-4-(1-hydroxyallyl)piperidine-1-carboxylate (26.7 g, 95 mmol) as colorless oil. $^1$H NMR (400 MHz, CHLOROFORM-d) δ ppm 9.52 (s, 1H), 5.56-5.75 (m, 1H), 5.05-5.18 (m, 2H), 3.80 (br. s., 2H), 2.97 (t, J=11.49 Hz, 2H), 2.26 (d, J=7.33 Hz, 2H), 1.96 (dt, J=13.83, 3.06 Hz, 2H), 1.49-1.60 (m, 2H), 1.41-1.49 (m, 9H). This compound was used in next step without further purification.

Step c:

A mixture of tert-butyl 4-allyl-4-(1-hydroxyallyl)piperidine-1-carboxylate (26.7 g, 95 mmol) and Dess-Martin periodinane (44.3 g, 105 mmol) in DCM (380 mL) was stirred for 1 h at RT. The mixture was poured into a separation funnel containing sat. aq $NaHCO_3:Na_2SO_3$ (1:1, 300 mL) and it was extracted with DCM (4×50 mL). The combined organic phases were dried over $MgSO_4$, filtered, and the volatiles were removed under reduced pressure to provide a white solid. This solid was suspended in heptane (250 mL) and sonicated for 5 min. The white suspension was filtered through a pad of Celite and the volatiles were removed under reduced pressure to give tert-butyl 4-acryloyl-4-allylpiperidine-1-carboxylate (26.5 g, 95 mmol) as yellow oil. $^1$H NMR (400 MHz, CHLOROFORM-d) δ ppm 6.81 (dd, J=16.93, 10.36 Hz, 1H), 6.40 (dd, J=16.80, 1.89 Hz, 1H), 5.71 (dd, J=10.36, 2.02 Hz, 1H), 5.46-5.66 (m, 1H), 4.91-5.14 (m, 2H), 3.78 (br. s., 2H), 2.96 (br. s., 2H), 2.25-2.39 (m, 2H), 1.97-2.15 (m, 2H), 1.37-1.57 (m, 11H). This compound was used in next step without further purification.

Step d:

To a solution of tert-butyl 4-acryloyl-4-allylpiperidine-1-carboxylate (26.5 g, 95 mmol) in toluene (degassed, 850 mL) was added Grubbs II catalyst (2.02 g, 2.38 mmol) in toluene (degassed, 100 mL). The resulting mixture was stirred for 45 min at 85° C. The solvent was removed under reduced pressure and the resulting residue was purified by silica chromatography (0 to 40% gradient of EtOAc/heptane) to give tert-butyl 1-oxo-8-azaspiro[4.5]dec-2-ene-8-carboxylate (20.76 g, 83 mmol) as brown solid. A solution of this compound and DDQ (565 mg, 2.49 mmol) in toluene (540 mL) was stirred for 15 min at RT. The resulting bright red solution was filtered through a pad of Celite. Charcoal (200 g) was added and the resulting suspension was stirred for 2 h at RT. The mixture was filtered through a pad of Celite and the volatiles were removed under reduce pressure. The resulting residue was purified by silica chromatography (0 to 40% gradient of EtOAc/heptane) to give tert-butyl 1-oxo-8-azaspiro[4.5]dec-2-ene-8-carboxylate (15.6 g, 62.3 mmol) as white solid. $^1$H NMR (400 MHz, CHLOROFORM-d) δ ppm 7.63-7.74 (m, 1H), 6.20 (dt, J=5.81, 2.15 Hz, 1H), 3.99-4.25 (m, 2 H), 2.92 (t, J=11.62 Hz, 2H), 2.63 (s, 2H), 1.72-1.86 (m, 2H), 1.49 (s, 9H), 1.29 (d, J=12.88 Hz, 2H).

Intermediate 25 tert-butyl 1-(1,1-dimethylethylsulfinamido)-3-methyl-8-azaspiro[4.5]decane-8-carboxylate

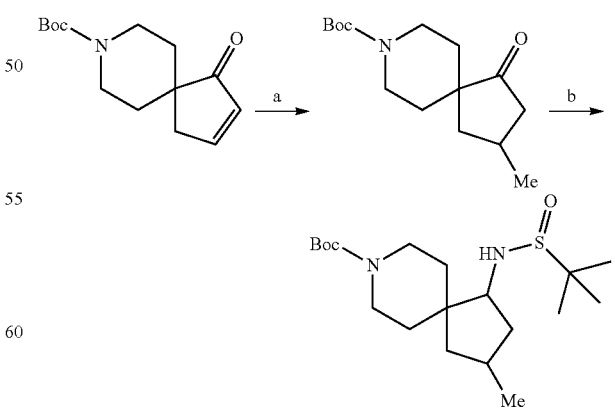

Step a:

To a suspension of tert-butyl 1-oxo-8-azaspiro[4.5]dec-2-ene-8-carboxylate (4.2 g, 16.71 mmol) and CuI (6.37 g, 33.4 mmol) in Et₂O (100 mL) was added (at 0° C. and under N₂) MeLi (1.6 M in THF, 31.3 mL, 50.1 mmol). After stirring for 90 min at 0° C., the mixture was poured into a separation funnel containing sat. aq NH₄Cl and it was extracted with EtOAc (3×15 mL). The combined organic phases were dried over MgSO₄, filtered and the volatiles were removed under reduced pressure. The resulting residue was purified by silica chromatography (0 to 50% gradient of EtOAc/heptane) to give tert-butyl 3-methyl-1-oxo-8-azaspiro[4.5]dec-2-ene-8-carboxylate (4.23 g, 15.82 mmol) as colorless oil. ¹H NMR (400 MHz, CHLOROFORM-d) δ ppm 3.89-4.00 (m, 1H), 3.83 (d, J=13.39 Hz, 1H), 3.11 (ddd, J=13.64, 10.36, 3.28 Hz, 1H), 2.99 (ddd, J=13.58, 10.42, 3.54 Hz, 1H), 2.47-2.59 (m, 1H), 2.19-2.36 (m, 2H), 1.74-1.97 (m, 2H), 1.50-1.65 (m, 2H), 1.48 (s, 9H), 1.33-1.44 (m, 2H), 1.17 (d, J=6.32 Hz, 3H).

Step b:

A solution of tert-butyl 3-methyl-1-oxo-8-azaspiro[4.5] dec-2-ene-8-carboxylate (502 mg, 1.878 mmol), titanium (IV) ethoxide (1.57 mL, 7.51 mmol), and 2-methylpropane-2-sulfinamide (455 mg, 3.76 mmol) in THF (12.5 mL) was stirred for 16 h at 65° C. After cooling to 0° C., MeOH (3 mL) was added followed by lithium borohydride (123 mg, 5.63 mmol). The resulting mixture was stirred at 0° C. for 1 h. sat. aq NH₄Cl was slowly added to quench the excess of borohydride followed by addition of EtOAc (30 mL). The resulting mixture was vigorously stirred for 15 min and then filtered through a pad of Celite. The volatiles were removed under reduced pressure and the resulting residue was purified by silica chromatography (0 to 75% gradient of EtOAc/heptane) to give tert-butyl 1-(1,1-dimethylethylsulfinamido)-3-methyl-8-azaspiro[4.5]decane-8-carboxylate (463 mg, 1.243 mmol) as a white solid.

Intermediates 26a/b (1R,3S)-benzyl 1-((R)-1,1-dimethlethylsulfinamido)-3-methyl-8-azaspiro[4.5]decane-8-carboxylate & (1R,3R)-benzyl 1-((R)-1,1-dimethylethylsulfinamido)-3-methyl-8-azaspiro[4.5]decane-8-carboxylate

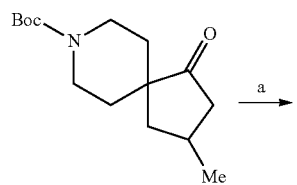

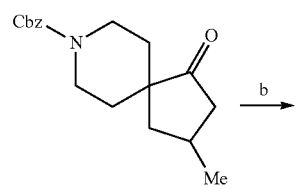

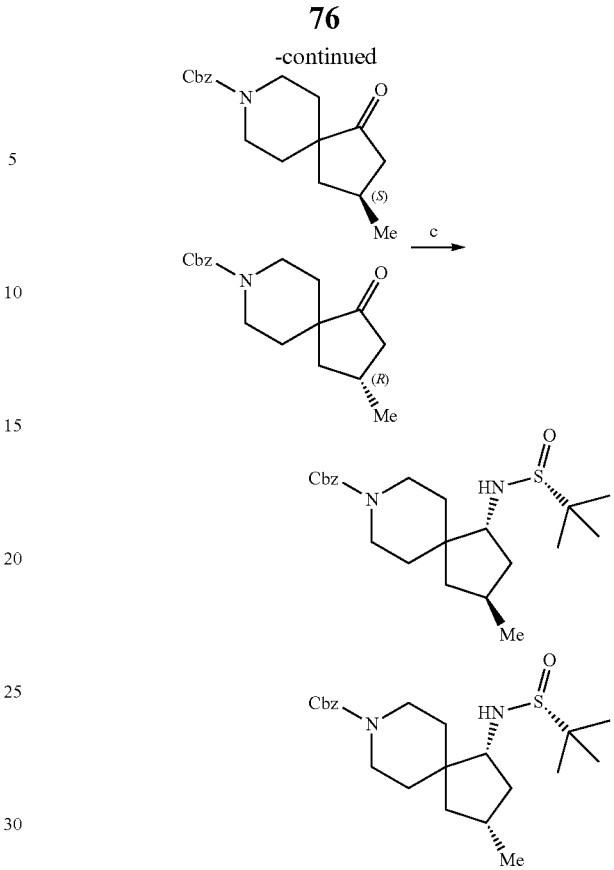

Step a:

A mixture of tert-butyl 3-methyl-1-oxo-8-azaspiro[4.5] dec-2-ene-8-carboxylate (4.23 g, 15.82 mmol) and TFA (17 mL) in DCM (80 mL) was stirred for 30 min at RT. The volatiles were removed under reduced pressure. A mixture of the resulting residue, DIPEA (13.82 mL, 79 mmol), and benzyl chloroformate (3.39 mL, 23.73 mmol) in DCM (80 mL) was stirred for 16 h at RT. The mixture was poured into a separation funnel containing sat. aq NH₄Cl and it was extracted with DCM (3×25 mL). The combined organic phases were dried over MgSO₄, filtered and the volatiles were removed under reduced pressure. The resulting residue was purified by silica chromatography (0 to 40% gradient of EtOAc/heptane) to give benzyl 3-methyl-1-oxo-8-azaspiro [4.5]decane-8-carboxylate (4.58 g, 15.20 mmol) as light yellow oil. MS m/z 302.2 (M+H)⁺.

Step b:

Benzyl 3-methyl-1-oxo-8-azaspiro[4.5]decane-8-carboxylate (4.58 g, 15.20 mmol) was further purified by chiral SFC as follows: column: IA 21×250 mm, flow rate: 70 g per minute, mobile phase: 45% (9:1 EtOH:MeCN) in CO₂, detection: 220 nm UV to give (R)-benzyl 3-methyl-1-oxo-8-azaspiro[4.5]decane-8-carboxylate (2.02 g, 6.70 mmol), R$_t$: 2.0 min; and (S)-benzyl 3-methyl-1-oxo-8-azaspiro[4.5] decane-8-carboxylate (2.11 g, 7.0 mmol), R$_t$: 3.6 min.

Step c:

A solution of (R)-benzyl 3-methyl-1-oxo-8-azaspiro[4.5] decane-8-carboxylate (2.02 g, 6.70 mmol), titanium(IV) ethoxide (5.62 mL, 26.8 mmol), and (R)-2-methylpropane-2-sulfinamide (1.625 g, 13.4 mmol) in THF (67 mL) was stirred for 16 h at 65° C. After cooling to −78° C., MeOH (12 mL) was added followed by lithium borohydride (0.438 g, 20.11 mmol). The resulting mixture was stirred for 16 h at −78° C. to RT. Sat. aq NH₄Cl was slowly added to quench the excess of borohydride followed by addition of EtOAc (100 mL). The resulting mixture was vigorously stirred for 15 min and then filtered through a pad of Celite. The volatiles were removed under reduced pressure and the resulting residue was purified by silica chromatography (5 to 90% gradient of EtOAc/heptane) to give (1R,3R)-benzyl 1-((R)-1,1-dimethylethylsulfinamido)-3-methyl-8-azaspiro [4.5]decane-8-carboxylate (1.94 g, 4.77 mmol) as a white solid. MS m/z 407.3 (M+H)+.

Step c (from Enantiomer):

The same procedure was followed starting from (S)-benzyl 3-methyl-1-oxo-8-azaspiro[4.5]decane-8-carboxylate to give (1R,3S)-benzyl 1-((R)-1,1-dimethylethylsulfinamido)-3-methyl-8-azaspiro[4.5]decane-8-carboxylate.

Intermediate 27

(1R,3R)-tert-butyl 3-((tert-butyldimethylsilyl)oxy)-1-((R)-1,1-dimethylethylsulfinamido)-8-azaspiro [4.5]decane-8-carboxylate)

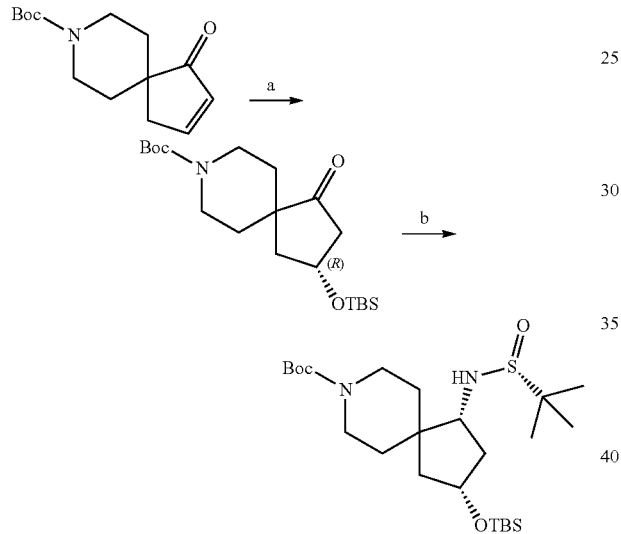

Step a:

A mixture of CuCl (142 mg, 1.432 mmol), (S)-TolBINAP (972 mg, 1.432 mmol), and sodium tert-butoxide (138 mg, 1.432 mmol) in THF (60 mL) was stirred for 30 min at RT. B$_2$pin$_2$ (13.34 g, 52.5 mmol) in THF (20 mL) was added and the resulting mixture was stirred for 10 min at RT. Tert-butyl 1-oxo-8-azaspiro[4.5]dec-2-ene-8-carboxylate (12.0 g, 47.7 mmol) in THF (50 mL) was added followed by MeOH (3.9 mL, 95 mmol). The resulting mixture was stirred for 16 h at RT. H$_2$O (150 mL) was added followed by sodium perborate (36.7 g, 239 mmol) and the resulting mixture was vigorously stirred for 1 h at RT. The resulting green suspension was filtered through a pad of Celite, poured into a separation funnel containing sat. aq NaHCO$_3$: sat. aq Na$_2$SO$_3$ (1:1, 300 mL) and extracted with EtOAc (4×40 mL). The combined organic phases were dried over MgSO$_4$, filtered, and the volatiles were removed under reduced pressure to give (R)-tert-butyl 3-hydroxy-1-oxo-8-azaspiro[4.5]decane-8-carboxylate crude. Enantiomeric determination of this mixture show 90% ee (R$_t$(S): 1.59 min, R$_t$(R): 1.80 min; chiral SFC; column: IA 4.6×100 mm, flow rate: 70 g per minute, mobile phase: 5-55% MeOH in CO$_2$, detection: 220 nm UV).

A mixture of (R)-tert-butyl 3-hydroxy-1-oxo-8-azaspiro [4.5]decane-8-carboxylate crude (theor 47.7 mmol), imidazole (4.87 g, 71.6 mmol), and TBSCl (8.99 g, 59.6 mmol) in DMF (120 mL) was stirred for 16 h at RT. The reaction mixture was poured into a separation funnel containing sat. aq NH$_4$Cl:H$_2$O (1:1, 250 mL) and it was extracted with Et$_2$O (5×50 mL). The combined organic phases were dried over MgSO$_4$, filtered and the volatiles were removed under reduced pressure. The resulting residue was purified by silica chromatography (0 to 30% gradient of EtOAc/heptane) to give (R)-tert-butyl 3-((tert-butyldimethylsilyl)oxy)-1-oxo-8-azaspiro[4.5]decane-8-carboxylate (13.115 g, 34.2 mmol) as colorless oil that solidify upon standing.

Step b:

A solution of (R)-tert-butyl 3-((tert-butyldimethylsilyl)oxy)-1-oxo-8-azaspiro[4.5]decane-8-carboxylate (8 g, 20.86 mmol), titanium(IV) ethoxide (17.49 mL, 83.0 mmol), and (R)-2-methylpropane-2-sulfinamide (5.06 g, 41.7 mmol) in THF (100 mL) was stirred for 16 h at 65° C. After cooling to −78° C., MeOH (15 mL) was added followed by lithium borohydride (1.363 g, 62.6 mmol). The resulting mixture was stirred for 16 h at −78° C. Sat. aq NH$_4$Cl was slowly added to quench the excess of borohydride followed by addition of EtOAc (100 mL). The resulting mixture was vigorously stirred for 15 min and then filtered through a pad of Celite. The volatiles were removed under reduced pressure and the resulting residue was purified by silica chromatography (0 to 50% gradient of EtOAc/heptane) to give (1R,3R)-tert-butyl 3-((tert-butyldimethylsilyl)oxy)-1-((R)-1,1-dimethylethylsulfinamido)-8-azaspiro[4.5]decane-8-carboxylate (5.3 g, 10.84 mmol) as a white solid. MS m/z 489.3 (M+H)+.

Intermediate 28

(1R,3S)-tert-butyl 1-((R)-1,1-dimethylethylsulfinamido)-3-hydroxy-8-azaspiro[4.5]decane-8-carboxylate)

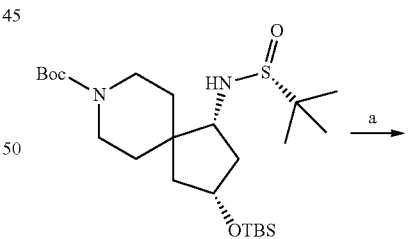

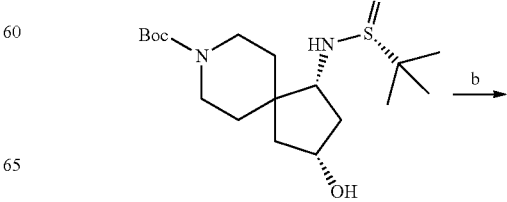

-continued

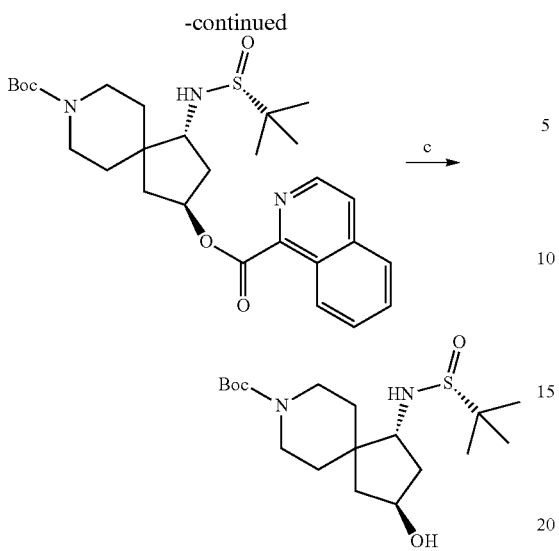

Step a:

A mixture of (1R,3R)-tert-butyl 3-((tert-butyldimethylsilyl)oxy)-1-((R)-1,1-dimethylethylsulfinamido)-8-azaspiro[4.5]decane-8-carboxylate (3.84 g, 7.86 mmol) and TBAF (1 M in THF; 8.64 mL, 8.64 mmol) in THF (40 mL) was stirred for 30 min at RT. The volatiles were removed under reduced pressure and the resulting residue was purified by silica chromatography (0 to 10% gradient of MeOH/DCM) to give (1R,3R)-tert-butyl 1-((R)-1,1-dimethylethylsulfinamido)-3-hydroxy-8-azaspiro[4.5]decane-8-carboxylate (2.94 g, 7.86 mmol). MS m/z 375.3 (M+H)+.

Step b:

To a solution of (1R,3R)-tert-butyl 1-((R)-1,1-dimethylethylsulfinamido)-3-hydroxy-8-azaspiro[4.5]decane-8-carboxylate (3.0 g, 8.01 mmol), triphenylphosphine (4.2 g, 16.02 mmol), and isoquinoline-1-carboxylic acid (4.16 g, 24.03 mmol) in THF (80 mL) was added DIAD (3.1 mL, 16.02 mmol). The resulting mixture was stirred for 1 h at RT. The reaction was diluted with EtOAc (50 mL), filtered through a pad of Celite, poured into a separation funnel containing sat. aq NaHCO₃ and extracted with EtOAc (3×25 mL). The combined organic phases were dried over MgSO₄, filtered and the volatiles were removed under reduced pressure. The resulting residue was purified by silica chromatography (0 to 4% gradient of MeOH/DCM) to give (2S, 4R)-8-(tert-butoxycarbonyl)-4-((R)-1,1-dimethylethylsulfinamido)-8-azaspiro[4.5]decan-2-yl isoquinoline-1-carboxylate (3.65 g, 6.89 mmol) as orange solid. MS m/z 530.3 (M+H)+.

Step c:

A mixture of (2S,4R)-8-(tert-butoxycarbonyl)-4-((R)-1,1-dimethylethylsulfinamido)-8-azaspiro[4.5]decan-2-yl isoquinoline-1-carboxylate (3.65 g, 6.89 mmol) and lithium hydroxide (2.95 g, 68.9 mmol) in THF:H₂O (1:1, 70 mL) was stirred for 2 h at RT. The mixture was poured into a separation funnel containing sat. aq NH₄Cl and it was extracted with EtOAc (3×15 mL). The combined organic phases were dried over MgSO₄, filtered and the volatiles were removed under reduced pressure. The resulting residue was purified by silica chromatography (0 to 10% gradient of MeOH/DCM) to give (1R,3S)-tert-butyl 1-((R)-1,1-dimethylethylsulfinamido)-3-hydroxy-8-azaspiro[4.5]decane-8-carboxylate (2.35 g, 6.27 mmol) as white solid. MS m/z 275.2 (M+H-Boc)+.

Intermediate 29

(1R,3S)-tert-butyl 1-((R)-1,1-dimethylethylsulfinamido)-3-(isobutyryloxy)-8-azaspiro[4.5]decane-8-carboxylate)

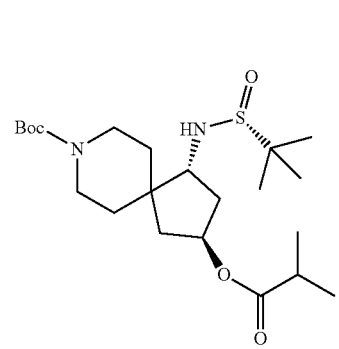

To a solution of (1R,3R)-tert-butyl 1-((R)-1,1-dimethylethylsulfinamido)-3-hydroxy-8-azaspiro[4.5]decane-8-carboxylate (200 mg, 0.534 mmol), triphenylphosphine (280 mg, 1.068 mmol), and isobutyric acid (146 μL, 1.602 mmol) in THF (5 mL) was added DIAD (208 μL, 1.068 mmol). The resulting mixture was stirred for 16 h at RT. The reaction was diluted with EtOAc (50 mL), filtered through a pad of Celite, poured into a separation funnel containing sat. aq NaHCO₃, and extracted with EtOAc (3×10 mL). The combined organic phases were dried over MgSO₄, filtered, and the volatiles were removed under reduced pressure. The resulting residue was purified by silica chromatography (0 to 7% gradient of MeOH/DCM) to give (1R,3S)-tert-butyl 1-((R)-1,1-dimethylethylsulfinamido)-3-(isobutyryloxy)-8-azaspiro[4.5]decane-8-carboxylate) (237 mg, 0.534 mmol). MS m/z 345.3 (M+H-Boc)+.

Intermediates 30a/b/c (1R,3R)-tert-butyl 1-((R)—N,2-dimethylpropan-2-ylsulfinamido)-3-hydroxy-8-azaspiro[4.5]decane-8-carboxylate, (1R,3R)-tert-butyl 1-((R)-1,1-dimethylethylsulfinamido)-3-methoxy-8-azaspiro[4.5]decane-8-carboxylate, & (1R,3R)-tert-butyl 1-((R)—N,2-dimethylpropan-2-ylsulfinamido)-3-methoxy-8-azaspiro[4.5]decane-8-carboxylate

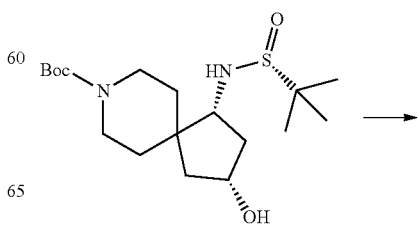

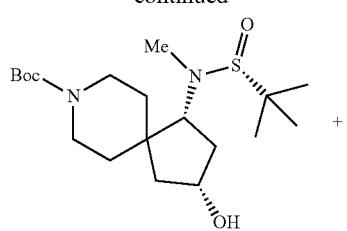

+

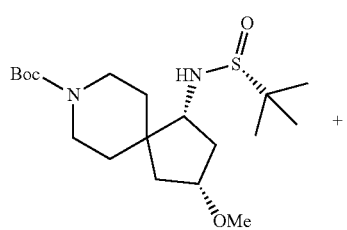

+

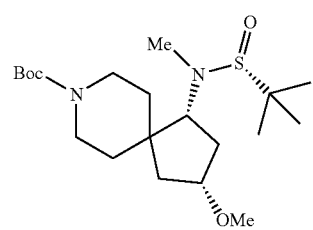

A mixture of (1R,3R)-tert-butyl 1-((R)-1,1-dimethylethylsulfinamido)-3-hydroxy-8-azaspiro[4.5]decane-8-carboxylate (142 mg, 0.378 mmol) and NaH (60% dispersion in mineral oil, 19 mg, 0.473 mmol) in THF was stirred for 20 min at 0° C. Iodomethane (47 µL, 0.756 mmol) was added and the resulting mixture was stirred for 4 h at RT. The volatiles were removed under reduced pressure and the resulting residue was purified by HPLC (gradient elution 25-50% acetonitrile in water, 5 mM NH$_4$OH modifier) to give (1R,3R)-tert-butyl 1-((R)—N,2-dimethylpropan-2-ylsulfinamido)-3-hydroxy-8-azaspiro[4.5]decane-8-carboxylate (15.0 mg, 0.039 mmol). MS m/z 289.2 (M+H-Boc)$^+$; (1R,3R)-tert-butyl 1-((R)-1,1-dimethylethylsulfinamido)-3-methoxy-8-azaspiro[4.5]decane-8-carboxylate. MS m/z 289.2 (M+H-Boc)$^+$; and (1R,3R)-tert-butyl 1-((R)—N,2-dimethylpropan-2-ylsulfinamido)-3-methoxy-8-azaspiro[4.5]decane-8-carboxylate. MS m/z 303.2 (M+H-Boc)$^+$.

Intermediate 31

(1R,3S)-tert-butyl 1-((R)-1,1-dimethylethylsulfinamido)-3-methoxy-8-azaspiro[4.5]decane-8-carboxylate

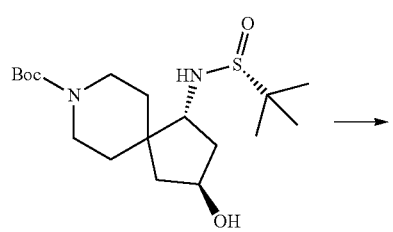

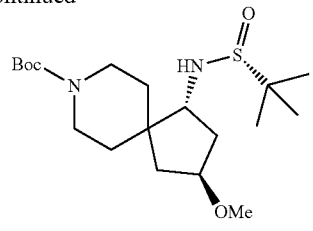

A mixture of (1R,3S)-tert-butyl 1-((R)-1,1-dimethylethylsulfinamido)-3-hydroxy-8-azaspiro[4.5]decane-8-carboxylate (500 mg, 1.335 mmol), silver (I) oxide (340 mg, 1.468 mmol), and iodomethane (250 µL, 4.0 mmol) in DCM (5 mL) was stirred (protected from the light) for 24 h at RT and 24 h at 45° C. After cooling to RT, the mixture was filtered through a pad of Celite, the volatiles were removed under reduced pressure, and the resulting residue was purified by silica chromatography (0 to 5% gradient of MeOH/DCM) to give (1R,3S)-tert-butyl 1-((R)-1,1-dimethylethylsulfinamido)-3-methoxy-8-azaspiro[4.5]decane-8-carboxylate (248 mg, 0.638 mmol). MS m/z 289.2 (M+H-Boc)$^+$.

Intermediate 32 racemic tert-butyl 1-((tert-butoxycarbonyl)amino)-3,3-difluoro-8-azaspiro[4.5]decane-8-carboxylate

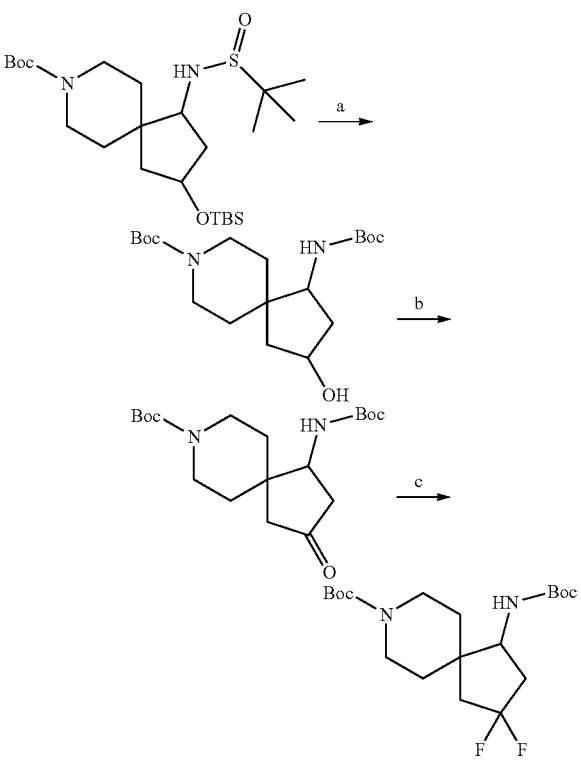

Step a:
A mixture of tert-butyl 3-((tert-butyldimethylsilyl)oxy)-1-(1,1-dimethylethylsulfinamido)-8-azaspiro[4.5]decane-8-carboxylate (365 mg, 0.746 mmol) and HCl (4 M in dioxane, 1.86 mL, 7.46 mmol) in MeOH (4 mL) was stirred for 1 h at 40° C. After cooling to RT, the volatiles were removed under reduced pressure to give a white solid. MS m/z 171.1 (M+H)+. A mixture of this residue, DIPEA (2.6 mL, 14.92 mmol), and Boc$_2$O (407 mg, 1.865 mmol) in THF (15 mL) was stirred for 16 h at RT. The mixture was poured into a separation funnel containing sat. aq NH$_4$Cl and it was extracted with Et$_2$O (5×10 mL). The combined organic phases were dried over MgSO$_4$, filtered and the volatiles were removed under reduced pressure. The resulting residue was purified by silica chromatography (10 to 80% gradient of EtOAc/heptane) to give tert-butyl 1-((tert-butoxycarbonyl)amino)-3-hydroxy-8-azaspiro[4.5]decane-8-carboxylate (275 mg, 0.742 mmol). MS m/z 271.3 (M+H-Boc)+.

Step b:

A mixture of tert-butyl 1-((tert-butoxycarbonyl)amino)-3-hydroxy-8-azaspiro[4.5]decane-8-carboxylate (275 mg, 0.742 mmol) and Dess-Martin periodinane (472 mg, 1.113 mmol) in DCM (7.5 mL) was stirred for 2 h at 0° C. The mixture was poured into a separation funnel containing sat. aq NaHCO$_3$ and it was extracted with DCM (3×10 mL). The combined organic phases were dried over MgSO$_4$, filtered and the volatiles were removed under reduced pressure. The resulting residue was purified by silica chromatography (5 to 75% gradient of EtOAc/heptane) to give tert-butyl 1-((tert-butoxycarbonyl)amino)-3-oxo-8-azaspiro[4.5]decane-8-carboxylate (135 mg, 0.366 mmol). $^1$H NMR (400 MHz, CHLOROFORM-d) δ ppm 4.57 (d, J=9.09 Hz, 1H), 4.16 (d, J=8.08 Hz, 1H), 3.89-4.08 (m, 2H), 2.77-2.93 (m, 2H), 2.71 (dd, J=18.95, 8.08 Hz, 1H), 2.50 (d, J=18.19 Hz, 1H), 2.07-2.24 (m, 2H), 1.76 (td, J=12.82, 4.67 Hz, 1H), 1.58-1.70 (m, 1H), 1.42-1.53 (m, 18H), 1.25-1.38 (m, 1H).

Step c:

A mixture of tert-butyl 1-((tert-butoxycarbonyl)amino)-3-oxo-8-azaspiro[4.5]decane-8-carboxylate (95 mg, 0.258 mmol) and DeoxoFluor (190 μL, 1.031 mmol) in DCM (1 mL) was stirred for 48 h at 50° C. The mixture was poured into a separation funnel containing sat. aq NaHCO$_3$/ice and it was extracted with EtOAc (3×5 mL). The combined organic phases were dried over MgSO$_4$, filtered and the volatiles were removed under reduced pressure. The resulting residue was purified by silica chromatography (0 to 30% gradient of EtOAc/heptane) to give tert-butyl 1-((tert-butoxycarbonyl)amino)-3,3-difluoro-8-azaspiro[4.5]decane-8-carboxylate (52 mg, 0.133 mmol). $^1$H NMR (400 MHz, CHLOROFORM-d) δ ppm 4.55 (d, J=9.35 Hz, 1H), 3.78-4.02 (m, 3H), 2.64-2.86 (m, 2H), 2.38-2.59 (m, 1H), 2.10-2.32 (m, 1H), 1.79-2.10 (m, 2H), 1.58 (qd, J=12.72, 3.79 Hz, 1H), 1.27-1.52 (m, 21H).

The following compounds were synthesized using the above procedure or modifications to the above procedure using the chirally pure (1R,3R)-tert-butyl 3-((tert-butyldimethylsilyl)oxy)-1-((R)-1,1-dimethylethylsulfinamido)-8-azaspiro[4.5]decane-8-carboxylate as starting material.

TABLE 2

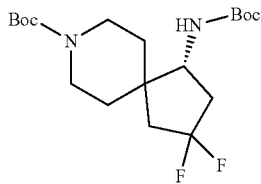

Intermediate 33

1-amino-2,8-diazaspiro[4.5]dec-1-en-3-one

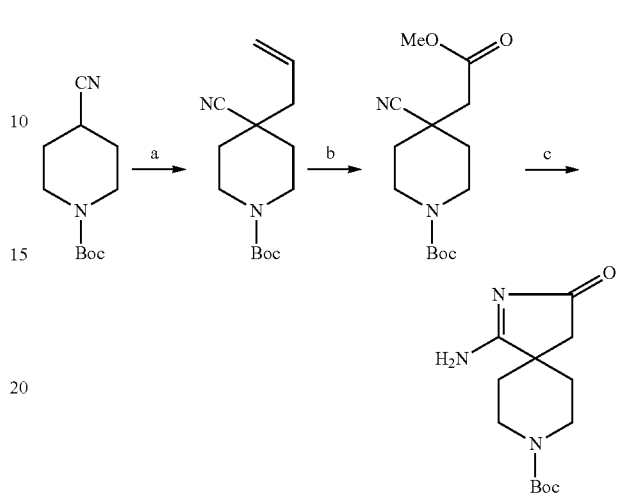

Step a:

A solution of diisopropylamine (0.320 mL, 2.245 mmol) in THF (4 mL) was cooled to −78° C. and treated with n-butyllithium (1.3 mL, 2.080 mmol) then stirred for 5 min at −78° C. and warmed to 0° C. giving a solution of LDA to be used subsequently. To a −78° C. solution of tert-butyl 4-cyanopiperidine-1-carboxylate (153 mg, 0.728 mmol) in THF (10 mL) was added the prepared solution of LDA (2.8 mL) dropwise and the resulting mixture stirred for 10 min at −78° C., then for 10 min at −10° C. Reaction was recooled to −78° C. and a solution of allyl-Br (80 μL, 0.924 mmol) in THF (2 mL) was added dropwise. The resulting reaction mixture was stirred for 1 h at RT and the volatiles were removed under reduced pressure. The aqueous was extracted with EtOAc, the combined organic phases were washed with water, brine, dried over Na$_2$SO$_4$, filtered and concentrated under reduced pressure. The residue was purified by silica chromatography (0 to 50% gradient of EtOAc/heptane) to give tert-butyl 4-allyl-4-cyanopiperidine-1-carboxylate (40 mg, 0.16 mmol) as a colorless oil. $^1$H NMR (400 MHz, DMSO-d$_6$) δ ppm 5.99-5.70 (m, 1H), 5.23 (q, J=1.1 Hz, 1H), 5.20 (dtd, J=3.3, 2.1, 1.1 Hz, 1H), 3.96 (d, J=13.7 Hz, 2H), 2.86 (s, 2H), 2.36 (dt, J=7.5, 1.3 Hz, 2H), 1.84 (dq, J=13.7, 2.6 Hz, 2H), 1.40 (s, 11H).

Step b:

A solution of tert-butyl 4-allyl-4-cyanopiperidine-1-carboxylate (22 mg, 0.088 mmol) in DCM (1.5 mL) and NaOH (2.5 M in MeOH, 0.176 mL, 0.439 mmol) was aerated with ozone (diffusing aerator) at −78° C. for 30 minutes. The reaction was purged with oxygen then partitioned between water and DCM. The phases were separated, the organic collected and the aqueous extracted with DCM (2×5 mL). The combined organic phases were concentrated under reduce pressure. The resulting residue was taken up in MeOH and stirred for 24 h at 65° C. After cooling to RT, the volatiles were removed under reduced pressure and the resulting residue was purified by silica chromatography (0 to 70% gradient of EtOAc/heptane) to give tert-butyl 4-cyano-4-(2-methoxy-2-oxoethyl)piperidine-1-carboxylate (21 mg, 0.074 mmol) as a colorless oil. $^1$H NMR (400 MHz, CHLOROFORM-d) δ ppm 4.14 (s, 2H), 3.75 (s, 3H), 3.08 (t, J=12.9 Hz, 2H), 2.62 (s, 2H), 2.15-2.02 (m, 2H), 1.59-1.48 (m, 2H), 1.46 (s, 9H). TLC (50% EtOAc/heptane (stained w/KMnO4), $R_f$=0.5).

Step c:

A solution of tert-butyl 4-cyano-4-(2-methoxy-2-oxoethyl)piperidine-1-carboxylate (287 mg, 1.017 mmol) and NH$_3$ (7 N in MeOH, 3.0 mL, 21.00 mmol) in MeOH (5 mL) was stirred in a sealed tube for 48 h at 120° C. After cooling to RT, the volatiles were removed under reduced pressure to give a white solid. The solid was triturated with EtOAc and filtered to give tert-butyl 1-amino-3-oxo-2,8-diazaspiro[4.5]dec-1-ene-8-carboxylate (157 mg, 0.587 mmol) as a white solid. $^1$H NMR (400 MHz, DMSO-d$_6$) δ ppm 8.44 (s, 1H), 8.02 (s, 1H), 3.98 (d, J=13.3 Hz, 2H), 2.71 (s, 2H), 2.34 (s, 2H), 1.81 (td, J=12.9, 4.6 Hz, 2H), 1.49-1.30 (m, 11H). MS m/z 268 (M+H)$^+$.

Intermediates 34a/b racemic tert-butyl 2-fluoro-1-oxo-8-azaspiro[4.5]decane-8-carboxylate & tert-butyl 2,2-difluoro-1-oxo-8-azaspiro[4.5]decane-8-carboxylate

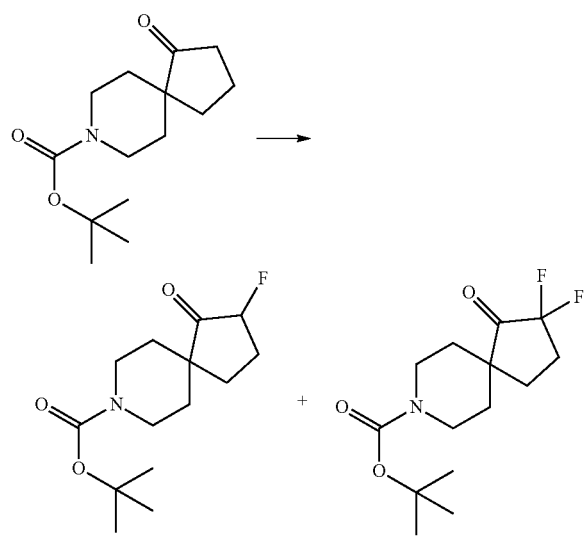

To a −78° C. solution of NaHMDS (1 M in THF, 8.68 mL, 8.68 mmol) was added a solution of tert-butyl 1-oxo-8-azaspiro[4.5]decane-8-carboxylate (2.0 g, 7.89 mmol) in THF (5 mL). After stirring for 30 min at this temperature, a solution of N-fluorobenzenesulfonamide (2.49 g, 7.89 mmol) in THF (10 mL) was added. After 3 h stirring at −78° C., it was diluted with sat. aq NaHCO$_3$ (100 mL) and extracted with DCM (3×100 mL). The combined organic phases were washed with brine, dried over Na$_2$SO$_4$, filtered, and concentrated under reduced pressure. The resulting residue was purified by silica chromatography (0 to 25% gradient of EtOAc/heptane) to give racemic tert-butyl 2-fluoro-1-oxo-8-azaspiro[4.5]decane-8-carboxylate (351 mg, 1.29 mmol). MS m/z 272.1 (M+H)$^+$ and difluoro ketone which coelutes with starting material. The combined coeluted fractions of difluoro ketone/starting were repurified by silica chromatography (0 to 5% gradient of MeOH/DCM) to give tert-butyl 2,2-difluoro-1-oxo-8-azaspiro[4.5]decane-8-carboxylate (573 mg, 1.98 mmol). MS m/z 290.1 (M+H)$^+$.

Intermediate 35

(S)-tert-butyl 4-((R)-1,1-dimethylethylsulfinamido)-2-oxa-8-azaspiro[4.5]decane-8-carboxylate

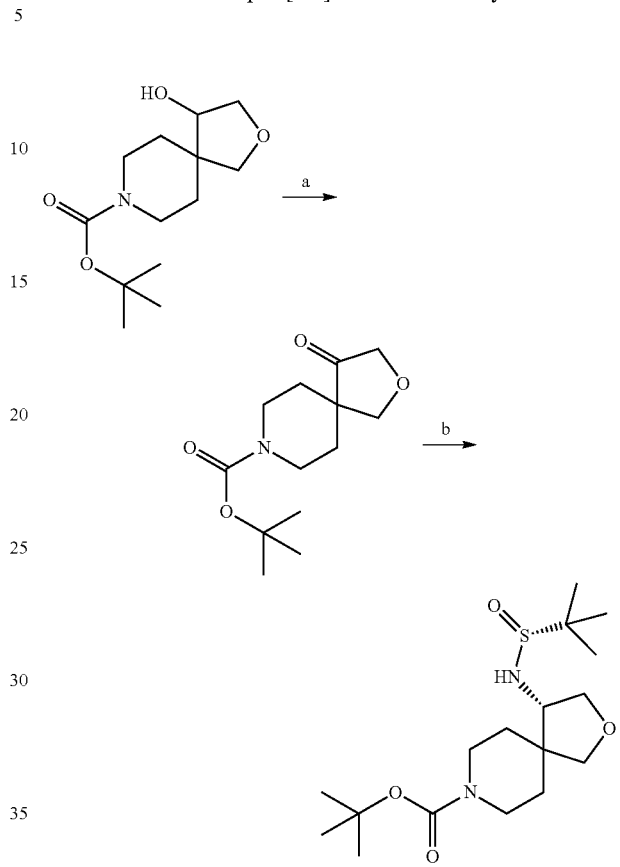

Step a:

A solution of tert-butyl 4-hydroxy-2-oxa-8-azaspiro[4.5]decane-8-carboxylate (544 mg, 2.11 mmol) and Dess-Martin periodinane (1.39 g, 3.17 mmol) in DCM (10 mL) was stirred for 2 h at 0° C. Sat. aq NaHCO$_3$:sat. aq Na$_2$S$_2$O$_3$ (1:1, 10 mL) was added, the organic phase was separated and the aqueous phase was extracted with DCM (3×10 mL). The combined organic phases were dried over Na$_2$SO$_4$, filtered and the volatiles were removed under reduced pressure. The resulting residue was purified by silica chromatography (0 to 50% gradient of EtOAc/heptane) to give tert-butyl 4-oxo-2-oxa-8-azaspiro[4.5]decane-8-carboxylate (470 mg, 1.84 mmol) as a colorless oil which crystallized upon standing. $^1$H NMR (400 MHz, CHLOROFORM-d) δ ppm 4.08 (s, 2H), 4.05 (s, 2H), 3.88 (dt, J=13.7, 4.9 Hz, 2H), 3.12 (ddd, J=13.6, 9.8, 3.6 Hz, 2H), 1.75 (ddd, J=13.9, 9.7, 4.2 Hz, 2H), 1.58-1.51 (m, 2H), 1.48 (s, 9H). MS m/z 256.2 (M+H)$^+$.

Step b:

A solution of tert-butyl 4-oxo-2-oxa-8-azaspiro[4.5]decane-8-carboxylate (220 mg, 0.86 mmol), titanium(IV) ethoxide (725 μL, 3.45 mmol), and (R)-2-methylpropane-2-sulfinamide (209 mg, 1.72 mmol) in THF (4 mL) was stirred for 1 h at 90° C. After cooling to 0° C., lithium borohydride (23 mg, 1.06 mmol) was added. After stirring for 30 min, the reaction mixture was quenched by addition of MeOH. The volatiles were removed under reduce pressure. The resulting residue was diluted with brine and it was extracted with EtOAc (4×10 mL). The combined organic phases were dried over Na$_2$SO$_4$, filtered, the volatiles were removed under reduced pressure, and the resulting residue was purified by silica chromatography (0 to 100% gradient of EtOAc/heptane) to give (S)-tert-butyl 4-((R)-1,1-dimethylethylsulfinamido)-2-oxa-8-azaspiro[4.5]decane-8-carboxylate (170 mg, 0.47 mmol). MS m/z 361.1 (M+H)+.

The following compounds were synthesized using the above procedure or modifications to the above procedure using the corresponding ketone and sulfonamide.

TABLE 3

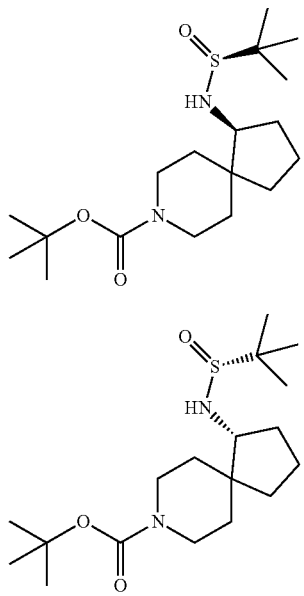

Intermediate 36

(1R)-tert-butyl 1-((R)-1,1-dimethylethylsulfinamido)-2-methyl-8-azaspiro[4.5]decane-8-carboxylate

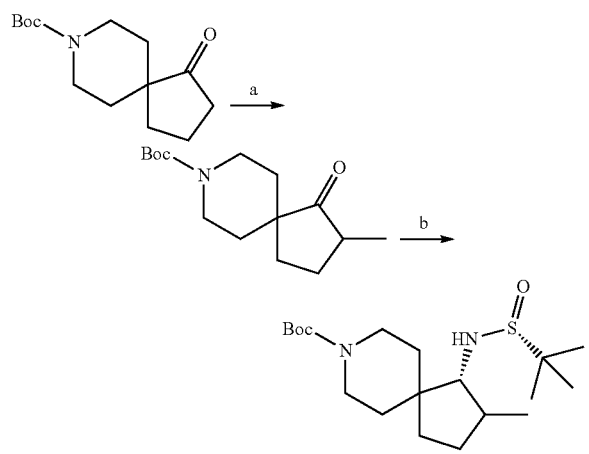

Step a:

To a solution of tert-butyl 1-oxo-8-azaspiro[4.5]decane-8-carboxylate (2.2 g, 8.68 mmol) in THF (24 mL) was added LiHMDS (1 M in THF, 8.68 mL, 8.68 mmol) at 0-5° C. After stirring the mixture for 30 min at this temperature, iodomethane (0.543 mL, 8.68 mmol) was added. The resulting mixture was allowed to warm to RT and stirred for 2 h. The reaction mixture was diluted with EtOAc and quenched with sat. aq NaHCO₃. The organic phase was washed with brine, dried over Na₂SO₄, filtered and concentrated under reduced pressure. The resulting brown oil was purified by silica chromatography (0 to 25% gradient of EtOAc/heptane) to give tert-butyl 2-methyl-1-oxo-8-azaspiro[4.5]decane-8-carboxylate (1.3 g, 4.86 mmol). MS m/z 268.1. (M+H)+.

Step b:

A solution of tert-butyl 2-methyl-1-oxo-8-azaspiro[4.5]decane-8-carboxylate (267 mg, 0.999 mmol), titanium(IV) ethoxide (837 µL, 3.99 mmol), and (R)-2-methylpropane-2-sulfinamide (242 mg, 1.997 mmol) in THF (10 mL) was stirred for 24 h at 85° C. After cooling to −78° C., MeOH (12 mL) was added followed by lithium borohydride (65.3 mg, 3.00 mmol). The resulting mixture was stirred at −78° C. to RT for 16 h. Sat. aq NH₄Cl was slowly added to quench the excess of borohydride followed by addition of EtOAc (100 mL). The resulting mixture was vigorously stirred for 15 min and then filtered through a pad of Celite. The volatiles were removed under reduced pressure and the resulting residue was purified by silica chromatography (0 to 60% gradient of EtOAc/heptane (containing 0.25% of Et₃N)) to give (1R)-tert-butyl 1-((R)-1,1-dimethylethylsulfinamido)-2-methyl-8-azaspiro[4.5]decane-8-carboxylate (92 mg, 0.247 mmol). MS m/z 373.1 (M+H)+.

Intermediates 37a/b (3S,4S)-tert-butyl 4-((R)-1,1-dimethylethylsulfinamido)-3-methyl-2-oxa-8-azaspiro[4.5]decane-8-carboxylate & (3R,4S)-tert-butyl 4-((R)-1,1-dimethylethylsulfinamido)-3-methyl-2-oxa-8-azaspiro[4.5]decane-8-carboxylate

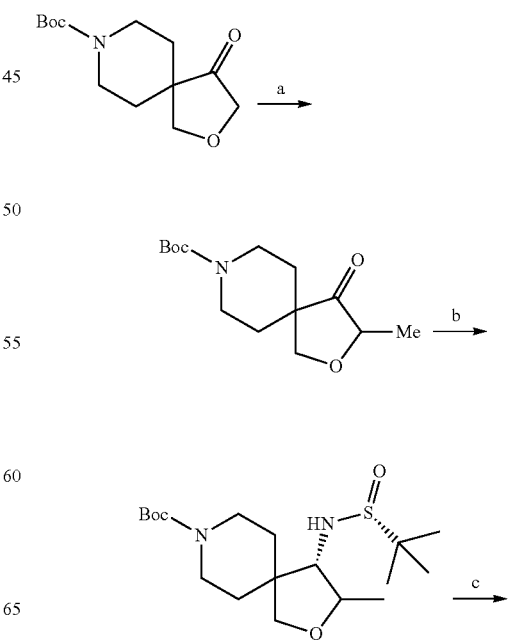

-continued

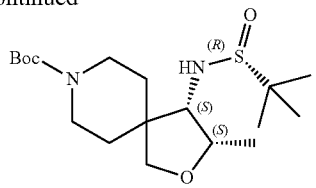

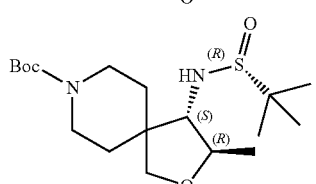

Step a:

To a solution of of tert-butyl 4-oxo-2-oxa-8-azaspiro[4.5]decane-8-(2.47 g, 9.67 mmol) in THF (24 mL) was added LiHMDS (1 M in THF, 9.67 mL, 9.67 mmol) at −78° C. After stirring the mixture for 30 min at this temperature, iodomethane (0.605 mL, 9.67 mmol) in THF (10 mL) was added. The resulting mixture was allowed to warm to RT and stirred for 1 h. The reaction mixture was diluted with EtOAc and quenched with sat. aq NaHCO$_3$. The organic phase was washed with brine, dried over Na$_2$SO$_4$, filtered, and concentrated under reduced pressure. The resulting brown oil was purified by silica chromatography (0 to 20% gradient of EtOAc/heptane) to give tert-butyl 3-methyl-4-oxo-2-oxa-8-azaspiro[4.5]decane-8-carboxylate (318 mg, 1.181 mmol). MS m/z 270.2. (M+H)$^+$.

Step b:

A solution of tert-butyl 3-methyl-4-oxo-2-oxa-8-azaspiro[4.5]decane-8-carboxylate (318 mg, 1.181 mmol), titanium (IV) ethoxide (990 μL, 4.72 mmol), and (R)-2-methylpropane-2-sulfinamide (286 mg, 2.361 mmol) in THF (4 mL) was stirred for 90 min at 90° C. After cooling to 0° C., lithium borohydride (65.3 mg, 3.00 mmol) was added in one portion and the resulting mixture was stirred stirred for 16 h at RT. Sat. aq NH$_4$Cl was slowly added to quench the excess of borohydride followed by addition of EtOAc (25 mL). The resulting mixture was vigorously stirred for 15 min and then filtered through a pad of Celite. The organic phase was washed with sat. aq NaHCO$_3$, brine, dried over Na$_2$SO$_4$, filtered, and the volatiles were removed under reduced pressure. The resulting residue was purified by silica chromatography (0 to 100% gradient of EtOAc/heptane) to give (4S)-tert-butyl 4-((R)-1,1-dimethylethylsulfinamido)-3-methyl-2-oxa-8-azaspiro[4.5]decane-8-carboxylate (88 mg, 0.235 mmol). MS m/z 375.2 (M+H)$^+$.

Step c:

The diastereomers were separated by chiral SFC as follows: column: LUXC4 30×250 mm, flow rate: 80 g per minute, mobile phase: 20% MeOH in CO$_2$, detection: 210 nm to give (3R,4S)-tert-butyl 4-((R)-1,1-dimethylethylsulfinamido)-3-methyl-2-oxa-8-azaspiro[4.5]decane-8-carboxylate, R$_t$=4.0 min; and (3S,4S)-tert-butyl 4-((R)-1,1-dimethylethylsulfinamido)-3-methyl-2-oxa-8-azaspiro[4.5]decane-8-carboxylate, R$_t$=4.55 min.

Intermediate 38

(3S,4S)-tert-butyl 4-((R)-1,1-dimethylethylsulfinamido)-3-methyl-2-oxa-8-azaspiro[4.5]decane-8-carboxylate

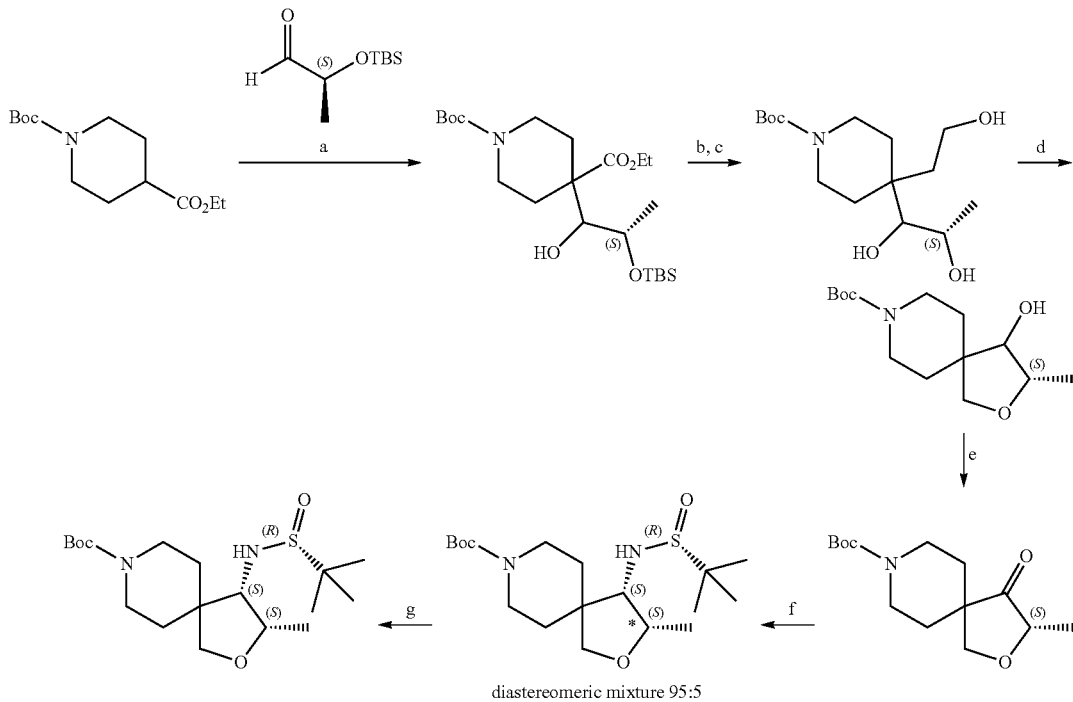

diastereomeric mixture 95:5

Step a:

To a −10° C. solution of diisopropylamine (23.4 mL, 166 mmol) in THF (220 mL) was added nBuLi (2.5 M in hexane, 64.1 mL, 160 mmol) dropwise. After stirring for 30 min at this temperature, 1-tert-butyl 4-ethyl piperidine-1,4-dicarboxylate (27.5 g, 107 mmol) in THF (50 mL) was added dropwise and the resulting mixture was stirred for 30 min at 0° C. (S)-2-((tert-butyldimethylsilyl)oxy)propanal (20.47 mL, 102 mmol) was added and the mixture was stirred for 1 h at 0° C. and 1 h at RT. The reaction was diluted with sat. aq NaHCO$_3$:H$_2$O (1:4, 125 mL), EtOAc (50 mL) was added, and the phases were separated. The aqueous phase was further extracted with EtOAc (3×100 mL). The combined organic phases were dried over Na$_2$SO$_4$, filtered, and the solvent was removed under reduced pressure. The resulting residue was used in next step without further purification. MS m/z 346.4 (M+H-Boc)$^+$.

Step b:

To a solution of crude 1-tert-butyl 4-ethyl 4-((2S)-2-((tert-butyldimethylsilyl)oxy)-1-hydroxypropyl)piperidine-1,4-dicarboxylate (95 g, 214 mmol) in THF (600 mL) was added portionwise LiBH$_4$ (7.0 g, 321 mmol) and the resulting mixture was stirred for 16 h at RT. After cooling to 0° C., sat. aq NaHCO$_3$:H$_2$O (1:2, 150 mL) was added and the resulting mixture was vigorously stirred until no more bubbling was observed. EtOAc (100 mL) was added, the mixture was filtered, the phases were separated, and the aqueous phase was further extracted with EtOAc (3×50 mL). The combined organic phases were washed with brine, dried over Na$_2$SO$_4$, filtered, and the volatiles were removed under reduced pressure to give tert-butyl 4-((2S)-2-((tert-butyldimethylsilyl)oxy)-1-hydroxypropyl)-4-(2-hydroxyethyl)piperidine-1-carboxylate (64.8 g, 161 mmol) which was used in next step without further purification.

Step c:

A solution of tert-butyl 4-((2S)-2-((tert-butyldimethylsilyl)oxy)-1-hydroxypropyl)-4-(2-hydroxyethyl)piperidine-1-carboxylate (64.8 g, 161 mmol) and TBAF (1 M in THF, 242 mL, 242 mmol) in THF (500 mL) was stirred for 2 h at RT. Sat. aq NaHCO$_3$:H$_2$O (1:2, 150 mL) were added, the phases were separated, and the aqueous phase was further extracted with EtOAc (3×100 mL). The combined organic phases were washed with brine, dried over Na$_2$SO$_4$, filtered, and the volatiles were removed under reduced pressure. The resulting residue was purified by silica chromatography (20 to 100% gradient of EtOAc/heptane) to give tert-butyl 4-((2S)-1,2-dihydroxypropyl)-4-(2-hydroxyethyl)piperidine-1-carboxylate (39.25 g, 136 mmol) as a semi-solid colorless oil.

Step d:

To a 0° C. suspension of NaH (10.60 g, 424 mmol) in THF (600 mL) was added dropwise a solution of tert-butyl 4-((2S)-1,2-dihydroxypropyl)-4-(2-hydroxyethyl)piperidine-1-carboxylate (35.06 g, 121 mmol) and TsCl (23.10 g, 121 mmol) in THF (200 mL). The resulting mixture was stirred for 1 h at 0° C. Sat. aq NH$_4$Cl (~5 mL) was added slowly at −20° C. and the reaction was vigorously stirred until no more bubbling was observed. At this point, sat. aq NH$_4$Cl (100 mL) was added followed by brine (100 mL) and the mixture was extracted with EtOAc (3×100 mL). The combined organic phases were dried over Na$_2$SO$_4$, filtered, and the solvent was removed under reduced pressure to give (3S)-tert-butyl 4-hydroxy-3-methyl-2-oxa-8-azaspiro[4.5]decane-8-carboxylate (32.19 g, 119 mmol) which was used in next step without further purification. MS m/z 171.1 (M-Boc)$^-$.

Step e:

A solution of (3S)-tert-butyl 4-hydroxy-3-methyl-2-oxa-8-azaspiro[4.5]decane-8-carboxylate (32.19 g, 119 mmol) and Dess-Martin periodinane (67.4 g, 154 mmol) in DCM (300 mL) was stirred for 2 h at 0° C. After warming to RT, the volatiles were removed under reduced pressure and the resulting residue was purified by silica chromatography (0 to 40% gradient of EtOAc/heptane) to give (S)-tert-butyl 3-methyl-4-oxo-2-oxa-8-azaspiro[4.5]decane-8-carboxylate (27.68 g, 92 mmol) as a pale yellow oil. $^1$H NMR (400 MHz, CHLOROFORM-d) δ ppm 4.09 (d, J=9.60 Hz, 1H), 3.66-3.86 (m, 4H), 3.03 (ddd, J=13.77, 9.73, 3.79 Hz, 1H), 2.90 (ddd, J=13.64, 10.23, 3.41 Hz, 1H), 1.68 (ddd, J=13.83, 9.92, 4.29 Hz, 1H), 1.41-1.59 (m, 2H), 1.30-1.40 (m, 10H), 1.20-1.25 (m, 3H).

Step f:

A solution of (3S)-tert-butyl 3-methyl-4-oxo-2-oxa-8-azaspiro[4.5]decane-8-carboxylate (22.52 g mg, 84 mmol), titanium(IV) ethoxide (70.1 mL, 334 mmol), and (R)-2-methylpropane-2-sulfinamide (21 g, 173 mmol) in THF (300 mL) was stirred for 21 h at 90° C. After cooling to −4° C., MeOH (30 mL) was added, followed by dropwise addition (maintaining reaction temperature below 2° C.) of lithium borohydride (1.82 g, 84 mmol) and the resulting mixture was stirred for 1 h at −4° C. Sat. aq NH$_4$Cl was slowly added to quench the excess of borohydride (gelatin-type formed) followed by addition of EtOAc (500 mL). The resulting mixture was vigorously stirred for 15 min at RT and then filtered through a pad of Celite followed by EtOAc (500 mL) wash. The volatiles were removed under reduced pressure and the resulting residue was purified by silica chromatography (0 to 100% gradient of EtOAc/heptane) to give (3S,4S)-tert-butyl 4-((R)-1,1-dimethylethylsulfinamido)-3-methyl-2-oxa-8-azaspiro[4.5]decane-8-carboxylate as a 95:5 diastereomeric mixture (minor diastereomer (3R,4S)-tert-butyl 4-((R)-1,1-dimethylethylsulfinamido)-3-methyl-2-oxa-8-azaspiro[4.5]decane-8-carboxylate).

Step g:

The diastereomers were separated by chiral SFC as follows: column: LC-4 30×250 mm, flow rate: 100 g per minute, mobile phase: 30% MeOH in CO$_2$, detection: 225 nm, R$_t$: 0.95 min (minor diastereomer R$_t$: 0.55 min) to give (3S,4S)-tert-butyl 4-((R)-1,1-dimethylethylsulfinamido)-3-methyl-2-oxa-8-azaspiro[4.5]decane-8-carboxylate (19 g, 50.68 mmol). MS m/z 375.2.

Intermediate 39

(4R)-4-amino-2-methyl-8-azaspiro[4.5]decan-2-ol

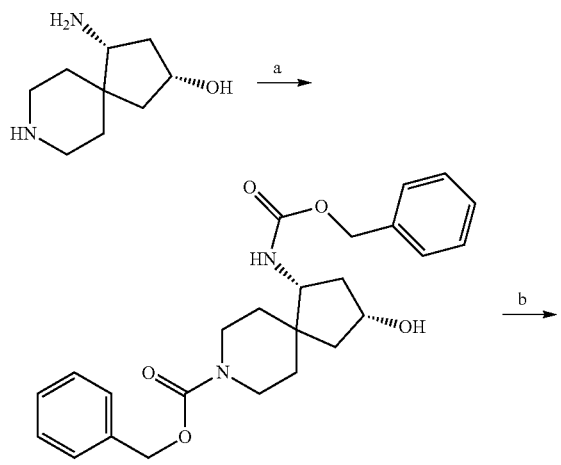

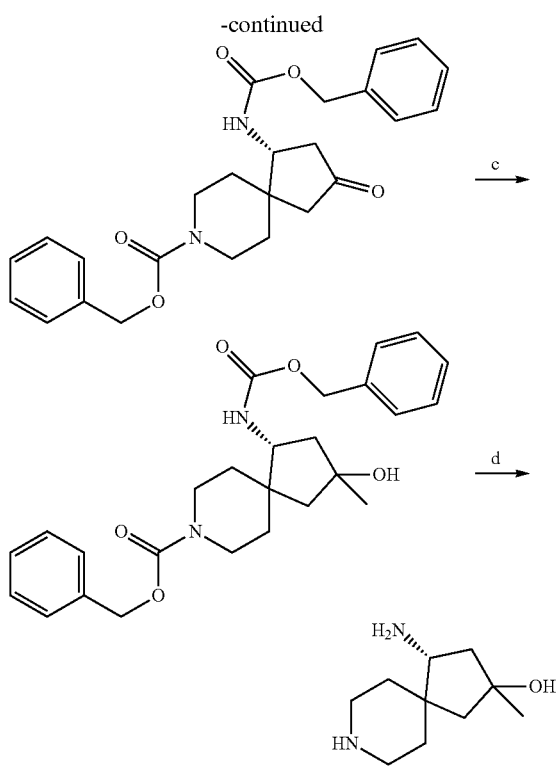

Step a:

A mixture of (2R,4R)-4-amino-8-azaspiro[4.5]decan-2-ol dihydrochloride salt (623 mg, 2.56 mmol), Na₂CO₃ (1357 mg, 12.80 mmol), and CbzCl (1048 mg, 6.14 mmol) in H₂O (5 mL) was stirred vigorously for 30 min at RT. THF (0.5 mL) was added and the resulting mixture was stirred for 18 h at RT. The mixture was diluted with water and DCM. The separated aqueous phase was extracted with DCM (2×10 mL). The combined organic phases were dried over Na₂SO₄, filtered, and concentrated under reduced pressure, and the resulting residue was purified by silica chromatography (0 to 100% gradient of EtOAc/heptane) to give (1R,3R)-benzyl 1-(((benzyloxy)carbonyl)amino)-3-hydroxy-8-azaspiro[4.5]decane-8-carboxylate (940 mg, 2.14 mmol) as a white foam. MS m/z 439.3 (M+H)⁺.

Step b:

A mixture of (1R,3R)-benzyl 1-(((benzyloxy)carbonyl)amino)-3-hydroxy-8-azaspiro[4.5]decane-8-carboxylate (440 mg, 1.003 mmol) and Dess-Martin periodinane (638 mg, 1.505 mmol) in DCM (6 mL) was stirred for 1 h at 0° C. and for 18 h at RT. The reaction mixture was diluted with sat. aq NaHCO₃:sat. aq Na₂S₂O₃ (1:1, 25 mL). The separated aqueous phase was extracted with DCM (3×15 mL). The combined organic phases were washed with brine, dried over MgSO₄, and concentrated under reduced pressure. The resulting residue was purified by silica chromatography (0 to 70% gradient of EtOAc/heptane) to give (R)-benzyl 1-(((benzyloxy)carbonyl)amino)-3-oxo-8-azaspiro[4.5]decane-8-carboxylate (415 mg, 0.951 mmol) as a white foam. MS m/z 437.2 (M+H)⁺.

Step c:

To a solution of MeLi (1.2 M in THF, 2.61 mL, 3.13 mmol) in THF (15 mL) was added dropwise (R)-benzyl 1-(((benzyloxy)carbonyl)amino)-3-oxo-8-azaspiro[4.5]decane-8-carboxylate (415 mg, 0.951 mmol) in THF (5 mL) at −30 to −40° C. The resulting mixture was stirred for 20 min at −30 to −40° C. The mixture was dilute with NaHSO₄ (10% solution in H₂O), diluted with EtOAc, and allowed to warm up to RT under vigorously stirring. The mixture was diluted with sat. aq NaHCO₃ and The separated aqueous phase was extracted with EtOAc (1×15 mL). The combined organic phases were dried over Na₂SO₄, filtered, and concentrated under reduced pressure. A solution of the resulting residue (313 mg), Na₂CO₃ (498 mg, 4.70 mmol), and CbzCl (295 mg, 1.729 mmol) in water (10 mL) and THF (1 mL) was vigorously stirred for 3 days at RT. The mixture was diluted with EtOAc and the separated aqueous phase was extracted with EtOAc (3×15 mL). The combined organic phases were concentrated under reduced pressure. The resulting residue was purified by silica chromatography (0 to 50% gradient of EtOAc/heptane) to give two diastereomers: diastereomer A (112 mg, 0.25 mmol) as a colorless semi-solid, MS m/z 453.3 (M+H)⁺ and diastereomer B (45 mg, 0.010 mmol) as white foam/solid, MS m/z 453.3 (M+H)⁺.

Step d:

A mixture of diastereomer A (50 mg, 0.11 mmol) and Pd/C (10 wt. %; 12 mg, 0.011 mmol) in MeOH (8 mL) was stirred vigorously under hydrogen atmosphere for 2 h. Celite was added and the mixture was filtered through a pad of Celite followed by DCM wash. The filtrate was concentrated under reduced pressure to give (4R)-4-amino-2-methyl-8-azaspiro[4.5]decan-2-ol as a colorless solid which was used without further purification. MS m/z 185.2 (M+H)⁺.

Intermediate 40

(1R,3S)-tert-butyl 1-((R)-1,1-dimethylethylsulfinamido)-3-fluoro-8-azaspiro[4.5]decane-8-carboxylate

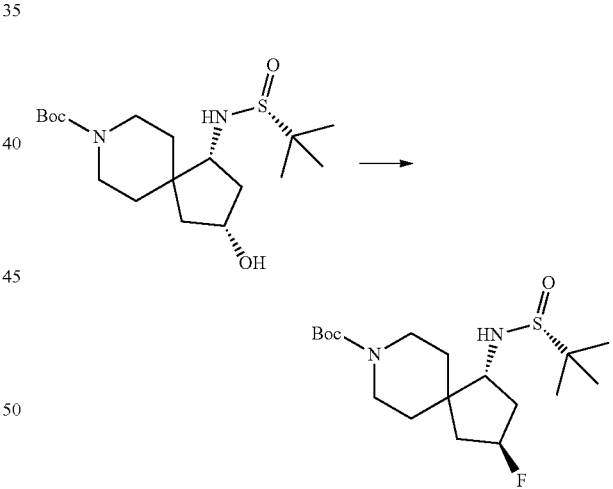

A mixture (1R,3R)-tert-butyl 1-((R)-1,1-dimethylethylsulfinamido)-3-hydroxy-8-azaspiro[4.5]decane-8-carboxylate (400 mg, 1.068 mmol) and DAST (1 M in DCM, 1.87 mL, 1.87 mmol) in DCM (8.5 mL) was stirred for 90 min at 0° C. The reaction mixture was quenched by addition of sat. aq NaHCO₃ (5 mL). After stirring for 10 min at 0° C., the phases were separated and the aqueous was stracted with DCM (2×5 mL). The combined organic phases were dried over MgSO₄, filtered, and the volatiles were removed under reduced pressure to give (1R,3S)-tert-butyl 1-((R)-1,1-dimethylethylsulfinamido)-3-fluoro-8-azaspiro[4.5]decane-8-carboxylate which was used in next step without further purification. MS m/z 277.2 (M+H-Boc)⁺.

Intermediate 41

(1R,3R)-tert-butyl 1-((R)-1,1-dimethylethylsulfinamido)-3-fluoro-8-azaspiro[4.5]decane-8-carboxylate

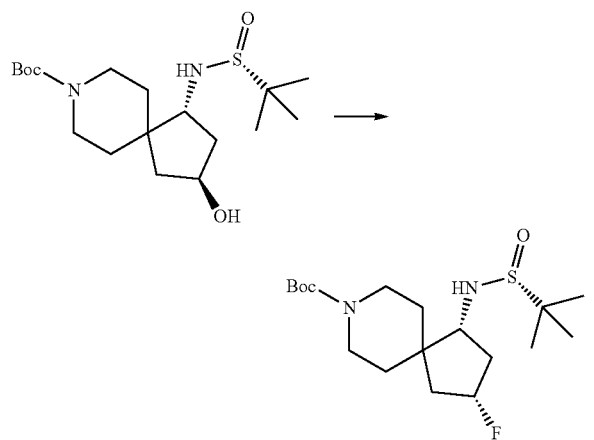

A mixture (1R,3S)-tert-butyl 1-((R)-1,1-dimethylethylsulfinamido)-3-hydroxy-8-azaspiro[4.5]decane-8-carboxylate (200 mg, 0.534 mmol) and DAST (1 M in DCM, 934 µL, 0.934 mmol) in DCM (5 mL) was stirred for 90 min at 0° C. The reaction mixture was quenched by addition of sat. aq NaHCO₃ (5 mL). After stirring for 10 min at RT, the phases were separated and the aqueous was stracted with DCM (2×5 mL). The combined organic phases were dried over MgSO₄, filtered, and the volatiles were removed under reduced pressure to give (1R,3R)-tert-butyl 1-((R)-1,1-dimethylethylsulfinamido)-3-fluoro-8-azaspiro[4.5]decane-8-carboxylate which was used in next step without further purification. MS m/z 277.2 (M+H-Boc)⁺.

Intermediate 42

3-((6-amino-2,3-dichloropyridin-4-yl)thio)-6-chloropyrazin-2-amine

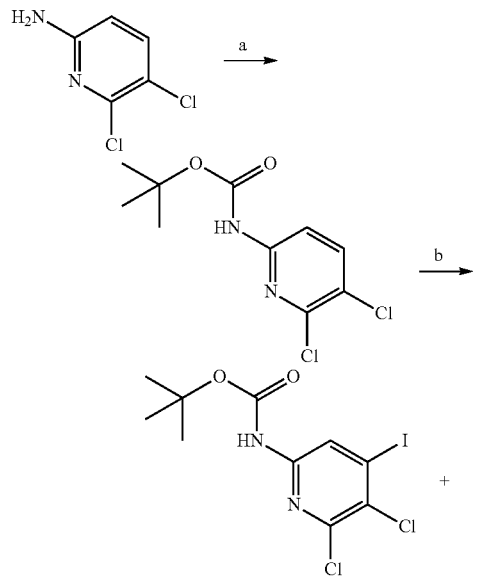

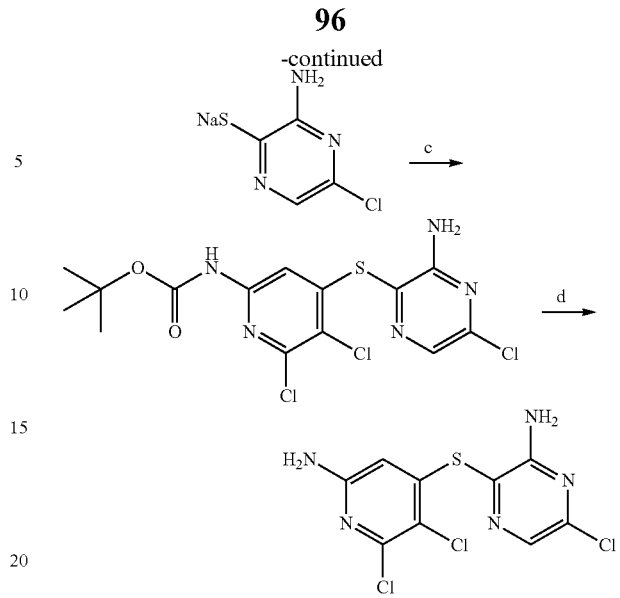

Step a:

To a solution of 5,6-dichloropyridin-2-amine (590 mg, 3.62 mmol) in THF (5 mL) was added LiHMDS (1 M in THF, 7.96 mL, 7.96 mmol) at 0° C. The reaction was stirred for 10 min at 0° C. then a solution of Boc₂O (869 mg, 3.98 mmol) in THF (5 mL) was added to reaction mixture. The resulting solution was stirred for 15 min at 0° C. then taken to pH 4 by addition of 1 M HCl. The solution was diluted with EtOAc, washed with sat. aq NaHCO₃, brine, dried over Na₂SO₄, filtered, and concentrated under reduced pressure. The resulting residue was purified by silica chromatography (0 to 40% gradient of EtOAc/heptane) to give tert-butyl (5,6-dichloropyridin-2-yl)carbamate (790 mg, 3.00 mmol). ¹H NMR (400 MHz, CHLOROFORM-d) δ ppm 7.86 (d, J=8.7 Hz, 1H), 7.70 (d, J=8.7 Hz, 1H), 7.20 (br s, 1H), 1.51 (s, 9H). MS m/z 232.9 (M+H–tBu)⁺.

Step b:

To a solution of diisopropylamine (1 mL, 7.07 mmol) in THF (5 mL) was added n-BuLi (2.5 M in hexanes, 2.83 mL, 7.07 mmol) at −78° C. and the resulting solution was stirred for 1 h at this temperature. Tert-butyl (5,6-dichloropyridin-2-yl)carbamate (930 mg, 3.53 mmol) in THF (5 mL) was added at −78° C. After stirring at this temperature for 2 h, iodine (987 mg, 3.89 mmol) in THF (5 mL) was added and the resulting mixture was stirred for 30 min at −78° C. After warming to RT, the reaction mixture was diluted with water and extracted with EtOAc (2×50 mL). The combined organic phases were washed with sat. aq Na₂S₂O₃, brine, dried over Na₂SO₄, filtered, and concentrated under reduced pressure. The resulting residue was purified by silica chromatography (0 to 40% gradient of EtOAc/heptane) to give tert-butyl (5,6-dichloro-4-iodopyridin-2-yl)carbamate (813 mg, 2.09 mmol). ¹H NMR (400 MHz, CHLOROFORM-d) δ ppm 8.45 (s, 1H), 7.12 (s, 1H), 1.52 (s, 9H). MS m/z 332.9 (M+H–tBu)⁺.

Step c:

A mixture of tert-butyl (5,6-dichloro-4-iodopyridin-2-yl)carbamate (610 mg, 1.57 mmol), sodium 3-amino-5-chloropyrazine-2-thiolate (302 mg, 1.65 mmol), Pd₂(dba)₃ (72 mg, 0.08 mmol), Xantphos (91 mg, 0.16 mmol), and DIPEA (0.55 mL, 3.14 mmol) in dioxane (7.8 mL) was stirred for 8 h at 110° C. After cooling to RT, the reaction mixture was filtered through a pad of Celite and the volatiles were removed under reduced pressure. The resulting residue was purified by silica chromatography (0 to 40% gradient of EtOAc/heptane) to give tert-butyl (4-((3-amino-5-chloropyrazin-2-yl)thio)-5,6-dichloropyridin-2-yl)carbamate (470 mg, 1.11 mmol). $^1$H NMR (400 MHz, DMSO) δ ppm 10.24 (s, 1H), 7.96 (s, 1H), 7.31 (br s, 2H), 7.16 (s, 1H), 1.38 (s, 9H). MS m/z 321.9 (M+H-Boc)$^+$.

Step d:

A mixture of tert-butyl (4-((3-amino-5-chloropyrazin-2-yl)thio)-5,6-dichloropyridin-2-yl)carbamate (470 mg, 1.11 mmol) and HCl (4 M in dioxane, 5.56 mL, 22.24 mmol) was stirred for 1 h at RT. The volatiles were removed under reduced pressure to give 3-((6-amino-2,3-dichloropyridin-4-yl)thio)-6-chloropyrazin-2-amine dihydrochloride (411 mg, 1.04 mmol) which was used without further purification. MS m/z 324.0 (M+H)$^+$.

Example 1

(S) and (R) 8-(6-amino-5-((2-(trifluoromethyl)pyridin-3-yl)thio)pyrazin-2-yl)-8-azaspiro[4.5]decan-1-amine

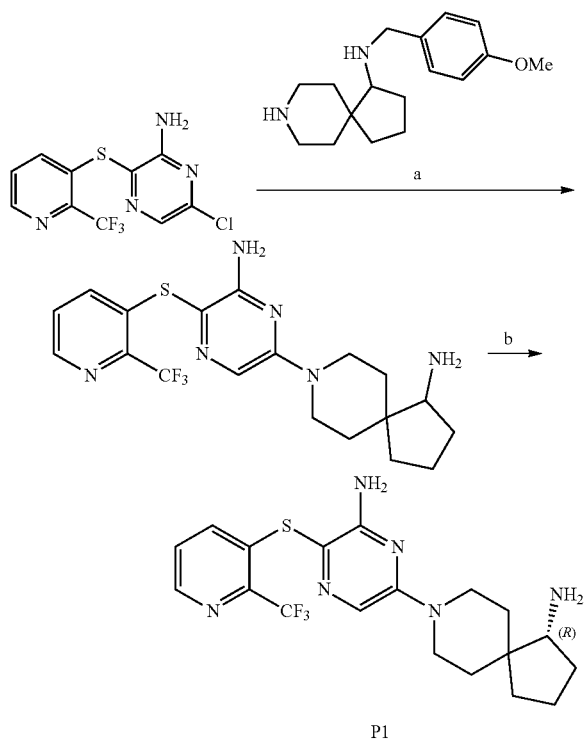

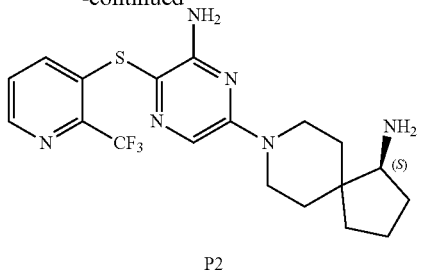

Step a:

A solution of 6-chloro-3-((2-(trifluoromethyl)pyridin-3-yl)thio)pyrazin-2-amine (200 mg, 0.652 mmol) and N-(4-methoxybenzyl)-8-azaspiro[4.5]decan-1-amine (358 mg, 1.304 mmol) in DIPEA (3 mL) was stirred for 60 h at 130° C. After cooling to RT, the volatiles were removed under reduced pressure. The resulting residue was dissolved in TFA (3 mL) and the solution was stirred in a microwave reactor for 1 h at 160° C. and for 15 min at 180° C. The volatiles were removed under reduced pressure and the resulting residue was purified by HPLC (gradient elution 25-50% acetonitrile in water, 5 mM NH$_4$OH modifier) to give 8-(6-amino-5-((2-(trifluoromethyl)pyridin-3-yl)thio)pyrazin-2-yl)-8-azaspiro[4.5]decan-1-amine (73 mg, 0.482 mmol; 83% pure based on HRMS). 19 mg of this compound were further purified by HPLC (gradient elution 25-50% acetonitrile in water, 0.1% TFA modifier) to give the title compound pure (9.5 mg). $^1$H NMR (400 MHz, METHANOL-d$_4$) δ ppm 8.29 (dd, J=4.42, 1.39 Hz, 1H), 7.48 (s, 1H), 7.19-7.41 (m, 2H), 4.06-4.26 (m, 2H), 2.89-3.14 (m, 2H), 2.71 (t, J=7.33 Hz, 1H), 1.86-2.00 (m, 1H), 1.73-1.84 (m, 1H), 1.43-1.72 (m, 5H), 1.27-1.42 (m, 2H), 1.17-1.27 (m, 1H). $^{19}$F NMR (376 MHz, METHANOL-d$_4$) δ ppm −66.45 (s). HRMS calcd for C$_{19}$H$_{24}$N$_6$F$_3$S (M+H)$^+$ 425.1735, found 425.1753. IC$_{50}$ is 0.023 μM.

Step b:

Chiral SFC purification of the above title compound performed as follows; column: ID 21×250 mm, flow rate: 75 g per minute, mobile phase: 35% MeOH and 10 mM NH$_4$OH in CO$_2$, detection: 270 nm UV to obtain single enantiomer R$_t$ (P1)=4.9 min; IC$_{50}$ is 0.011 μM and R$_t$ (P2)=6.4 min; IC$_{50}$ is 0.167 μM.

The following compounds of Formula I, as identified in table 4, were made using the above procedure or modifications to the above procedure using the corresponding tiopyrazin-2-amine derivative and protected amine.

TABLE 4

| Example | Compound | Characterization | IC$_{50}$ (μM) |
|---|---|---|---|
| 2 | (structure shown, racemic) | $^1$H NMR (400 MHz, DMSO-d$_6$) δ ppm 7.62 (s, 1 H), 7.39 (d, J = 7.83 Hz, 1 H), 7.22 (t, J = 8.08 Hz, 1 H), 6.57 (d, J = 7.83 Hz, 1 H), 6.13 (s, 2 H), 4.03-4.21 (m, 2 H), 2.96-3.13 (m, 2 H), 2.63-2.72 (m, 1 H), 1.73-1.89 (m, 2 H), 1.48-1.69 (m, 3 H), 1.13-1.40 (m, 5 H). HRMS calcd for C$_{19}$H$_{24}$Cl$_2$N$_5$S (M + H)$^+$ 424.1129, found 424.1131. | 0.025 |

TABLE 4-continued

| Example | Compound | Characterization | IC$_{50}$ (μM) |
|---|---|---|---|
| 3 | (2,3-dichlorophenylthio-pyrazin-amine with 8-azaspiro[4.5]decane-NH$_2$, (R)) | $^1$H NMR (400 MHz, DMSO-d$_6$) δ ppm 7.63 (s, 1 H), 7.39 (d, J = 8.08 Hz, 1 H), 7.22 (t, J = 7.96 Hz, 1 H), 6.58 (d, J = 8.08 Hz, 1 H), 6.13 (s, 2 H), 4.06-4.21 (m, 2 H), 2.96-3.13 (m, 2 H), 2.71 (t, J = 7.45 Hz, 1 H), 1.71-1.93 (m, 2 H), 1.45-1.64 (m, 3 H), 1.13-1.42 (m, 5 H). HRMS calcd for C$_{19}$H$_{24}$Cl$_2$N$_5$S (M + H)$^+$ 424.1129, found 424.1129. | 0.010 |
| 4 | (2,3-dichlorophenylthio-pyrazin-amine with spiro[5.5]undecane-NH$_2$, racemic) | $^1$H NMR (400 MHz, DMSO-d$_6$) δ ppm 7.59 (s, 1 H), 7.39 (dd, J = 8.08, 1.26 Hz, 1 H), 7.18-7.25 (m, 1 H), 6.11 (s, 2 H), 3.94-4.05 (m, 2 H), 3.07-3.21 (m, 2 H), 2.40 (d, J = 4.55 Hz, 1 H), 1.81-2.00 (m, 2 H), 1.13-1.67 (m, 9 H), 0.96-1.07 (m, 1 H). HRMS calcd for C$_{20}$H$_{26}$Cl$_2$N$_5$S (M + H)$^+$ 438.1286, found 438.1283. | 0.032 |
| 5 | (2-(trifluoromethyl)pyridin-3-ylthio-pyrazin-amine with oxa-azaspiro-NH$_2$, chiral); (second structure shown below) | $^1$H NMR (400 MHz, CDCl$_3$) δ ppm 8.35 (dd, J = 4.5, 1.5 Hz, 1 H), 7.58 (s, 1 H), 7.42 (d, J = 8.1 Hz, 1 H), 7.24-7.15 (m, 1 H), 4.77 (s, 2 H), 4.13 (m, 2 H), 3.90 (m, 1 H), 3.78 (m, 1 H), 3.28-3.17 (m, 2 H), 3.06 (t, J = 6.9 Hz, 1 H), 2.27 (2, 1 H), 1.74-1.63 (m, 1 H), 1.63-1.54 (m, 3 H), 1.53-1.46 (m, 1 H), 1.21 (br. s, 2 H). HRMS calcd for C$_{18}$H$_{22}$F$_3$N$_6$OS (M + H)$^+$ 427.1528, found 427.1526. | 0.349 |
| 6 | (2,3-dichlorophenyl-pyrazin-amine with 8-azaspiro[4.5]decane-NH$_2$ cyclohexyl variant, racemic) | $^1$H NMR (400 MHz, DMSO-d$_6$) δ ppm 7.61 (dd, J = 7.96, 1.39 Hz, 1 H), 7.43-7.48 (m, 1 H), 7.35-7.42 (m, 1 H), 7.27-7.33 (m, 1 H), 5.57 (br. s., 2 H), 3.94 (dd, J = 12.76, 5.18 Hz, 2 H), 3.00-3.14 (m, 2 H), 2.40 (d, J = 4.55 Hz, 1 H), 1.79-1.99 (m, 2 H), 1.15-1.66 (m, 9 H), 0.96-1.07 (m, 1 H). HRMS calcd for C$_{20}$H$_{26}$Cl$_2$N$_5$ (M + H)$^+$ 406.1565, found 406.1563 | 0.074 |
| 7 | (2,3-dichlorophenyl-pyrazin-amine with spiro cyclopentyl-NH$_2$, racemic) | $^1$H NMR (400 MHz, DMSO-d$_6$) δ ppm 7.61 (dd, J = 7.96, 1.64 Hz, 1 H), 7.48 (s, 1 H), 7.35-7.42 (m, 1 H), 7.28-7.33 (m, 1 H), 5.53-5.63 (m, 2 H), 4.01-4.13 (m, 2 H), 2.99 (qd, J = 12.38, 2.78 Hz, 2 H), 1.71-1.91 (m, 2 H), 1.47-1.66 (m, 4 H), 1.13-1.40 (m, 5 H). HRMS calcd for C$_{19}$H$_{24}$Cl$_2$N$_5$ (M + H)$^+$ 392.1409, found 392.1417. | 0.073 |

Example 8

(R) and (S)-2-(6-amino-5-((2,3-dichlorophenyl)thio)pyrazin-2-yl)-2-azaspiro[3.3]heptan-5-amine

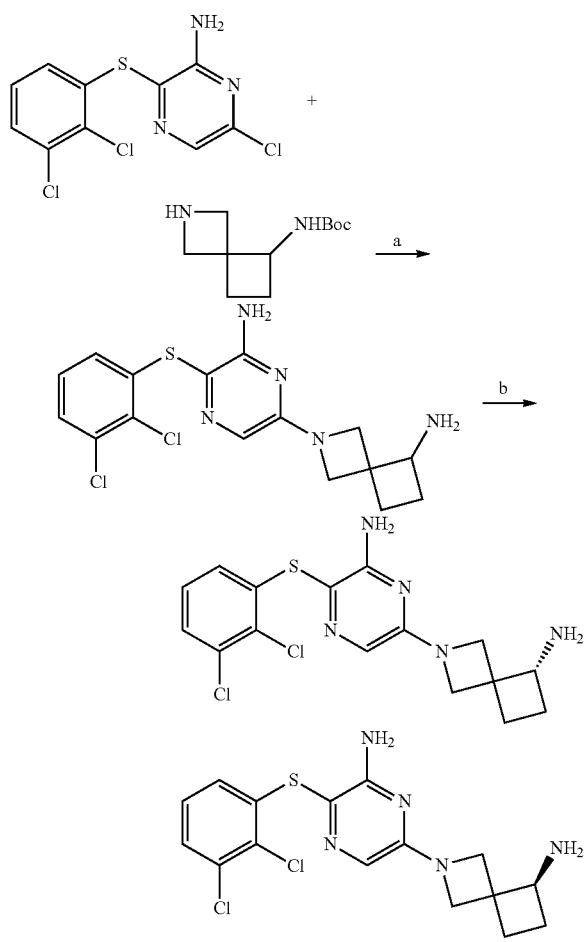

Step a:

A solution of 6-chloro-3-((2,3-dichlorophenyl)thio)pyrazin-2-amine (140 mg, 0.457 mmol) and tert-butyl 2-azaspiro[3.3]heptan-5-ylcarbamate (HCl salt, 125 mg, 0.502 mmol) in DIPEA (1 mL) was stirred for 24 h at 130° C. After cooling to RT, the volatiles were removed under reduced pressure. The resulting residue was dissolved in DCM (5 mL), TFA (0.5 mL) was added and the resulting mixture was stirred for 30 min at RT. The volatiles were removed under reduced pressure and the resulting residue was purified by HPLC (gradient elution 25-50% acetonitrile in water, 5 mM NH$_4$OH modifier) to give 2-(6-amino-5-((2,3-dichlorophenyl)thio)pyrazin-2-yl)-2-azaspiro[3.3]heptan-5-amine (75 mg, 0.186 mmol). $^1$H NMR (400 MHz, METHANOL-d$_4$) δ ppm 7.31 (dd, J=8.03, 1.51 Hz, 1H), 7.18 (s, 1H), 7.11 (t, J=8.03 Hz, 1H), 6.60 (dd, J=8.03, 1.51 Hz, 1H), 4.45 (d, J=8.78 Hz, 1H), 4.03 (d, J=9.03 Hz, 1H), 3.96 (d, J=9.03 Hz, 1H), 3.90 (d, J=8.78 Hz, 1H), 3.34-3.39 (partially overlapped with solvent, m, 1H), 2.12-2.25 (m, 1H), 1.90-2.11 (m, 2H), 1.52-1.67 (m, 1H). HRMS calcd for C$_{16}$H$_{18}$Cl$_2$N$_5$S (M+H)$^+$ 382.0660, found 382.0585. IC$_{50}$ is 5.36 μM.

Step b:

2-(6-amino-5-((2,3-dichlorophenyl)thio)pyrazin-2-yl)-2-azaspiro[3.3]heptan-5-amine (53.9 mg, 0.141 mmol) was further purified by Chiral SFC; column: OJ-H 21×250 mm, flow rate: 80 g per minute, mobile phase: 26% MeOH and 10 mM NH$_4$OH in CO$_2$, detection: 269 nm UV to obtain single enantiomer R$_t$ (P1)=3.7 min; IC$_{50}$ is 17.49 μM and R$_t$ (P2)=4.7 min.; IC$_{50}$ is 3.31 μM.

The following compounds of Formula I, as identified in table 5, were made using the above procedure or modifications to the above procedure using the corresponding pyrazin-2-amine derivative and protected amine.

TABLE 5

| Example | Compound | Characterization | IC$_{50}$ (μM) |
|---|---|---|---|
| 9 | racemic | $^1$H NMR (400 MHz, METHANOL-d$_4$) δ ppm 7.50 (dd, J = 7.91, 1.63 Hz, 1H), 7.29 (t, J = 7.91, Hz, 1 H), 7.21 (dd, J = 7.65, 1.63 Hz, 1 H), 6.98 (s, 1 H), 4.29 (d, J = 8.53 Hz, 1 H), 3.89 (d, J = 8.53 Hz, 1 H), 3.82 (d, J = 8.53 Hz, 1 H), 3.76 (d, J = 8.78 Hz, 1 H), 3.27 (partially overlapped with solvent, t, J = 8.41 Hz, 1 H), 2.03-2.16 (m, 1 H), 1.92-2.03 (m, 1 H), 1.82-1.92 (m, 1 H), 1.45-1.61 (m, 1 H). HRMS calcd for C$_{16}$H$_{18}$Cl$_2$N$_5$ (M + H)$^+$ 350.0939, found 350.0876. | 1.106 |

TABLE 5-continued

| Example | Compound | Characterization | IC$_{50}$ (μM) |
|---|---|---|---|
| 10a & 10b | | Chiral SFC purification performed as follows; column: Cellulos LUX-2 21 × 250 mm, flow rate: 75 g per minute, mobile phase: 45% MeOH and 10 mM NH$_4$OH in CO$_2$, detection: 354 nm UV to obtain single enantiomer R$_t$ (P1) = 3.3 min, R$_t$ (P2) = 5.6 min. $^1$H NMR (400 MHz, METHANOL-d$_4$) δ ppm 7.61 (dd, J = 7.78, 1.76 Hz, 1 H), 7.40 (t, J = 7.78 Hz, 1 H), 7.35 (dd, J = 7.53, 1.76 Hz, 1 H), 7.22 (s, 1 H), 3.80 (d, J = 10.79 Hz, 1 H), 3.35-3.61 (m, 4 H), 2.18-2.36 (m, 1 H), 2.05-2.18 (m, 1 H), 1.95-2.05 (m, 1 H), 1.66-1.90 (m, 3 H). HRMS calcd for C$_{17}$H$_{20}$C$_2$N$_5$ (M + H)$^+$ 364.1096, found 364.1078. | P1 = 0.548  P2 = 0.189 |
| 11a & 11b | | Chiral SFC purification performed as follows; column: AD-H 21 × 250 mm, flow rate: 75 g per minute, mobile phase: 50% MeOH and 10 mM NH$_4$OH in CO$_2$, detection: 354 nm UV to obtain single enantiomer R$_t$ (P1) = 2.2 min, R$_t$ (P2) = 3.6 min. $^1$H NMR (400 MHz, METHANOL-d$_4$) δ ppm 7.48 (dd, J = 7.78, 1.76 Hz, 1 H), 7.28 (t, J = 7.78 Hz, 1 H), 7.22 (dd, J = 7.53, 1.76 Hz, 1 H), 7.04 (s, 1 H), 3.55 (br. s., 1 H), 3.28-3.42 (m, 4 H), 2.05-2.20 (m, 2 H), 1.79-1.89 (m, 1 H), 1.60-1.73 (m, 3 H). HRMS calcd for C$_{17}$H$_{20}$Cl$_2$N$_5$ (M + H)$^+$ 364.1096, found 364.1082. | P1 = 0.365  P2 = 0.145 |

TABLE 5-continued

| Example | Compound | Characterization | IC$_{50}$ (μM) |
|---|---|---|---|
| | (structure) | | |
| | (structure) | | |
| 12a & 12b | (structures) | Chiral SFC purification performed as follows; column: AS-H 21 × 250 mm, flow rate: 75 g per minute, mobile phase: 40% IPA and 0.2% diethylamine in CO$_2$, detection: 354 nm UV to obtain single enantiomer R$_t$ (P1) = 2.0 min, R$_t$ (P2) = 3.1 min. $^1$H NMR (400 MHz, METHANOL-d$_4$) δ ppm 7.23 (s, 1 H), 7.18 (dd, J = 8.03, 1.51 Hz, 1 H), 6.93-7.05 (m, 1 H), 6.50 (dd, J = 8.03, 1.51 Hz, 1 H), 3.70 (d, J = 11.04 Hz, 1 H), 3.24-3.51 (m, 3 H), 2.07-2.24 (m, 1 H), 1.94-2.07 (m, 1 H), 1.89 (d, J = 5.77 Hz, 1 H), 1.54-1.82 (m, 4 H). HRMS calcd for C$_{17}$H$_{20}$Cl$_2$N$_5$S (M + H)$^+$ 396.0816, found 396.0798. | P1 = 5.787 P2 = 3.933 |
| 13a & 13b | (structures) | Chiral SFC purification performed as follows; column: AS-H 21 × 250 mm, flow rate: 75 g per minute, mobile phase: 45% IPA and 0.2% diethylamine in CO$_2$, detection: 354 nm UV to obtain single enantiomer R$_t$ (P1) = 2.1 min, R$_t$ (P2) = 3.5 min. $^1$H NMR (400 MHz, METHANOL-d$_4$) δ ppm 7.27-7.32 (m, 2 H), 7.11 (t, J = 7.91 Hz, 1 H), 6.60 (dd, J = 8.16, 1.38 Hz, 1 H), 3.64-3.76 (m, 1 H), 3.39-3.57 (m, 4 H), 2.14-2.32 (m, 2 H), 1.88-2.04 (m, 2 H), 1.68-1.88 (m, 2 H). HRMS calcd for C$_{17}$H$_{20}$Cl$_2$N$_5$S (M + H)$^+$ 396.0816, found 396.0799. | P1 = 0.354 P2 = 1.510 |

TABLE 5-continued

| Example | Compound | Characterization | IC$_{50}$ (μM) |
|---------|----------|------------------|----------------|

Example 14

7-(6-amino-5-((2,3-dichlorophenyl)thio)pyrazin-2-yl)-7-azaspiro[3.5]nonan-1-amine

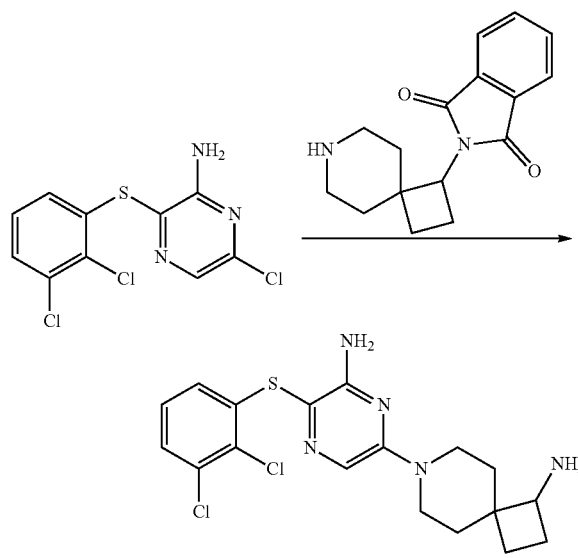

A solution of 6-chloro-3-((2,3-dichlorophenyl)thio)pyrazin-2-amine (140 mg, 0.457 mmol) and 2-(7-azaspiro[3.5]nonan-1-yl)isoindoline-1,3-dione (HCl salt, 154 mg, 0.502 mmol) in DIPEA (1 mL) was stirred for 16 h at 130° C. After cooling to RT, the volatiles were removed under reduced pressure. A solution of the resulting residue and hydrazine hydrate (29 μL, 0.602 mmol) in THF:MeOH (1:1, 1 mL) was stirred for 16 h at 55° C. After cooling to RT, the volatiles were removed under reduced pressure and the resulting residue was purified by HPLC (gradient elution 35-60% acetonitrile in water, 5 mM NH$_4$OH modifier) to give the title compound (78 mg, 0.502 mmol). $^1$H NMR (400 MHz, METHANOL-d$_4$) δ ppm 7.59 (s, 1H), 7.31 (dd, J=8.03, 1.51 Hz, 1H), 7.12 (t, J=8.03 Hz, 1H), 6.62 (dd, J=8.03, 1.51 Hz, 1H), 4.37 (d, J=13.55 Hz, 1H), 4.26 (d, J=13.55 Hz, 1H), 3.24-3.30 (partially overlapped with solvent, m, 1H), 3.07-3.20 (m, 1H), 2.92-3.06 (m, 1H), 2.26-2.39 (m, 1H), 1.87-2.07 (m, 2H), 1.57-1.87 (m, 4H), 1.34-1.42 (m, 1H). HRMS calcd for C$_{18}$H$_{22}$Cl$_2$N$_5$S (M+H)$^+$ 410.0973, found 410.1018; (racemic). IC$_{50}$ is 0.056 μM.

Chiral SFC purification of the above title compound performed as follows; column: AD-H 21×250 mm, flow rate: 80 g per minute, mobile phase: 46% MeOH and 10 mM NH$_4$OH in CO$_2$, detection: 274 nm UV to obtain single enantiomer R$_t$ (P1)=4.0 min and R$_t$ (P2)=5.5 min. (P1 (S-enantiomer (determined by X-ray)); IC$_{50}$ is 0.019 μM; (P2 (R-enantiomer)); IC$_{50}$ is 0.414 μM.

The following compounds of Formula I, as identified in table 6, were made using the above procedure or modifications to the above procedure using the corresponding pyrazin-2-amine derivative and phthalamide-protected amine.

TABLE 6

| Example | Compound | Characterization | IC$_{50}$ (μM) |
|---------|----------|------------------|----------------|
| 15 | | $^1$H NMR (400 MHz, METHANOL-d$_4$) δ ppm 7.53 (s, 1H), 6.86 (t, J = 8.0 Hz, 1 H), 6.62 (dd, J = 1.3, 8.1 Hz, 1 H), 6.02 (dd, J = 1.3, 7.8 Hz, 1 H), 4.37-4.10 (m, 2 H), 3.21-2.92 (m, 3 H), 2.32-2.18 (m, 1 H), 1.92-1.62 (m, 5 H), 1.61-1.49 (m, 2H). HRMS calcd for C$_{18}$H$_{24}$ClN$_6$S (M + H)$^+$ 391.1472, found 391.1486. | 0.016 |

TABLE 6-continued

| Example | Compound | Characterization | IC$_{50}$ (μM) |
|---|---|---|---|
| 16 | 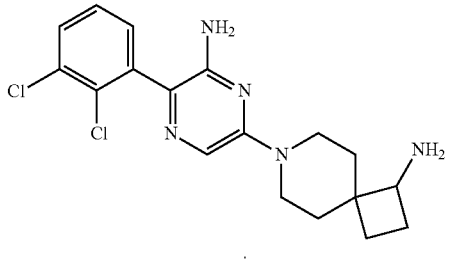 racemic | $^1$H NMR (400 MHz, DMSO-d6) δ ppm 7.61 (dd, J = 8.03, 1.51 Hz, 1 H), 7.49 (s, 1 H), 7.38 (t, J = 7.78 Hz, 1 H), 7.30 (dd, J = 7.53, 1.51 Hz, 1 H), 5.63 (s, 2 H), 4.03-4.19 (m, 1 H), 3.89-4.03 (m, 1 H), 3.34 (s, 2 H), 3.05 (ddd, J = 13.55, 8.53, 5.52 Hz, 1 H), 2.86-2.99 (m, 2 H), 2.00-2.14 (m, 1 H), 1.47-1.71 (m, 5 H), 1.28-1.47 (m, 2 H). HRMS calcd for C$_{18}$H$_{22}$Cl$_2$N$_5$ (M + H)$^+$ 378.1252, found 378.1217. | 0.145 |
| 17a & 17b | 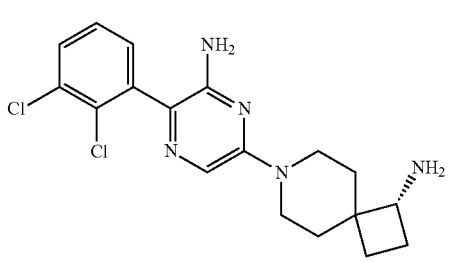 | Chiral SFC purification performed as follows; column: AD-H 21 × 250 mm, flow rate: 75 g per minute, mobile phase: 45% IPA and 10 mM NH$_4$OH in CO$_2$, detection: 354 nm UV to obtain single enantiomer R$_t$ (P1) = 3.4 min, R$_t$ (P2) = 4.6 min. $^1$H NMR (400 MHz, DMSO-d$_6$) δ ppm 7.61 (dd, J = 8.03, 1.51 Hz, 1 H), 7.49 (s, 1 H), 7.38 (t, J = 7.78 Hz, 1 H), 7.30 (dd, J = 7.53, 1.51 Hz, 1 H), 5.63 (s, 2 H), 4.03-4.19 (m, 1 H), 3.89-4.03 (m, 1 H), 3.34 (s, 2 H), 3.05 (ddd, J = 13.55, 8.53, 5.52 Hz, 1 H), 2.86-2.99 (m, 2 H), 2.00-2.14 (m, 1 H), 1.47-1.71 (m, 5 H), 1.28-1.47 (m, 2 H). HRMS calcd for C$_{18}$H$_{22}$Cl$_2$N$_5$ (M + H)$^+$ 378.1252, found 378.1245. | P1 = 0.120 P2 = 0.445 |
| 18 | 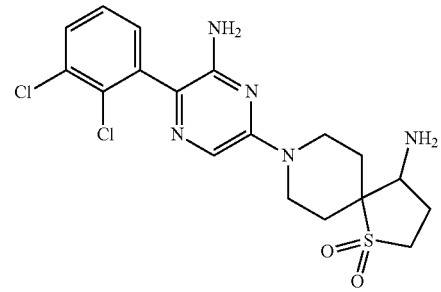 racemic | $^1$H NMR (400 MHz, METHANOL-d$_4$) δ ppm 7.53 (dd, J = 8.08, 1.77 Hz, 1 H) 7.41 (s, 1 H) 7.31 (t, J = 7.83 Hz, 1 H) 7.23 (dd, J = 7.71, 1.64 Hz, 1 H) 4.18 (m, 2 H), 3.73 (t, J = 7.20 Hz, 1 H) 3.44-3.61 (m, 2 H) 3.26-3.44 (m, 2 H) 2.54 (dddd, J = 13.99, 9.32, 6.88, 4.42 Hz, 1 H) 2.03-2.29 (m, 3 H) 1.86-2.01 (m, 1 H) 1.68-1.86 (m, 1 H). HRMS calcd for C$_{18}$H$_{22}$Cl$_2$N$_5$O$_2$S (M + H)$^+$ 442.0871, found 442.0848. | 3.552 |
| 19 | 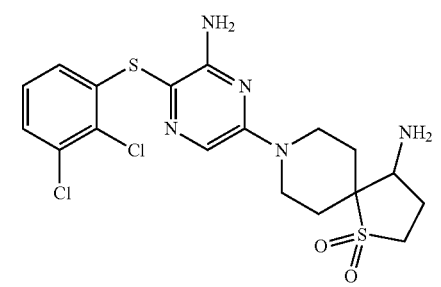 racemic | $^1$H NMR (400 MHz, METHANOL-d$_4$) δ ppm 7.52 (s, 1 H) 7.21 (dd, J = 8.08, 1.52 Hz, 1 H) 7.01 (t, J = 7.96 Hz, 1 H) 6.55 (dd, J = 8.08, 1.26 Hz, 1 H) 4.11-4.29 (m, 2 H), 3.73 (t, J = 7.20 Hz, 1 H) 3.52 (dtd, J = 13.93, 10.97, 10.97, 2.78 Hz, 2 H) 3.34-3.44 (m, 1 H) 3.25-3.34 (m, 1 H) 2.55 (dddd, J = 13.93, 9.38, 6.88, 4.42 Hz, 1 H) 2.04-2.28 (m, 3 H) 1.85-2.00 (m, 1 H) 1.68-1.85 (m, 1 H). HRMS calcd for C$_{18}$H$_{22}$Cl$_2$N$_5$O$_2$S$_2$ (M + H)$^+$ 474.0592, found 474.0569. | 4.094 |

Example 20

(S)-7-(6-amino-5-((2-(trifluoromethyl)pyridin-3-yl)thio)pyrazin-2-yl)-7-azaspiro[3.5]nonan-1-amine

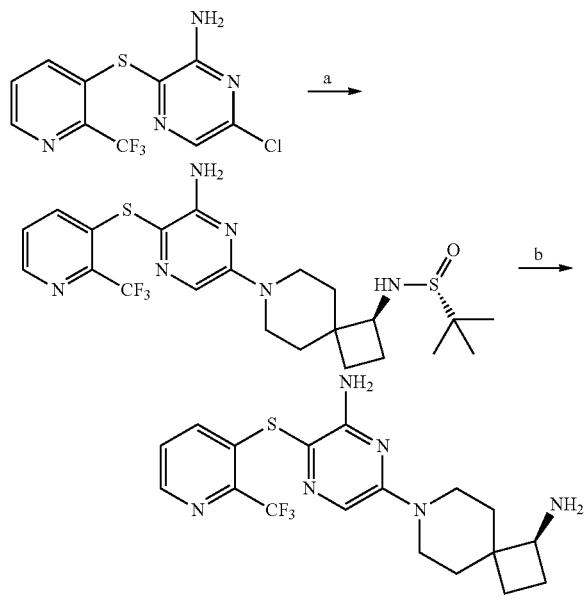

Step a:

A mixture of 6-chloro-3-((2-(trifluoromethyl)pyridin-3-yl)thio)pyrazin-2-amine (230 mg, 0.750 mmol) and (R)-2-methyl-N—((S)-7-azaspiro[3.5]nonan-1-yl)propane-2-sulfinamide (238 mg, 0.975 mmol) in DIPEA (3.7 mL) was stirred for 10 h at 105° C. After cooling to RT, the volatiles were removed under reduced pressure and the resulting residue was purified by silica chromatography (5 to 70% gradient of EtOAc/heptane) to give (R)—N—((S)-7-(6-amino-5-((2-(trifluoromethyl)pyridin-3-yl)thio)pyrazin-2-yl)-7-azaspiro[3.5]nonan-1-yl)-2-methylpropane-2-sulfinamide (172 mg, 0.334 mmol) as a white solid. MS m/z 515.2 (M+H)$^+$.

Step b:

A solution of (R)—N—((S)-7-(6-amino-5-((2-(trifluoromethyl)pyridin-3-yl)thio)pyrazin-2-yl)-7-azaspiro[3.5]nonan-1-yl)-2-methylpropane-2-sulfinamide (142 mg, 0.376 mmol) and HCl (4 M in dioxane, 414 μL, 1.66 mmol) in DCM (1.4 mL) was stirred for 20 min at 40° C. After cooling to RT, HCl (1 M in H$_2$O) was added and the resulting aqueous mixture was extracted with DCM. The aqueous phase was basified with NH$_4$OH (28% in H$_2$O) until pH 12 and it was extracted with DCM (3×20 mL). The combined organic layers were washed with brine, dried over MgSO$_4$, filtered and the volatiles were removed under reduced pressure to give (S)-7-(6-amino-5-((2-(trifluoromethyl)pyridin-3-yl)thio)pyrazin-2-yl)-7-azaspiro[3.5]nonan-1-amine (93 mg, 0.227 mmol). $^1$H NMR (400 MHz, DMSO-d$_6$) δ ppm 8.40-8.53 (m, 1H), 7.61-7.69 (m, 1H), 7.55 (dd, J=8.0, 4.5 Hz, 1H), 7.29 (d, J=8.0 Hz, 1H), 6.19 (s, 2H), 4.11-4.24 (m, 1H), 3.99-4.06 (m, 1H), 3.06-3.20 (m, 2H), 2.90-3.06 (m, 2H), 1.50-1.74 (m, 4H), 1.33-1.49 (m, 2H). HRMS calcd for C$_{18}$H$_{21}$F$_3$N$_6$S (M+H)$^+$ 411.1566, found 411.1579. IC$_{50}$ is 0.038 μM.

Example 21

(S)-5-amino-3-(1-amino-8-azaspiro[4.5]decan-8-yl)-6-((2-(trifluoromethyl)pyridin-3-yl)thio)pyrazine-2-carboxamide

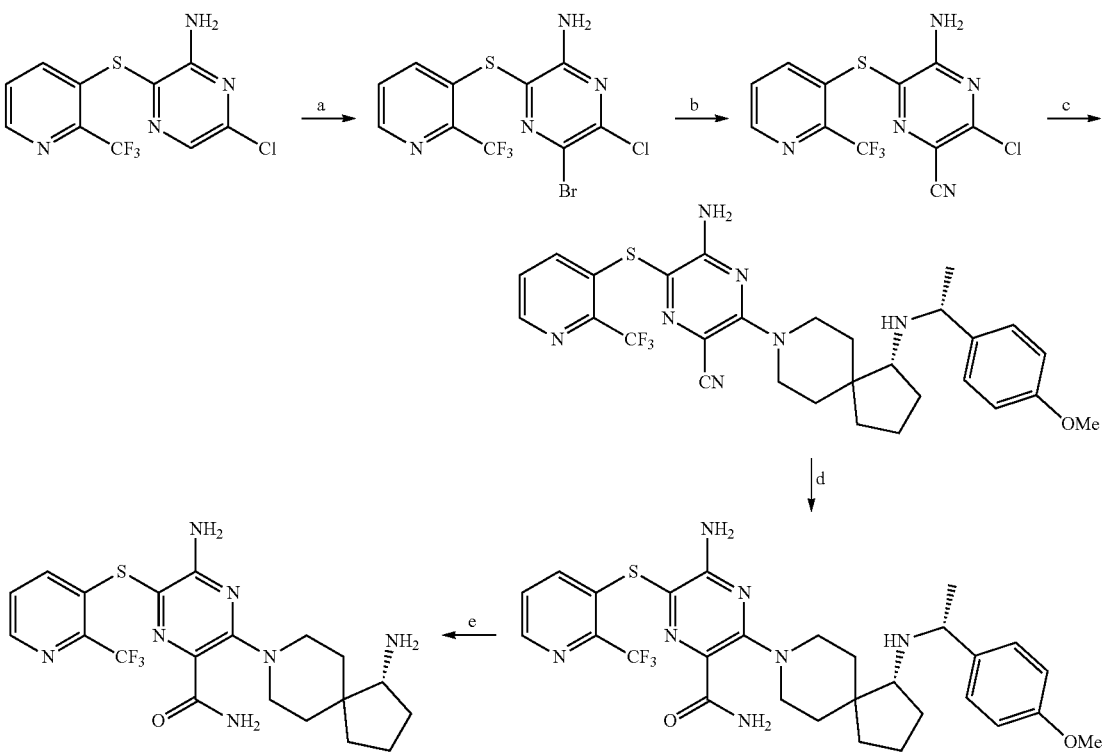

Step a:
To a solution of 6-chloro-3-((2-(trifluoromethyl)pyridin-3-yl)thio)pyrazin-2-amine (1.2 g, 2.119 mmol) in DCM (30 mL) was added at 0° C. NBS (745 mg, 4.19 mmol) in one portion. The resulting mixture was stirred vigorously for 30 min at 0° C. and for 1 h at RT. The clear solution was quenched with water and extracted with DCM. The combined organic layers were subsequently washed with water, brine, dried over $Na_2SO_4$, filtered and concentrated. The resulting residue was purified by silica chromatography (0 to 50% gradient of EtOAc/heptane) to give 5-bromo-6-chloro-3-((2-(trifluoromethyl)pyridin-3-yl)thio)pyrazin-2-amine (938 mg, 2.51 mmol). MS m/z 387.2 $(M+H)^+$.

Step b:
A mixture of 5-bromo-6-chloro-3-((2-(trifluoromethyl)pyridin-3-yl)thio)pyrazin-2-amine (750 mg, 1.945 mmol) and copper(I) cyanide (348 mg, 3.89 mmol) in DMF (7 mL) was stirred for 14 h at 120° C. After cooling to RT, the reaction was filtered through a pad of Celite followed by MeOH (50 mL) wash. The volatiles were removed under reduced pressure and the resulting residue was purified by silica chromatography (0 to 100% gradient of EtOAc/heptane) to afford 5-amino-3-chloro-6-((2-(trifluoromethyl)pyridin-3-yl)thio)pyrazine-2-carbonitrile (301 mg, 0.907 mmol). MS m/z 332.3 $(M+H)^+$.

Step c:
A mixture of 5-amino-3-chloro-6-((2-(trifluoromethyl)pyridin-3-yl)thio)pyrazine-2-carbonitrile (52 mg, 0.157 mmol) and (S)—N—((R)-1-(4-methoxyphenyl)ethyl)-8-azaspiro[4.5]decan-1-amine (90 mg, 0.314 mmol) in DIPEA (0.246 mL) was stirred for 1 h at 135° C. After cooling to RT, volatiles were removed under reduced pressure and the resulting residue was purified by silica chromatography (0 to 100% gradient of EtOAc/heptane) to afford 5-amino-3-((S)-1-(((R)-1-(4-methoxyphenyl)ethyl)amino)-8-azaspiro[4.5]decan-8-yl)-6-((2-(trifluoromethyl)pyridin-3-yl)thio)pyrazine-2-carbonitrile (77 mg, 0.132 mmol). MS m/z 584.5 $(M+H)^+$.

Step d:
A mixture of 5-amino-3-((S)-1-(((R)-1-(4-methoxyphenyl)ethyl)amino)-8-azaspiro[4.5]decan-8-yl)-6-((2-(trifluoromethyl)pyridin-3-yl)thio)pyrazine-2-carbonitrile (77 mg, 0.132 mmol) and NaOH (1 M in $H_2O$, 1.451 mL, 1.451 mmol) in MeOH (3.5 mL) was stirred in a microwave reactor for 35 min at 110° C. After cooling to RT, the volatiles were removed under reduced pressure to give 5-amino-3-((S)-1-(((R)-1-(4-methoxyphenyl)ethyl)amino)-8-azaspiro[4.5]decan-8-yl)-6-((2-(trifluoromethyl)pyridin-3-yl)thio)pyrazine-2-carboxamide (79 mg, 0.132 mmol) which was used in next step without further purification. MS m/z 602.5 $(M+H)^+$.

Step e:
A solution of 5-amino-3-((S)-1-(((R)-1-(4-methoxyphenyl)ethyl)amino)-8-azaspiro[4.5]decan-8-yl)-6-((2-(trifluoromethyl)pyridin-3-yl)thio)pyrazine-2-carboxamide (79 mg, 0.132 mmol) in TFA (1.2 mL, 15.76 mmol) was stirred in a microwave reactor at 100° C. until no starting material remained (3 h, monitored by LCMS). The volatiles were removed under reduced pressure and the resulting residue was purified by HPLC (gradient elution 25-50% acetonitrile in water, 5 mM $NH_4OH$ modifier) to give (S)-5-amino-3-(1-amino-8-azaspiro[4.5]decan-8-yl)-6-((2-(trifluoromethyl)pyridin-3-yl)thio)pyrazine-2-carboxamide (18.8 mg, 0.039 mmol). $^1H$ NMR (400 MHz, METHANOL-$d_4$) δ ppm 8.43 (dd, J=4.5, 1.4 Hz, 1H), 7.57 (dd, J=8.1, 1.3 Hz, 1H), 7.46 (dd, J=8.2, 4.5 Hz, 1H), 3.92-3.88 (m, 2H), 3.20-3.08 (m, 2H), 2.77 (t, J=7.4 Hz, 1H), 2.04-1.96 (m, 1H), 1.829-1.82 (m, 1H), 1.78-1.61 (m, 4H), 1.53 (ddd, J=12.3, 9.2, 5.7 Hz, 1H), 1.43 (ddd, J=9.8, 4.9, 2.0 Hz, 1H), 1.39-1.32 (m, 1H), 1.30-1.23 (m, 1H). HRMS calcd for $C_{20}H_{25}F_3N_7OS$ $(M+H)^+$ 468.1715, found 468.1761; $IC_{50}$ is 0.010 μM.

The following compounds of Formula I, as identified in table 7, were made using the above procedure or modifications to the above procedure using the corresponding amine and amine deprotection method.

TABLE 7

| Example | Compound | Characterization | $IC_{50}$ (μM) |
|---|---|---|---|
| 22 | ![structure] | $^1H$ NMR (400 MHz, METHANOL-$d_4$) δ ppm 8.33 (dd, J = 1.3, 4.5 Hz, 1 H), 7.50-7.43 (m, 1 H), 7.36 (dd, J = 4.5, 8.1 Hz, 1 H), 3.92-3.81 (m, 1 H), 3.81-3.69 (m, 1 H), 3.11-3.00 (m, 1 H), 3.00-2.86 (m, 2 H), 2.18-2.06 (m, 1 H), 1.76-1.52 (m, 5 H), 1.48-1.36 (m, 2 H). HRMS calcd for $C_{19}H_{23}F3N_7OS$ $(M + H)^+$ 454.1673, found 454.1645 | 0.053 |

Example 23

(S)-8-(5-amino-6-((2-(trifluoromethyl)pyridin-3-yl)thio)-1,2,4-triazin-3-yl)-8-azaspiro[4.5]decan-1-amine

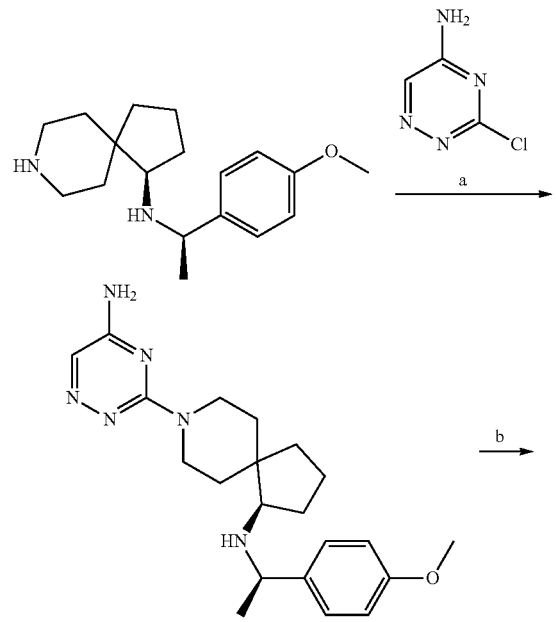

-continued

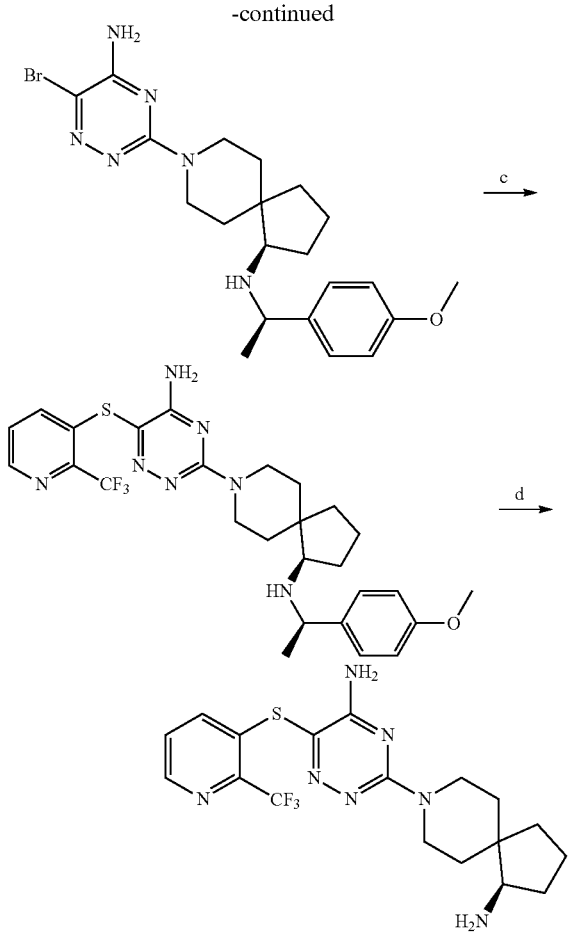

Step a:

A mixture of 3-chloro-1,2,4-triazin-5-amine (70 mg, 0.536 mmol), (S)—N—((R)-1-(4-methoxyphenyl)ethyl)-8-azaspiro[4.5]decan-1-amine (247 mg, 0.644 mmol), and N-methylmorpholine (177 μL, 1.609 mmol) in MeCN (1 mL) and NMP (0.1 mL) was irradiated in a microwave reactor for 45 min at 90° C. After cooling to RT, the resulting residue was directly purified by silica chromatography (0 to 5% gradient of MeOH/DCM) to afford (S)-8-(5-amino-1,2,4-triazin-3-yl)-N—((R)-1-(4-methoxyphenyl)ethyl)-8-azaspiro[4.5]decan-1-amine that was used in next step without further purification. MS m/z 383.5 (M+H)$^+$.

Step b:

To a solution of (S)-8-(5-amino-1,2,4-triazin-3-yl)-N—((R)-1-(4-methoxyphenyl)ethyl)-8-azaspiro[4.5]decan-1-amine (194 mg, 0.507 mmol) in DCM (8 mL) was added, at 0° C., NBS (97 mg, 0.543 mmol) in one portion. After stirring for 20 min at 0° C., the clear solution was quenched with few drops of $Na_2CO_3$ aq. and it was extracted with DCM. The combined organic layer was dried over $MgSO_4$, filtered and the volatiles were removed under reduced pressure. The resulting residue was purified by silica chromatography (0 to 100% gradient of EtOAc/heptane) to give (S)-8-(5-amino-6-bromo-1,2,4-triazin-3-yl)-N—((R)-1-(4-methoxyphenyl)ethyl)-8-azaspiro[4.5]decan-1-amine (77.9 mg, 0.169 mmol). MS m/z 463.4 (M+H)$^+$.

Step c:

A mixture of (S)-8-(5-amino-6-bromo-1,2,4-triazin-3-yl)-N—((R)-1-(4-methoxyphenyl)ethyl)-8-azaspiro[4.5]decan-1-amine (54.1 mg, 0.117 mmol), 2-(trifluoromethyl)pyridine-3-thiol (21 mg, 0.117 mmol), XantPhos (7.46 mg, 0.013 mmol), $Pd_2(dba)_3$ (5.37 mg, 0.0058 mmol), and DIPEA (0.041 mL, 0.234 mmol) in dioxane (1 mL) was stirred in a microwave reactor for 1.5 h at 130° C. After cooling to RT, the reaction was filtered through a pad of Celite followed by EtOAc (10 mL) wash. The volatiles were removed under reduced pressure to give (S)-8-(5-amino-6-((2-(trifluoromethyl)pyridin-3-yl)thio)-1,2,4-triazin-3-yl)-N—((R)-1-(4-methoxyphenyl)ethyl)-8-azaspiro[4.5]decan-1-amine (65 mg, 0.116 mmol). MS m/z 560.5 (M+H)$^+$.

Step d:

A solution of (S)-8-(5-amino-6-((2-(trifluoromethyl)pyridin-3-yl)thio)-1,2,4-triazin-3-yl)-N—((R)-1-(4-methoxyphenyl)ethyl)-8-azaspiro[4.5]decan-1-amine (65 mg, 0.116 mmol) in TFA (1.253 mL, 16.26 mmol) was stirred at 100° C. until no starting material remained (1.5 h, monitored by LC/MS), the volatiles were removed under reduced pressure, the resulting residue was diluted with water, and it was extracted with $Et_2O$ (3×10 mL). The aqueous layer was basified to pH 12 using $NH_4OH$ (28% in water), and it was extracted with DCM (3×10 mL). The combined organic layers were washed with brine, dried over $Na_2SO_4$, filtered and the volatiles were removed under reduced pressure. The resulting residue was purified by HPLC (gradient elution 25-50% acetonitrile in water, 5 mM $NH_4OH$ modifier) to give (S)-8-(5-amino-6-((2-(trifluoromethyl)pyridin-3-yl)thio)-1,2,4-triazin-3-yl)-8-azaspiro[4.5]decan-1-amine (14.5 mg, 0.032 mmol). $^1$H NMR (400 MHz, METHANOL-$d_4$) δ ppm 8.50-8.45 (m, 1H), 7.60-7.54 (m, 1H), 7.53-7.46 (m, 1H), 4.64-4.50 (m, 2H), 3.22-3.09 (m, 2H), 2.88 (t, J=7.3 Hz, 1H), 2.11-2.00 (m, 1H), 1.94-1.86 (m, 1H), 1.84-1.74 (m, 1H), 1.74-1.63 (m, 3H), 1.59-1.46 (m, 2H), 1.45-1.39 (m, 1H), 1.39-1.31 (m, 1H). HRMS calcd for $C_{18}H_{23}F_3N_7S$ (M+H)$^+$ 426.1688, found 426.1667. $IC_{50}$ is 0.290 μM.

Example 24

(S)-8-(4-amino-5-((2-(trifluoromethyl)pyridin-3-yl)thio)pyrimidin-2-yl)-8-azaspiro[4.5]decan-1-amine

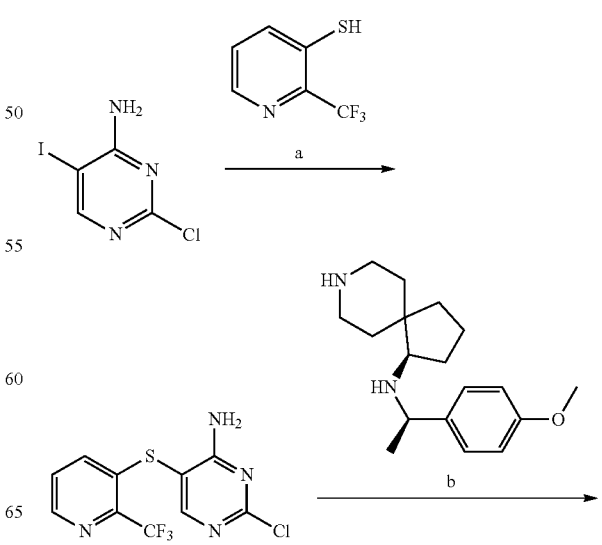

-continued

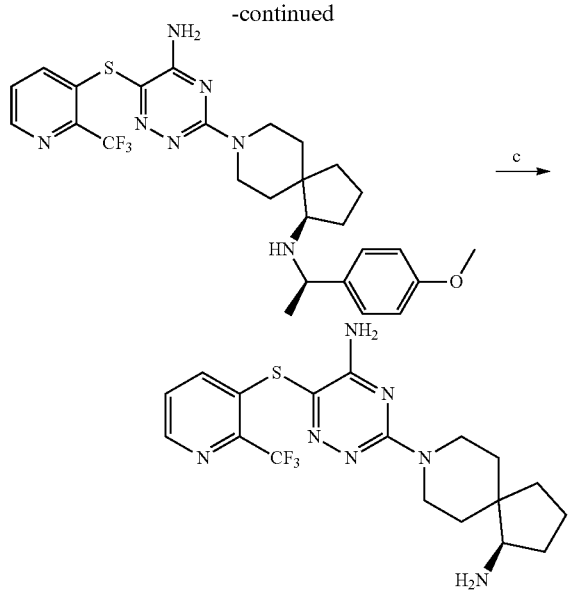

Step a:

A mixture of 2-(trifluoromethyl)pyridine-3-thiol (150 mg, 0.837 mmol), 2-chloro-5-iodopyrimidin-4-amine (267 mg, 1.047 mmol), XantPhos (53.3 mg, 0.092 mmol), Pd$_2$(dba)$_3$ (38.3 mg, 0.042 mmol), and DIPEA (0.292 mL, 1.674 mmol) in dioxane (1 mL) was stirred in a microwave reactor for 1.5 h at 130° C. After cooling to RT, the reaction was filtered through a pad of Celite followed by EtOAc (10 mL) wash. The volatiles were removed under reduced pressure to give 2-chloro-5-((2-(trifluoromethyl)pyridin-3-yl)thio)pyrimidin-4-amine (141 mg, 0.460 mmol). MS m/z 307.4 (M+H)$^+$.

Step b:

A mixture of 2-chloro-5-((2-(trifluoromethyl)pyridin-3-yl)thio)pyrimidin-4-amine (70 mg, 0.228 mmol) and (S)—N—((R)-1-(4-methoxyphenyl)ethyl)-8-azaspiro[4.5]decan-1-amine (105 mg, 0.274 mmol) in DIPEA (0.359 mL) was stirred in a microwave reactor for 1.5 h at 135° C. After cooling to RT, the volatiles were removed under reduced pressure to give (S)-8-(4-amino-5-((2-(trifluoromethyl)pyridin-3-yl)thio)pyrimidin-2-yl)-N—((R)-1-(4-methoxyphenyl)ethyl)-8-azaspiro[4.5]decan-1-amine (128 mg, 0.228 mmol). MS m/z 559.5 (M+H)$^+$.

Step c:

A solution of (S)-8-(4-amino-5-((2-(trifluoromethyl)pyridin-3-yl)thio)pyrimidin-2-yl)-N—((R)-1-(4-methoxyphenyl)ethyl)-8-azaspiro[4.5]decan-1-amine (128 mg, 0.229 mmol) in TFA (2.471 mL, 32.1 mmol) was stirred at 100° C. until no starting material remained (1.5 h, monitored by LCMS), the volatiles were removed under reduced pressure, the resulting residue was diluted with water, and it was then extracted with Et$_2$O (3×10 mL). The aqueous layer was basified to pH 12 using NH$_4$OH (28% in water), and it was extracted with DCM (3×10 mL). The combined organic layers were washed with brine, dried over Na$_2$SO$_4$, filtered and the volatiles were removed under reduced pressure. The resulting residue was purified by HPLC (gradient elution 35-60% acetonitrile in water, 5 mM NH$_4$OH modifier), to give (S)-8-(4-amino-5-((2-(trifluoromethyl)pyridin-3-yl)thio)pyrimidin-2-yl)-8-azaspiro[4.5]decan-1-amine (32 mg, 0.072 mmol). $^1$H NMR (400 MHz, METHANOL-d$_4$) δ ppm 8.41-8.35 (m, 1H), 8.00 (s, 1H), 7.47-7.43 (m, 2H), 4.66-4.45 (m, 2H), 3.18-3.06 (m, 2H), 2.81 (t, J=7.3 Hz, 1H), 2.09-1.97 (m, 1H), 1.94-1.86 (m, 1H), 1.81-1.72 (m, 1H), 1.69-1.62 (m, 2H), 1.59-1.53 (m, 2H), 1.49-1.44 (m, 1H), 1.40-1.35 (m, 1H), 1.33-1.25 (m, 1H). HRMS calcd for C$_{19}$H$_{24}$F$_3$N$_6$S (M+H)$^+$425.1735, found 425.1741; IC$_{50}$ is 2.78 μM.

Example 25

(R)-5-amino-3-(1-amino-8-azaspiro[4.5]decan-8-yl)-6-((3-chloro-2-(trifluoromethyl)pyridin-4-yl)thio)pyrazine-2-carboxamide

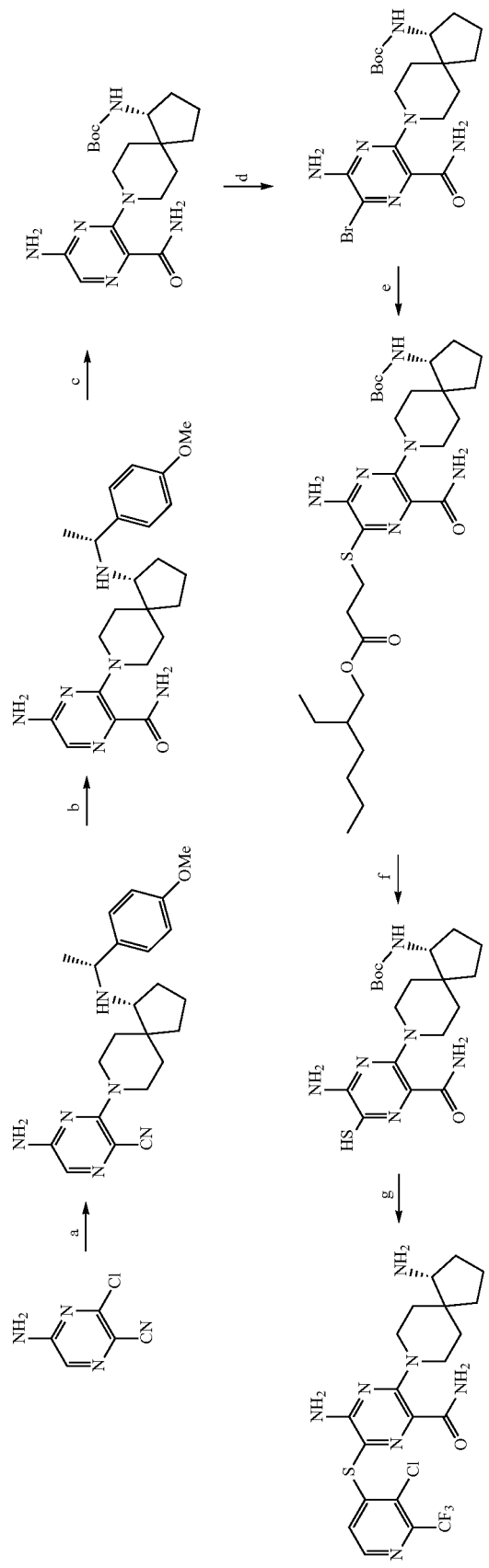

Step a:

A solution of 5-amino-3-chloropyrazine-2-carbonitrile (1.55 g, 10.0 mmol) and (R)—N—((R)-1-(4-methoxyphenyl)ethyl)-8-azaspiro[4.5]decan-1-amine (2.88 g, 10.0 mmol) in DIPEA (10 µL) and NMP (5 mL) was stirred for 16 h at 110° C. After cooling to RT, the reaction mixture was poured into a separation funnel containing NaHCO$_3$ aq. and it was extracted with EtOAc. The combined organic phases were dried over MgSO$_4$, filtered and the volatiles were removed under reduced pressure. The resulting residue was purified by silica chromatography (0 to 5% gradient of MeOH/DCM) to give 5-amino-3-((R)-1-(((R)-1-(4-methoxyphenyl)ethyl)amino)-8-azaspiro[4.5]decan-8-yl)pyrazine-2-carbonitrile (2.74 g, 6.74 mmol). MS m/z 407.3 (M+H)$^+$.

Step b:

(Note: This reaction was run in 4 batches of 500 mg each). A solution of 5-amino-3-((R)-1-(((R)-1-(4-methoxyphenyl)ethyl)amino)-8-azaspiro[4.5]decan-8-yl)pyrazine-2-carbonitrile (500 mg, 1.23 mmol) in MeOH (8 mL) and NaOH (2.5 M in H$_2$O, 5 mL, 12.3 mmol) was stirred in a microwave reactor for 90 min at 130° C. After cooling to RT, the resulting mixture was purified by HPLC (35-60% gradient of acetonitrile/water, 5 mM NH$_4$OH modifier) to give 5-amino-3-((R)-1-(((R)-1-(4-methoxyphenyl)ethyl)amino)-8-azaspiro[4.5]decan-8-yl)pyrazine-2-carboxamide (160 mg/reaction, 640 mg total, 1.51 mmol). MS m/z 425.3 (M+H)$^+$.

Step c:

A solution of 5-amino-3-((R)-1-(((R)-1-(4-methoxyphenyl)ethyl)amino)-8-azaspiro[4.5]decan-8-yl)pyrazine-2-carboxamide (615 mg, 1.45 mmol) in TFA (11 mL) was stirred for 1 h at 100° C. The volatiles were removed under reduced pressure. A solution of the resulting residue, DIPEA (1.2 mL, 6.89 mmol), and Boc$_2$O (330 mg, 1.516 mmol) in DCM (15 mL) was stirred for 2 h at RT. The volatiles were removed under reduced pressure and the resulting residue was purified by silica chromatography (1 to 10% gradient of MeOH/DCM) to give (R)-tert-butyl (8-(6-amino-3-carbamoylpyrazin-2-yl)-8-azaspiro[4.5]decan-1-yl)carbamate (538 mg, 1.378 mmol). MS m/z 391.0 (M+H)$^+$.

Step d:

A solution of (R)-tert-butyl (8-(6-amino-3-carbamoylpyrazin-2-yl)-8-azaspiro[4.5]decan-1-yl)carbamate (538 mg, 1.378 mmol), and NBS (270 mg, 1.516 mmol) in DCM (5 mL) was stirred for 20 min at 0° C. The reaction mixture was quenched with MeOH (2 mL) and stirred for 20 min at RT. The resulting mixture was poured into a separation funnel containing aq NaHCO$_3$. and it was extracted with DCM. The combined organic phases were dried over MgSO$_4$, filtered and the volatiles were removed under reduced pressure to give (R)-tert-butyl (8-(6-amino-5-bromo-3-carbamoylpyrazin-2-yl)-8-azaspiro[4.5]decan-1-yl)carbamate (627 mg, 1.336 mmol). MS m/z 471.2 (M+H)$^+$.

Step e:

To a solution of (R)-tert-butyl (8-(6-amino-5-bromo-3-carbamoylpyrazin-2-yl)-8-azaspiro[4.5]decan-1-yl)carbamate (627 mg, 1.336 mmol), XantPhos (77 mg, 0.134 mmol), and Pd$_2$(dba)$_3$ (61.2 mg, 0.067 mmol) in dioxane (3 mL) was added (at RT and under N$_2$) 2-ethylhexyl-3-mercaptopropanoate (334 µL, 1.469 mmol) followed by addition of DIPEA (467 µL, 2.67 mmol). The resulting solution was stirred in a microwave reactor for 1 h at 90° C. After cooling to RT, the reaction was filtered through a pad of Celite followed by EtOAc (5 mL) wash. The combined filtrates were concentrated and the resulting residue was purified by silica chromatography (0 to 10% gradient of MeOH/DCM) to give 2-ethylhexyl 3-((3-amino-5-((R)-1-((tert-butoxycarbonyl)amino)-8-azaspiro[4.5]decan-8-yl)-6-carbamoylpyrazin-2-yl)thio)propanoate (574 mg, 0.946 mmol). MS m/z 607.4 (M+H)$^+$.

Step f:

To a solution of 2-ethylhexyl 3-((3-amino-5-((R)-1-((tert-butoxycarbonyl)amino)-8-azaspiro[4.5]decan-8-yl)-6-carbamoylpyrazin-2-yl)thio)propanoate (574 mg, 0.946 mmol) in THF (3 mL) was added (at −78° C. and under N$_2$) potassium tert-butoxide (1 M in THF, 2.84 mL, 2.84 mmol). After stirring vigorously at −78° C. for 10 min, the reaction was quenched with K$_2$CO$_3$ aq. (2 M, 500 µL) and the volatiles were removed under reduced pressure. The resulting residue was purified by HPLC (15 to 40% gradient of acetonitrile/water, 5 mM NH$_4$OH modifier) to give (R)-tert-butyl (8-(6-amino-3-carbamoyl-5-mercaptopyrazin-2-yl)-8-azaspiro[4.5]decan-1-yl)carbamate (280 mg, 0.663 mmol). MS m/z 423.4 (M+H)$^+$.

Step g:

To a solution of (R)-tert-butyl (8-(6-amino-3-carbamoyl-5-mercaptopyrazin-2-yl)-8-azaspiro[4.5]decan-1-yl)carbamate (88 mg, 0.208 mmol), 3-chloro-4-iodo-2-(trifluoromethyl)pyridine (80 mg, 0.260 mmol), XantPhos (12.1 mg, 0.021 mmol), and Pd$_2$(dba)$_3$ (9.6 mg, 0.01 mmol) in dioxane (0.5 mL) was added (at RT and under N$_2$) DIPEA (110 µL, 0.625 mmol). The resulting solution was stirred in a microwave reactor for 1 h at 90° C. After cooling to RT, the reaction was diluted with EtOAc and it was filtered through a pad of Celite followed by EtOAc (5 mL) wash. The combined filtrates were concentrated and dried under vacuum. A solution of the resulting residue in DCM (1 mL) and TFA (400 µL) was stirred for 10 min at RT. The volatiles were removed under reduce pressure and the resulting residue was purified by HPLC (gradient elution 25-50% acetonitrile in water, 5 mM NH$_4$OH modifier) to give (R)-5-amino-3-(1-amino-8-azaspiro[4.5]decan-8-yl)-6-((3-chloro-2-(trifluoromethyl)pyridin-4-yl)thio)pyrazine-2-carboxamide (60 mg, 0.120 mmol). $^1$H NMR (400 MHz, METHANOL-d$_4$) δ ppm 8.18 (d, J=5.05 Hz, 1H). 6.85 (d, J=5.31 Hz, 1H). 3.87 (t, J=13.89 Hz, 2H). 2.98-3.14 (m, 2H), 2.72 (t, J=7.33 Hz, 1H). 1.86-2.02 (m, 1H). 1.73-1.81 (m, 1H). 1.43-1.72 (m, 5H). 1.17-1.41 (m, 3H). $^{19}$F NMR (376 MHz, METHANOL-d$_4$) δ ppm −67.22 (s, 1F). HRMS calcd for C$_{20}$H$_{24}$ClF$_3$N$_7$OS (M+H)$^+$ 502.1404, found 502.1398. IC$_{50}$ is 0.058 µM.

Example 26

(R)-8-(6-amino-5-((2-amino-3-chloropyridin-4-yl)thio)pyrazin-2-yl)-8-azaspiro[4.5]decan-1-amine

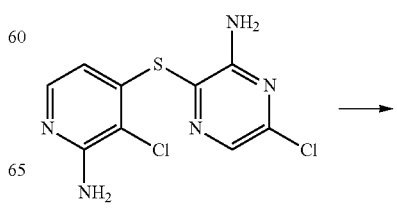

123

-continued

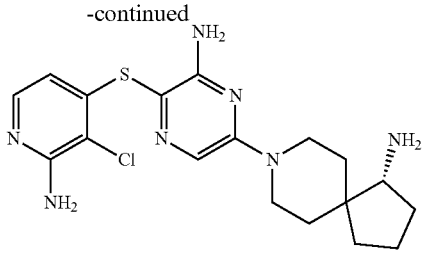

A mixture of 3-((2-amino-3-chloropyridin-4-yl)thio)-6-chloropyrazin-2-amine (67 mg, 0.233 mmol) and (R)-2-methyl-N—((R)-8-azaspiro[4.5]decan-1-yl)propane-2-sulfinamide (120 mg, 0.465 mmol) in DIPEA (2 mL) was stirred for 5 h at 130° C. After cooling to RT, the volatiles were removed under reduced pressure. A solution of the resulting residue in dioxane (5 mL) and HCl (4 M in dioxane, 1 mL) was stirred for 1 h at 40° C. The volatiles were remove under reduced pressure and the resulting residue was purified by HPLC (gradient elution 25-50% acetonitrile in water, 5 mM NH$_4$OH modifier). The resulting residue was further purified by SFC (Princeton DEAP 20×150 mm, flow rate: 80 g per minute, mobile phase: 20-40% MeOH in CO$_2$ within 5.7 min, mass triggered collection, oven temperature 40° C., back pressure 120 bar) to give (R)-8-(6-amino-5-((2-amino-3-chloropyridin-4-yl)thio)pyrazin-2-yl)-8-azaspiro[4.5]decan-1-amine (23 mg, 0.057 mmol). $^1$H NMR (400 MHz, METHANOL-d$_4$) δ ppm 7.50-7.64 (m, 2H), 5.91 (d, J=5.77 Hz, 1H), 4.26 (t, J=13.18 Hz, 2H), 3.03-3.20 (m, 2H), 2.79 (t, J=7.53 Hz, 1H), 1.95-2.11 (m, 1H), 1.83-1.95 (m, 1H), 1.52-1.82 (m, 5H), 1.37-1.52 (m, 2H), 1.32 (dd, J=13.30, 2.01 Hz, 1H). HRMS calcd for C$_{18}$H$_{25}$ClN$_7$S (M+H)$^+$ 406.1581, found 406.1576. IC$_{50}$ is 0.014 μM.

The following compounds were synthesized using the above procedure or modifications to the above procedure using the corresponding amine protected amine.

124

-continued

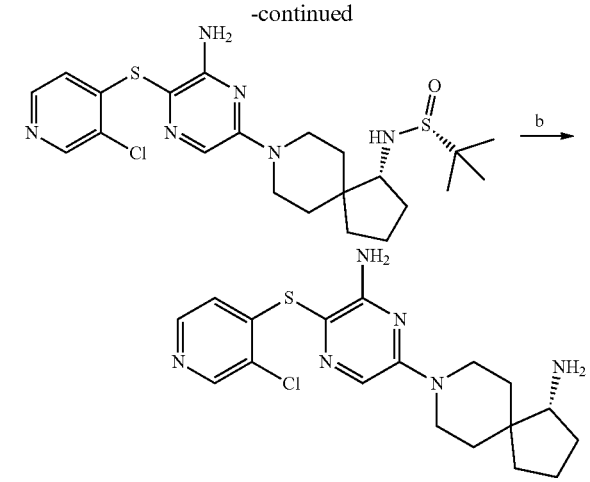

Step a:

To a suspension of 6-chloro-3-((3-chloropyridin-4-yl)thio)pyrazin-2-amine (53 mg, 0.194 mmol) in DIPEA (2 mL) was added (R)-2-methyl-N—((R)-8-azaspiro[4.5]decan-1-yl)propane-2-sulfinamide (65 mg, 0.252 mmol). The resulting mixture was stirred at 90° C. for 10 h and then concentrated. The crude was purified by silica chromatography (0-50% gradient of EtOAc/heptane; EtOAc containing 10% MeOH, heptane containing 2% Et$_3$N) to afford (R)—N—((R)-8-(6-amino-5-((3-chloropyridin-4-yl)thio)pyrazin-2-yl)-8-azaspiro[4.5]decan-1-yl)-2-methylpropane-2-sulfinamide (40 mg, 0.081 mmol) as an off-white solid. MS m/z 495.0 (M+H)$^+$.

Step b:

To a solution of (R)—N—((R)-8-(6-amino-5-((3-chloropyridin-4-yl)thio)pyrazin-2-yl)-8-azaspiro[4.5]decan-1-yl)-2-methylpropane-2-sulfinamide (40 mg, 0.081 mmol) in

TABLE 8

| Example | Compound | Characterization | IC$_{50}$ (μM) |
|---|---|---|---|
| 27 | 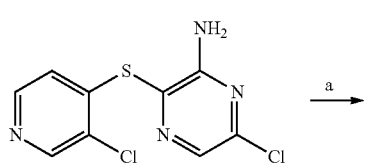 | $^1$H NMR (400 MHz, METHANOL-d$_4$) δ ppm 7.50-7.64 (m, 2 H), 5.90 (d, J = 5.52 Hz, 1 H), 4.30 (d, J = 13.55 Hz, 1 H), 4.19 (d, J = 13.55 Hz, 1 H), 2.94-3.19 (m, 3 H), 2.15-2.29 (m, 1 H), 1.60-1.89 (m, 5 H), 1.47-1.60 (m, 2 H). HRMS calcd for C$_{17}$H$_{23}$ClN$_7$S (M + H)$^+$ 392.1424, found 392.1434. | 0.042 |

Example 28

(R)-8-(6-amino-5-((3-chloropyridin-4-yl)thio)pyrazin-2-yl)-8-azaspiro[4.5]decan-1-amine DCM (0.8 mL), a solution of HCl (4 M in dioxane, 101 μL, 0.404 mmol) was added and the resulting mixture was stirred at 40° C. for 1 h. An aqueous solution of HCl (2 M, 2 mL) was added and the resulting mixture was extracted with DCM (2×). The aqueous mixture was basified with ammonium hydroxide (28% in water) until pH=12 and it was extracted with DCM (3×). The organic layers were combined, washed with brine, dried with Na$_2$SO$_4$, filtered and concentrated to afford (R)-8-(6-amino-5-((3-chloropyridin-4-yl)thio)pyrazin-2-yl)-8-azaspiro[4.5]decan-1-amine (24 mg, 0.061 mmol). $^1$H NMR (400 MHz, DMSO-d$_6$) δ ppm 8.49 (s, 1H), 8.25 (d, J=5.3 Hz, 1H), 7.66 (s, 1H), 6.56 (d, J=5.3 Hz, 1H), 6.24 (s, 2H), 4.07-4.26 (m, 2H), 2.98-3.13

(m, 2H), 2.70 (t, J=7.4 Hz, 1H), 1.11-1.94 (m, 10H). HRMS calcd for $C_{18}H_{24}ClN_6S$ (M+H)$^+$ 391.1472, found 391.1480. IC$_{50}$ is 0.023 µM.

Example 29

(R)-8-(6-amino-5-((2-chloropyridin-3-yl)thio)pyrazin-2-yl)-8-azaspiro[4.5]decan-1-amine

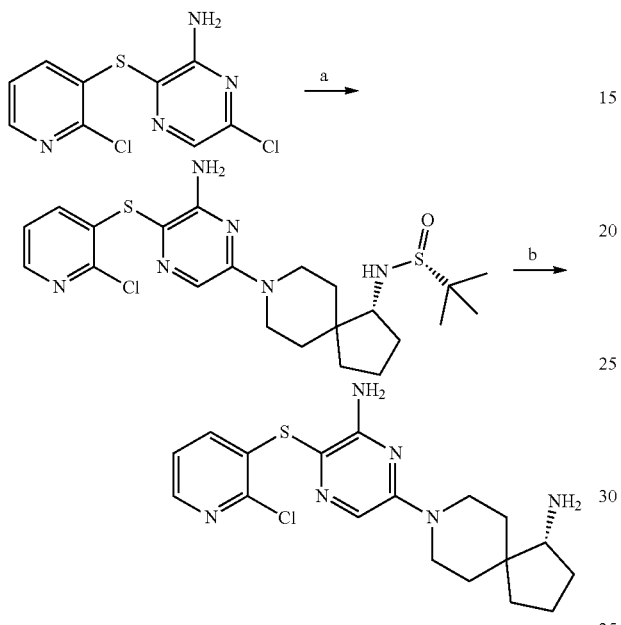

Step a:

To a suspension of 6-chloro-3-((2-chloropyridin-3-yl)thio)pyrazin-2-amine (85 mg, 0.311 mmol) in DIPEA (1.6 mL), was added (R)-2-methyl-N—((R)-8-azaspiro[4.5]decan-1-yl)propane-2-sulfinamide (105 mg, 0.405 mmol). The resulting mixture was stirred at 90° C. for 10 h and then concentrated. The crude was purified by silica chromatograpahy (0-50% gradient of EtOAc/heptane; EtOAc containing 10% MeOH, heptane containing 2% Et$_3$N) to afford (R)—N—((R)-8-(6-amino-5-((2-chloropyridin-3-yl)thio)pyrazin-2-yl)-8-azaspiro[4.5]decan-1-yl)-2-methylpropane-2-sulfinamide (40 mg, 0.081 mmol) as an off-white solid. $^1$H NMR (400 MHz, CHLOROFORM-d) δ ppm 8.15 (dd, J=4.5, 1.8 Hz, 1H), 7.64 (s, 1H), 7.01-7.18 (m, 2H), 4.87 (br. s, 2H), 4.24 (s, 2H), 3.29-3.45 (m, 1H), 3.20 (d, J=5.8 Hz, 1H) 2.98-3.13 (m, 2H), 1.98-2.21 (m, 1H), 1.36-1.94 (m, 9H), 1.22 (s, 9H). MS m/z 495.0 (M+H)$^+$.

Step b:

To a solution of (R)—N—((R)-8-(6-amino-5-((2-chloropyridin-3-yl)thio)pyrazin-2-yl)-8-azaspiro[4.5]decan-1-yl)-2-methylpropane-2-sulfinamide (66 mg, 0.133 mmol) in DCM (2 mL), was added a solution of HCl (4 M in dioxane, 167 µL, 0.667 mmol) and the resulting mixture was stirred at 40° C. for 1 h. An aqueous solution of HCl (2 M, 2 mL) was added and the resulting mixture was extracted with DCM (2×). The aqueous mixture was basified with ammonium hydroxide (28% in water) until pH=12 and it was extracted with DCM (3×). The organic layers were combined, washed with brine, dried with Na$_2$SO$_4$, filtered and concentrated to afford (R)-8-(6-amino-5-((2-chloropyridin-3-yl)thio)pyrazin-2-yl)-8-azaspiro[4.5]decan-1-amine (24 mg, 0.062 mmol) as a tan solid. $^1$H NMR (400 MHz, METHANOL-d$_4$) δ ppm 8.01 (dd, J=4.8, 1.8 Hz, 1H), 7.43-7.52 (m, 1H), 7.12 (dd, J=7.9, 4.6 Hz, 1H), 7.00 (dd, J=7.9, 1.6 Hz, 1H), 4.11-4.26 (m, 2H), 2.96-3.10 (m, 2H), 2.67-2.81 (m, 1H), 1.06-2.05 (m, 10H). HRMS calcd for $C_{18}H_{24}ClN_6S$ (M+H)$^+$ 391.1472, found 391.1470. IC$_{50}$ is 0.015 µM.

Example 30

(R)-8-(6-amino-5-((2,3-dichloropyridin-4-yl)thio)pyrazin-2-yl)-8-azaspiro[4.5]decan-1-amine

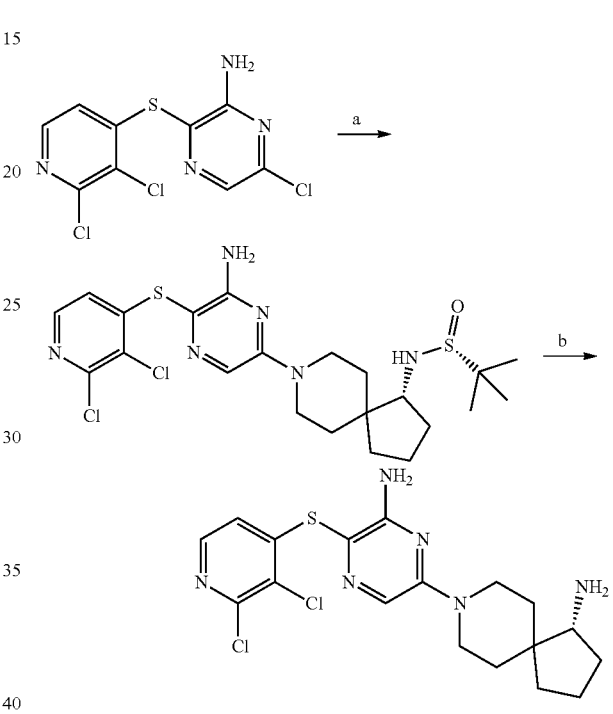

Step a:

To a suspension 6-chloro-3-((2,3-dichloropyridin-4-yl)thio)pyrazin-2-amine (34 mg, 0.111 mmol) in DIPEA (0.55 mL), (R)-2-methyl-N—((R)-8-azaspiro[4.5]decan-1-yl)propane-2-sulfinamide (37 mg, 0.144 mmol) was added. The resulting mixture was stirred at 90° C. for 10 h and then concentrated. The crude was purified by silica chromatography (0-50% gradient of EtOAc/heptane; EtOAc containing 10% MeOH, heptane containing 2% Et$_3$N) to afford (R)—N—((R)-8-(6-amino-5-((2,3-dichloropyridin-4-yl)thio)pyrazin-2-yl)-8-azaspiro[4.5]decan-1-yl)-2-methylpropane-2-sulfinamide (33 mg, 0.062 mmol) as an off-white solid. $^1$H NMR (400 MHz, CHLOROFORM-d) δ ppm 8.02 (d, J=5.3 Hz, 1H), 7.66 (s, 1H), 6.60 (d, J=5.3 Hz, 1H), 4.82 (s, 2H), 4.21-4.34 (m, 2H), 3.34-3.42 (m, 1H), 3.20 (d, J=5.8 Hz, 1H), 2.99-3.15 (m, 2H), 2.08-2.21 (m, 1H), 1.26-1.97 (m, 9H), 1.23 (s, 9H). MS m/z 529.1 (M+H)$^+$.

Step b:

To a solution of (R)—N—((R)-8-(6-amino-5-((2,3-dichloropyridin-4-yl)thio)pyrazin-2-yl)-8-azaspiro[4.5]decan-1-yl)-2-methylpropane-2-sulfinamide (20 mg, 0.038 mmol) in DCM (0.38 mL), was added a solution of HCl (4 M in dioxane, 47 µL, 0.189 mmol) and the resulting mixture was stirred at 40° C. for 1 h. The reaction mixture was concentrated and dissolved in MeOH. The crude was purified by HPLC (gradient elution 15-40% acetonitrile in water, 5 mM NH₄OH modifier) to afford (R)-8-(6-amino-5-((2,3-dichloropyridin-4-yl)thio)pyrazin-2-yl)-8-azaspiro[4.5]decan-1-amine (7 mg, 0.016 mmol) as a white solid. ¹H NMR (400 MHz, METHANOL-d₄) δ ppm 7.91-8.04 (m, 1H), 7.52-7.65 (m, 1H), 6.61 (d, J=5.3 Hz, 1H), 4.29 (t, J=14.2 Hz, 2H), 3.06-3.22 (m, 2H), 2.88 (t, J=7.4 Hz, 1H), 1.21-2.17 (m, 10H). HRMS calcd for C₁₈H₂₃Cl₂N₆S (M+H)⁺ 425.1082, found 425.1095. IC₅₀ is 0.003 µM.

Example 31

(S)-7-(6-amino-5-((2,3-dichloropyridin-4-yl)thio)pyrazin-2-yl)-7-azaspiro[3.5]nonan-1-amine

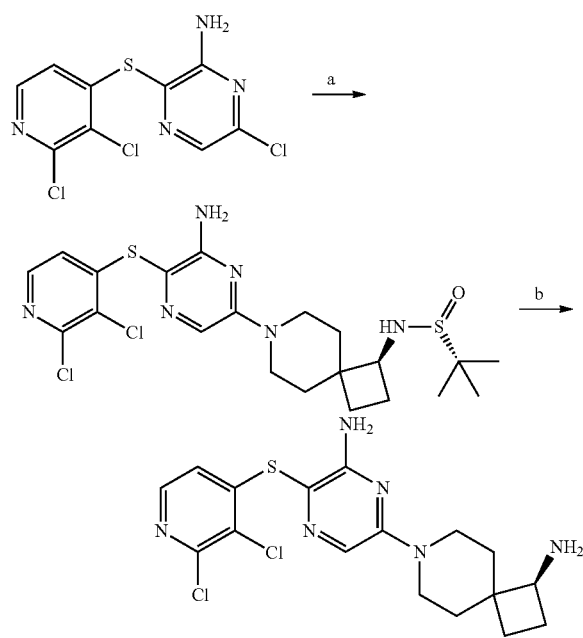

Step a:
To a suspension of 6-chloro-3-((2,3-dichloropyridin-4-yl)thio)pyrazin-2-amine (54 mg, 0.176 mmol) in DIPEA (1.8 mL), was added (R)-2-methyl-N—((R)-8-azaspiro[4.5]decan-1-yl)propane-2-sulfinamide (86 mg, 0.351 mmol). The resulting mixture was stirred at 90° C. for 10 h and then concentrated. The crude was purified by silica chromatography (0-50% gradient EtOAc/heptane; EtOAc containing 10% MeOH, heptane containing 2% Et₃N) to afford (R)—N—((S)-7-(6-amino-5-((2,3-dichloropyridin-4-yl)thio)pyrazin-2-yl)-7-azaspiro[3.5]nonan-1-yl)-2-methylpropane-2-sulfinamide (52 mg, 0.102 mmol) as an off-white solid. MS m/z 514.9 (M+H)⁺.

Step b:
To a solution of (R)—N—((S)-7-(6-amino-5-((2,3-dichloropyridin-4-yl)thio)pyrazin-2-yl)-7-azaspiro[3.5]nonan-1-yl)-2-methylpropane-2-sulfinamide (20 mg, 0.039 mmol) in DCM (0.38 mL), was added a solution of HCl (4 M in dioxane, 47 µL, 0.189 mmol) and the resulting mixture was stirred at 40° C. for 1 h. The reaction mixture was concentrated and dissolved in MeOH. The crude was purified by HPLC (gradient elution 15-40% acetonitrile in water, 5 mM NH₄OH modifier) to afford (S)-7-(6-amino-5-((2,3-dichloropyridin-4-yl)thio)pyrazin-2-yl)-7-azaspiro[3.5]nonan-1-amine (7 mg, 0.017 mmol) as a white solid. ¹H NMR (400 MHz, METHANOL-d₄) δ ppm 7.89 (d, J=5.5 Hz, 1H), 7.50 (s, 1H), 6.51 (d, J=5.5 Hz, 1H), 3.94-4.31 (m, 2H), 2.76-3.11 (m, 3H), 2.06-2.24 (m, 1H), 1.36-1.82 (m, 7H). HRMS calcd for C₁₇H₂₁Cl₂N₆S (M+H)⁺ 411.0925, found 411.0938. IC₅₀ is 0.028 µM.

Example 32

(R)-8-(6-amino-5-((2,3-dichloropyridin-4-yl)thio)pyrazin-2-yl)-8-azaspiro[4.5]decan-1-amine

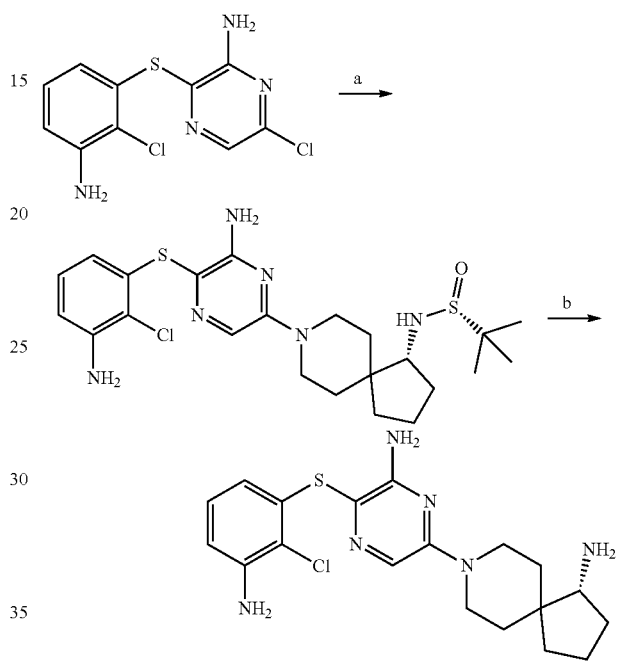

Step a:
To a suspension 3-((3-amino-2-chlorophenyl)thio)-6-chloropyrazin-2-amine (60 mg, 0.209 mmol) in DIPEA (1.5 mL) was added (R)-2-methyl-N—((R)-8-azaspiro[4.5]decan-1-yl)propane-2-sulfinamide (70 mg, 0.272 mmol). The resulting mixture was stirred at 90° C. for 10 h and then concentrated. The crude was purified by silica chromatography (0-50% gradient of EtOAc/heptane; heptane containing 2% Et₃N) to afford (R)—N—((R)-8-(6-amino-5-((3-amino-2-chlorophenyl)thio)pyrazin-2-yl)-8-azaspiro[4.5]decan-1-yl)-2-methylpropane-2-sulfinamide (31 mg, 0.061 mmol) as an off-white solid. MS m/z 509.0 (M+H)⁺.

Step b:
To a solution of (R)—N—((R)-8-(6-amino-5-((3-amino-2-chlorophenyl)thio)pyrazin-2-yl)-8-azaspiro[4.5]decan-1-yl)-2-methylpropane-2-sulfinamide (31 mg, 0.061 mmol) in DCM (0.6 mL) was added a solution of HCl (4 M in dioxane, 76 µL, 0.304 mmol) and the resulting mixture was stirred at 40° C. for 1 h. An aqueous solution of HCl (2 M, 2 mL) was added and the resulting mixture was extracted with DCM (2×). The aqueous mixture was basified with ammonium hydroxide (28% in water) until pH=12 and it was extracted with DCM (3×). The organic layers were combined, washed with brine, dried over Na₂SO₄, filtered, and concentrated to afford (R)-8-(6-amino-5-((3-amino-2-chlorophenyl)thio)pyrazin-2-yl)-8-azaspiro[4.5]decan-1-amine (18 mg, 0.042 mmol) as a yellow solid. ¹H NMR (400 MHz, METHANOL-d₄) δ ppm 7.40 (s, 1H), 6.73 (t, J=8.0 Hz, 1H), 6.50 (dd, J=8.1, 1.3 Hz, 1H), 5.90 (dd, J=7.8, 1.3 Hz, 1H), 4.02-4.18 (m, 2H), 3.21 (dt, J=3.2, 1.5 Hz, 1H), 2.98 (d, J=11.4 Hz, 2H), 2.67 (t, J=7.5 Hz, 1H), 1.04-2.02 (m, 10H). HRMS calcd for $C_{19}H_{26}ClN_6S$ (M+H)$^+$ 405.1628, found 405.1639. IC$_{50}$ is 0.011 µM.

Example 33

(R)-8-(6-amino-5-((3-chloro-2-fluoropyridin-4-yl)thio)pyrazin-2-yl)-8-azaspiro[4.5]decan-1-amine

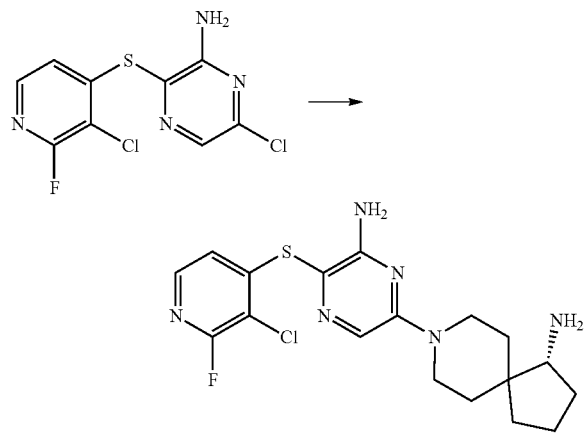

To a suspension of 6-chloro-3-((3-chloro-2-fluoropyridin-4-yl)thio)pyrazin-2-amine (40 mg, 0.137 mmol) in DIPEA (0.7 mL) was added (R)-2-methyl-N—((R)-8-azaspiro[4.5]decan-1-yl)propane-2-sulfinamide (71 mg, 0.0275 mmol). The resulting mixture was stirred at 90° C. for 10 h and then concentrated. The crude was dissolved in DCM (0.7 mL), a solution of HCl (4 M in dioxane, 34 µL, 0.137 mmol) was added and the resulting mixture was stirred at 40° C. for 1 h. The reaction mixture was concentrated and the crude was purified by HPLC (gradient elution 15 to 40% acetonitrile in water, 0.1% TFA modifier) to afford (R)-8-(6-amino-5-((3-chloro-2-fluoropyridin-4-yl)thio)pyrazin-2-yl)-8-azaspiro[4.5]decan-1-amine (TFA salt: 17 mg, 0.042 mmol). $^1$H NMR (400 MHz, DMSO-d$_6$) δ ppm 7.94 (d, J=5.3 Hz, 1H), 7.79 (br. s., 3H), 7.69 (br. s., 1H), 6.51 (d, J=5.5 Hz, 1H), 6.34 (br. s., 2H), 4.12-4.32 (m, 2H), 2.99-3.24 (m, 3H), 2.00-2.12 (m, 1H), 1.30-1.90 (m, 9H). HRMS calcd for $C_{18}H_{23}ClFN_6S$ (M+H)$^+$ 409.1377, found 409.1385. IC$_{50}$ is 0.005 µM.

Example 34

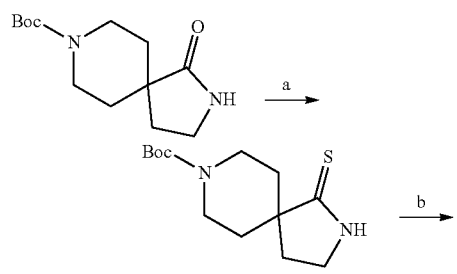

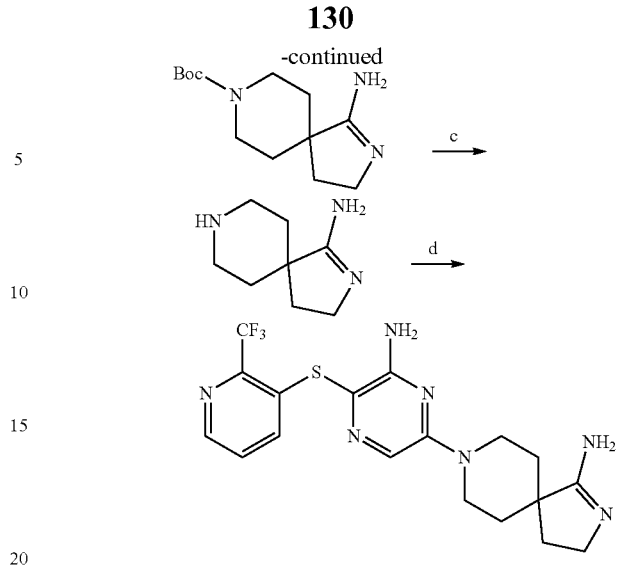

Step a:
To a RT solution of tert-butyl 2-oxo-1,8-diazaspiro[4.5]decane-8-carboxylate (300 mg, 1.180 mmol) in dichloromethane (3 mL) was added phosphorus pentasulfide (110 mg, 0.495 mmol) followed by hexamethyldisiloxane (2.256 mL, 10.62 mmol). The reaction was stirred for 3 h at RT then diluted with EtOAc and filtered through Celite. The filtrate was concentrated under reduced pressure. Crude product was purified by silica chromatography (0 to 80% gradient of EtOAc/heptane) giving tert-butyl 1-thioxo-2,8-diazaspiro[4.5]decane-8-carboxylate (0.290 g, 1.07 mmol) as a white solid. $^1$H NMR (400 MHz, DMSO-d$_6$) δ 10.39 (s, 1H), 3.66 (dt, J=13.6, 4.9 Hz, 2H), 3.09 (s, 2H), 2.78 (t, J=7.8 Hz, 2H), 1.95 (t, J=7.8 Hz, 2H), 1.57 (dd, J=6.6, 4.8 Hz, 4H), 1.39 (s, 9H). MS m/z 271 (M+H)$^+$.

Step b:
To a solution of 1-thioxo-2,8-diazaspiro[4.5]decane-8-carboxylate (100 mg, 0.370 mmol) in THF (3 mL) was added dropwise iodomethane (0.231 mL, 3.70 mmol). The resulting solution was stirred at RT for 16 h. Throughout the course of the reaction the mixture slowly became more yellow in color and resulted in a light yellow precipitate after stirring the allotted reaction time. The reaction mixture was concentrated and dried under vacuum giving a yellow solid. The yellow solid was taken up in MeOH (2 mL) and treated with 7 M ammonia in methanol (3 mL) then heated in a sealed tube to 100° C. for 8 h. The reaction was cooled to RT and concentrated under reduced pressure giving a solid that was sonicated with acetonitrile and filtered. The filtrate was concentrated and the residue purified by silica chromatography (0 to 30% gradient of MeOH/DCM) giving tert-butyl 1-amino-2,8-diazaspiro[4.5]dec-1-ene-8-carboxylate (87 mg, 0.343 mmol). $^1$H NMR (400 MHz, DMSO-d$_6$) δ 9.38 (s, 1H), 8.81 (d, J=25.2 Hz, 2H), 3.98 (s, 2H), 3.55 (t, J=7.0 Hz, 2H), 2.82 (s, 2H), 2.12 (t, J=7.1 Hz, 2H), 1.74 (td, J=12.9, 4.7 Hz, 2H), 1.57 (d, J=12.7 Hz, 2H), 1.41 (s, 9H). MS m/z 254 (M+H)$^+$.

Step c:
To a solution of tert-butyl 1-amino-2,8-diazaspiro[4.5]dec-1-ene-8-carboxylate (86 mg, 0.339 mmol) in DCM (3 mL) was added HCl in dioxane (4 M, 0.500 mL, 2.0 mmol) at RT and the reaction stirred for 16 h. The reaction mixture was concentrated and residue was triturated from acetonitrile and filtered giving 2,8-diazaspiro[4.5]dec-1-en-1-amine (57.7 mg, 0.254 mmol) as a tan solid. $^1$H NMR (400 MHz, DMSO-d$_6$) δ 9.64 (s, 1H), 9.39-9.23 (m, 1H), 9.15 (s, 1H), 9.07 (s, 1H), 8.70 (d, J=12.5 Hz, 1H), 3.54 (t, J=6.9 Hz, 2H), 3.32 (d, J=13.3 Hz, 2H), 3.05-2.88 (m, 2H), 2.18 (t, J=6.9 Hz, 2H), 2.01 (td, J=13.7, 4.3 Hz, 2H), 1.80 (d, J=13.8 Hz, 2H). MS m/z 154 (M+H)$^+$.

Step d:

To a suspension of 6-chloro-3-((2-(trifluoromethyl)pyridin-3-yl)thio)pyrazin-2-amine (250 mg, 0.815 mmol) and 2,8-diazaspiro[4.5]dec-1-en-1-amine (210 mg, 1.371 mmol) in N-methyl-2-pyrrolidinone (4 mL) was added DIPEA (1.4 mL, 8.02 mmol) and the reaction heated to 140° C. for 16 h. The resulting dark mixture was cooled to RT and diluted with EtOAc and water. The layers were partitioned and the organic discarded. The aqueous layer was extracted with 20% isopropanol/chloroform mixture (2×30 mL), the combined organics dried over $Na_2SO_4$, filtered and concentrated. The crude residue was purified using preparative HPLC (gradient elution, 5 to 40% ACN in water, 0.1% TFA modifier) and half the pooled fractions were lyophilized giving 8-(6-amino-5-((2-(trifluoromethyl)pyridin-3-yl)thio)pyrazin-2-yl)-2,8-diazaspiro[4.5]dec-1-en-1-amine (TFA salt: 61.4 mg, 0.082 mmol). The remaining fractions were combined and neutralized by stirring for 10 minutes vigorously with 50% saturated $NaHCO_3$. The resulting solution was extracted with 20% isopropanol/chloroform mixture (3×30 mL), the combined organics dried over $Na_2SO_4$, filtered and concentrated giving 8-(6-amino-5-((2-(trifluoromethyl)pyridin-3-yl)thio)pyrazin-2-yl)-2,8-diazaspiro[4.5]dec-1-en-1-amine (22 mg, 0.052 mmol) as the free base. $^1$H NMR (400 MHz, DMSO-$d_6$) δ 8.46 (d, J=4.4 Hz, 1H), 7.67 (s, 1H), 7.55 (dd, J=8.2, 4.5 Hz, 1H), 7.31 (d, J=8.1 Hz, 1H), 6.19 (s, 2H), 5.74 (s, 2H), 4.40 (d, J=13.4 Hz, 2H), 3.43-3.34 (m, 2H), 2.90 (t, J=12.2 Hz, 2H), 1.97-1.89 (m, 2H), 1.83 (td, J=13.0, 4.1 Hz, 2H), 1.36 (d, J=12.9 Hz, 2H). MS m/z 424.1541 (M+H)$^+$. $IC_{50}$ is 0.032 μM The following compound was made using the above amine and coupled using the standard procedures described herein.

Dissolved racemic-2-(8-(6-amino-5-((2-(trifluoromethyl)pyridin-3-yl)thio)pyrazin-2-yl)-2-oxa-8-azaspiro[4.5]decan-4-yl)isoindoline-1,3-dione (40 mg, 0.072 mmol) in ethanol (1 mL) in a 5 mL conical microwave vial, added hydrazine hydrate (0.070 mL, 1.44 mmol), capped and heated on a 90° C. aluminum bead bath for 2 h. Vacuum filtered suspension through 0.45 m PTFE membrane and washed with ethanol. HPLC purification (gradient elution 15 to 40% acetonitrile in water, 0.1% TFA modifier), then diluted with EtOAc and washed with sat. aq bicarbonate, then brine. Concentrated, diluted with 1 mL DCM and added HCl (100 μL, 4 M in dioxane) to obtain precipitate. Concentrated to obtain 8-(6-amino-5-((2-(trifluoromethyl) pyridin-3-yl)thio)pyrazin-2-yl)-2-oxa-8-azaspiro[4.5]decan-4-amine (HCl salt: 1 mg, 0.002 mmol). $^1$H NMR (400 MHz, Methanol-$d_4$) δ 8.43-8.39 (m, 1H), 7.65 (s, 1H), 7.46-7.39 (m, 2H), 4.35-4.14 (m, 2H), 3.98 (d, J=9.2 Hz, 1H), 3.90 (d, J=9.2 Hz, 1H), 3.58 (d, J=5.3 Hz, 1H), 3.29-3.12 (m, 3H), 1.76 (m, 4H). HRMS calcd for $C_{18}H_{22}F_3N_6OS$ (M+H)$^+$ 427.1528, found 427.1537. $IC_{50}$ is 0.07 μM.

| Example | Compound | Characterization | $IC_{50}$ (μM) |
|---|---|---|---|
| 35 | 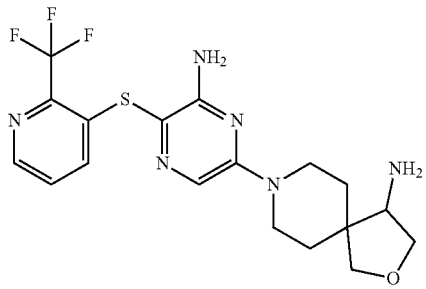 [SMILES: Nc1nc(N2CCC3(CC2)COCC3N)cnc1Sc1cccnc1C(F)(F)F] | $^1$H NMR (400 MHz, Chloroform-d) δ ppm 8.35 (dd, J = 4.5, 1.5 Hz, 1 H), 7.58 (s, 1 H), 7.42 (d, J = 8.1 Hz, 1 H), 7.24-7.15 (m, 1 H), 4.77 (s, 2 H), 4.13 (m, 2 H), 3.90 (m, 1 H), 3.78 (m, 1 H), 3.28-3.17 (m, 2 H), 3.06 (t, J = 6.9 Hz, 1 H), 2.27 (2, 1 H), 1.74-1.63 (m, 1 H), 1.69-1.54 (m, 3 H), 1.53-1.46 (m, 1 H), 1.21 (br. s, 2 H). HRMS calcd for $C_{18}H_{22}F_3N_6OS$ (M + H)$^+$ 427.1528, found 427.1526. | 0.232 |

Example 36 racemic-8-(6-amino-5-((2-(trifluoromethyl)pyridin-3-yl)thio)pyrazin-2-yl)-2-oxa-8-azaspiro[4.5]decan-4-amine Example 37

(R) and (S)-8-(6-amino-5-((2-(trifluoromethyl)pyridin-3-yl)thio)pyrazin-2-yl)-2-oxa-8-azaspiro[4.5]decan-4-amine

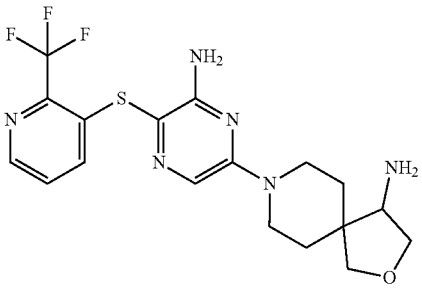 [SMILES: Nc1nc(N2CCC3(CC2)COCC3N)cnc1Sc1cccnc1C(F)(F)F]

Dissolved the single enantiomer P1, 2-(8-(6-amino-5-((2-(trifluoromethyl)pyridin-3-yl)thio)pyrazin-2-yl)-2-oxa-8-azaspiro[4.5]decan-4-yl)isoindoline-1,3-dione (49 mg, 0.088 mmol) in ethanol (1 mL) in a 5 mL conical microwave vial, added hydrazine hydrate (0.080 mL, 1.65 mmol), capped and heated on a 90° C. aluminum bead bath for 2 h. Vacuum filtered the suspension through 0.45 m PTFE membrane and washed with ethanol. HPLC purification (gradient elution 15 to 40% acetonitrile in water, 5 mM NH$_4$OH modifier) resulted in the isolation of 8-(6-amino-5-((2-(trifluoromethyl) pyridin-3-yl)thio)pyrazin-2-yl)-2-oxa-8-azaspiro[4.5]decan-4-amine (13 mg, 0.029 mmol). Chiral analytical HPLC: LC-3 4.6×100 mm, 5 μm, mobile phase: 45% MeOH with 10 mM ammonia, 5 mL/min, single enantiomer peak 1 (P1), R$_t$: 0.88 min, >99% single enantiomer. $^1$H NMR (400 MHz, Methanol-d4) δ 8.39 (dd, J=4.3, 1.6 Hz, 1H), 7.60 (s, 1H), 7.41 (m, 2H), 4.21-4.07 (m, 3H), 3.86 (d, J=8.7 Hz, 1H), 3.79 (d, J=8.7 Hz, 1H), 3.51 (dd, J=9.0, 5.2 Hz, 1H), 3.24 (m, 2H), 3.15 (m, 1H), 1.73 (m, 2H), 1.59 (m, 1.8 Hz, 2H). HRMS calcd for C$_{18}$H$_{22}$F$_3$N$_6$OS (M+H)$^+$ 427.1528, found 427.1542. IC$_{50}$ is 0.025 μM.

Example 38

(R) and (S)-8-(6-amino-5-((2-(trifluoromethyl)pyridin-3-yl)thio)pyrazin-2-yl)-2-oxa-8-azaspiro[4.5]decan-4-amine

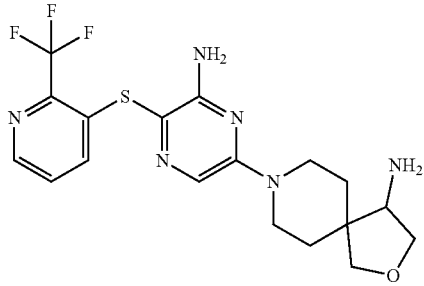 [SMILES: Nc1nc(N2CCC3(CC2)COCC3N)cnc1Sc1cccnc1C(F)(F)F]

Dissolved the single enantiomer P2, 2-(8-(6-amino-5-((2-(trifluoromethyl)pyridin-3-yl)thio)pyrazin-2-yl)-2-oxa-8-azaspiro[4.5]decan-4-yl)isoindoline-1,3-dione (42 mg, 0.075 mmol) in ethanol (1 mL) in a 5 mL conical microwave vial, added hydrazine hydrate (0.080 mL, 1.65 mmol), capped and heated on a 90° C. aluminum bead bath for 2 h. Vacuum filtered the suspension through 0.45 m PTFE membrane and washed with ethanol. HPLC purification (gradient elution 15 to 40% acetonitrile in water, 5 mM NH$_4$OH modifier) resulted in the isolation of 8-(6-amino-5-((2-(trifluoromethyl) pyridin-3-yl)thio)pyrazin-2-yl)-2-oxa-8-azaspiro[4.5]decan-4-amine (13 mg, 0.029 mmol). Chiral analytical HPLC: LC-3 4.6×100 mm, 5 μm, mobile phase: 45% MeOH with 10 mM ammonia, 5 mL/min, single enantiomer peak 2 (P2), R$_t$: 1.33 min, >99% single enantiomer. $^1$H NMR (400 MHz, Methanol-d4) δ 8.39 (dd, J=4.3, 1.6 Hz, 1H), 7.60 (s, 1H), 7.41 (m, 2H), 4.21-4.07 (m, 3H), 3.86 (d, J=8.6 Hz, 1H), 3.79 (d, J=8.8 Hz, 1H), 3.50 (dd, J=9.0, 5.2 Hz, 1H), 3.24 (m, 2H), 3.15 (m, 1H), 1.80-1.67 (m, 2H), 1.64-1.50 (m, 2H). HRMS calcd for C$_{18}$H$_{22}$F$_3$N$_6$OS (M+H)$^+$ 427.1528, found 427.1536. IC$_{50}$ is 0.983 μM.

Example 39

(R)-6-amino-2-(1-amino-8-azaspiro[4.5]decan-8-yl)-5-((2-(trifluoromethyl)pyridin-3-yl)thio)nicotinamide

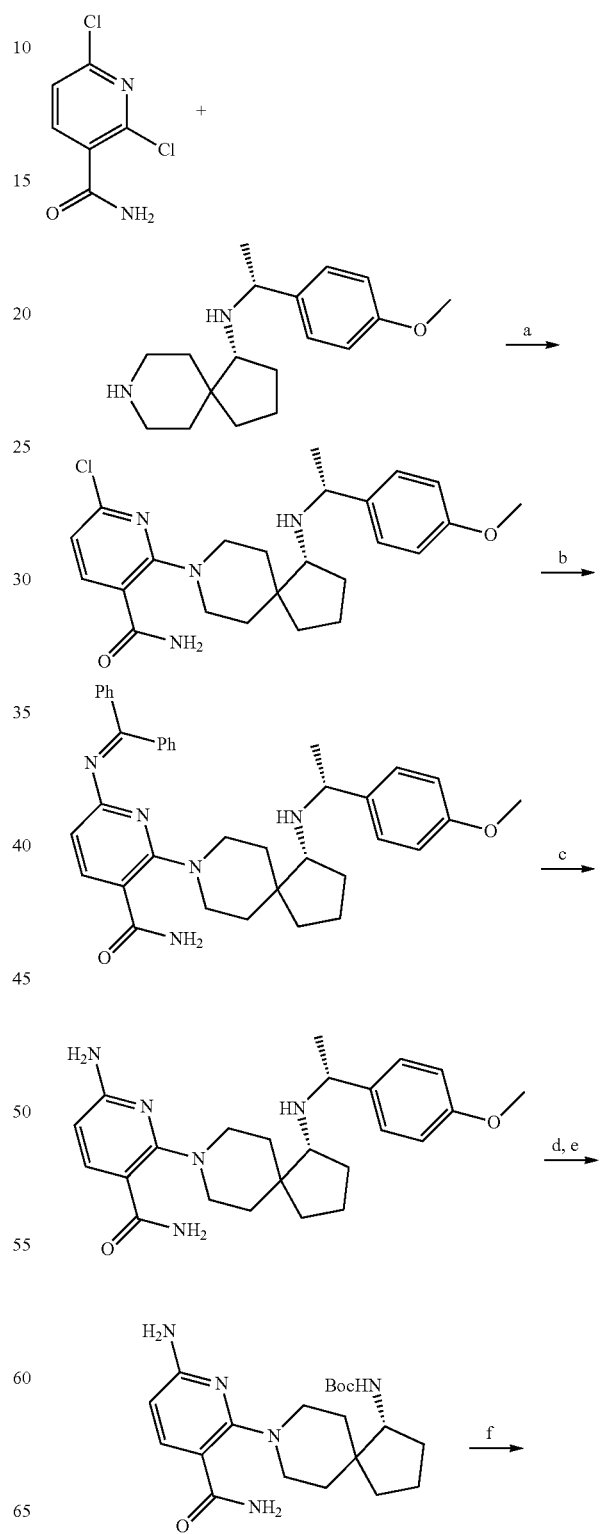

-continued

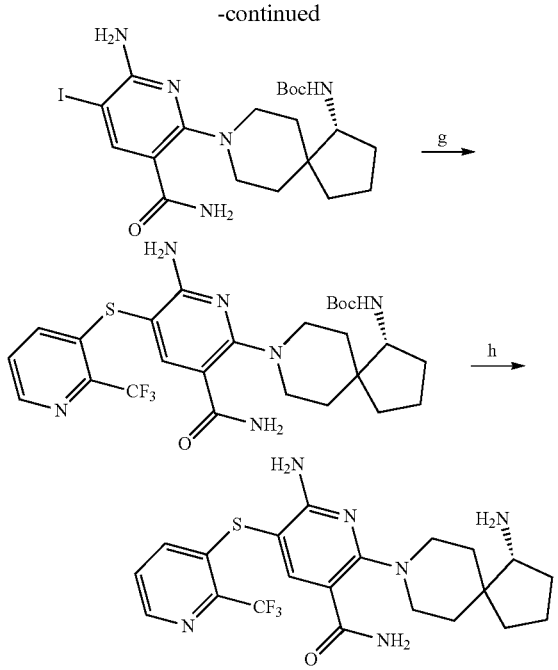

Step a:

To a solution of 2,6-dichloropyridine-3-carboxamide (0.728 g, 3.81 mmol) in 1-methyl pyrrolidinone (7 mL) was added N-methyl morpholine (1.14 mL, 10.40 mmol) and (R)—N—((R)-1-(4-methoxyphenyl)ethyl)-8-azaspiro[4.5]decan-1-amine (1 g, 3.47 mmol). The resulting mixture was heated to 100° C. under refluxing conditions for 24 h. The reaction mixture was diluted with ethyl acetate, treated with concentrated sodium bicarbonate and filtered. The organic layer was separated, dried over sodium sulfate, filtered and concentrated under reduced pressure. The resulting dark red oil was purified by silica chromatography (0 to 50% gradient of ethyl acetate/heptane containing 0.25% triethylamine) to furnish 6-chloro-2-((R)-1-(((R)-1-(4-methoxyphenyl)ethyl)amino)-8-azaspiro[4.5]decan-8-yl)nicotinamide (0.998 g, 2.25 mmol). $^1$H NMR (400 MHz, Methanol-$d_4$) δ 7.81 (d, J=7.8 Hz, 1H), 7.26 (d, J=8.6 Hz, 2H), 6.86 (m, 3H), 3.82 (m, 1H), 3.77 (s, 3H), 3.75-3.63 (m, 2H), 3.03 (m, 2H), 2.59 (m, 1H), 2.01-1.92 (m, 1H), 1.88-1.52 (m, 5H), 1.51-1.36 (m, 3H), 1.32 (d, J=6.5 Hz, 3H), 1.25 (m, 2H). MS m/z 442.9 (M+H)$^+$.

Step b:

To a solution of 6-chloro-2-((R)-1-(((R)-1-(4-methoxyphenyl)ethyl)amino)-8-azaspiro[4.5]decan-8-yl)nicotinamide (242 mg, 0.546 mmol), in toluene (11 mL), was added Pd$_2$(dba)$_3$ (97 mg, 0.169 mmol), and (oxybis(2,1-phenylene))bis(diphenylphosphine) (103 mg, 0.191 mmol). The reaction mixture was sparged with nitrogen, and benzophenone imine (0.11 mL, 0.656 mmol) and potassium tert-butoxide (0.710 mL, 1 M in tetrahydrofuran, 0.710 mmol) were added under nitrogen. The reaction mixture was heated to 80° C. for 2 h, and the mixture was allowed to cool to RT, filtered through a pad of Celite, and washed with ethyl acetate. The filtrate was concentrated under reduced pressure, and the residue was purified by silica chromatography (0 to 50% gradient of ethyl acetate/heptane) to furnish 6-((diphenylmethylene)amino)-2-((R)-1-(((R)-1-(4-methoxyphenyl)ethyl)amino)-8-azaspiro[4.5]decan-8-yl)nicotinamide (250 mg, 0.425 mmol). MS m/z 588.3 (M+H)$^+$.

Step c:

To a suspension of 6-((diphenylmethylene)amino)-2-((R)-1-(((R)-1-(4-methoxyphenyl)ethyl)amino)-8-azaspiro[4.5]decan-8-yl)nicotinamide (130 mg, 0.221 mmol) in THF (6 mL), was added HCl (2 M, 0.1 mL, 0.200 mmol) and the resulting solution stirred at RT for 30 minutes. The reaction mixture was concentrated under reduced pressure and the residue was purified by silica chromatography (0 to 50% gradient of ethyl acetate/heptane, containing 0.25% triethylamine) to furnish 6-amino-2-((R)-1-(((R)-1-(4-methoxyphenyl)ethyl)amino)-8-azaspiro[4.5]decan-8-yl)nicotinamide (43 mg, 0.102 mmol). MS m/z 424.1 (M+H)$^+$.

Step d:

A solution of 6-amino-2-((R)-1-(((R)-1-(4-methoxyphenyl)ethyl)amino)-8-azaspiro[4.5]decan-8-yl)nicotinamide (199 mg, 0.470 mmol) in trifluoroacetic acid (3 mL) was heated to 100° C. for 30 min. The mixture was concentrated under reduced pressure and the residue was used in the next step without further purification. (R)-6-amino-2-(1-amino-8-azaspiro[4.5]decan-8-yl)nicotinamide. MS m/z 290.2 (M+H)$^+$.

Step e:

To a solution of (R)-6-amino-2-(1-amino-8-azaspiro[4.5]decan-8-yl)nicotinamide in dichloromethane (2 mL) was added triethylamine (0.196 mL, 1.410 mmol) and di-tert-butyl dicarbonate (113 mg, 0.517 mmol) and the resulting mixture was stirred for 2 h at RT. The reaction mixture was concentrated under reduced pressure, and the residue purified by silica chromatography (0 to 50% gradient of ethyl acetate/heptane, containing 0.25% triethylamine) to furnish (R)-tert-butyl(8-(6-amino-3-carbamoylpyridin-2-yl)-8-azaspiro[4.5]decan-1-yl)carbamate (147 mg, 0.377 mmol). $^1$H NMR (400 MHz, Methanol-$d_4$) δ 7.88 (d, J=8.5 Hz, 1H), 6.19 (d, J=8.5 Hz, 1H), 3.66 (t, J=7.7 Hz, 1H), 3.27-3.15 (m, 2H), 2.98 (t, J=12.4 Hz, 2H), 2.05-1.94 (m, 1H), 1.86-1.46 (m, 8H), 1.45 (s, 9H), 1.41 (d, J=6.0 Hz, 1H). MS m/z 390.3 (M+H)$^+$.

Step f:

To a solution of (R)-tert-butyl (8-(6-amino-3-carbamoylpyridin-2-yl)-8-azaspiro[4.5]decan-1-yl)carbamate (136 mg, 0.349 mmol) in dichloromethane (5 mL), cooled on an ice bath, was added N-iodosuccinimide (86 mg, 0.384 mmol). The resulting mixture was stirred at 5° C. for 2 h. The reaction was quenched by adding 2 mL of methanol, and the mixture allowed to warm up to RT. The solvents were removed under reduced pressure. The crude product was extracted with dichloromethane and washed with brine. The organic layer was dried over sodium sulfate, filtered and concentrated under reduced pressure to yield (R)-tert-butyl (8-(6-amino-3-carbamoyl-5-iodopyridin-2-yl)-8-azaspiro[4.5]decan-1-yl)carbamate (170 mg, 0.330 mmol) which was used in the next step without further purification. MS m/z 516.1 (M+H)$^+$.

Step g:

To a solution of (R)-tert-butyl (8-(6-amino-3-carbamoyl-5-iodopyridin-2-yl)-8-azaspiro[4.5]decan-1-yl)carbamate (177 mg, 0.343 mmol) in dioxane (10 mL), was added Pd$_2$(dba)$_3$ (31.4 mg, 0.034 mmol), (9,9-dimethyl-9H-xanthene-4,5-diyl)bis(diphenylphosphine) (39.7 mg, 0.069 mmol), 2-(trifluoromethyl)pyridine-3-thiol (67.7 mg, 0.378 mmol), and N,N-diisopropylethylamine (0.120 mL, 0.687 mmol). The resulting mixture was heated to 120° C. for 2 h, then allowed to cool to RT. The reaction mixture was diluted with ethyl acetate and filtered through a short pad of Celite. The filtrate was concentrated under reduced pressure and purified by silica chromatography (0 to 50% gradient of ethyl acetate/heptane, containing 0.25% triethylamine) to furnish (R)-tert-butyl (8-(6-amino-3-carbamoyl-5-((2-(trifluoromethyl)pyridin-3-yl)thio)pyridin-2-yl)-8-azaspiro[4.5]decan-1-yl)carbamate (115 mg, 0.203 mmol). MS m/z 567.2 (M+H)+.

Step h:

To a solution of (R)-tert-butyl (8-(6-amino-3-carbamoyl-5-((2-(trifluoromethyl)pyridin-3-yl)thio)pyridin-2-yl)-8-azaspiro[4.5]decan-1-yl)carbamate (110 mL, 0.194 mmol) in dichloromethane (2 mL) was added trifluoroacetic acid (2 mL, 26 mmol) and the resulting mixture was allowed to stir at RT for 1 h. The solvents were removed under reduced pressure, and the residue purified by HPLC (gradient elution: 35 to 60% acetonitrile in water, 5 mM NH$_4$OH modifier) to furnish (R)-6-amino-2-(1-amino-8-azaspiro[4.5]decan-8-yl)-5-((2-(trifluoromethyl)pyridin-3-yl)thio)nicotinamide (40 mg, 0.084 mmol). $^1$H NMR (400 MHz, Methanol-d$_4$) δ 8.38 (dd, J=4.1, 1.9 Hz, 1H), 7.93 (s, 1H), 7.56-7.31 (m, 2H), 3.77-3.55 (m, 2H), 3.16-2.98 (m, 2H), 2.82 (t, J=7.4 Hz, 1H), 2.03 (m, 1H), 1.94-1.60 (m, 5H), 1.60-1.20 (m, 4H). $^{19}$F NMR (376 MHz, Methanol-d4) δ −66.48. HRMS calcd for C$_{21}$H$_{26}$F$_3$N$_6$OS (M+H)+ 467.1841, found 467.1837. IC$_{50}$ is 0.118 µM.

Example 40

(R)-3-((3-amino-5-(1-amino-8-azaspiro[4.5]decan-8-yl)pyrazin-2-yl)thio)-2-chlorobenzamide

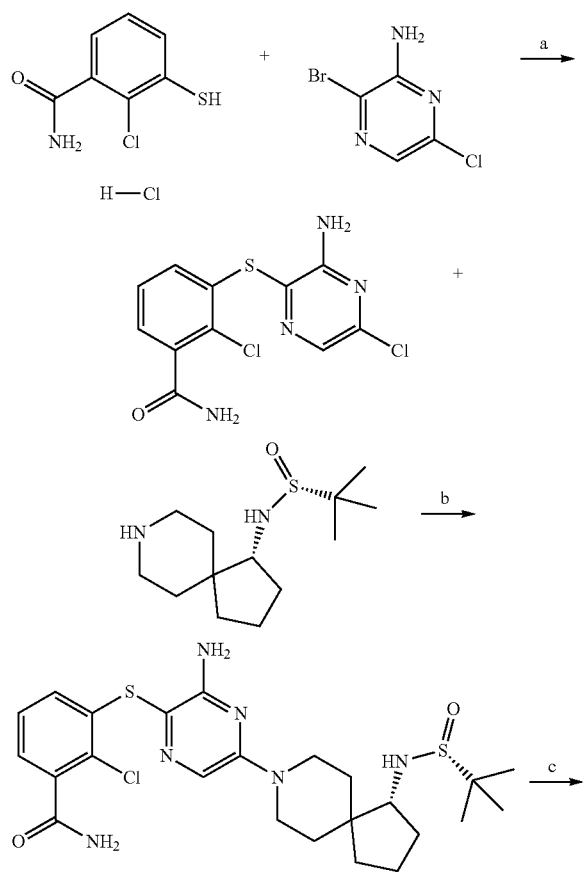

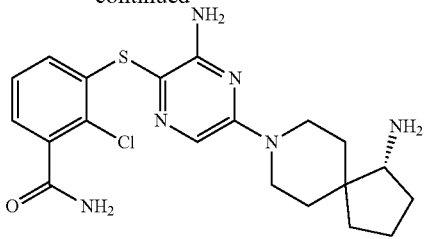

Step a:

A mixture of 2-chloro-3-mercaptobenzamide (HCl salt, 145 mg, 0.647 mmol), 3-bromo-6-chloropyrazin-2-amine (299 mg, 1.436 mmol), copper (I) iodide (49.3 mg, 0.259 mmol), potassium phosphate (412 mg, 1.941 mmol), and 1,10-phenanthroline (58.3 mg, 0.324 mmol) in dioxane (5 mL, degassed) was stirred in a microwave reactor for 4 h at 130° C. After cooling to RT, the reaction was filtered through a pad of Celite followed by EtOAc (50 mL) wash. The combined filtrates were concentrated and the resulting residue was purified by silica chromatography (0 to 100% gradient of EtOAc/heptane) to afford 3-((3-amino-5-chloropyrazin-2-yl)thio)-2-chlorobenzamide (140 mg, 0.444 mmol). MS m/z 315.0 (M+H)+

Step b:

A mixture of 3-((3-amino-5-chloropyrazin-2-yl)thio)-2-chlorobenzamide (130 mg, 0.412 mmol) and (R)-2-methyl-N—((R)-8-azaspiro[4.5]decan-1-yl)propane-2-sulfinamide (139 mg, 0.536 mmol) in DIPEA (0.648 mL) was stirred in a microwave reactor for 14 h at 95° C. After cooling to RT, the volatiles were removed under reduced pressure and the resulting residue was purified by silica chromatography (0 to 100% gradient of MeOH/DCM containing 0.25% TEA) to afford 3-((3-amino-5-((R)-1-((R)-1,1-dimethylethylsulfinamido)-8-azaspiro[4.5]decan-8-yl)pyrazin-2-yl)thio)-2-chlorobenzamide (65 mg, 0.121 mmol). MS m/z 537.2 (M+H)+.

Step c:

3-((3-amino-5-((R)-1-((R)-1,1-dimethylethylsulfinamido)-8-azaspiro[4.5]decan-8-yl)pyrazin-2-yl)thio)-2-chlorobenzamide (65 mg, 0.121 mmol) was dissolved in HCl/dioxane (4 M, 0.121 mL, 0.484 mmol) and stirred at 22° C. until no starting material remained (1 h, monitored by LCMS). The volatiles were removed under reduced pressure and the resulting residue was purified by HPLC (gradient elution: 25 to 50% acetonitrile in water, 5 mM NH$_4$OH modifier), to give R)-3-((3-amino-5-(1-amino-8-azaspiro[4.5]decan-8-yl)pyrazin-2-yl)thio)-2-chlorobenzamide (25.5 mg, 0.058 mmol). $^1$H NMR (400 MHz, DMSO-d$_6$) δ 7.90 (s, 1H), 7.63 (s, 1H), 7.62 (br. s., 1H), 7.28-7.18 (m, 1H), 7.18-7.09 (m, 1H), 6.64 (dd, J=1.6, 7.9 Hz, 1H), 6.08 (s, 2H), 4.18-4.07 (m, 2H), 3.12-2.95 (m, 2H), 2.74-2.64 (m, 1H), 1.91-1.73 (m, 2H), 1.66-1.47 (m, 4H), 1.39-1.14 (m, 4H). HRMS calcd for C$_{20}$H$_{26}$ClN$_6$OS (M+H)+ 433.1577, found 433.1598; IC$_{50}$ is 0.016 µM.

Example 41

(2R,4R)-4-amino-8-(6-amino-5-((2-amino-3-chloro-pyridin-4-yl)thio)pyrazin-2-yl)-8-azaspiro[4.5]decan-2-ol

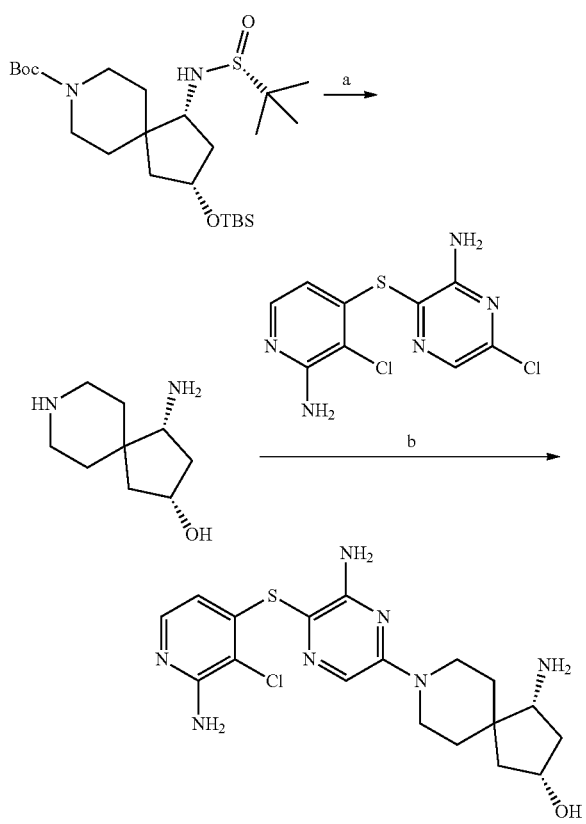

Step a:

A mixture of (1R,3R)-tert-butyl 3-((tert-butyldimethylsilyl)oxy)-1-((R)-1,1-dimethylethylsulfinamido)-8-azaspiro[4.5]decane-8-carboxylate (100 mg, 0.205 mmol) and HCl (4 M in dioxane, 510 µL, 2.05 mmol) in MeOH (1 mL) was stirred for 1 h at 40° C. The volatiles were removed under reduced pressure and the resulting white residue was dried under vacuum for 1 h. MS m/z 171.1 (M+H)$^+$.

Step b:

A mixture of this white residue and 3-((2-amino-3-chloropyridin-4-yl)thio)-6-chloropyrazin-2-amine (65 mg, 0.226 mmol) in DIPEA:NMP (2:1; 1.5 mL) was vigorously stirred for 40 h at 100° C. After cooling to RT, the volatiles were removed under reduced pressure and the resulting crude was purified by HPLC (gradient elution 7.5-20% acetonitrile in water, 0.1% TFA modifier). The volatiles were removed under reduced pressure and the resulting residue was further purified by HPLC (gradient elution 15-40% acetonitrile in water, 5 mM NH$_4$OH modifier) to give (2R,4R)-4-amino-8-(6-amino-5-((2-amino-3-chloropyridin-4-yl)thio)pyrazin-2-yl)-8-azaspiro[4.5]decan-2-ol (44 mg, 0.102 mmol) as a white solid. $^1$H NMR (400 MHz, METHANOL-d$_4$) δ ppm 7.51-7.64 (m, 2H), 5.92 (d, J=5.56 Hz, 1H), 4.16-4.39 (m, 3H), 3.00-3.21 (m, 2H), 2.80 (dd, J=8.08, 7.07 Hz, 1H), 2.33 (dt, J=13.45, 6.79 Hz, 1H), 1.95 (dd, J=13.89, 7.58 Hz, 1H), 1.83 (dd, J=14.02, 4.17 Hz, 1H), 1.61-1.74 (m, 3H), 1.56 (ddd, J=13.39, 8.08, 5.81 Hz, 1H), 1.30 (d, J=13.14 Hz, 1H). HRMS calcd for C$_{18}$H$_{25}$ClN$_7$OS (M+H)$^+$ 422.1557, found 422.1569. IC$_{50}$ is 0.007 µM.

The following compounds of table 9 were synthesized using the above procedure or modifications to the above procedure using the corresponding protected amine and chloro-pyrazine intermediate.

TABLE 9

| Example | Compound | Characterization | IC$_{50}$ (µM) |
|---|---|---|---|
| 42 | (structure) | $^1$H NMR (400 MHz, METHANOL-d$_4$) δ ppm 8.39 (dd, J = 4.42, 1.39 Hz, 1 H), 7.59 (s, 1 H), 7.22-7.50 (m, 2 H), 4.20-4.38 (m, 3 H), 2.97-3.22 (m, 2 H), 2.84 (t, J = 7.45 Hz, 1 H), 2.34 (dt, J = 13.39, 6.69 Hz, 1 H), 1.89-2.07 (m, 1 H), 1.78-1.89 (m, 1 H), 1.51-1.75 (m, 4 H), 1.32 (d, J = 12.88 Hz, 1 H). $^{19}$F NMR (376 MHz, METHANOL-d$_4$) δ ppm −66.48. HRMS calcd for C$_{19}$H$_{24}$F$_3$N$_6$OS (M + H)$^+$ 441.1684, found 441.1657. | 0.007 |

TABLE 9-continued

| Example | Compound | Characterization | IC$_{50}$ (μM) |
|---|---|---|---|
| 43 | (structure) | $^1$H NMR (400 MHz, METHANOL-d$_4$) δ ppm 8.34-8.47 (m, 1 H), 7.59 (s, 1 H), 7.32-7.49 (m, 2 H), 4.34 (td, J = 6.69, 3.28 Hz, 3 H), 2.96-3.18 (m, 3 H), 2.28 (dd, J = 14.15, 7.07 Hz, 1 H), 1.99 (ddd, J = 13.58, 6.88, 2.53 Hz, 1 H), 1.68-1.87 (m, 2 H), 1.52-1.62 (m, 2 H), 1.52-1.62 (m, 2 H), 1.49 (dd, J = 13.26, 2.15 Hz, 1 H), 1.24-1.41 (m, 1 H). $^{19}$F NMR (376 MHz, METHANOL-d$_4$) δ ppm −66.48. HRMS calcd for C$_{19}$H$_{24}$F$_3$N$_6$OS (M + H)$^+$ 441.1684, found 441.1651. | 0.006 |
| 44 | (structure) | $^1$H NMR (400 MHz, METHANOL-d$_4$) δ ppm 8.39 (dd, J = 4.42, 1.39 Hz, 1 H), 7.59 (s, 1 H), 7.30-7.50 (m, 2 H), 4.15-4.42 (m, 3 H), 2.98-3.21 (m, 2 H), 2.83 (t, J = 7.45 Hz, 1 H), 2.34 (dt, J = 13.45, 6.79 Hz, 1 H), 1.89-2.04 (m, 1 H), 1.76-1.89 (m, 1 H), 1.51-1.76 (m, 4 H), 1.32 (d, J = 12.88 Hz, 1 H). $^{19}$F NMR (376 MHz, METHANOL-d$_4$) δ ppm −66.48. HRMS calcd for C$_{19}$H$_{24}$F$_3$N$_6$OS (M + H)$^+$ 441.1684, found 441.1721. | 0.135 |
| 45 | (structure) | $^1$H NMR (400 MHz, METHANOL-d$_4$) δ ppm 7.48-7.67 (m, 2 H), 5.92 (d, J = 5.56 Hz, 1 H), 4.21-4.38 (m, 2 H), 3.92 (dt, J = 7.07, 3.54 Hz, 1 H), 3.28 (s, 3 H), 2.94-3.18 (m, 3 H), 2.25 (dd, J = 14.02, 7.20 Hz, 1 H), 2.07 (ddd, J = 13.77, 6.95, 2.53 Hz, 1 H), 1.68-1.83 (m, 2 H), 1.51-1.68 (m, 2 H), 1.42 (dd, J = 13.14, 2.27 Hz, 1 H), 1.28-1.38 (m, 1 H), 1.08-1.20 (m, 2 H). HRMS calcd for C$_{19}$H$_{27}$ClN$_7$OS (M + H)$^+$ 436.1686, found 436.1666. | 0.044 |
| 46 | (structure) | $^1$H NMR (400 MHz, METHANOL-d$_4$) δ ppm 7.99 (d, J = 5.31 Hz, 1 H), 7.60 (s, 1 H), 6.61 (d, J = 5.31 Hz, 1 H), 4.24-4.42 (m, 2 H), 3.92 (tt, J = 6.88, 3.35 Hz, 1 H), 3.28 (s, 3 H), 3.03-3.18 (m, 2 H), 3.00 (dd, J = 8.72, 7.20 Hz, 1 H), 2.25 (dd, J = 14.15, 7.33 Hz, 1 H), 2.08 (ddd, J = 13.83, 6.88, 2.53 Hz, 1 H), 1.68-1.82 (m, 2 H), 1.51-1.68 (m, 2 H), 1.44 (dd, J = 13.14, 2.27 Hz, 1 H), 1.29-1.40 (m, 1 H). HRMS calcd for C$_{19}$H$_{25}$Cl$_2$N$_6$OS (M + H)$^+$ 455.1188, found 455.1166. | 0.038 |
| 47 | (structure) racemic | $^1$H NMR (400 MHz, METHANOL-d$_4$) δ ppm 8.39 (dd, J = 4.29, 1.26 Hz, 1 H), 7.60 (s, 1 H), 7.30-7.51 (m, 2 H), 4.20-4.44 (m, 2 H), 2.94-3.20 (m, 3 H), 2.35-2.61 (m, 2 H), 1.94-2.20 (m, 2 H), 1.81 (td, J = 12.69, 4.17 Hz, 1 H), 1.69 (td, J = 12.69, 3.92 Hz, 1 H), 1.48-1.59 (m, 1 H), 1.44 (dd, J = 13.39, 2.27 Hz, 1 H). $^{19}$F NMR (376 MHz, METHANOL-d$_4$) δ ppm −66.46, −84.76, −85.11. HRMS calcd for C$_{19}$H$_{22}$F$_5$N$_6$S (M + H)$^+$ 461.1547, found 461.1548. | 0.021 |

TABLE 9-continued

| Example | Compound | Characterization | IC$_{50}$ (μM) |
|---|---|---|---|
| 48 | | $^1$H NMR (400 MHz, METHANOL-d$_4$) δ ppm 8.38 (dd, J = 4.29, 1.26 Hz, 1 H), 7.54-7.63 (m, 1 H), 7.31-7.49 (m, 2 H), 4.15-4.38 (m, 2 H), 3.81-3.96 (m, 1 H), 3.27-3.29 (m, 3 H), 3.02-3.19 (m, 2 H), 2.82 (t, J = 7.58 Hz, 1 H), 2.34 (dt, J = 13.71, 6.92 Hz, 1 H), 1.93-2.06 (m, 1 H), 1.75-1.93 (m, 1 H), 1.50-1.75 (m, 4 H), 1.24-1.39 (m, 1 H). $^{19}$F NMR (376 MHz, METHANOL-d$_4$) δ ppm −66.43. HRMS calcd for C$_{20}$H$_{26}$F$_3$N$_6$OS (M + H)$^+$ 455.1841, found 455.1801. | 0.009 |
| 49 | | $^1$H NMR (400 MHz, METHANOL-d$_4$) δ ppm 8.38 (dd, J = 4.29, 1.26 Hz, 1 H), 7.58 (s, 1 H), 7.33-7.46 (m, 2 H), 4.21-4.40 (m, 3 H), 2.97-3.17 (m, 2 H), 2.56 (dd, J = 9.22, 6.44 Hz, 1 H), 2.34-2.46 (m, 4 H), 1.91-2.05 (m, 1 H), 1.74-1.91 (m, 2 H), 1.68 (dd, J = 7.83, 3.79 Hz, 2 H), 1.56 (ddd, J = 12.82, 9.16, 6.57 Hz, 1 H), 1.34 (d, J = 13.39 Hz, 1 H). $^{19}$F NMR (376 MHz, METHANOL-d$_4$) δ ppm −66.46. HRMS calcd for C$_{20}$H$_{26}$F$_3$N$_6$OS (M + H)$^+$ 455.1841, found 455.1861. | 0.234 |
| 50 | | $^1$H NMR (400 MHz, DMSO-d$_6$) δ 8.47 (dd, J = 4.4, 1.4 Hz, 1 H), 8.43 (s, 1 H), 8.03 (s, 1 H), 7.70 (s, 1 H), 7.56 (dd, J = 8.2, 4.6 Hz, 1 H), 7.31 (d, J = 8.1 Hz, 1 H), 6.23 (s, 2 H), 4.44 (d, J = 13.5 Hz, 2 H), 2.97-2.80 (m, 2 H), 2.46 (s, 2 H), 1.94 (td, J = 13.1, 4.3 Hz, 2 H), 1.48 (d, J = 12.6 Hz, 2H). HRMS calcd for C$_{18}$H$_{19}$F$_3$N$_7$OS (M + H)$^+$ 438.1318, found 438.1418. | 0.610 |
| 51 | | $^1$H NMR (400 MHz, METHANOL-d$_4$) δ ppm 7.76 (s, 1 H), 7.60 (s, 1 H), 5.90 (s, 1 H), 4.27 (t, J = 13.01 Hz, 2 H), 3.08-3.21 (m, 2 H), 2.83 (t, J = 7.45 Hz, 1 H), 1.99-2.11 (m, 1 H), 1.29-1.96 (m, 9 H). HRMS calcd for C$_{18}$H$_{25}$ClN$_7$S (M + H)$^+$ 406.1581, found 406.1595. | 0.010 |
| 52 | | $^1$H NMR (400 MHz, METHANOL-d$_4$) δ 7.64-7.59 (m, 2 H), 6.14 (dd, J = 6.5, 2.2 Hz, 1 H), 4.36-4.21 (m, 2 H), 4.18 (dd, J = 10.6, 5.6 Hz, 1 H), 3.97 (d, J = 9.2 Hz, 1 H), 3.90 (d, J = 9.2 Hz, 1 H), 3.84 (dd, J = 10.7, 2.8 Hz, 1 H), 3.58 (dd, J = 5.6, 2.8 Hz, 1 H), 3.28-3.11 (m, 2 H), 1.85-1.71 (m, 4 H). HRMS calcd for C$_{17}$H$_{23}$ClN$_7$OS (M + H)$^+$ 408.1373, found 408.1475. | 0.007 |

TABLE 9-continued

| Example | Compound | Characterization | IC$_{50}$ (μM) |
|---|---|---|---|
| 53 | (structure) | $^1$H NMR (400 MHz, METHANOL-d$_4$) δ 7.65-7.57 (m, 2 H), 6.14 (dd, J = 6.5, 2.2 Hz, 1 H), 4.34-4.21 (m, 2 H), 4.18 (dd, J = 10.6, 5.6 Hz, 1 H), 3.97 (d, J = 9.2 Hz, 1 H), 3.90 (d, J = 9.2 Hz, 1 H), 3.84 (dd, J = 10.7, 2.8 Hz, 1 H), 3.58 (dd, J = 5.6, 2.8 Hz, 1 H), 3.27-3.09 (m, 2 H), 1.85-1.71 (m, 4 H). HRMS calcd for C$_{17}$H$_{23}$ClN$_7$OS (M + H)$^+$ 408.1373, found 408.1474. | 0.298 |
| 54 | (structure) | $^1$H NMR (400 MHz, METHANOL-d$_4$) δ 8.10 (dd, J = 4.7, 1.8 Hz, 1 H), 7.58 (s, 1 H), 7.21 (dd, J = 7.9, 4.7 Hz, 1 H), 7.11 (dd, J = 7.9, 1.7 Hz, 1 H), 4.22-4.07 (m, 3 H), 3.86 (d, J = 8.6 Hz, 1 H), 3.79 (d, J = 8.7 Hz, 1 H), 3.50 (dd, J = 9.0, 5.2 Hz, 1 H), 3.28-3.11 (m, 3 H), 1.82-1.65 (m, 2 H), 1.65-1.50 (m, 2 H). HRMS calcd for C$_{17}$H$_{22}$ClN$_6$OS (M + H)$^+$ 393.1264, found 393.1278. | 0.010 |
| 55 | (structure) | $^1$H NMR (400 MHz, DMSO-d$_6$) δ 8.86 (d, J = 5.3 Hz, 1 H), 7.68 (s, 1 H), 6.83 (d, J = 5.4 Hz, 1 H), 6.34 (s, 2 H), 4.11-3.90 (m, 3 H), 3.65 (dd, J = 46.4, 8.4 Hz, 2 H), 3.27-3.16 (m, 3 H), 3.05 (t, J = 6.2 Hz, 1 H), 1.73-1.49 (m, 3 H), 1.47-1.35 (m, 2 H). HRMS calcd for C$_{16}$H$_{21}$ClN$_7$OS (M + H)$^+$ 394.1217, found 394.0713. | 0.073 |
| 56 | (structure)<br><br>(structure)<br><br>2:1 diastereomer mixture | Major diastereomer. $^1$H NMR (400 MHz, METHANOL-d$_4$) δ 7.68-7.48 (m, 2 H), 5.92 (d, J = 5.5 Hz, 1 H), 4.21-4.04 (m, 2 H), 3.28-3.10 (m, 2 H), 2.79 (d, J = 5.9 Hz, 1 H), 2.44-2.23 (m, 1 H), 1.94-1.40 (m, 8 H), 1.01 (d, J = 7.0 Hz, 3 H). HRMS calcd for C$_{19}$H$_{27}$ClN$_7$S (M + H)$^+$ 420.1737, found 420.1748.<br>Minor diastereomer. $^1$H NMR (400 MHz, METHANOL-d$_4$) δ 7.66-7.49 (m, 2 H), 5.92 (d, J = 5.5 Hz, 1 H), 4.36 (t, J = 12.0 Hz, 2 H), 3.16-2.90 (m, 2 H), 2.17 (d, J = 10.0 Hz, 1 H), 1.94-1.53 (m, 6 H), 1.37-1.27 (m, 3 H), 1.08 (d, J = 6.5 Hz, 3 H). HRMS calcd for C$_{19}$H$_{27}$ClN$_7$S (M + H)$^+$ 420.1737, found 420.1748. | 0.009 |
| 57 | (structure) | $^1$H NMR (400 MHz, METHANOL-d$_4$) δ ppm 7.99 (d, J = 5.56 Hz, 1 H), 7.61 (s, 1 H), 6.61 (d, J = 5.31 Hz, 1 H), 4.36 (dt, J = 6.63, 3.38 Hz, 3 H), 2.99-3.19 (m, 3 H), 2.28 (dd, J = 14.02, 6.95 Hz, 1 H), 1.95-2.08 (m, 1 H), 1.72-1.90 (m, 2 H), 1.44-1.68 (m, 3 H), 1.36 (d, J = 11.12 Hz, 1 H). HRMS calcd for C$_{18}$H$_{23}$Cl$_2$N$_6$OS (M + H)$^+$ 441.1031, found 441.0937. | 0.003 |

TABLE 9-continued

| Example | Compound | Characterization | IC$_{50}$ (μM) |
|---|---|---|---|
| 58 | (structure) | $^1$H NMR (400 MHz, METHANOL-d$_4$) δ ppm 7.99 (d, J = 5.31 Hz, 1 H), 7.61 (s, 1 H), 6.61 (d, J = 5.31 Hz, 1 H), 4.23-4.39 (m, 3 H), 3.01-3.22 (m, 2 H), 2.85 (t, J = 7.33 Hz, 1 H), 2.34 (dt, J = 13.39, 6.69 Hz, 1 H), 1.97 (dd, J = 14.15, 7.33 Hz, 1 H), 1.85 (dd, J = 14.02, 3.92 Hz, 1 H), 1.50-1.74 (m, 4 H), 1.33 (d, J = 13.64 Hz, 1 H). HRMS calcd for C$_{18}$H$_{23}$Cl$_2$N$_6$OS 441.1031, (M + H)$^+$, found 441.1020. | 0.004 |
| 59 | (structure) | $^1$H NMR (400 MHz, METHANOL-d$_4$) δ ppm 7.51-7.64 (m, 2 H) 5.91 (d, J = 5.56 Hz, 1 H) 4.19-4.37 (m, 2 H) 3.83-3.96 (m, 1 H) 3.28 (s, 3 H) 3.01-3.20 (m, 2 H) 2.80 (t, J = 7.58 Hz, 1 H) 2.34 (dt, J = 13.71, 6.92 Hz, 1 H) 1.94-2.04 (m, 1 H) 1.78-1.90 (m, 1 H) 1.53-1.75 (m, 4 H) 1.30 (d, J = 13.39 Hz, 1 H). HRMS calcd for C$_{19}$H$_{26}$ClN$_6$OS (M + H)$^+$ 436.1686, found 436.1663. | 0.010 |
| 60 | (structure) | $^1$H NMR (400 MHz, METHANOL-d$_4$) δ ppm 7.51-7.64 (m, 2 H) 5.91 (d, J = 5.56 Hz, 1 H) 4.19-4.37 (m, 2 H) 3.83-3.96 (m, 1 H) 3.28 (s, 3 H) 3.01-3.20 (m, 2 H) 2.80 (t, J = 7.58 Hz, 1 H) 2.34 (dt, J = 13.71, 6.92 Hz, 1 H) 1.94-2.04 (m, 1 H) 1.78-1.90 (m, 1 H) 1.53-1.75 (m, 4 H) 1.30 (d, J = 13.39 Hz, 1 H). HRMS calcd for C$_{19}$H$_{26}$ClN$_6$OS (M + H)$^+$ 436.1188, found 455.1234. | 0.004 |
| 61 | (structure) | Chiral SFC purification performed as follow; column: ADH 21 × 250 mm, flow rate: 80 g per minute, mobile phase: 30% IPA and 5 mM NH$_4$OH in CO$_2$, detection: 260 nm UV to obtain two peaks R$_t$(Peak 1) = 3.5 min. NMR was a mixture of diastereomers (as depicted). Major diastereomer: $^1$H NMR (400 MHz, METHANOL-d$_4$) δ ppm 8.38 (dd, J = 4.42, 1.39 Hz, 1 H), 7.51-7.66 (m, 1 H) 7.33-7.48 (m, 2 H), 4.14-4.38 (m, 2 H), 2.95-3.21 (m, 2 H), 2.72-2.95 (m, 1 H), 2.19-2.34 (m, 1 H), 1.86-2.19 (m, 1 H), 1.52-1.81 (m, 3 H), 1.24-1.48 (m, 3 H), 0.93-1.20 (m, 4 H). HRMS calcd for C$_{20}$H$_{26}$F$_3$N$_6$S (M + H)$^+$ 439.1892, found 439.1897. | 0.007 |

TABLE 9-continued

| Example | Compound | Characterization | IC$_{50}$ (μM) |
|---|---|---|---|
| 62 | | Chiral SFC purification performed as follow; column: ADH 21 × 250 mm, flow rate: 80 g per minute, mobile phase: 30% IPA and 5 mM NH$_4$OH in CO$_2$, detection: 260 nm UV to obtain two peaks R$_t$(Peak 2) = 4.5 min. NMR was a mixture of diastereomers (as depicted). Major diastereomer: $^1$H NMR (400 MHz, METHANOL-d$_4$) δ ppm 8.38 (dd, J = 4.55, 1.26 Hz, 1 H), 7.54-7.66 (m, 1 H), 7.32-7.49 (m, 2 H), 4.15-4.39 (m, 2 H), 2.98-3.19 (m, 2 H), 2.76-2.98 (m, 1 H), 2.19-2.31 (m, 1 H), 1.91-2.14 (m, 1 H), 1.52-1.81 (m, 3 H), 1.26-1.49 (m, 3 H), 0.99-1.21 (m, 4 H). HRMS calcd for C$_{20}$H$_{26}$F$_3$N$_6$S (M + H)$^+$ 439.1892, found 439.1927. | 0.100 |
| 63 | | $^1$H NMR (400 MHz, DMSO-d$_6$) δ ppm 8.10 (d, J = 5.3 Hz, 1 H), 7.67 (s, 1 H), 6.52-6.62 (m, 1 H), 6.32 (br. s, 2 H), 3.97-4.11 (m, 2 H), 3.95 (dd, J = 8.5, 6.5 Hz, 1 H), 3.71 (d, J = 8.5 Hz, 1 H), 3.59 (d, J = 8.3 Hz, 1 H), 3.29 (dd, J = 8.5, 5.8 Hz, 1 H), 3.15-3.25 (m, 2 H), 3.04 (t, J = 6.1 Hz, 1 H), 1.51-1.70 (m, 4 H), 1.35-1.46 (m, 2 H). HRMS calcd for C$_{17}$H$_{21}$Cl$_2$N$_6$OS (M + H)$^+$ 427.3513, found 427.0852. | 0.007 |
| 64 | | $^1$H NMR (400 MHz, DMSO-d$_6$) δ ppm 7.93 (d, J = 5.0 Hz, 1 H), 7.67 (s, 1 H), 6.52 (d, J = 5.5 Hz, 1 H), 6.32 (s, 2 H), 3.97-4.10 (m, 2 H), 3.95 (dd, J = 8.5, 6.8 Hz, 1 H), 3.71 (d, J = 8.5 Hz, 1 H), 3.60 (d, J = 8.3 Hz, 1 H), 3.30 (dd, J = 8.5, 5.8 Hz, 1 H), 3.20 (ddd, J = 13.4, 10.5, 3.0 Hz, 2 H), 3.05 (t, J = 6.1 Hz, 1 H), 1.52-1.70 (m, 2 H), 1.41 (td, J = 8.8, 4.6 Hz, 2 H). HRMS calcd for C$_{17}$H$_{21}$ClFN$_6$OS (M + H)$^+$ 411.1170, found 411.1165. | 0.013 |
| 65 | | $^1$H NMR (400 MHz, METHANOL-d$_4$) δ ppm 8.09 (s, 1 H), 7.62 (s, 1 H), 6.21 (d, J = 1.8 Hz, 1 H), 4.30 (t, J = 13.5 Hz, 2 H), 3.22-3.07 (m, 2 H), 2.82 (br s, 1 H), 2.09-1.98 (m, 1 H), 1.95-1.86 (m, 1 H), 1.83-1.55 (m, 5 H), 1.52-1.28 (m, 3 H). HRMS calcd for C$_{18}$H$_{23}$ClFN$_6$S (M + H)$^+$ 409.1377, found 409.1369. | 0.310 |

TABLE 9-continued

| Example | Compound | Characterization | IC$_{50}$ (μM) |
|---|---|---|---|
| 66 | | $^1$H NMR (400 MHz, METHANOL-d$_4$) δ ppm 7.99 (d, J = 5.52 Hz, 1 H), 7.61 (s, 1 H), 6.61 (d, J = 5.27 Hz, 1 H), 5.19 (td, J = 6.84, 3.39 Hz, 1 H), 4.20-4.44 (m, 2 H), 2.96-3.19 (m, 3 H), 2.52 (quin, J = 6.96 Hz, 1 H), 2.38 (dd, J = 14.56, 7.28 Hz, 1 H), 1.98-2.11 (m, 1 H), 1.86-1.98 (m, 1 H), 1.72-1.86 (m, 1 H), 1.54-1.72 (m, 2 H), 1.33-1.51 (m, 2 H), 1.05-1.18 (m, 6 H). HRMS calcd for C$_{22}$H$_{29}$Cl$_2$N$_6$O$_2$S (M + H)$^+$ 511.1450, found 511.1453. | 0.065 |
| 67 | | $^1$H NMR (400 MHz, METHANOL-d$_4$) δ ppm 7.53-7.64 (m, 2 H), 5.91 (d, J = 5.56 Hz, 1 H), 4.24-4.43 (m, 2 H), 2.95-3.18 (m, 3 H), 2.36-2.61 (m, 2 H), 1.95-2.19 (m, 2 H), 1.81 (td, J = 12.76, 4.29 Hz, 1 H), 1.69 (td, J = 12.69, 3.92 Hz, 1 H), 1.54 (dd, J = 13.26, 2.15 Hz, 1 H), 1.43 (dd, J = 13.39, 2.53 Hz, 1 H). $^{19}$F NMR (376 MHz, METHANOL-d$_4$) δ ppm −84.69, −85.07. HRMS calcd for C$_{18}$H$_{23}$ClF$_2$N$_7$O$_2$S (M + H)$^+$ 442.1392, found 442.1443. | 0.010 |

Example 68

(3R,4S)-8-(6-amino-5-((2-amino-3-chloropyridin-4-yl)thio)pyrazin-2-yl)-3-methyl-2-oxa-8-azaspiro[4.5]decan-4-amine

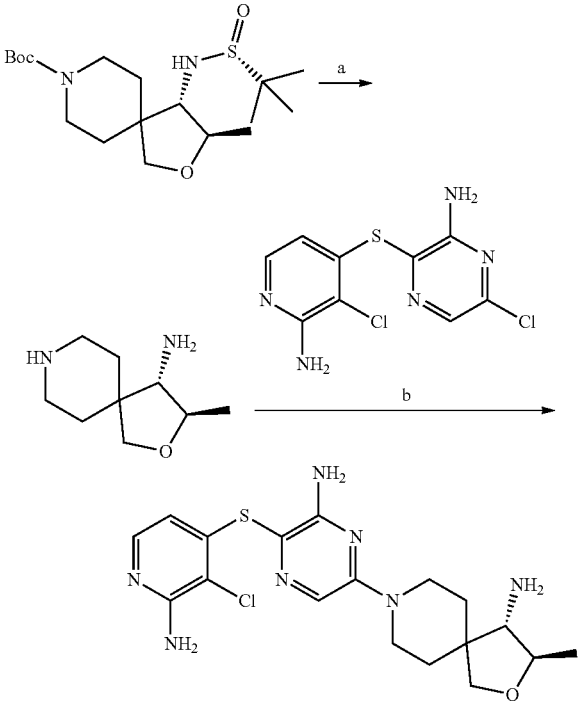

Step a:

A mixture of (3R,4S)-tert-butyl 4-((R)-1,1-dimethylethylsulfinamido)-3-methyl-2-oxa-8-azaspiro[4.5]decane-8-carboxylate (53 mg, 0.142 mmol) and HCl (4 M in dioxane, 354 μL, 1.415 mmol) in MeOH (5 mL) was stirred for 1 h at 40° C. After cooling to RT, the volatiles were removed under reduced pressure to give (3R,4S)-3-methyl-2-oxa-8-azaspiro[4.5]decane-4-amine which was used in next step without further purification. MS m/z 171.1 (M+H)$^+$.

Step b:

A mixture of (3R,4S)-3-methyl-2-oxa-8-azaspiro[4.5]decane-4-amine crude, 3-((2-amino-3-chloropyridin-4-yl)thio)-6-chloropyrazin-2-amine (35.5 mg, 0.123 mmol), and DIPEA (193 μL, 1.11 mmol) in DMSO (600 μL) was stirred for 16 h at 100° C. After cooling to RT, the volatiles were removed under reduced pressure and the resulting residue was purified by HPLC (gradient elution 15-40% acetonitrile in water, 5 mM NH$_4$OH modifier) to give (3R,4S)-8-(6-amino-5-((2-amino-3-chloropyridin-4-yl)thio)pyrazin-2-yl)-3-methyl-2-oxa-8-azaspiro[4.5]decan-4-amine (13 mg, 0.030 mmol). $^1$H NMR (400 MHz, METHANOL-d$_4$) δ ppm 7.72-7.51 (m, 2H), 5.92 (d, J=5.5 Hz, 1H), 4.31 (m, 2H), 4.01-3.78 (m, 2H), 3.58 (dq, J=8.1, 6.0 Hz, 1H), 3.04 (m, 2H), 2.48 (d, J=8.1 Hz, 1H), 1.75 (m, 2H), 1.61-1.47 (m, 2H), 1.31 (d, J=6.1 Hz, 3H). HRMS calcd for C$_{18}$H$_{25}$ClN$_7$OS (M+H)$^+$ 422.1530, found 422.1505. IC$_{50}$ is 0.010 μM.

Example 69

(3S,4S)-8-(6-amino-5-((2-amino-3-chloropyridin-4-yl)thio)pyrazin-2-yl)-3-methyl-2-oxa-8-azaspiro[4.5]decan-4-amine

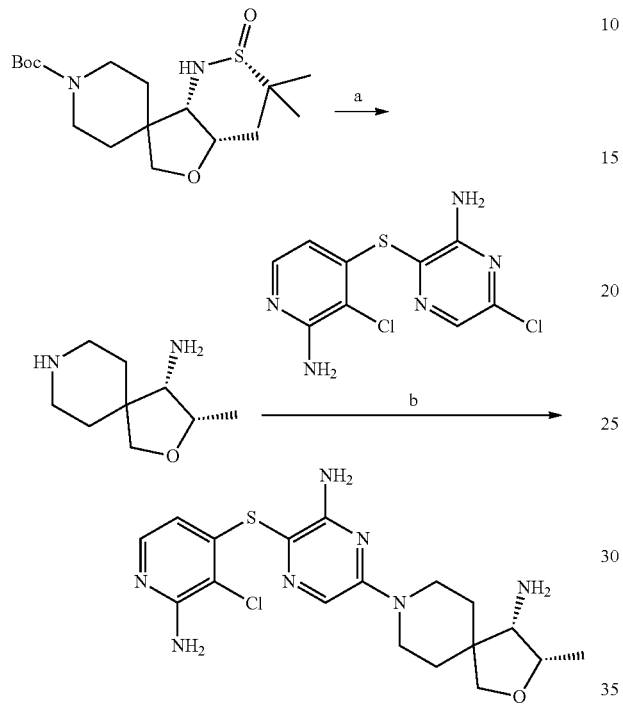

Step a:

A mixture of (3S,4S)-tert-butyl 4-((R)-1,1-dimethylethyl-sulfinamido)-3-methyl-2-oxa-8-azaspiro[4.5]decane-8-carboxylate (51 mg, 0.136 mmol) and HCl (4 M in dioxane, 340 µL, 1.362 mmol) in MeOH (5 mL) was stirred for 1 h at 40° C. After cooling to RT, the volatiles were removed under reduced pressure to give (3S,4S)-3-methyl-2-oxa-8-azaspiro[4.5]decane-4-amine which was used in next step without further purification. MS m/z 171.1 (M+H)$^+$.

Step b:

A mixture of (3S,4S)-3-methyl-2-oxa-8-azaspiro[4.5]decane-4-amine crude, 3-((2-amino-3-chloropyridin-4-yl)thio)-6-chloropyrazin-2-amine (35.5 mg, 0.123 mmol), and DIPEA (193 µL, 1.11 mmol) in DMSO (600 µL) was stirred for 16 h at 100° C. After cooling to RT, the volatiles were removed under reduced pressure and the resulting residue was purified by HPLC (gradient elution 15-40% acetonitrile in water, 5 mM NH$_4$OH modifier) to give (3S,4S)-8-(6-amino-5-((2-amino-3-chloropyridin-4-yl)thio)pyrazin-2-yl)-3-methyl-2-oxa-8-azaspiro[4.5]decan-4-amine (11 mg, 0.026 mmol). $^1$H NMR (400 MHz, METHANOL-d$_4$) δ ppm 7.67-7.47 (m, 2H), 5.91 (d, J=5.5 Hz, 1H), 4.22 (qd, J=6.4, 4.8 Hz, 1H), 4.03 (ddt, J=13.5, 8.9, 4.7 Hz, 2H), 3.86 (d, J=8.7 Hz, 1H), 3.71 (d, J=8.7 Hz, 1H), 3.37 (td, J=9.9, 4.9 Hz, 1H), 3.29-3.23 (m, 1H), 3.00 (d, J=5.0 Hz, 1H) 1.91-1.56 (m, 4H), 1.21 (d, J=6.4 Hz, 3H). HRMS calcd for C$_{18}$H$_{25}$ClN$_7$OS (M+H)$^+$ 422.1530, found 422.1514. IC$_{50}$ is 0.010 µM.

Example 70

(1R,3R)-8-(6-amino-5-((2-amino-3-chloropyridin-4-yl)thio)pyrazin-2-yl)-3-methyl-8-azaspiro[4.5]decan-1-amine

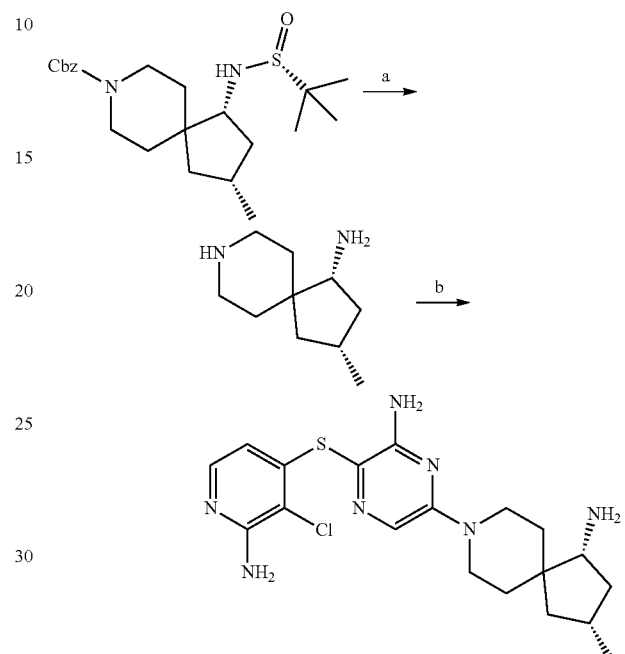

Step a:

A mixture of (1R,3R)-benzyl 1-((R)-1,1-dimethylethyl-sulfinamido)-3-methyl-8-azaspiro[4.5]decane-8-carboxylate (100 mg, 0.246 mmol) and HCl (4 M in dioxane, 1.5 mL, 6.5 mmol) in MeOH (1.5 mL) was stirred in a microwave reactor for 14 h at 140° C. After cooling to RT, the volatiles were removed under reduced pressure to give (1R,3R)-3-methyl-8-azaspiro[4.5]decan-1-amine which was used in next step without further purification. MS m/z 169.2 (M+H)$^+$.

Step b:

A mixture of (1R,3R)-3-methyl-8-azaspiro[4.5]decan-1-amine crude (theor 0.246 mmol) and 3-((2-amino-3-chloropyridin-4-yl)thio)-6-chloropyrazin-2-amine (70.9 mg, 0.246 mmol) in DIPEA (1 mL) and DMSO (0.5 mL) was stirred for 2 h at 130° C. After cooling to RT, the volatiles were removed under reduced pressure and the resulting residue was purified by HPLC (gradient elution 15-40% acetonitrile in water, 5 mM NH$_4$OH modifier) to give (1R,3R)-8-(6-amino-5-((2-amino-3-chloropyridin-4-yl)thio)pyrazin-2-yl)-3-methyl-8-azaspiro[4.5]decan-1-amine (23 mg, 0.055 mmol). $^1$H NMR (400 MHz, METHANOL-d$_4$) δ ppm 7.51-7.64 (m, 2H), 5.91 (d, J=5.31 Hz, 1H), 4.18-4.37 (m, 2H), 3.02-3.18 (m, 2H), 2.82 (dd, J=9.60, 6.32 Hz, 1H), 2.09-2.20 (m, 1H), 2.00-2.09 (m, 1H), 1.91-2.00 (m, 1H), 1.58-1.74 (m, 2H), 1.24-1.48 (m, 3H), 1.09-1.20 (m, 1H), 1.01-1.09 (m, 3H). HRMS cald for C$_{19}$H$_{27}$ClN$_7$S (M+H)$^+$ 420.1737, found 420.1719. IC$_{50}$ is 0.005 µM.

Example 71

(1R,3S)-8-(6-amino-5-((2-amino-3-chloropyridin-4-yl)thio)pyrazin-2-yl)-3-methyl-8-azaspiro[4.5]decan-1-amine

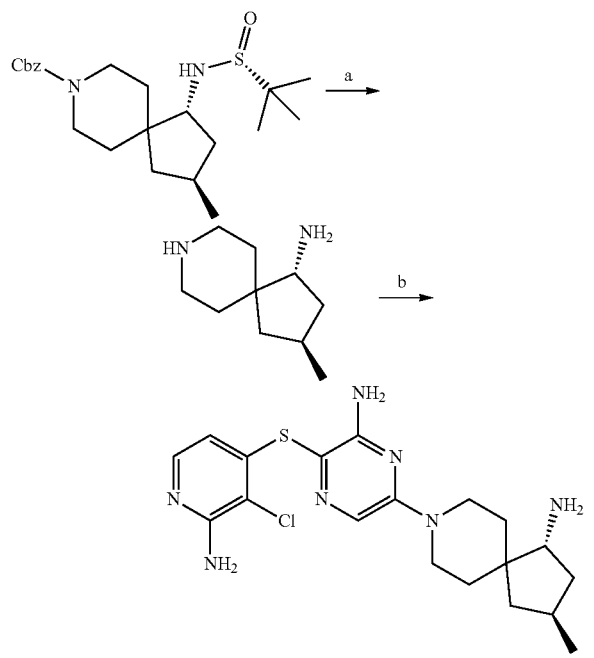

Step a:

A suspension of (1R,3S)-benzyl 1-((R)-1,1-dimethylethylsulfinamido)-3-methyl-8-azaspiro[4.5]decane-8-carboxylate (600 mg, 1.476 mmol) and Pd(OH)$_2$ (104 mg, 0.148 mmol) in EtOAc:THF (1:2 75 mL) was stirred vigorously under H$_2$ atmosphere for 48 h. The reaction mixture was filtered through a pad of Celite followed by MeOH (50 mL) wash. The volatiles were removed under reduced pressure. A solution of the resulting residue and HCl (4 M in dioxane, 1.0 mL, 4.0 mmol) was stirred for 2 h at 45° C. After cooling to RT, the volatiles were removed under reduced pressure. A suspension of the resulting residue and Pd/C (10% in charcoal, 200 mg) in MeOH (20 mL) was shaked for 2 h under 60 psi H$_2$ atmosphere. The reaction mixture was filtered through a pad of Celite followed by MeOH (50 mL) wash. The volatiles were removed under reduced pressure to afford (1R,3S)-3-methyl-8-azaspiro[4.5]decan-1-amine which was used in next step without further purification. MS m/z 169.1 (M+H)$^+$.

Step b:

A mixture of (1R,3S)-3-methyl-8-azaspiro[4.5]decan-1-amine crude (0.729 mmol) and 3-((2-amino-3-chloropyridin-4-yl)thio)-6-chloropyrazin-2-amine (150 mg, 0.521 mmol) in DIPEA (3.2 mL) and DMA (6 mL) was stirred for 14 h at 100° C. After cooling to RT, the volatiles were removed under reduced pressure and the resulting residue was purified by HPLC (gradient elution 10-30% acetonitrile in water, 0.1% TFA modifier) to give crude solid. This crude solid was further purified by HPLC (gradient elution 15-40% acetonitrile in water, 5 mM NH$_4$OH modifier) to give (1R,3S)-8-(6-amino-5-((2-amino-3-chloropyridin-4-yl)thio)pyrazin-2-yl)-3-methyl-8-azaspiro[4.5]decan-1-amine (80 mg, 0.189 mmol). $^1$H NMR (400 MHz, METHANOL-d$_4$) δ ppm 7.65-7.49 (m, 2H), 5.91 (d, J=5.5 Hz, 1H), 4.30 (ddt, J=12.4, 9.7, 3.6 Hz, 2H), 3.34 (s, 1H), 3.19-2.95 (m, 1H), 2.92-2.80 (m, 1H), 2.34-2.16 (m, 2H), 1.85-1.49 (m, 4H), 1.41 (dq, J=13.5, 2.7 Hz, 1H), 1.30 (dq, J=13.5, 2.6 Hz, 1H), 1.13-0.92 (m, 4H). HRMS cald for C$_{19}$H$_{27}$ClN$_7$S (M+H)$^+$ 420.1737, found 420.1716. IC$_{50}$ is 0.005 μM.

Example 72

8-(6-amino-5-((2-(trifluoromethyl)pyridin-3-yl)thio)pyrazin-2-yl)-1-oxa-3,8-diazaspiro[4.5]dec-2-en-2-amine

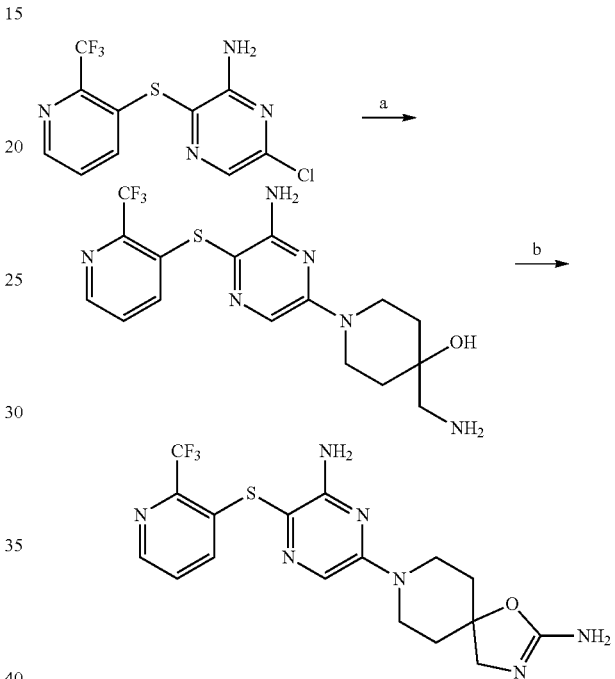

Step a:

A solution of 6-chloro-3-((2-(trifluoromethyl)pyridin-3-yl)thio)pyrazin-2-amine (70 mg, 0.304 mmol), tert-butyl ((4-hydroxypiperidine-4-yl)methyl)carbamate (103 mg, 0.336 mmol), and DIPEA (2.0 mL, 11.45 mmol) in NMP (1 mL) was stirred for 3 h at 120° C. After cooling to RT, the reaction was diluted with EtOAc, the organic phase was washed with water, brine, dried over Na$_2$SO$_4$, and the volatiles were removed under reduced pressure to give a brown oily residue. This residue was taken up in DCM (5 mL) and HCl (4 M in dioxane; 760 μL, 3.04 mmol) was added in two portions (half at the beginning of the reaction and the other half 3 h later). The reaction was stirred a total of 4 h. The volatiles were removed under reduced pressure and the resulting residue was triturated with MeCN to give a brown solid. The resulting crude was freebased suspending in 5% MeOH/DCM and adding sat. aq NaHCO$_3$. The resulting layers were separated and the aqueous was extracted again with 5% MeOH/DCM. The combine organic phases were concentrated under reduced pressure to give 1-(6-amino-5-((2-(trifluoromethyl)pyridin-3-yl)thio)pyrazin-2-yl)-4-(aminomethyl)piperidin-4-ol (65 mg, 0.149 mmol) as an off-white-tan solid. $^1$H NMR (400 MHz, DMSO-d$_6$) δ ppm 8.47 (dd, J=4.6, 1.4 Hz, 1H), 7.68 (s, 1H), 7.55 (dd, J=8.3, 4.5 Hz, 1H) 7.32 (dd, J=8.3, 1.4 Hz, 1H), 4.04 (dt, J=13.8, 4.2 Hz, 2H), 3.38-3.28 (m, 2H), 2.83 (s, 2H), 1.70-1.48 (m, 4H). MS m/z 401.2 (M+H)+.

Step b:

A solution of 1-(6-amino-5-((2-(trifluoromethyl)pyridin-3-yl)thio)pyrazin-2-yl)-4-(aminomethyl)piperidin-4-ol (65 mg, 0.162 mmol) in EtOH (3 mL) was treated in succession with cyanogen bromide (0.541 mL, 1.623 mmol) followed by NaHCO$_3$ (68.2 mg, 0.812 mmol) and the resulting mixture was stirred for 16 h at RT. The volatiles were removed under reduced pressure and the resulting residue was purified by HPLC (gradient elution 15-40% acetonitrile in water, 5 mM NH$_4$OH modifier) to give 8-(6-amino-5-((2-(trifluoromethyl)pyridin-3-yl)thio)pyrazin-2-yl)-1-oxa-3,8-diazaspiro[4.5]dec-2-en-2-amine (12.5 mg, 0.029 mmol). $^1$H NMR (400 MHz, DMSO-d$_6$) δ ppm 8.46 (dd, J=4.5, 1.4 Hz, 1H), 7.68 (s, 1H), 7.55 (dd, J=8.3, 4.6 Hz, 1H), 7.31 (dd, J=8.2, 1.5 Hz, 1H), 6.22 (s, 2H), 5.78 (s, 2H), 3.94-3.73 (m, 2H), 3.64-3.45 (m, 2H), 3.36 (s, 2H), 1.88-1.56 (m, 4H). HRMS calcd for C$_{17}$H$_{19}$F$_3$N$_7$OS (M+H)+ 426.1318, found 426.1296. IC$_{50}$ is 0.193 µM.

The following compounds of table 10 were synthesized using the above procedure or modifications to the above procedure using the corresponding protected amine and chloro-pyrazine intermediate.

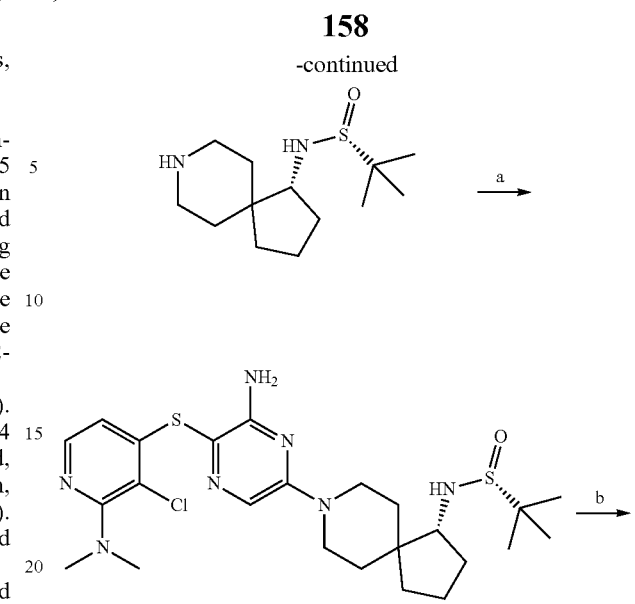

TABLE 10

| Example | Compound | Characterization | IC$_{50}$ (µM) |
|---|---|---|---|
| 73 | (structure with NH$_2$, S, pyridine with 2 Cl, pyrazine, piperidine spiro oxazoline-NH$_2$) | $^1$H NMR (400 MHz, DMSO-d$_6$) δ ppm 8.10 (d, J = 5.2 Hz, 1 H), 7.69 (s, 1 H), 6.57 (d, J = 5.3 Hz, 1 H), 6.30 (s, 2 H), 4.06 (s, 2 H), 3.79-3.60 (m, 4 H), 1.75-1.52 (m, 4 H). HRMS calcd for C$_{16}$H$_{18}$Cl$_2$N$_7$OS (M + H)+ 426.0665, found 426.0628. | 0.020 |
| 74 | (structure with CF$_3$, pyridine, S, pyrazine-NH$_2$, piperidine spiro oxazoline-NH$_2$) | $^1$H NMR (400 MHz, METHANOL-d$_4$) δ ppm 8.40 (dd, J = 4.3, 1.7 Hz, 1 H), 7.64 (s, 1 H), 7.52-7.30 (m, 2 H), 4.72 (s, 2 H), 4.00 (dt, J = 14.2, 5.1 Hz, 2 H), 3.54 (ddd, J = 13.5, 8.7, 3.8 Hz, 2 H), 1.97 (dtq, J = 17.6, 8.6, 4.1 Hz, 4 H). HRMS calcd for C$_{17}$H$_{19}$F$_3$N$_7$OS (M + H)+ 426.1318, found 426.1344. | 0.056 |

Example 75

(R)-8-(6-amino-5-((3-chloro-2-(dimethylamino)pyridin-4-yl)thio)pyrazin-2-yl)-8-azaspiro[4.5]decan-1-amine

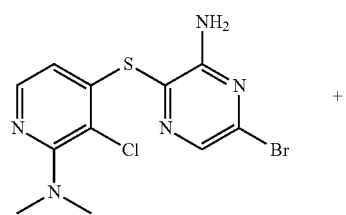

Step a:

A mixture of 6-bromo-3-((3-chloro-2-(dimethylamino)pyridin-4-yl)thio)pyrazin-2-amine (124 mg, 0.392 mmol) and (R)-2-methyl-N—((R)-8-azaspiro[4.5]decan-1-yl)propane-2-sulfinamide (111 mg, 0.431 mmol) in DIPEA (2.6 mL) was stirred for 10 h at 90° C. After cooling to RT, the volatiles were removed under reduced pressure and the resulting residue was purified by silica chromatography (0 to 10% gradient of EtOAc (containing 10% of MeOH)/heptane (containing 25 of Et₃N)) to give (R)—N—((R)-8-(6-amino-5-((3-chloro-2-(dimethylamino)pyridin-4-yl)thio)pyrazin-2-yl)-8-azaspiro[4.5]decan-1-yl)-2-methylpropane-2-sulfinamide (75 mg, 0.139 mmol). MS m/z 538.3 (M+H)⁺.

Step b:

A mixture of (R)—N—((R)-8-(6-amino-5-((3-chloro-2-(dimethylamino)pyridin-4-yl)thio)pyrazin-2-yl)-8-azaspiro[4.5]decan-1-yl)-2-methylpropane-2-sulfinamide (75 mg, 0.139 mmol) and HCl (4 M in dioxane, 174 µL, 0.697 mmol) in DCM (2 mL) was stirred for 30 min at RT. The volatiles were removed under reduced pressure and the resulting residue was purified by HPLC (gradient elution 35-60% acetonitrile in water, 5 mM NH₄OH modifier) to give (R)-8-(6-amino-5-((3-chloro-2-(dimethylamino)pyridin-4-yl)thio)pyrazin-2-yl)-8-azaspiro[4.5]decan-1-amine (28 mg, 0.064 mmol) as a white solid. $^1$H NMR (400 MHz, DMSO-$d_6$) δ ppm 7.85-7.92 (m, 1H), 7.63 (s, 1H), 6.16 (br. s, 2H), 6.04-6.10 (m, 1H), 4.06-4.23 (m, 2H), 2.97-3.15 (m, 2H), 2.87 (s, 6H), 2.64-2.73 (m, 1H), 1.11-1.97 (m, 10H). HRMS calcd for $C_{20}H_{29}ClN_7S$ (M+H)⁺ 434.1894, found 434.1883. IC₅₀ is 0.010 µM.

The following compounds of table 11 were synthesized using the above procedure or modifications to the above procedure using the corresponding protected amine and chloro-pyrazine intermediate.

TABLE 11

| Example | Compound | Characterization | IC₅₀ (µM) |
|---|---|---|---|
| 76 | (3-chloropyridazin-4-yl thio pyrazine linked to 8-azaspiro[4.5]decan-1-amine) | $^1$H NMR (400 MHz, DMSO-$d_6$) δ ppm 8.79 (d, J = 5.3 Hz, 1 H), 7.59 (s, 1 H), 6.76 (d, J = 5.5 Hz, 1 H), 6.24 (s, 2 H), 4.09 (m, 2 H), 3.00 (m, 3 H), 2.65 (t, J = 7.4 Hz, 1 H), 1.76 (m, 2 H), 1.50 (m, 4 H), 1.37-1.05 (m, 5 H). HRMS calcd for $C_{17}H_{23}ClN_7S$ (M + H)⁺ 392.1424, found 392.0977. | 0.078 |
| 77 | (3-chloro-2-fluoropyridin-4-yl thio pyrazine linked to 8-azaspiro[4.5]decan-1-amine) | TFA salt. $^1$H NMR (400 MHz, DMSO-$d_6$) δ ppm 7.94 (d, J = 5.3 Hz, 1 H), 7.79 (br. s., 3 H), 7.69 (br. s., 1 H), 6.51 (d, J = 5.5 Hz, 1 H), 6.34 (br. s., 2 H), 4.12-4.32 (m, 2 H), 2.99-3.24 (m, 3 H), 2.00-2.12 (m, 1 H), 1.30-1.90 (m, 9 H). HRMS calcd for $C_{18}H_{23}ClFN_6S$ (M + H)⁺ 409.1377, found 409.1385. | 0.005 |
| 78 | (3-chloro-2-methoxypyridin-4-yl thio pyrazine linked to 8-azaspiro[4.5]decan-1-amine) | $^1$H NMR (400 MHz, METHANOL-$d_4$) δ ppm 7.70-7.87 (m, 1 H), 7.52-7.64 (m, 1 H), 6.22 (d, J = 5.5 Hz, 1 H), 4.27 (t, J = 13.7 Hz, 2 H), 3.97 (br. s., 3 H), 3.03-3.20 (m, 2 H), 2.82 (t, J = 7.5 Hz, 1 H), 1.98-2.18 (m, 1 H), 1.24-1.96 (m, 9 H). HRMS calcd for $C_{19}H_{26}ClN_6OS$ (M + H)⁺ 421.1577, found 421.1594. | 0.015 |
| 79 | (3-chloropyridin-4-yl thio pyrazine linked to 8-azaspiro[4.5]decan-1-amine) | $^1$H NMR (400 MHz, DMSO-$d_6$) δ ppm 8.49 (s, 1 H), 8.25 (d, J = 5.3 Hz, 1 H), 7.66 (s, 1 H), 6.56 (d, J = 5.3 Hz, 1 H), 6.24 (s, 2 H), 4.07-4.26 (m, 2 H), 2.98-3.13 (m, 2 H), 2.70 (t, J = 7.4 Hz, 1 H), 1.11-1.94 (m, 10 H). HRMS calcd for $C_{18}H_{24}ClN_6S$ (M + H)⁺ 391.1472, found 391.1480. | 0.023 |
| 80 | (3-trifluoromethylpyridin-4-yl thio pyrazine linked to 8-azaspiro[4.5]decan-1-amine) | $^1$H NMR (400 MHz, DMSO-$d_6$) δ ppm 8.77 (s, 1 H), 8.25 (d, J = 5.5 Hz, 1 H), 7.68 (s, 1 H), 6.77 (d, J = 5.5 Hz, 1 H), 6.23 (br. s, 2 H), 4.18 (t, J = 11.8 Hz, 2 H), 2.97-3.16 (m, 2 H), 2.72 (t, J = 7.5 Hz, 1 H), 1.09-1.97 (m, 10 H). HRMS calcd for $C_{19}H_{24}F_3N_6S$ (M + H)⁺ 425.1735, found 425.1727. | 0.042 |

Example 81

(R)-4-((3-amino-5-(1-amino-8-azaspiro[4.5]decan-8-yl)pyrazin-2-yl)thio)-3-chloropyridin-2(1H)-one

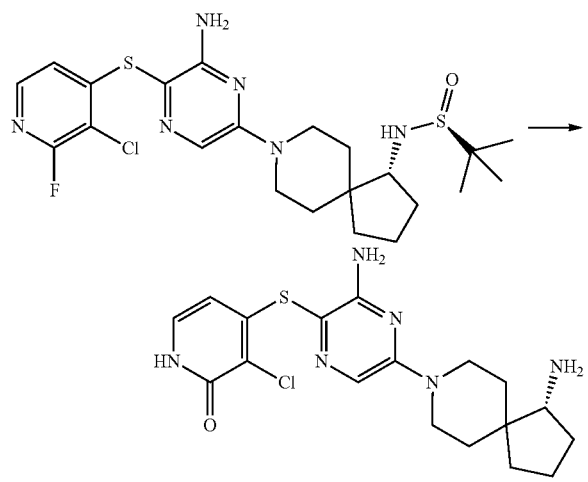

A mixture of (S)—N—((R)-8-(6-amino-5-((3-chloro-2-fluoropyridin-4-yl)thio)pyrazin-2-yl)-8-azaspiro[4.5]decan-1-yl)-2-methylpropane-2-sulfinamide (17 mg, 0.033 mmol), lithium hydroxide (2 mg, 0.040 mmol), and water (0.07 mL) in DMSO (0.3 mL) was stirred in a microwave reactor for 45 min at 90° C. After cooling to RT, MeOH (0.5 mL) was added followed by HCl (4 M in dioxane, 2.0 mL, 8.0 mmol) and the resulting mixture was stirred for 1 h at 40° C. The volatiles were removed under reduced pressure and the resulting residue was purified by HPLC (gradient elution 15-40% acetonitrile in water, 5 mM NH$_4$OH modifier) to give (R)-4-((3-amino-5-(1-amino-8-azaspiro[4.5]decan-8-yl)pyrazin-2-yl)thio)-3-chloropyridin-2(1H)one (5 mg, 0.012 mmol) as a white solid. $^1$H NMR (400 MHz, METHANOL-d$_4$) δ ppm 7.53-7.61 (m, 1H), 7.19 (d, J=7.1 Hz, 1H), 5.72 (d, J=7.1 Hz, 1H), 4.26 (t, J=13.1 Hz, 2H), 3.06-3.20 (m, 2H), 2.81 (t, J=7.5 Hz, 1H), 1.27-2.11 (m, 10H). HRMS calcd for C$_{18}$H$_{24}$ClN$_6$OS (M+H)$^+$ 407.1448, found 407.1433. IC$_{50}$ is 0.020 µM.

Example 82 racemic-8-(6-amino-5-((2-(trifluoromethyl)pyridin-3-yl)thio)pyrazin-2-yl)-2,2-difluoro-8-azaspiro[4.5]decan-1-amine

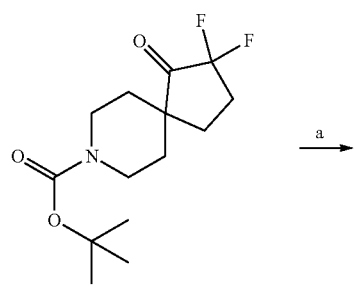

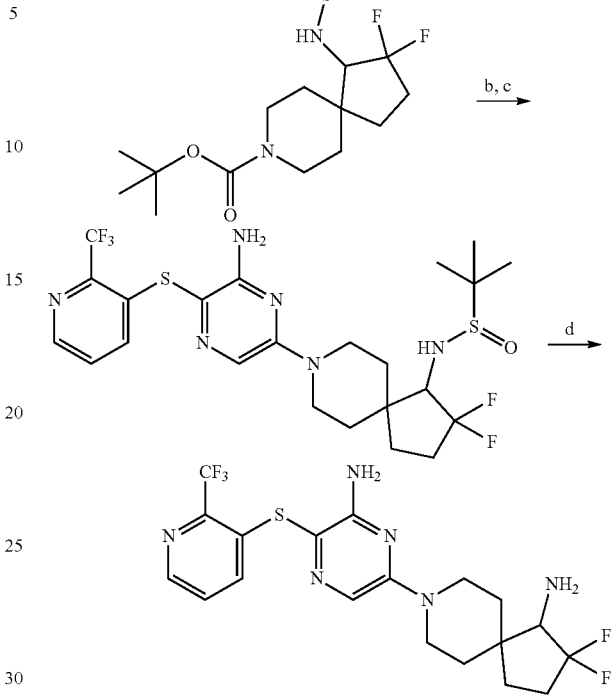

Step a:

A solution of tert-butyl 2,2-difluoro-1-oxo-8-azaspiro[4.5]decane-8-carboxylate (220 mg, 0.76 mmol), racemic 2-methylpropane-2-sulfinamide (184 mg, 1.52 mmol), and titanium(IV) ethoxide (0.640 mL, 3.0 mmol) in THF (4 mL) was stirred for 30 min at 90° C. After cooling to 0° C., lithium borohydride (33 mg, 1.5 mmol) was added in one portion. After stirring for 30 min, the reaction mixture was quenched by addition of MeOH. The volatiles were removed under reduce pressure. The resulting residue was diluted with brine, it was extracted with EtOAc (4×10 mL), the combined organic phases were dried over Na$_2$SO$_4$, filtered, and concentrated under under reduced pressure. The resulting residue was purified by silica chromatography (10 to 50% gradient of EtOAc/heptane) to give tert-butyl 1-(1,1-dimethylethylsulfinamido)-2,2-difluoro-8-azaspiro[4.5]decane-8-carboxylate as white powder (190 mg, 0.48 mmol). MS m/z 395.2 (M+H)$^+$.

Step b:

A solution of tert-butyl 1-(1,1-dimethylethylsulfinamido)-2,2-difluoro-8-azaspiro[4.5]decane-8-carboxylate (190 mg, 0.48 mmol) and TFA (1 mL) in DCM (4 mL) was stirred for 20 min at 0° C. The volatiles were removed under reduced pressure to give N-(2,2-difluoro-8-azaspiro[4.5]decan-1-yl)-2-methylpropane-2-sulfinamide which was used in next step without further purification.

Step c:

A solution of N-(2,2-difluoro-8-azaspiro[4.5]decan-1-yl)-2-methylpropane-2-sulfinamide (theor 0.48 mmol) and 6-chloro-3-((2-(trifluoro methyl)pyridin-3-yl)thio)pyrazin-2-amine (148 mg, 0.480 mmol) in DIPEA (0.8 mL) was stirred for 1 h at 100° C. After cooling to RT, the volatiles were removed under reduced pressure and the resulting residue was purified by silica chromatography (0 to 100% gradient of EtOAc/heptane) to give N-(8-(6-amino-5-((2-(trifluoromethyl)pyridin-3-yl)thio)pyrazin-2-yl)-2,2-difluoro-8-azaspiro[4.5]decan-1-yl)-2-methylpropane-2-sulfinamide (174 mg, 0.28 mmol) as an orange powder. A portion of this material was progressed to step d, the remaining material was separated by chiral chromatography (see example 83).

Step d:

A solution N-(8-(6-amino-5-((2-(trifluoromethyl) pyridin-3-yl)thio) pyrazin-2-yl)-2,2-difluoro-8-azaspiro[4.5]decan-1-yl)-2-methylpropane-2-sulfinamide (54 mg, 0.096 mmol) and HCl (4 M in dioxane, 0.239 mL, 0.96 mmol) in DCM (1 mL) was stirred for 30 min at 40° C. After cooling to RT, the volatiles were removed under reduced pressure. This residue was triturated with MeCN to give racemic-8-(6-amino-5-((2-(trifluoromethyl)pyridin-3-yl)thio)pyrazin-2-yl)-2,2-difluoro-8-azaspiro[4.5]decan-1-amine (HCl salt, 38 mg, 0.075 mmol) as a pale tan powder. $^1$H NMR (400 MHz, METHANOL-$d_4$) δ ppm 8.52-8.38 (m, 1H), 7.71 (s, 1H), 7.50-7.43 (m, 2H), 4.44 (dd, J=21.0, 14.2 Hz, 2H), 3.67 (dd, J=15.1, 11.2 Hz, 1H), 3.23-3.08 (m, 2H), 2.47-2.34 (m, 2H), 2.27 (dt, J=14.6, 7.4 Hz, 1H), 2.01-1.88 (m, 2H), 1.75-1.54 (m, 3H). HRMS calcd for $C_{19}H_{22}F_5N_6S$ (M+H)$^+$ 461.1547, found 461.1540. $IC_{50}$ is 0.380 µM.

Step b:

A mixture of pure enantiomer and HCl (4 M in dioxane, 200 µL, 0.8 mmol) in DCM (2 mL) was stirred for 1 h at 40° C. The volatiles were removed under reduced pressure and the resulting residue was triturated with MeCN to give the title compounds as HCl salts:

(R)-Enantiomer: $^1$H NMR (400 MHz, METHANOL-$d_4$) δ ppm 8.46 (dd, J=3.7, 2.3 Hz, 1H), 7.73 (s, 1H), 7.53-7.45 (m, 2H), 4.52-4.36 (m, 2H), 3.68 (dd, J=15.0, 11.2 Hz, 1H), 3.24-3.09 (m, 2H), 2.47-2.34 (m, 2H), 2.32-2.21 (m, 1H), 2.05-1.90 (m, 2H), 1.74-1.55 (m, 3H). $^{19}$F NMR (376 MHz, METHANOL-$d_4$) δ −66.19, −98.51 (d, J=234.5 Hz), −101.83 (d, J=234.6 Hz). HRMS calcd for $C_{19}H_{22}F_5N_6S$ (M+H)$^+$ 461.1547, found 461.1540. $IC_{50}$ is 0.882 µM.

(S)-Enantiomer: $^1$H NMR (400 MHz, METHANOL-$d_4$) δ ppm 8.50-8.41 (m, 1H), 7.70 (s, 1H), 7.47 (m, 2H), 4.52-4.35 (m, 2H), 3.67 (dd, J=15.1, 11.2 Hz, 1H), 3.24-3.05 (m, 2H), 2.49-2.32 (m, 2H), 2.31-2.19 (m, 1H), 2.02-1.88 (m, 2H), 1.73-1.51 (m, 3H). $^{19}$F NMR (376 MHz, METHANOL-$d_4$) δ −66.24, −98.47 (d, J=234.4 Hz), −101.77 (d, J=234.6 Hz). HRMS calcd for $C_{19}H_{22}F_5N_6S$ (M+H)$^+$ 461.1547, found 461.1541. $IC_{50}$ is 0.306 µM.

Example 83a/b (R) and (S)-8-(6-amino-5-((2-(trifluoromethyl)pyridin-3-yl)thio)pyrazin-2-yl)-2,2-difluoro-8-azaspiro[4.5]decan-1-amine Example 84

8-(6-amino-5-((2-(trifluoromethyl)pyridin-3-yl)thio)pyrazin-2-yl)-2-fluoro-8-azaspiro[4.5]decan-1-amine

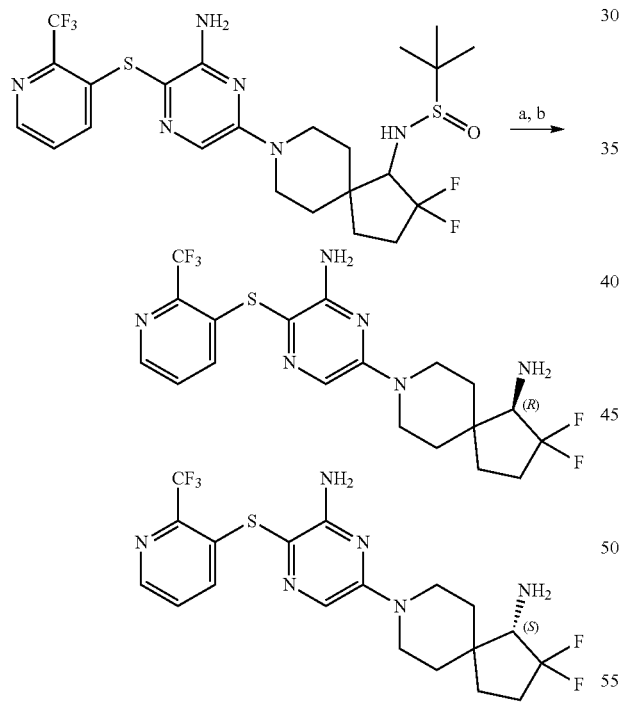

Step a:

N-(8-(6-amino-5-((2-(trifluoromethyl)pyridin-3-yl)thio)pyrazin-2-yl)-2,2-difluoro-8-azaspiro[4.5]decan-1-yl)-2-methylpropane-2-sulfinamide (100 mg, 0.177 mmol) was further purified by chiral SFC as follows: column: WHO-1 21×250 mm, flow rate: 80 g per minute, mobile phase: 45% MeOH and 5 mM NH$_4$OH in CO$_2$, detection: mass triggered to obtain single enantiomers R$_t$ (enantiomer R): 2.6 min (44 mg, 0.078 mmol) and R$_t$ (enantiomer S): 5.8 min (41 mg, 0.073 mmol).

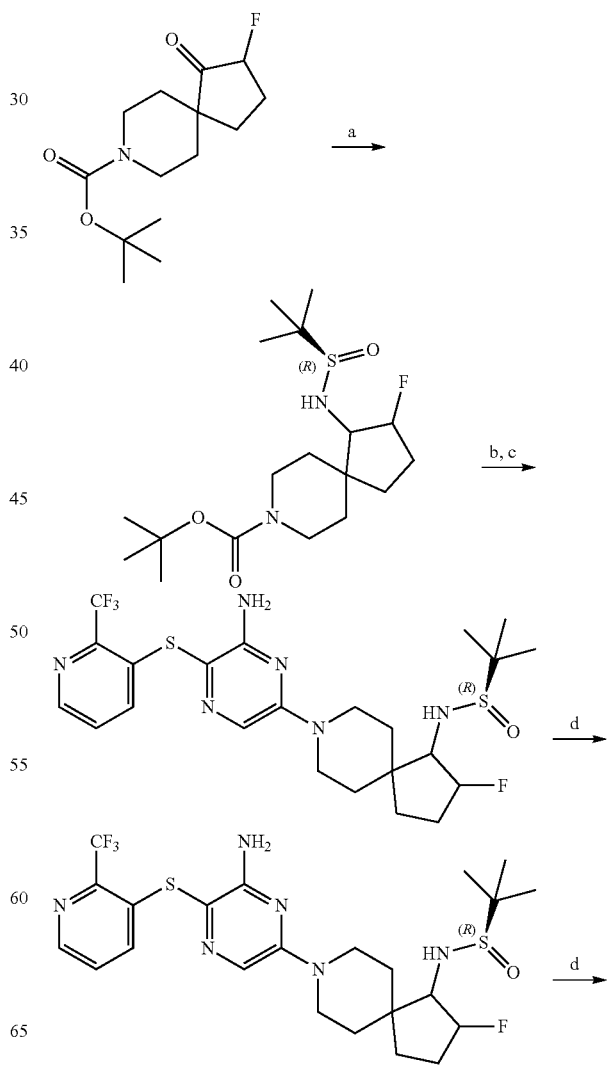

-continued

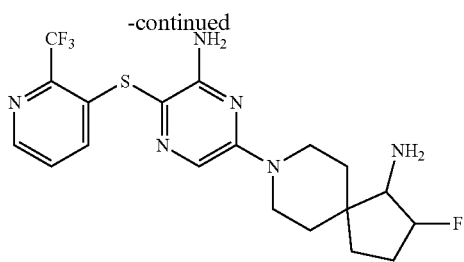

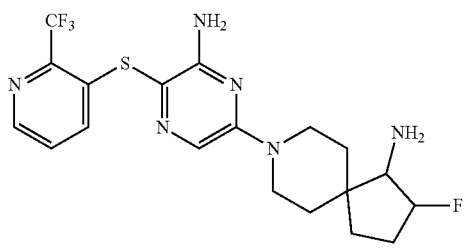

Step a:
A solution of racemic tert-butyl 2-fluoro-1-oxo-8-azaspiro[4.5]decane-8-carboxylate (78 mg, 0.28 mmol), titanium(IV) ethoxide (235 µL, 1.1 mmol), and (R)-2-methylpropane-2-sulfinamide (68 mg, 0.56 mmol) in THF (1.5 mL) was stirred for 1 h at 90° C. After cooling to 0° C., lithium borohydride (12 mg, 0.56 mmol) was added in one portion. After stirring for 30 min, the reaction mixture was quenched by addition of MeOH. The volatiles were removed under reduce pressure. The resulting residue was diluted with brine, it was extracted with EtOAc (4×10 mL), the combined organic phases were dried over $Na_2SO_4$, filtered, and concentrated under reduced pressure. The resulting residue was purified by silica chromatography (0 to 50% gradient of EtOAc/heptane) to give tert-butyl 1-((R)-1,1-dimethylethylsulfinamido)-2-fluoro-8-azaspiro[4.5]decane-8-carboxylate (64 mg, 0.17 mmol). MS m/z 377.3 $(M+H)^+$.

Step b:
A mixture of tert-butyl 1-((R)-1,1-dimethylethylsulfinamido)-2-fluoro-8-azaspiro[4.5]decane-8-carboxylate (64 mg, 0.17 mmol) and TFA (1 mL) in DCM (4 mL) was stirred for 10 min at 0° C. The volatiles were removed under reduced pressure and the resulting residue was use in next step without further purification.

Step c:
A mixture of the former residue and 6-chloro-3-((2-(trifluoro methyl)pyridin-3-yl)thio)pyrazin-2-amine (51 mg, 0.17 mmol) in DIPEA (0.3 mL) was stirred for 2 h at 100° C. After cooling to RT, the volatiles were removed under reduced pressure and the resulting residue was purified by silica chromatography (0 to 10% gradient of MeOH/DCM (containing 0.25% $Et_3N$)) to give N-(8-(6-amino-5-((2-(trifluoromethyl)pyridin-3-yl)thio)pyrazin-2-yl)-2-fluoro-8-azaspiro[4.5]decan-1-yl)-2-methylpropane-2-sulfinamide (41 mg, 0.075 mmol). MS m/z 547.2 $(M+H)^+$ as mixture of diastereomers. Further purification using chiral SFC was performed as follows: column: ID 21×250 mm, flow rate: 80 g per minute, mobile phase: 45% iPrOH and 10 mM $NH_4OH$ in $CO_2$, detection: mass triggered to give single enantiomers $R_t$(P1)=2.7 min (17 mg, 0.031 mmol) and $R_t$ (enant-P1)=4.4 min (17 mg, 0.031 mmol).

Step d:
A solution of each pure isomer and HCl (4 M in dioxane, 100 µL, 0.4 mmol) in DCM (0.1 mL) was stirred for 1 h at 40° C. After cooling to RT, the volatiles were removed under reduced pressure and the resulting residue was triturated with MeCN to give the title compounds as HCl salts.

TABLE 12

| Example | Compound | Characterization | IC$_{50}$ (µM) |
| --- | --- | --- | --- |
| 85 | | HCl salt. P1: $^1$H NMR (400 MHz, METHANOL-d$_4$) δ ppm 8.45 (dd, J = 3.7, 2.3 Hz, 1 H), 7.70 (s, 1 H), 7.51-7.43 (m, 2 H), 5.31-5.08 (m, 1 H), 4.46 (t, J = 15.0 Hz, 2 H), 3.36 (d, J = 4.2 Hz, 1 H), 3.20-3.06 (m, 2 H), 2.28-2.06 (m, 3 H), 1.96-1.82 (m, 2 H), 1.74-1.50 (m, 3 H). $^{19}$F NMR (376 MHz, METHANOL-d$_4$) δ −65.01, −66.44. HRMS calcd for $C_{19}H_{23}F_4N_6S$ $(M + H)^+$ 443.1641, found 443.1642. | P1 = 0.100 enant-P1 = 0.113 |
| | | HCl salt. enant-P1: $^1$H NMR (400 MHz, METHANOL-d$_4$) δ ppm 8.48-8.44 (m, 1 H), 7.71 (s, 1 H), 7.51-7.42 (m, 2 H), 5.30-5.10 (m, 1 H), 4.47 (t, J = 15.1 Hz, 2 H), 3.37-3.34 (m, 1 H), 3.21-3.06 (m, 2 H), 2.28-2.08 (m, 3 H), 1.95-1.82 (m, 2 H), 1.76-1.47 (m, 3 H). $^{19}$F NMR (376 MHz, METHANOL-d$_4$) δ −65.01, −66.42. HRMS calcd for $C_{19}H_{23}F_4N_6S$ $(M + H)^+$ 443.1641, found 443.1633. | |

TABLE 12-continued

| Example | Compound | Characterization | IC$_{50}$ (μM) |
|---|---|---|---|
| | 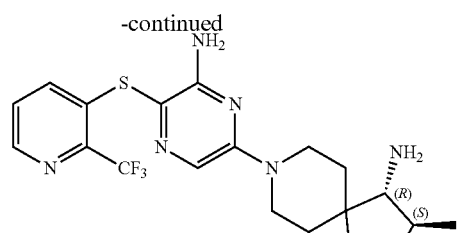 | | |
| | 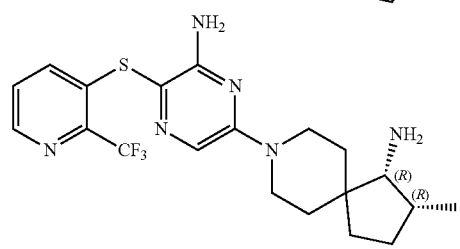 | | |

Example 86a/b (1R)-8-(6-amino-5-((2-(trifluoromethyl)pyridin-3-yl)thio)pyrazin-2-yl)-2-methyl-8-azaspiro[4.5]decan-1-amine

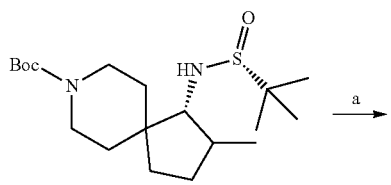
→ a

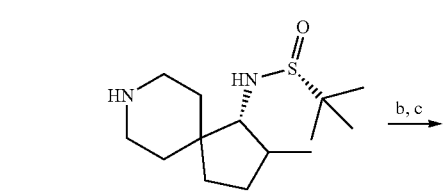
→ b, c

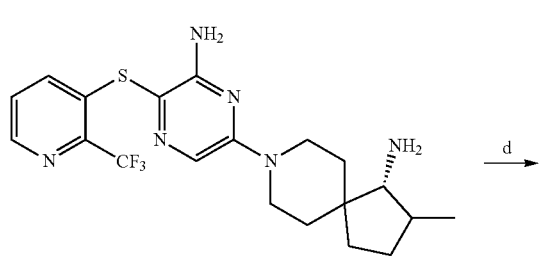
→ d

Step a:

A solution of (1R)-tert-butyl 1-((R)-1,1-dimethylethylsulfinamido)-2-methyl-8-azaspiro[4.5]decane-8-carboxylate (32 mg, 0.086 mmol) and TFA (0.2 mL, 2.60 mmol) in DCM (2 mL) was stirred for 30 min at RT. The volatiles were removed under reduced pressure to give (R)-2-methyl-N-((1R)-2-methyl-8-azaspiro[4.5]decan-1-yl)propane-2-sulfinamide. MS m/z 273.0 (M+H)$^+$. The crude product was used in the next step without further purification.

Step b:

A mixture of (R)-2-methyl-N-((1R)-2-methyl-8-azaspiro[4.5]decan-1-yl)propane-2-sulfinamide (23 mg, 0.084 mmol), 6-chloro-3-((2-(trifluoromethyl)pyridin-3-yl)thio)pyrazin-2-amine (23 mg, 0.075 mmol), and NMP (0.1 mL) in DIPEA (1 mL) was stirred for 6 h at 115° C. After cooling to RT, the volatiles were removed under reduce pressure to give (R)—N-((1R)-8-(6-amino-5-((2-(trifluoromethyl)pyridin-3-yl)thio)pyrazin-2-yl)-2-methyl-8-azaspiro[4.5]decan-1-yl)-2-methylpropane-2-sulfinamide as a black oil which was used in the next step without purification.

Step c:

A mixture of (R)—N-((1R)-8-(6-amino-5-((2-(trifluoromethyl)pyridin-3-yl)thio)pyrazin-2-yl)-2-methyl-8- azaspiro[4.5]decan-1-yl)-2-methylpropane-2-sulfinamide and HCl (4 M in dioxane, 84 µL, 0.338 mmol) in DCM (2 mL) was stirred for 1 h at 40° C. After cooling to RT, the volatiles were removed under reduced pressure and the resulting residue was purified by HPLC (gradient elution 35-60% acetonitrile in water, 0.1% TFA modifier) to give 8-(6-amino-5-((2-(trifluoromethyl)pyridin-3-yl)thio)pyrazin-2-yl)-2-methyl-8-azaspiro[4.5]decan-1-amine TFA salt. HRMS calcd for $C_{20}H_{26}F_3N_6S$ 439.1892 (M+H)$^+$, found 439.1872. $IC_{50}$ is 0.0010 M.

Step d:
Chiral separation (see table 13 for details).

TABLE 13

| Example | Compound | Characterization | $IC_{50}$ (µM) |
|---|---|---|---|
| 86a | | Chiral SFC purification performed as follows: column: ADH 21 × 250 mm, flow rate: 80 g per minute, mobile phase: 30% MeOH and 5 mM NH$_4$OH in CO$_2$, detection: 270 nm UV to obtain a single isomer R$_t$(P1) = 3.3 min. $^1$H NMR (400 MHz, METHANOL-d$_4$) δ ppm 8.39 (dd, J = 4.4, 1.6 Hz, 1 H), 7.59 (s, 1 H), 7.47-7.35 (m, 2 H), 4.46-4.31 (m, 2 H), 3.15-2.95 (m, 2 H), 2.44 (d, J = 9.5 Hz, 1 H), 2.02-1.67 (m, 5 H), 1.61-1.36 (m, 4 H), 1.12 (d, J = 6.3 Hz, 3 H). HRMS calcd for $C_{20}H_{26}F_3N_6S$ 439.1892 (M + H)$^+$, found 439.1900. | 0.010 |
| 86b | | Chiral SFC purification performed as follows: column: ADH 21 × 250 mm, flow rate: 80 g per minute, mobile phase: 30% MeOH and 5 mM NH$_4$OH in CO$_2$, detection: 270 nm UV to obtain a single isomer R$_t$(P2) = 4.3 min. $^1$H NMR (400 MHz, METHANOL-d$_4$) δ ppm 8.38 (dd, J = 4.4, 1.6 Hz, 1 H), 7.58 (s, 1 H), 7.49-7.31 (m, 2 H), 4.19-4.00 (m, 2 H), 3.29-3.12 (m, 2 H), 2.80 (d, J = 5.9 Hz, 1 H), 2.38-2.24 (m, 1 H), 1.91-1.47 (m, 8 H), 1.01 (d, J = 7.0 Hz, 3 H). HRMS calcd for $C_{20}H_{26}F_3N_6S$ 439.1892 (M + H)$^+$, found 439.1880. | 0.010 |
| 87 | | TFA salt. $^1$H NMR (400 MHz, METHANOL-d$_4$) δ ppm 7.59 (s, 1 H), 5.77 (s, 1 H), 4.41-4.22 (m, 2 H), 3.24 (t, J = 6.8 Hz, 1 H), 3.21-3.08 (m, 2 H), 2.29-2.16 (m, 1 H), 1.97-1.79 (m, 4 H), 1.78-1.65 (m, 2 H), 1.65-1.48 (m, 3 H). HRMS calcd for $C_{18}H_{24}Cl_2N_7S$ (M + H)$^+$ 440.1191, found 440.1169. | 0.0093 |
| 88 | | TFA salt. $^1$H NMR (400 MHz, METHANOL-d$_4$) δ ppm 7.60 (s, 1 H), 5.76 (s, 1 H), 4.37-4.19 (m, 3 H), 3.98 (d, J = 9.2 Hz, 1 H), 3.88 (d, J = 9.2 Hz, 1 H), 3.42 (d, J = 4.0 Hz, 1 H), 3.13 (dddd, J = 26.3, 14.0, 11.0, 3.2 Hz, 2 H), 1.92-1.74 (m, 3 H), 1.73-1.63 (m, 1 H), 1.31 (d, J = 6.5 Hz, 3 H). HRMS calcd for $C_{18}H_{24}Cl_2N_7OS$ (M + H)$^+$ 456.1140, found 456.1118. | 0.004 |
| 89 | | TFA salt. $^1$H NMR (400 MHz, METHANOL-d$_4$) δ ppm 7.61 (s, 1 H), 5.77 (s, 1 H), 4.35-4.14 (m, 3 H), 3.98 (d, J = 9.2 Hz, 1 H), 3.89 (d, J = 9.2 Hz, 1 H), 3.82 (dd, J = 10.7, 2.6 Hz, 1 H), 3.57 (dd, J = 5.3, 2.5 Hz, 1 H), 3.23 (ddd, J = 14.1, 8.8, 5.5 Hz, 1 H), 3.14 (ddd, J = 13.8, 10.7, 3.3 Hz, 1 H), 1.86-1.63 (m, 4 H). HRMS calcd for $C_{17}H_{22}Cl_2N_7OS$ (M + H)$^+$ 442.0984, found 442.0961. | 0.0118 |

TABLE 13-continued

| Example | Compound | Characterization | IC$_{50}$ (μM) |
|---|---|---|---|
| 90 | | TFA salt. $^1$H NMR (400 MHz, METHANOL-d$_4$) δ ppm 7.60 (s, 1 H), 5.77 (s, 1 H), 4.51-4.32 (m, 3 H), 3.47 (dd, J = 9.3, 7.2 Hz, 1 H), 3.13-2.94 (m, 2 H), 2.28-2.11 (m, 2 H), 2.01 (ddd, J = 13.8, 9.5, 6.0 Hz, 1 H), 1.92-1.78 (m, 2 H), 1.70 (d, J = 13.2 Hz, 1 H), 1.55-1.47 (m, 2 H). HRMS calcd for C$_{18}$H$_{24}$Cl$_2$N$_7$OS (M + H)$^+$ 456.1140, found 456.1111. | 0.004 |
| 91 | | $^1$H NMR (400 MHz, METHANOL-d$_4$) δ ppm 7.52-7.64 (m, 2 H), 5.92 (d, J = 5.56 Hz, 1 H), 5.13 (td, J = 56.0, 6.69, Hz, 1 H), 4.21-4.42 (m, 2 H), 3.00-3.22 (m, 2 H), 2.83 (t, J = 7.71 Hz, 1 H), 2.37-2.58 (m, 1 H), 2.16-2.37 (m, 1 H), 1.62-1.92 (m, 5 H), 1.21-1.36 (m, 1 H). $^{19}$F NMR (376 MHz, METHANOL-d$_4$) δ ppm −162.81. HRMS calcd for C$_{18}$H$_{24}$ClFN$_7$S (M + H)$^+$ 424.1486, found 424.1491. | 0.008 |
| 92 | | $^1$H NMR (400 MHz, METHANOL-d$_4$) δ ppm 7.50-7.65 (m, 2 H), 5.92 (d, J = 5.56 Hz, 1 H), 5.13 (dt, J = 56 Hz, 5.94 Hz, 1 H) 4.21-4.40 (m, 2 H), 2.97-3.19 (m, 3 H), 2.13-2.35 (m, 2 H), 1.70-2.00 (m, 3 H), 1.62 (td, J = 12.63, 4.29 Hz, 1 H), 1.47 (dd, J = 13.26, 2.40 Hz, 1 H), 1.33 (dd, J = 13.39, 2.27 Hz, 1 H). $^{19}$F NMR (376 MHz, METHANOL-d$_4$) δ ppm −166.11. HRMS calcd for C$_{18}$H$_{24}$ClFN$_7$S (M + H)$^+$ 424.1486, found 424.1486. | 0.010 |

The following examples of Table 14 can be made using the above methods and appropriate starting materials:

TABLE 14

TABLE 14-continued

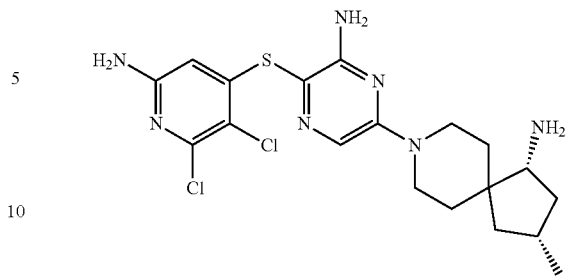

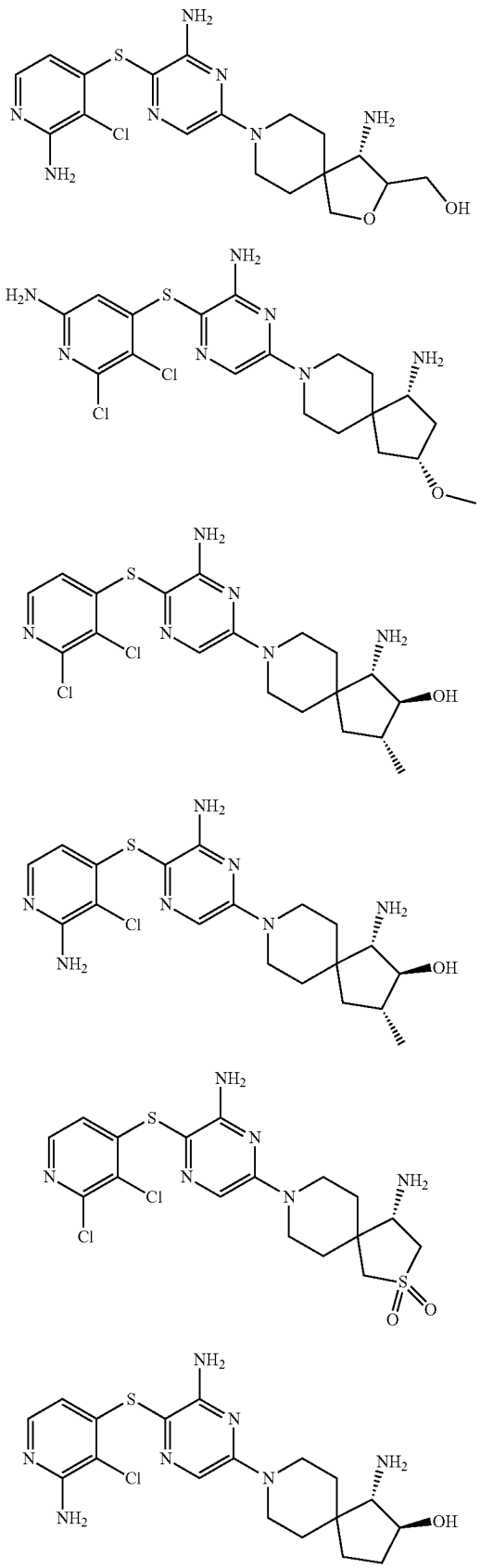

Assays

Compounds of the invention were assessed for their ability to selectively inhibit SHP2 activity. The inhibitory properties of the compounds of the invention described herein can be evidenced by testing in any one of the following assays.

SHP2 Allosteric Inhibition Assay

SHP2 is allosterically activated through binding of bis-tyrosyl-phorphorylated peptides to its Src Homology 2 (SH2) domains. The latter activation step leads to the release of the auto-inhibitory interface of SHP2, which in turn renders the SHP2 protein tyrosine phosphatase (PTP) active and available for substrate recognition and reaction catalysis. The catalytic activity of SHP2 was monitored using the surrogate substrate DiFMUP in a prompt fluorescence assay format.

More specifically, the phosphatase reactions were performed at room temperature in 384-well black polystyrene plate, flat bottom, low flange, non-binding surface (Corning, Cat#3575) using a final reaction volume of 25 µL and the following assay buffer conditions: 60 mM HEPES, pH 7.2, 75 mM NaCl, 75 mM KCl, 1 mM EDTA, 0.05% P-20, 5 mM DTT.

The inhibition of SHP2 by compounds of the invention (concentrations varying from 0.003-100 µM) was monitored using an assay in which 0.5 nM of SHP2 was incubated with of 0.5 µM of peptide IRS1_pY1172(dPEG8)pY1222 (sequence: H2N-LN(pY)IDLDLV(dPEG8)LST(pY)ASIN-FQK-amide) (SEQ ID NO:1). After 30-60 minutes incubation at 25° C., the surrogate substrate DiFMUP (Invitrogen, cat# D6567) was added to the reaction and incubated at 25° C. for 30 minutes. The reaction was then quenched by the addition of 5 µl of a 160 µM solution of bpV(Phen) (Enzo Life Sciences cat# ALX-270-204). The fluorescence signal was monitored using a microplate reader (Envision, Perki-Elmer) using excitation and emission wavelengths of 340 nm and 450 nm, respectively. The inhibitor dose response curves were analyzed using normalized $IC_{50}$ regression curve fitting with control based normalization. $IC_{50}$ results for compounds of the invention are shown in examples and tables 1-7, above.

p-ERK Cellular Assay p-ERK cellular assay using the AlphaScreen® SureFire™ Phospho-ERK 1/2 Kit (PerkinElmer): KYSE-520 cells (30,000 cells/well) were grown in 96-well plate culture overnight and treated with Shp2 inhibitors at concentrations of 20, 6.6, 2.2, 0.74, 0.24, 0.08, 0.027 µM for 2 hrs at 37° C. Incubations were terminated by addition of 30 µL of lysis buffer (PerkinElmer) supplied with the SureFire phospho-extracellular signal-regulated kinase (pERK) assay kit (PerkinElmer). Samples were processed according to the manufacturer's directions. The fluorescence signal from pERK was measured in duplicate using a 2101 multilabel reader (Perkin Elmer Envision). The percentage of inhibition was normalized by the total ERK signal and compared with the DMSO vehicle control.

Colony Formation Assay and Cell Proliferation Assay

KYSE-520 Cells (1500 cells/well) were plated onto 24-well plates in 300 μL medium (RPMI-1640 containing 10% FBS, Lonza). For drug treatment, compounds of the invention at various concentrations (20, 10, 5, 2.5, 1.25 μM) were added 24 hours and 5 days after cell plating. At day 11, colonies were stained with 0.2% crystal violet (MP Biomedicals) and subsequently dissolved in 20% acetic acid for quantitation using a Spectramax reader (Thermo Scientific). In cell proliferation assay, cells (1500-cells/well) were plated onto 96-well plates in 100 μL medium (RPMI-1640 containing 10% FBS, Lonza). At day 6, 50 μL Celltiter-Glo reagent (Promega) was added, and the luminescent signal was determined according to the supplier's instruction (Promega).

It is understood that the examples and embodiments described herein are for illustrative purposes only and that various modifications or changes in light thereof will be suggested to persons skilled in the art and are to be included within the spirit and purview of this application and scope of the appended claims.

We claim:

1. A method of treatment of lung cancer comprising administering a compound of formula I, or a pharmaceutically acceptable salt thereof, to a person in need of such treatment in an effective amount for the therapeutic treatment of lung cancer:

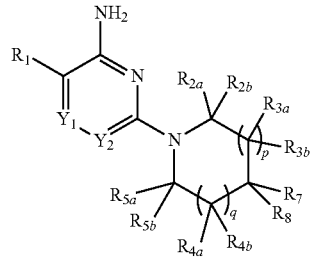

in which:
p is selected from 0 and 1;
q is selected from 0 and 1;
$Y_1$ is N;
$Y_2$ is $CR_6$;
$R_1$ is $-XR_{1a}$; wherein $R_{1a}$ is selected from $C_{6-10}$aryl, $C_{3-8}$cycloalkyl, $C_{3-8}$cycloalkenyl and a 5-9 member heteroaryl group containing from 1 to 4 heteroatoms or groups independently selected from N, C(O), O and S; wherein said aryl or heteroaryl of $R_{1a}$ is substituted with 1 to 5 $R_9$ groups independently selected from halo, amino, hydroxy, $N_3$, $C_{1-4}$alkyl, C$_{1-4}$alkoxy, dimethyl-amino, hydroxy-substituted-C$_{1-4}$alkyl, halo-substituted-C$_{1-4}$alkyl, amino-substituted-C$_{1-4}$alkyl, —C(O)OR$_{10}$, —C(O)NH$_2$ and —NHC(O)R$_{10}$, wherein R$_{10}$ is selected from hydrogen, phenyl and naphthyl; wherein said phenyl of R$_{10}$ is unsubstituted or substituted with methoxy; and X is selected from a bond, S(O)$_m$, O, C(O), CR$_{10a}$R$_{10b}$, NR$_{11}$; wherein m is selected from 0, 1 and 2; each R$_{10a}$ and R$_{10b}$ is independently selected from halo and C$_{1-4}$alkyl; and R$_{11}$ is selected from hydrogen and C$_{1-4}$alkyl;

R$_{2a}$ and R$_{2b}$ are independently selected from hydrogen, C$_{1-4}$alkyl, C$_{1-4}$alkoxy, amino, hydroxy, C$_{3-8}$cycloalkyl and C$_{1-4}$alkyl-amino;

R$_{3a}$ and R$_{3b}$ are independently selected from hydrogen, halo, C$_{1-4}$alkyl, C$_{1-4}$alkoxy, amino, hydroxy, C$_{3-8}$cycloalkyl and C$_{1-4}$alkyl-amino;

R$_{4a}$ and R$_{4b}$ are independently selected from hydrogen, halo, C$_{1-4}$alkyl, C$_{1-4}$alkoxy, amino, hydroxy, C$_{3-8}$cycloalkyl and C$_{1-4}$alkyl-amino;

R$_{5a}$ and R$_{5b}$ are independently selected from hydrogen, C$_{1-4}$alkyl, C$_{1-4}$alkoxy, amino, hydroxy, C$_{3-8}$cycloalkyl and C$_{1-4}$alkyl-amino;

R$_6$ is selected from hydrogen, halo, cyano, C$_{1-4}$alkyl, C$_{1-4}$alkoxy, amino-carbonyl, halo-substituted C$_{1-4}$alkyl, halo-substituted C$_{1-4}$alkoxy, hydroxy-substituted C$_{1-4}$alkyl, amino-substituted C$_{1-4}$alkyl, —S(O)$_{1-2}$R$_{6a}$, —C(S)R$_{6a}$, —C(O)NR$_{6a}$R$_{6b}$, —C(NH)NR$_{6a}$R$_{6b}$ and —NR$_{6a}$C(O)R$_{6b}$; wherein R$_{6a}$ and R$_{6b}$ are independently selected from hydrogen and C$_{1-4}$alkyl;

R$_7$ and R$_8$ together with the carbon atom to which they are both attached form a 3 to 7 member saturated or partially unsaturated ring that can optionally contain 1 to 3 heteroatoms or groups independently selected from N, C(O), O and S(O)$_m$; wherein m is selected from 0, 1 and 2; wherein said saturated ring formed by R$_7$ and R$_8$ can be unsubstituted or substituted with 1 to 3 groups independently selected from amino, hydroxy, methoxy, halo, methyl, amino-methyl, methyl-amino and isobutyryloxy.

2. The method of claim 1 wherein the compound is a compound of Formula Ia:

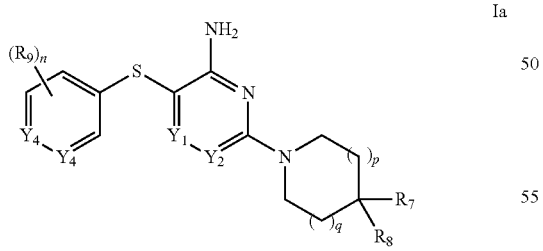

Ia in which:
n is selected from 1, 2, 3 and 4;
p is selected from 0 and 1;
q is selected from 0 and 1;
Y$_1$ is N;
Y$_2$ is CR$_6$;
each Y$_4$ is independently selected from N and CR$_9$;
R$_6$ is selected from hydrogen, halo, methyl and amino-carbonyl;

R$_7$ and R$_8$ together with the carbon atom to which they are both attached form a 3 to 7 member saturated or partially unsaturated ring that can optionally contain a heteroatom selected from N, O, C(O) and S(O)$_m$; wherein m is selected from 0, 1 and 2; wherein said saturated ring formed by R$_7$ and R$_8$ can be unsubstituted or substituted with 1 to 3 groups independently selected from amino, halo, hydroxy, methyl, methoxy, amino-methyl, methyl-amino and isobutyryloxy;

R$_9$ is selected from halo, amino, hydroxy, N$_3$, dimethyl-amino, C$_{1-4}$alkyl, halo-substituted-C$_{1-4}$alkyl, C$_{1-4}$alkoxy, —C(O)OR$_{10}$, —C(O)NH$_2$ and —NHC(O)R$_{10}$;

R$_{10}$ is selected from hydrogen, phenyl and naphthyl; wherein said phenyl of R$_{10}$ is unsubstituted or substituted with methoxy;

or a pharmaceutically acceptable salt thereof.

3. The method of claim 2 in which R$_7$ and R$_8$ together with the carbon atom to which they are both attached form a 5 member saturated or partially unsaturated ring that can optionally contain 1 to 2 heteroatoms or groups independently selected from N, O, C(O) and S(O)$_m$; wherein m is selected from 0, 1 and 2; wherein said saturated ring formed by R$_7$ and R$_8$ is substituted with 1 to 3 groups independently selected from amino, hydroxy, methoxy, halo, methyl, methyl-amino and isobutyryloxy; or a pharmaceutically acceptable salt thereof.

4. The method of claim 3, wherein the compound, or the pharmaceutically acceptable salt thereof, is selected from:

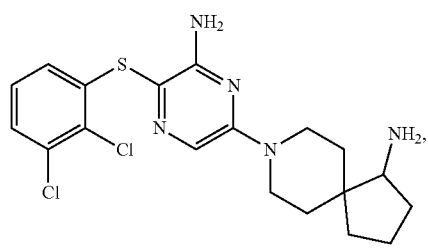

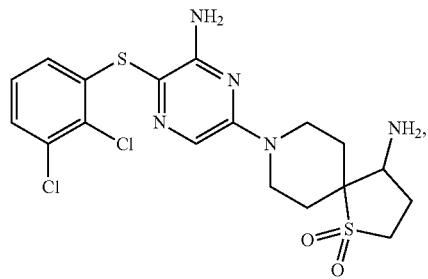

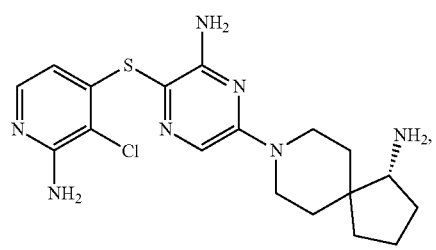

-continued
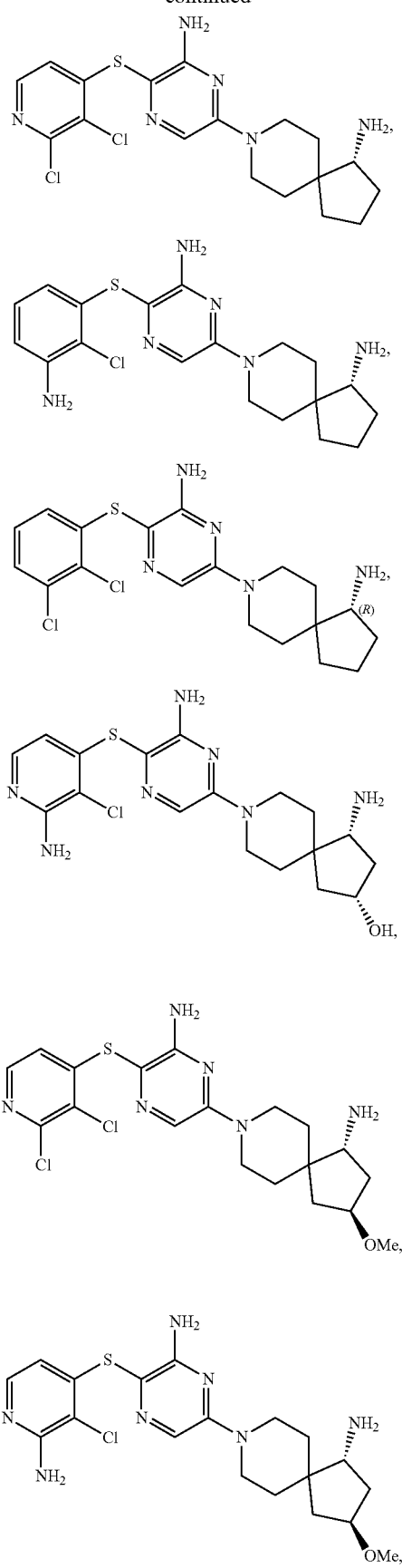
-continued
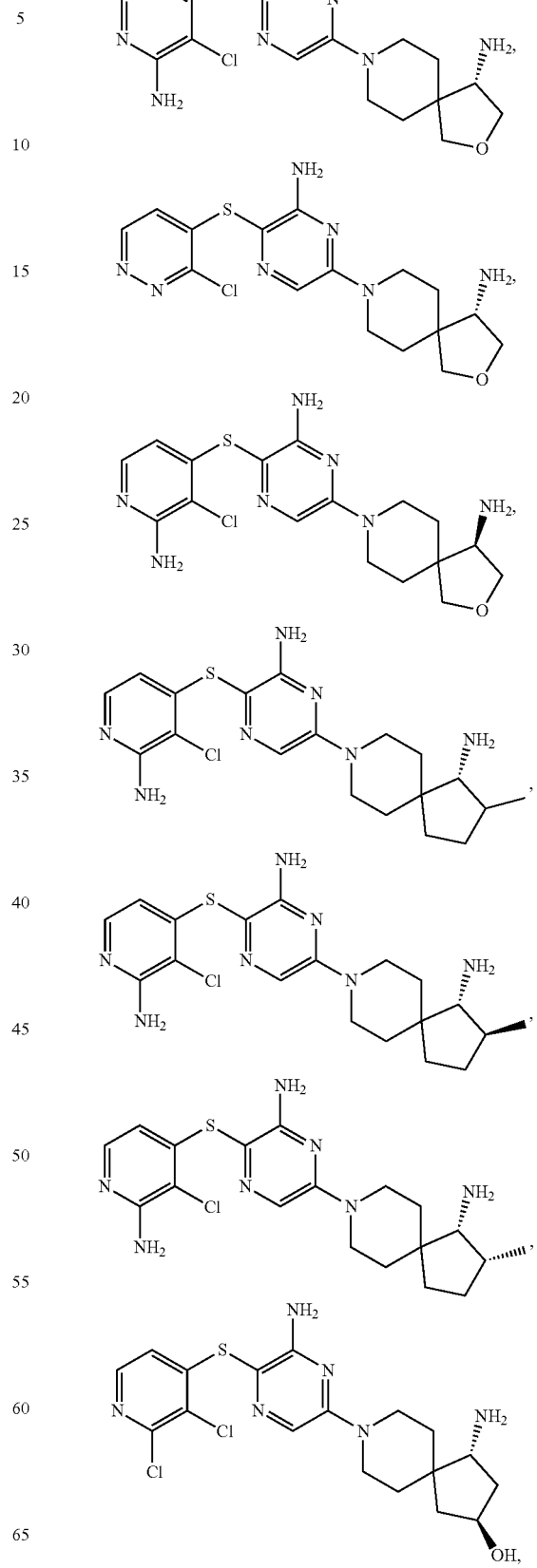

-continued
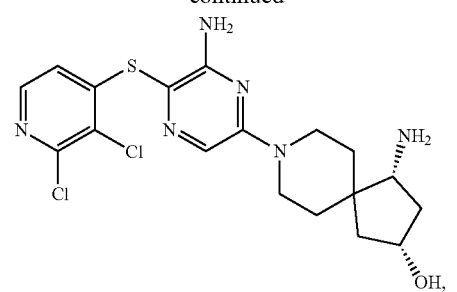
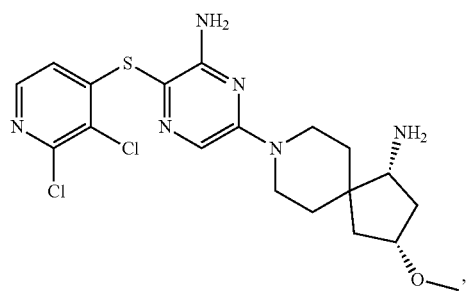
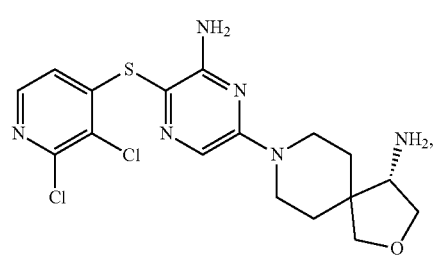
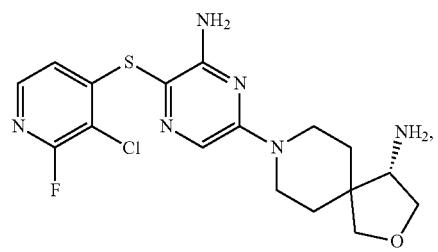
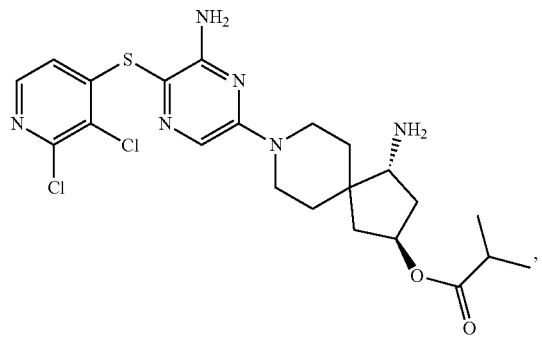
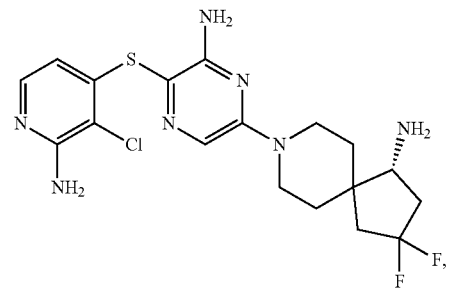
-continued
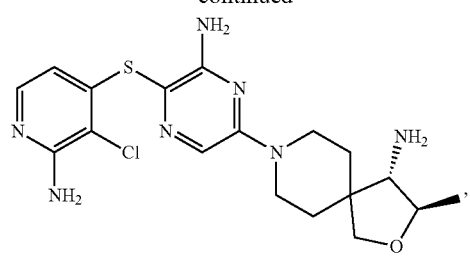
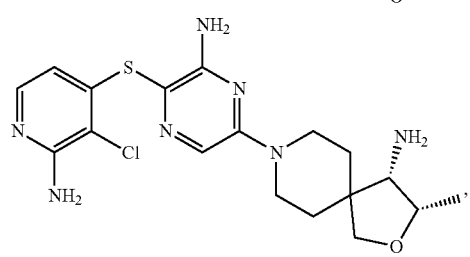
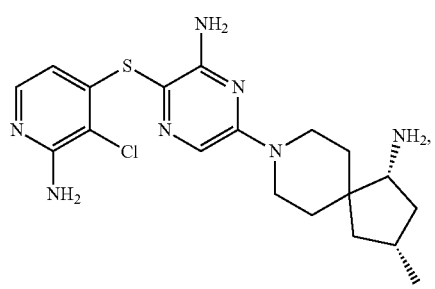
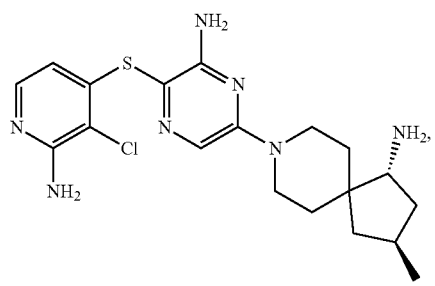
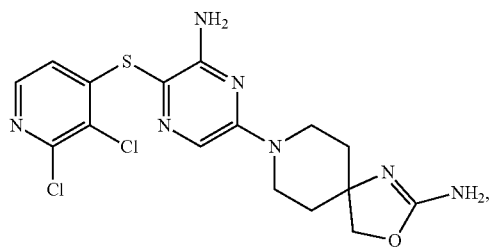
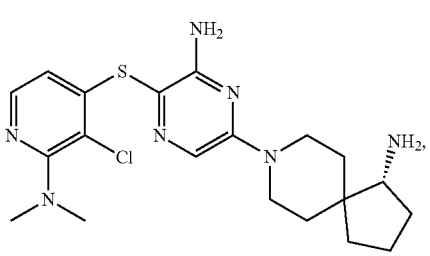

-continued

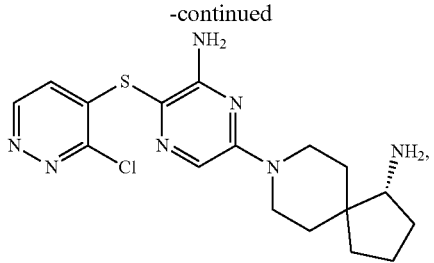

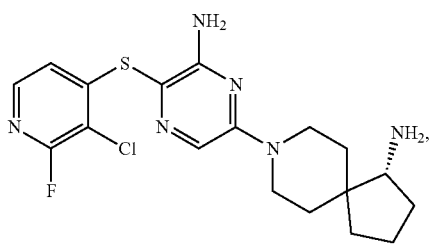

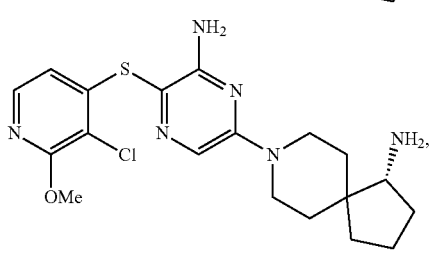

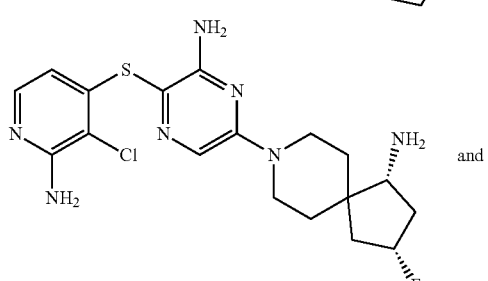

and

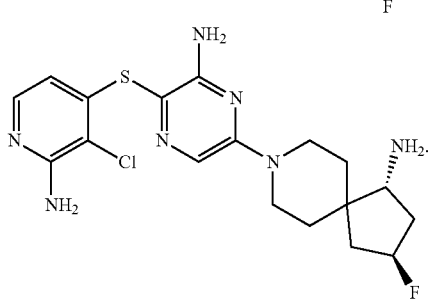

5. The method of claim 2 in which R$_7$ and R$_8$ together with the carbon atom to which they are both attached form a 6 member saturated or partially unsaturated ring that can optionally contain a heteroatom selected from N, O and S(O)$_m$; wherein m is selected from 0, 1 and 2; wherein said saturated ring formed by R$_7$ and R$_8$ is substituted with amino; or a pharmaceutically acceptable salt thereof.

6. The method of claim 5, wherein the compound, or the pharmaceutically acceptable salt thereof, is

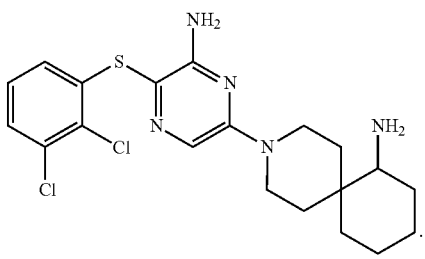 [SMILES: Nc1nc(N2CCC3(CCCCC3N)CC2)cnc1Sc1cccc(Cl)c1Cl]

7. The method of claim 2 in which R$_7$ and R$_8$ together with the carbon atom to which they are both attached form a 4 member saturated or partially unsaturated ring that can optionally contain a heteroatom selected from N, O and S(O)$_m$; wherein m is selected from 0, 1 and 2; wherein said saturated ring formed by R$_7$ and R$_8$ is substituted with a group selected from amino, amino-methyl and methyl-amino; or a pharmaceutically acceptable salt thereof.

8. The method of claim 7, wherein the compound, or the pharmaceutically acceptable salt thereof, is selected from:

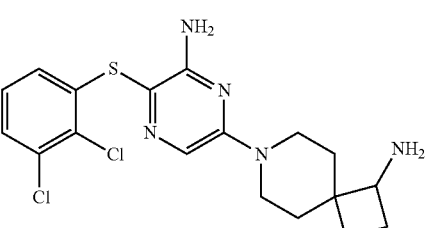

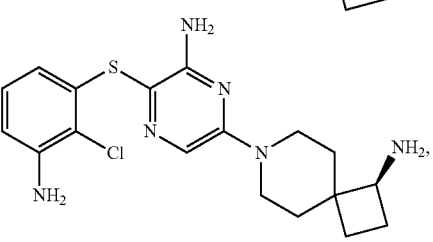

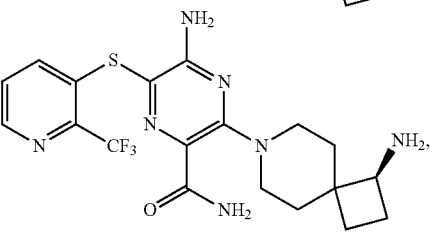

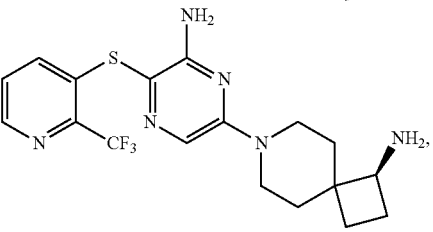

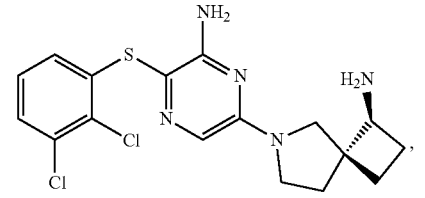

-continued

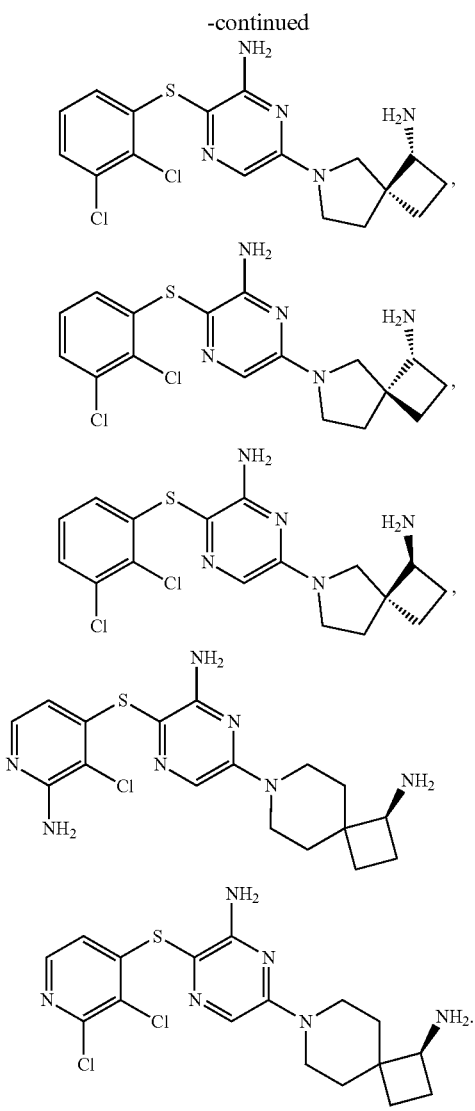

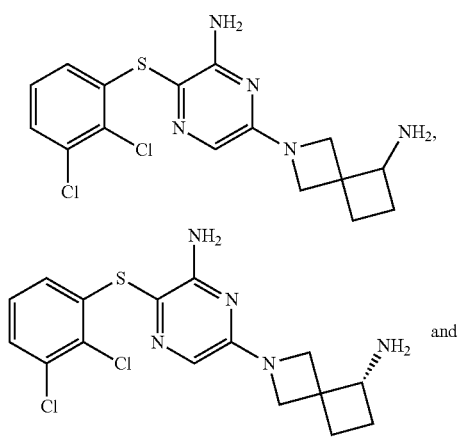

9. The method of claim 2 in which p and q are both 0; or the pharmaceutically acceptable salt thereof.

10. The method of claim 9, wherein the compound, or the pharmaceutically acceptable salt thereof, selected from:

-continued

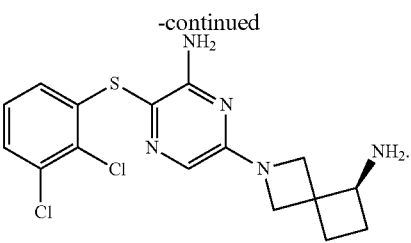

11. The method of claim 1, wherein the compound is a compound of formula II:

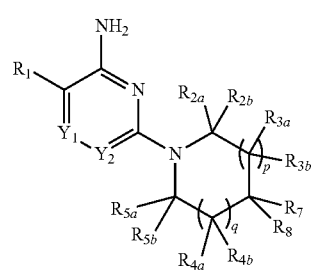

in which:
p is selected from 0 and 1;
q is selected from 0 and 1;
$Y_1$ is N;
$Y_2$ is $CR_6$;
$R_1$ is —$XR_{1a}$; wherein X is a bond and $R_{1a}$ is selected from $C_{6-10}$aryl, $C_{3-8}$cycloalkyl, $C_{3-8}$cycloalkenyl and a 5-9 member heteroaryl group containing from 1 to 4 heteroatoms selected from N, O and S; wherein said aryl or heteroaryl of $R_{1a}$ is substituted with 1 to 5 $R_9$ groups independently selected from halo, amino, hydroxy, $N_3$, $C_{1-4}$alkyl, hydroxy-substituted-$C_{1-4}$alkyl, halo-substituted-$C_{1-4}$alkyl, amino-substituted-$C_{1-4}$alkyl, —C(O)$OR_{10}$ and —NHC(O)$R_{10}$, wherein $R_{10}$ is selected from hydrogen, phenyl and naphthyl; wherein said phenyl of $R_{10}$ is unsubstituted or substituted with methoxy;
$R_{2a}$ and $R_{2b}$ are independently selected from hydrogen, $C_{1-4}$alkyl, $C_{1-4}$alkoxy, amino, hydroxy, $C_{3-8}$cycloalkyl and $C_{1-4}$alkyl-amino;
$R_{3a}$ and $R_{3b}$ are independently selected from hydrogen, halo, $C_{1-4}$alkyl, $C_{1-4}$alkoxy, amino, hydroxy, $C_{3-8}$cycloalkyl and $C_{1-4}$alkyl-amino;
$R_{4a}$ and $R_{4b}$ are independently selected from hydrogen, halo, $C_{1-4}$alkyl, $C_{1-4}$alkoxy, amino, hydroxy, $C_{3-8}$cycloalkyl and $C_{1-4}$alkyl-amino;
$R_{5a}$ and $R_{5b}$ are independently selected from hydrogen, $C_{1-4}$alkyl, $C_{1-4}$alkoxy, amino, hydroxy, $C_{3-8}$cycloalkyl and $C_{1-4}$alkyl-amino;
$R_6$ is selected from hydrogen, halo, cyano, $C_{1-4}$alkyl, $C_{1-4}$alkoxy, amino-carbonyl, halo-substituted $C_{1-4}$alkyl, halo-substituted $C_{1-4}$alkoxy, hydroxy-substituted $C_{1-4}$alkyl and amino-substituted $C_{1-4}$alkyl;
$R_7$ and $R_8$ together with the carbon atom to which they are both attached form a 3 to 7 member saturated or partially unsaturated ring that can optionally contain a heteroatom selected from N, O and S(O)$_m$; wherein m is selected from 0, 1 and 2; wherein said saturated ring formed by $R_7$ and $R_8$ can be unsubstituted or substituted with 1 to 3 groups independently selected from amino, halo, hydroxy, amino-methyl and methyl-amino;
or a pharmaceutically acceptable salt thereof.

12. The method of claim 11, wherein the compound is a compound of Formula IIa:

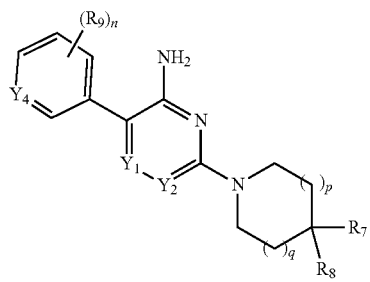

in which:
n is selected from 1, 2, 3 and 4;
p is selected from 0 and 1;
q is selected from 0 and 1;
$Y_1$ is selected from N;
$Y_2$ is selected from $CR_6$
$Y_4$ is selected from N and $CR_9$;
$R_6$ is selected from hydrogen, halo, methyl and aminocarbonyl;
$R_7$ and $R_8$ together with the carbon atom to which they are both attached form a 3 to 7 member saturated or partially unsaturated ring that can optionally contain a heteroatom selected from N, O and $S(O)_m$; wherein m is selected from 0, 1 and 2; wherein said saturated ring formed by $R_7$ and $R_8$ can be unsubstituted or substituted with a group selected from amino, amino-methyl and methyl-amino;
$R_9$ is selected from halo, amino, hydroxy, $N_3$, $C_{1-4}$alkyl, halo-substituted-$C_{1-4}$alkyl, —C(O)O$R_{10}$ and —NHC(O)$R_{10}$;
$R_{10}$ is selected from hydrogen, phenyl and naphthyl; wherein said phenyl of $R_{10}$ is unsubstituted or substituted with methoxy;
or a pharmaceutically acceptable salt thereof.

13. The method of claim 12 in which $R_7$ and $R_8$ together with the carbon atom to which they are both attached form a 5 member saturated or partially unsaturated ring that can optionally contain a heteroatom selected from N, O and $S(O)_m$; wherein m is selected from 0, 1 and 2; wherein said saturated ring formed by $R_7$ and $R_8$ is substituted with amino; or a pharmaceutically acceptable salt thereof.

14. The method of claim 13, wherein the compound, or the pharmaceutically acceptable salt thereof, is selected from:

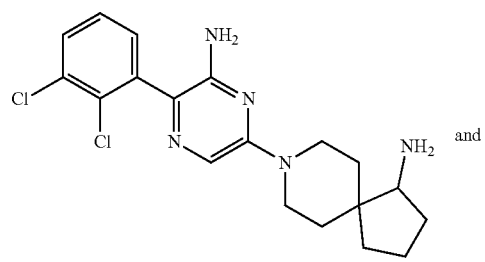

and

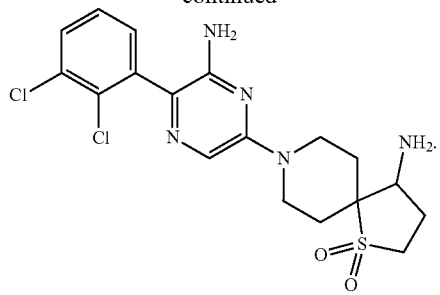

15. The method of claim 12 in which $R_7$ and $R_8$ together with the carbon atom to which they are both attached form a 6 member saturated ring that can optionally contain a heteroatom selected from N, O and $S(O)_m$; wherein m is selected from 0, 1 and 2; wherein said saturated ring formed by $R_7$ and $R_8$ is substituted with amino; or a pharmaceutically acceptable salt thereof.

16. The method of claim 15, wherein the compound, or the pharmaceutically acceptable salt thereof, is

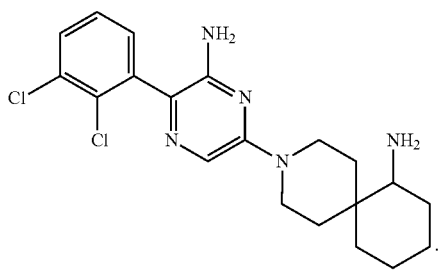 [SMILES: Nc1nc(N2CCC3(CCCCC3N)CC2)cnc1-c1cccc(Cl)c1Cl]

17. The method of claim 12 in which $R_7$ and $R_8$ together with the carbon atom to which they are both attached form a 4 member saturated ring that can optionally contain a heteroatom selected from N, O and $S(O)_m$; wherein m is selected from 0, 1 and 2; wherein said saturated ring formed by $R_7$ and $R_8$ is substituted with amino; or a pharmaceutically acceptable salt thereof.

18. The method of claim 17, wherein the compound, or the pharmaceutically acceptable salt thereof, is selected from:

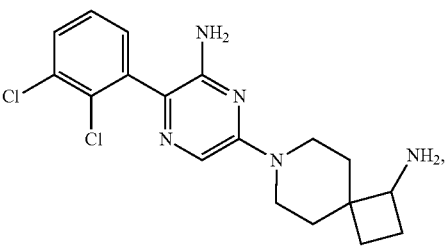

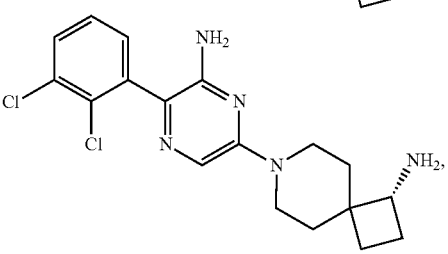

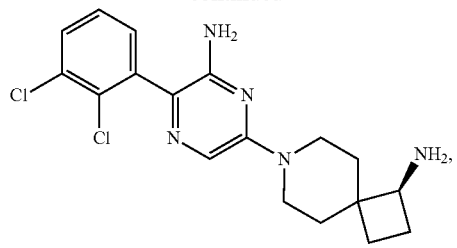
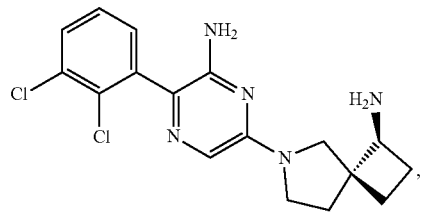
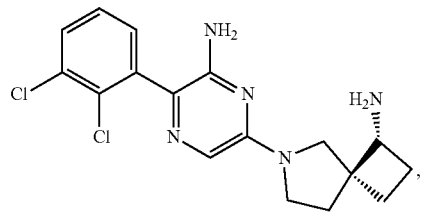
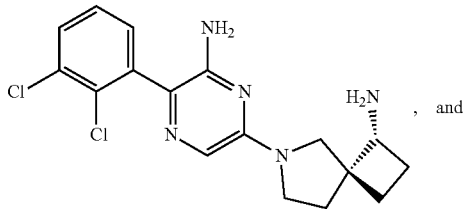
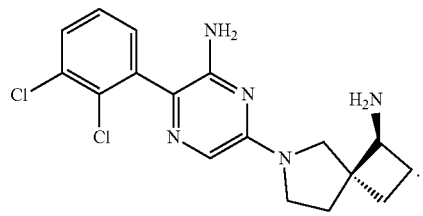 [SMILES: Nc1nc(N2CC[C@@]3(CC[C@@H]3N)C2)cnc1-c1cccc(Cl)c1Cl]
, and
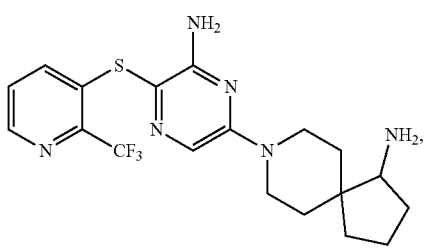
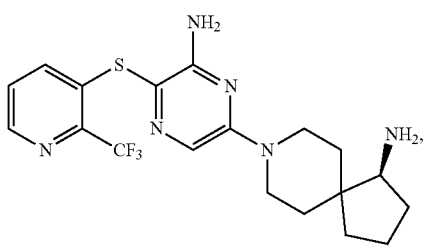
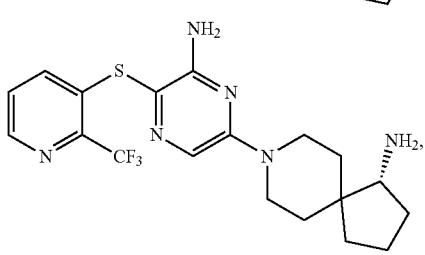
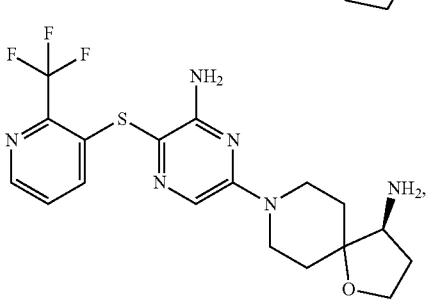
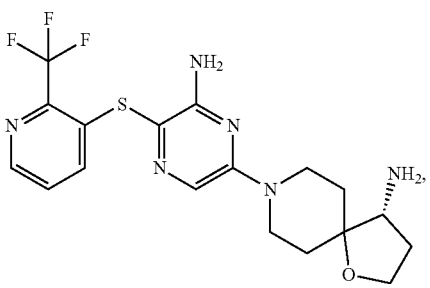
19. The method of claim 12 in which p and q are both 0; or the pharmaceutically acceptable salt thereof.
20. The method of claim 19, wherein the compound, or the pharmaceutically acceptable salt thereof, is
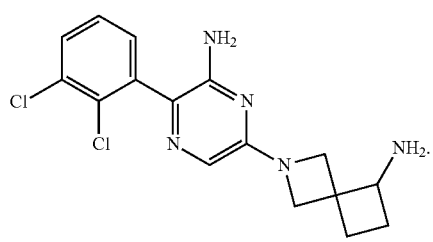 [SMILES: Nc1nc(N2CC3(CCC3N)C2)cnc1-c1cccc(Cl)c1Cl]
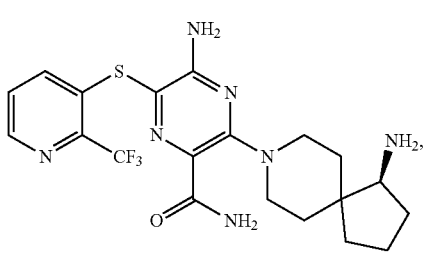
21. The method of claim 1, wherein the compound, or the pharmaceutically acceptable salt thereof, is selected from:

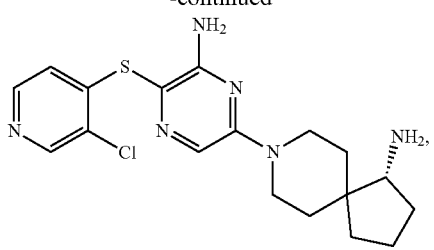
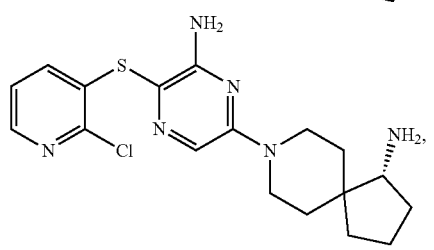
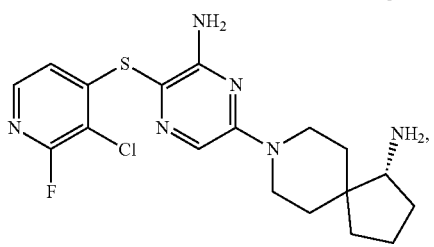
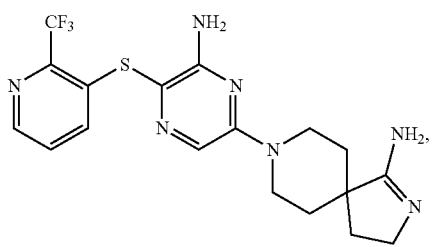
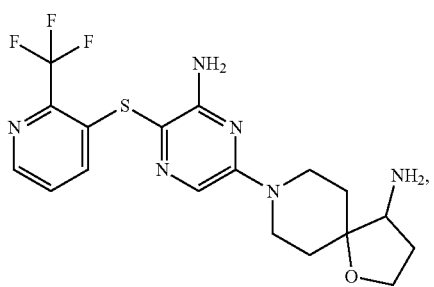
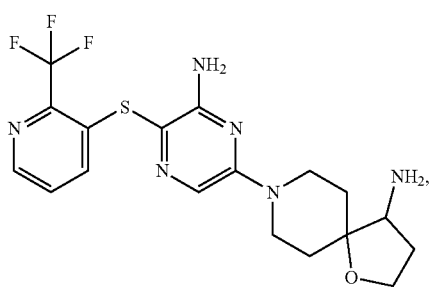
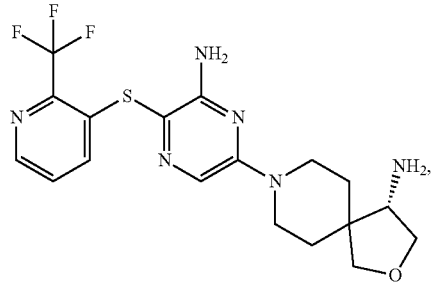
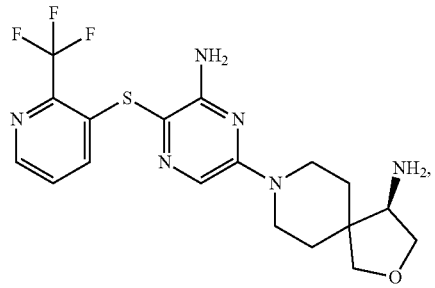
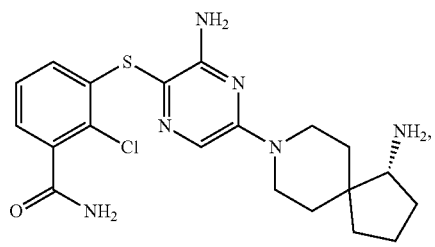
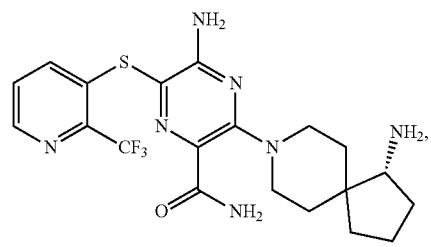
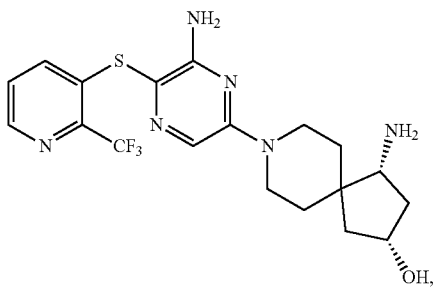
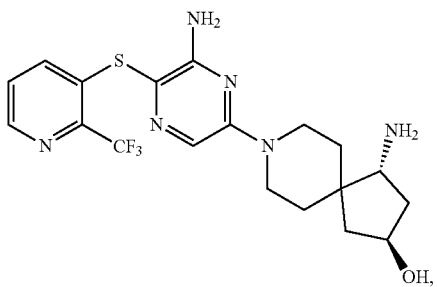

-continued
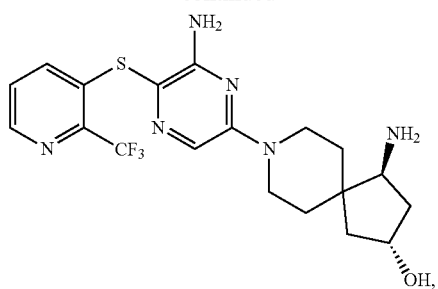
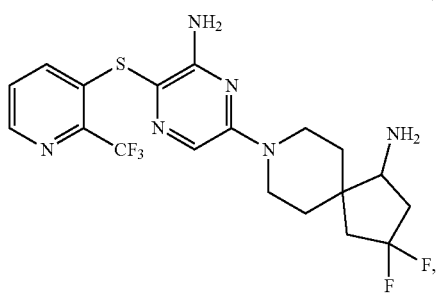
racemic
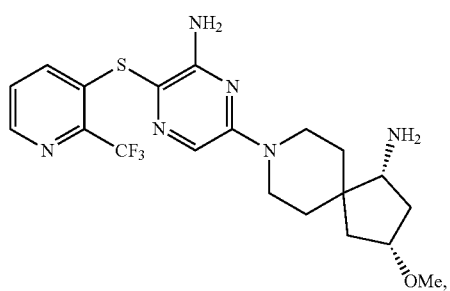
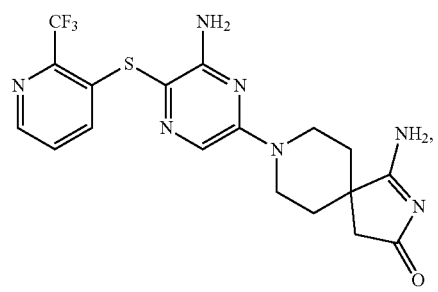
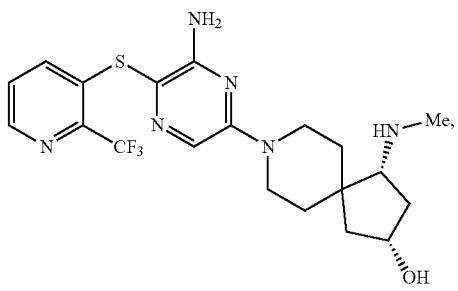
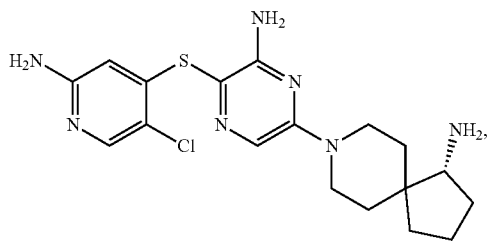
-continued
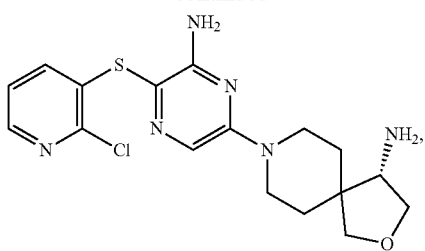
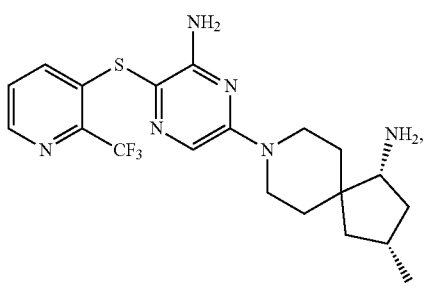
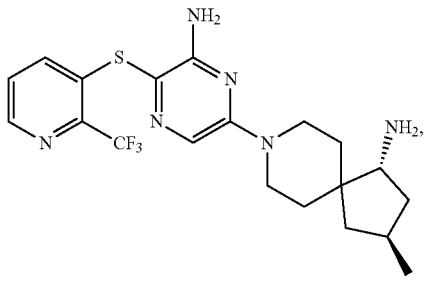
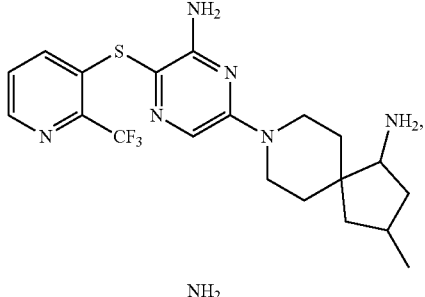
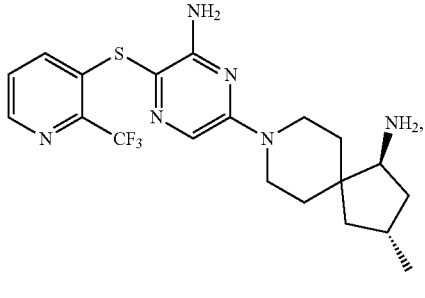
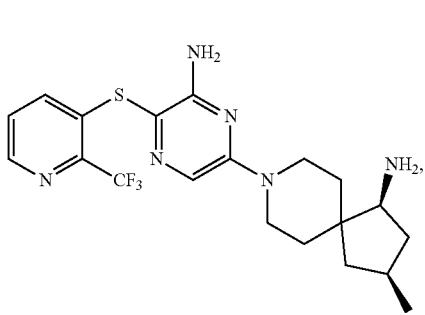

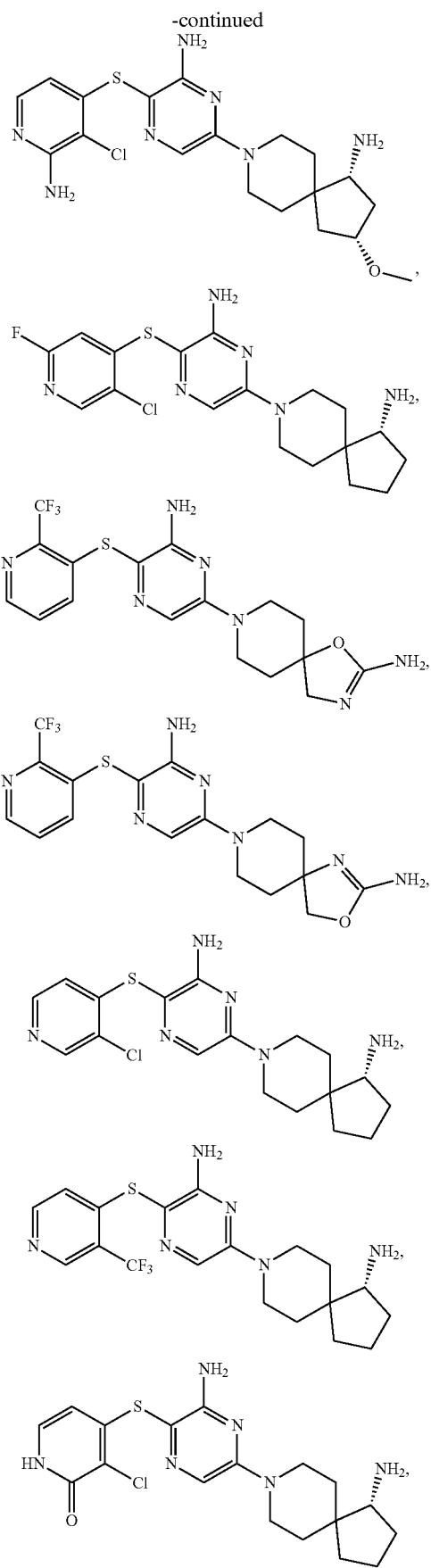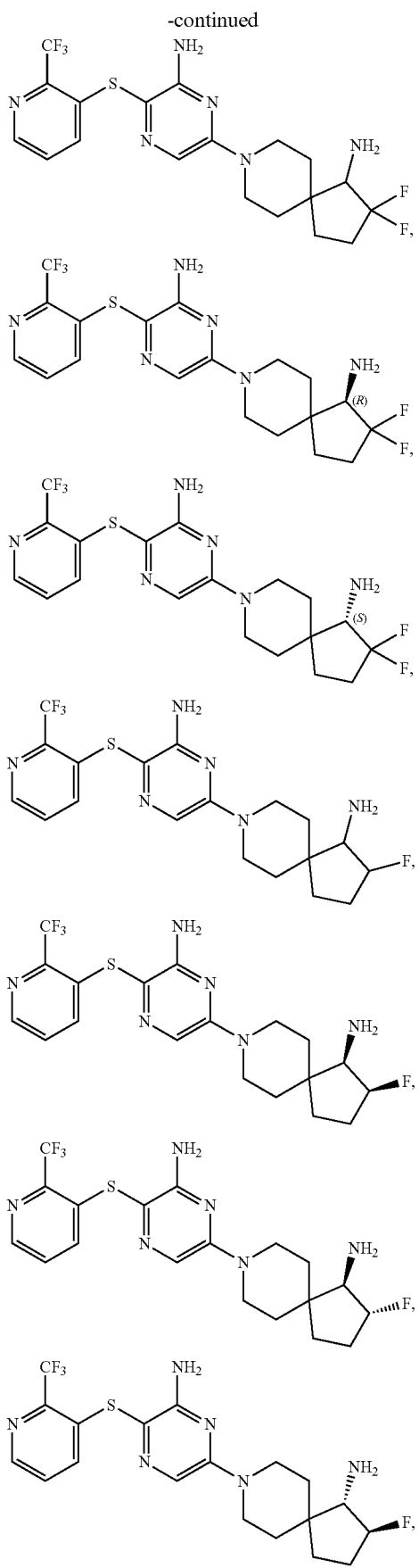

-continued
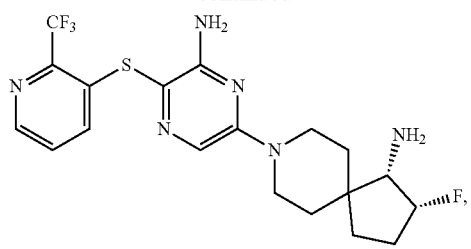
-continued
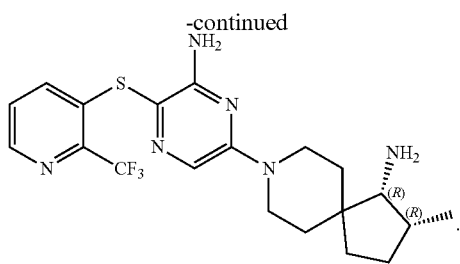
22. A method of treatment comprising administering:
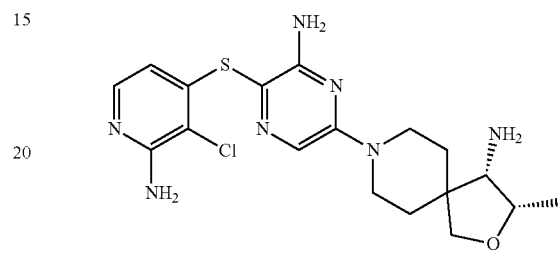
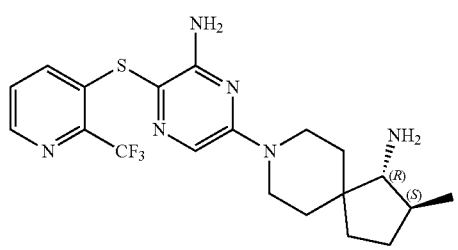
and
or a pharmaceutically acceptable salt thereof, to a person in need of such treatment in an effective amount for the therapeutic treatment of lung cancer.
* * * * *

SEQUENCE LISTING

```
<160> NUMBER OF SEQ ID NOS: 1

<210> SEQ ID NO 1
<211> LENGTH: 20
<212> TYPE: PRT
<213> ORGANISM: Artificial Sequence
<220> FEATURE:
<223> OTHER INFORMATION: biphosphorylated peptide derived from insulin
      receptor substrate-1 (IRS-1)
<220> FEATURE:
<221> NAME/KEY: MOD_RES
<222> LOCATION: (3)..(3)
<223> OTHER INFORMATION: PHOSPHORYLATED TYROSINE
<220> FEATURE:
<221> NAME/KEY: MOD_RES
<222> LOCATION: (9)..(9)
<223> OTHER INFORMATION: dPEG8 from valine residue 9 to leucine residue
      10
<220> FEATURE:
<221> NAME/KEY: MOD_RES
<222> LOCATION: (10)..(10)
<223> OTHER INFORMATION: dPEG8 from leucine residue 10 to valine residue
      9
<220> FEATURE:
<221> NAME/KEY: MOD_RES
<222> LOCATION: (13)..(13)
<223> OTHER INFORMATION: PHOSPHORYLATED TYROSINE
<220> FEATURE:
<221> NAME/KEY: MOD_RES
<222> LOCATION: (20)..(20)
<223> OTHER INFORMATION: AMIDATED LYSINE

<400> SEQUENCE: 1

Leu Asn Tyr Ile Asp Leu Asp Leu Val Leu Ser Thr Tyr Ala Ser Ile
1               5                   10                  15

Asn Phe Gln Lys
            20
```